US012630516B2

(12) United States Patent
Miller et al.

(10) Patent No.: US 12,630,516 B2
(45) Date of Patent: May 19, 2026

(54) COMPOUNDS

(71) Applicant: NRG Therapeutics Ltd., Stevenage (GB)

(72) Inventors: Neil Miller, Stevenage (GB); Richard Rutter, Stevenage (GB); Jan Kulagowski, London (GB); Richard Morphy, London (GB); Tammy Ladduwahetty, Cardiff (GB); John Maclean, Cardiff (GB); Mustafa Moroglu, Cardiff (GB); Eric Talbot, Cardiff (GB); Michael Rowley, London (GB)

(73) Assignee: NRG THERAPEUTICS LTD., Stevenage (GB)

( * ) Notice: Subject to any disclaimer, the term of this patent is extended or adjusted under 35 U.S.C. 154(b) by 496 days.

(21) Appl. No.: 18/023,558

(22) PCT Filed: Sep. 1, 2021

(86) PCT No.: PCT/GB2021/052261
§ 371 (c)(1),
(2) Date: Feb. 27, 2023

(87) PCT Pub. No.: WO2022/049376
PCT Pub. Date: Mar. 10, 2022

(65) Prior Publication Data
US 2024/0067614 A1 Feb. 29, 2024

(30) Foreign Application Priority Data
Sep. 1, 2020 (GB) ...................................... 2013728

(51) Int. Cl.

| | |
|---|---|
| ***C07D 249/18*** | (2006.01) |
| ***C07D 209/34*** | (2006.01) |
| ***C07D 209/96*** | (2006.01) |
| ***C07D 231/56*** | (2006.01) |
| ***C07D 235/26*** | (2006.01) |
| ***C07D 263/58*** | (2006.01) |
| ***C07D 277/68*** | (2006.01) |
| ***C07D 405/12*** | (2006.01) |

(52) U.S. Cl.
CPC ......... *C07D 249/18* (2013.01); *C07D 209/34* (2013.01); *C07D 209/96* (2013.01); *C07D 231/56* (2013.01); *C07D 235/26* (2013.01); *C07D 263/58* (2013.01); *C07D 277/68* (2013.01); *C07D 405/12* (2013.01)

(58) Field of Classification Search
CPC .................................................... C07D 249/18
See application file for complete search history.

(56) References Cited

U.S. PATENT DOCUMENTS

| | | | |
|---|---|---|---|
| 4,948,796 A | 8/1990 | Hiraiwa et al. | |
| 7,915,304 B2 | 3/2011 | Pellicci et al. | |
| 2014/0005221 A1 | 1/2014 | Nagai et al. | |

FOREIGN PATENT DOCUMENTS

| | | | |
|---|---|---|---|
| CA | 2 884 607 A1 | 9/2016 | |
| EP | 1 424 078 A1 | 6/2004 | |
| EP | 2 179 984 A1 | 4/2010 | |
| WO | WO 03/051876 A1 | 6/2003 | |
| WO | WO 2004/037751 A2 | 5/2004 | |
| WO | WO 2008/067863 A2 | 6/2008 | |
| WO | WO 2010/049768 A1 | 5/2010 | |
| WO | WO 2011/087051 A1 | 7/2011 | |
| WO | WO 2016/073633 A1 | 5/2016 | |
| WO | WO 2019/002624 A1 | 1/2019 | |
| WO | WO 2022/049377 A1 | 3/2022 | |

OTHER PUBLICATIONS

Antonucci et al., "A novel class of cardioprotective small-molecule PTP inhibitors," Pharmacological Research, vol. 151, 2020, pp. 1-26.
Chen et al., "Probing Mitochondrial Permeability Transition Pore Activity in Nucleated Cells and Platelets by High-Throughput Screening Assays Suggests Involvement of Protein Phosphatase 2B in Mitochondrial Dynamics,"Assay and Drug Development Technologies, vol. 16, No. 8, 2018, pp. 445-455, 12 pages total.
Fancelli et al., "Cinnamic Anilides as New Mitochondrial Permeability Transition Pore Inhibitors Endowed with Ischemia-Reperfusion Injury Protective Effect in Vivo," Journal of Medicinal Chemistry, vol. 57, 2014, pp. 5333-5347.
Jang et al., "Proximal tubule cyclophilin D mediates kidney fibrogenesis in obstructive nephropathy," American Journal of Physiology Renal Physiology, vol. 321, 2021, pp. F431-F442.
Lacroix, "The design, synthesis and optimisation of calcium release-activated calcium (CRAC) channel inhibitors and mitochondrial permeability transition pore (mPTP) modulators, using phenotypic screening," University of Strathclyde, 2015, 421 pages total.
(Continued)

*Primary Examiner* — Golam M Shameem
(74) *Attorney, Agent, or Firm* — Birch, Stewart, Kolasch & Birch, LLP

(57) ABSTRACT

The invention relates to compounds of formula (I): and related aspects.

(I)

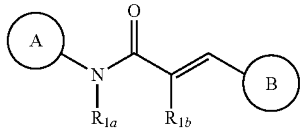

20 Claims, No Drawings

(56) References Cited

OTHER PUBLICATIONS

Martin et al., "GNX-4728, a novel small molecule drug inhibitor of mitochondrial permeability transition, is therapeutic in a mouse model of amyotrophic lateral sclerosis," Frontiers in Cellular Neuroscience, vol. 8, 2014, pp. 1-7.
Roy et al., "Discovery, Synthesis, and Optimization of Diarylisoxazole-3-carboxamides as Potent Inhibitors of the Mitochondrial Permeability Transition Pore," ChemMedChem, vol. 10, No. 10, 2015, pp. 1655-1671.
Song et al., "Design and synthesis of Factor Xa Inhibitors and Their Prodrugs," Bioorganic & Medicinal Chemistry Letters, vol. 13, 2003, pp. 297-300.
Yu et al., "TDP-43 Triggers Mitochondrial DNA Release via mPTP to Activate cGAS/STING in ALS," Cell, vol. 183, 2020, pp. 636-649.
CAS RN : 1268319-90-9, STN, Registry, Mar. 13, 2011.
CAS RN : 2362016-29-1, STN, Registry, Jul. 30, 2019.
CAS RN : 76381-40-3, 76381-39-0, 76381-38-9, STN, Registry, Nov. 16, 1984.
Lacroix, "The design, synthesis and optimisation of calcium release-activated calcium (CRAC) channel inhibitors and mitochondrial permeability transition pore (mPTP) modulators, using phenotypic screening," University of Strathclyde, Nov. 1, 2021, 421 pages total.

COMPOUNDS

FIELD OF THE INVENTION

The invention relates to novel compounds which are inhibitors of the mitochondrial permeability transition pore (mPTP). The invention also inter alia relates to such compounds for use as medicaments, in particular, for the treatment or prevention of degenerative, neurodegenerative or mitochondrial diseases or other diseases or disorders in which inhibition of mPTP provides a therapeutic or prophylactic effect.

BACKGROUND TO THE INVENTION

The mitochondria permeability transition pore (mPTP) is a high conductance channel residing on the inner mitochondrial membrane that is activated under certain conditions of cellular stress, in particular excessive $Ca^{2+}$ loading and oxidative stress. It is permeable to solutes with molecular mass <1.5 kDa, is voltage and $Ca^{2+}$ dependent and exhibits a characteristic large conductance. Once activated, oxidative phosphorylation is uncoupled resulting in the loss of the mitochondria membrane potential and disrupted mitochondria metabolism. In addition, solutes enter the mitochondrial matrix resulting in swelling, eventual rupture of the outer membrane with consequent release of apoptotic factors as well as sequestered $Ca^{2+}$, leading to eventual cell death via apoptosis or necrosis depending on the type and physiology of the cell. As such it has been implicated as a key pathological event in multiple degenerative and metabolic diseases.

Under normal physiological conditions mitochondria play a key role in regulating cellular $Ca^{2+}$ homeostasis. $Ca^{2+}$ entering the cell via cell surface channels, a common mechanism of cell signalling, is rapidly sequestered by mitochondria, preventing excessive and toxic $Ca^{2+}$ accumulation in the cell cytoplasm. In cell types such as neurons, skeletal muscle myofibers and cardiomyocytes which undergo high levels of $Ca^{2+}$ flux, this $Ca^{2+}$ 'buffering' effect of mitochondria is critical to maintain cell health. However, there is a limit to the capacity of mitochondria to sequester $Ca^{2+}$ and if intramitochondrial $Ca^{2+}$ levels reach a certain threshold the $Ca^{2+}$ sensitive mPTP is activated, resulting in collapse of the mitochondria and initiation of cell death. Activation of the mPTP in degenerative diseases may occur in a variety of ways depending on the disease, for example: 1) excessive $Ca^{2+}$ entry into cells and overload of the mitochondria with $Ca^{2+}$ 2) dysfunctional mitochondrial $Ca^{2+}$ efflux mechanisms, in particular decreased activity of the $Ca^{2+}$ efflux transporter NCLX resulting in $Ca^{2+}$ overload 3) overactivity or upregulation of the $Ca^{2+}$ uptake mechanisms in mitochondria 4) oxidative stress 5) sensitization of the mPTP due to compromised mitochondrial function i.e. mPTP activation at lower intramitochondrial concentrations of $Ca^{2+}$ 6) excessive transfer of $Ca^{2+}$ from the endoplasmic reticulum into the mitochondria at contact points between the two organelles known as mitochondria-associated-membranes.

While the properties and function of the mPTP can be studied in simple in vitro assays in isolated mitochondria, the molecular identity of the mPTP is not known. Multiple proteins have been proposed to comprise the pore forming complex, including the ATP synthase and the adenine nucleotide transporter (ANT) family of proteins but no single protein is widely accepted as being responsible for formation of the pore. However, the peptidyl prolyl cis-trans isomerase F (Ppif), also known as cyclophilin D, is well accepted to be a key regulator of the pore, though not forming a transmembrane channel in its own right. Genetic or pharmacological inhibition of Ppif significantly decreases the sensitivity of pore opening in response to $Ca^{2+}$ loading and other mPTP activators. Genetic ablation or pharmacological inhibition of Ppif has therefore been utilised to evaluate involvement of the mPTP in pathological pathways in cell and animal disease models. In this way, inhibition of the mPTP has been shown to be protective in numerous models of disease, in particular those where $Ca^{2+}$ dysregulation and oxidative stress are known to contribute to cellular degeneration. Notably, genetic knockout of Ppif was shown to be protective in various preclinical in vivo transgenic models of neurodegenerative disease including Alzheimer's disease, Parkinson's disease and motor neuron disease, demonstrating the therapeutic potential of mPTP inhibition. In each of these diseases, genetic mutations in particular proteins that cause inherited forms of disease (i.e. amyloid precursor protein, alpha-synuclein and superoxide dismutase 1 respectively), and are expressed in the mouse models, have been shown to cause either $Ca^{2+}$ overload of the mitochondria or sensitization of the mPTP. Recent evidence suggests this may occur through a common mechanism in Alzheimer's, Parkinson's and Friedreich's ataxia. In each case, it has been reported that in cells expressing the mutated disease associated proteins (amyloid precursor protein, PINK1 and frataxin respectively), the activity or expression of the mitochondrial $Ca^{2+}$ efflux transporter, NCLX, is decreased, resulting in $Ca^{2+}$ overload of the mitochondria. In the case of Parkinson's disease, the pathological aggregated form of the protein alpha-synuclein, a common misfolded protein in sporadic and inherited cases of Parkinson's disease, has also been shown to sensitise and activate the mPTP.

Genetic ablation of Ppif has been shown to be beneficial in numerous other preclinical models of degenerative disease, therefore demonstrating the potential of mPTP inhibitors in Duchenne and congenital forms of muscular dystrophy, ischemia-reperfusion injury, bone repair, pancreatitis and inter alia other associated disorders.

In addition to the demonstrated benefit of Ppif inhibition in preclinical models, mPTP function has been shown to be dysregulated in multiple other disease indications. In particular, in a number of diseases the threshold for mPTP activation in response to $Ca^{2+}$ loading appears to be sensitised suggesting that mPTP activation may occur aberrantly under physiological conditions and drive tissue degeneration. For example, in muscle mitochondria from elderly human muscle biopsies, the threshold for mPTP activation is reduced compared to healthy control. In these diseases, this sensitization of mPTP activity underlies additional rationale for the therapeutic potential of mPTP inhibitors.

mPTP inhibitors may also have therapeutic potential in other diseases where mitochondrial dysfunction, oxidative stress, inflammatory stress or $Ca^{2+}$ dysregulation occur during disease pathogenesis.

The discovery and development of inhibitors of the mPTP has largely been focussed on identification of Ppif inhibitors. Cyclosporin A (CsA), originally identified as an immunosuppressant by virtue of its inhibitory activity at calcineurin, was also found to inhibit Ppif as well as other members of the peptidyl prolyl cis-trans isomerase (Ppi) enzyme family. Several cyclosporin A derivatives e.g. Debio-25, NIM811 were subsequently developed that retained broad activity against the Ppi enzyme family without inhibiting calcineurin, however none of these progressed to market. To date, no potent brain penetrant selective Ppif inhibitors have been reported. Other more recent approaches to discover mPTP inhibitors, have utilised phenotypic screens in isolated mitochondria. These have successfully identified potent small molecule mPTP inhibitors with a Ppif-independent mode of action.

Yu et al., (2020, Cell, 183, 1-14) relates to the link between mPTP activation and the mechanism of TDP-43 proteinopathy such as TAR DNA-binding protein 43 (TDP-43) associated neurodegeneration. Cytoplasmic neuronal accumulation of the normally nuclear protein TDP-43 is a disease hallmark for almost all cases of ALS and 40-50% of Frontotemporal Lobar Degeneration (FTLD), with some familial cases caused by mutant forms of the protein. Both diseases are associated with a neuroinflammatory cytokine profile related to upregulation of NF-κB and type I IFN pathways, directly suggesting a role for TDP-43 in neuroinflammation. Mutant or overexpressed WT TDP-43 in neurons mis-localises to the mitochondria and induces the release of mitochondrial DNA (mtDNA) into the cytoplasm. This mtDNA then activates the immune sensor cGAS-STING triggering the induction of innate immune genes such as IL-6, TNFα, and interferons. Inhibition of the mPTP with cyclosporin A or via CypD knockout, prevents the TDP-43 induced release of mtDNA and subsequent induction of innate immune response genes. Furthermore, inhibition of cGAS-STING extends the survival of mutant mice expressing a mutant TDP-43. The data implicates mPTP activation in mediating the toxic effects of TDP-43 in ALS and other disease where either mutations in the TDP-43 gene causes disease or where TDP-43 proteinopathy is observed.

Jang et al., (2021 American Journal of Physiology: Renal physiology, doi: 10.1152/ajprenal.00171.2021. Epub ahead of print. PMID: 34396791.) highlighted the potential therapeutic benefit of mPTP inhibition (via CypD knockout) in a mouse model a kidney fibrosis. Unilateral ureteral obstruction was used to induce kidney fibrosis in WT and CypD KO mice. Inflammation, proximal tubule atrophy and markers of fibrosis were reduced in the CypD KO mice versus WT. Measures of fibrosis included collagen deposition, α-SMA and TGFβ expression, and interstitial cell proliferation. This highlights the potential role of the mPTP in cell injury/death-mediated tissue remodelling and fibrogenesis. mPTP inhibitors may therefore be beneficial in diseases where fibrosis is a key pathological mechanism, e,g, chronic kidney disease, idiopathic pulmonary fibrosis, non-alcoholic steatohepatitis, primary biliary cholangitis and systemic sclerosis.

CYP2D6 is one of the major members of the human drug metabolising cytochrome P450 enzyme system. It is involved in the hepatic metabolism of a significant proportion of clinically used drugs. Inhibition of CYP2D6 can drive drug-drug interactions with co-prescribed medications metabolised by the same enzyme, which result in increased plasma concentrations potentially to levels which may cause adverse effects. CYP2D6 is predominately expressed in the liver but also, to a lesser degree, in the central nervous system (CNS). In the CNS it is involved in the synthesis of different neurotransmitters such as dopamine. Consequently, inhibition of CYP2D6 particularly at the level of the central nervous system can potentially have detrimental effects via impairment of pathways such as the production of dopamine. In Parkinson's disease, which is characterized by the loss of dopaminergic neurons in the Substantia Nigra, further depletion of dopamine levels through inhibition of CYP2D6 may not be tolerated.

When dosed orally, the oral bioavailability and systemic exposure of a drug are largely determined by the degree of absorption from the gastrointestinal tract and the extent of first-pass metabolism in the liver. Properties such as high solubility (as measured in phosphate-buffered saline (PBS) or in the more biologically relevant Fasted State Simulated Intestinal Fluid (FaSSIF)) and high metabolic stability (as measured in vitro in either isolated liver microsomes or in hepatocytes from rat and human) are therefore predictive of improved oral bioavailability and/or systemic exposure in patients.

WO2010/049768 relates to acrylamido derivatives and their use as therapeutic agents, particularly for the prevention and/or treatment of diseases associated with the activity of the mPTP (see also Plyte et al. J. Med Chem. 2014, 57, 5333-47). Chen et al. (Assay and Drug Development Technologies, 2018, 16, 445-455) relates to phenotypic screening for mPTP modulators using platelets, and discloses further acrylamido derivatives. CA2884607A1 relates to acrylamido and maleimide compounds which are said to be useful in the treatment of mitochondrial diseases.

There remains a need to find further compounds which are inhibitors of mPTP, and in particular those that combine inhibition of mPTP with low CYP2D6 inhibition. Such compounds may also display other desirable pharmacological properties, such as improved oral bioavailability and/or improved systemic exposure.

SUMMARY OF THE INVENTION

The invention provides a compound of formula (I):

(I)

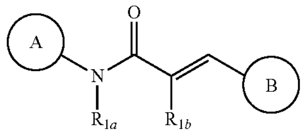

wherein:

$R_{1a}$ is H or methyl;

$R_{1b}$ is H or F;

A is group (Aa), (Ab), (Ac) or (Ad):

wherein group (Aa) is:

(Aa)

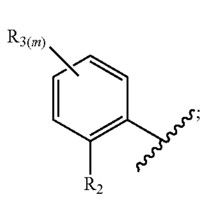

wherein:

$R_2$ is H, $C_{1-4}$alkyl, $C_{1-4}$alkylene(aryl), $C_{1-4}$alkylene(OH), $C_{1-4}$alkylene($C_{3-6}$cycloalkyl), $C_{1-4}$alkylene(4-7 membered heterocycloalkyl), $C_{1-4}$alkoxy, $OC_{1-4}$alkylene(aryl), $C_{1-4}$alkyleneO$C_{1-4}$alkyl, $C_{1-4}$alkyleneO$C_{3-6}$cycloalkyl, $C_{1-4}$alkyleneO(4-7 membered heterocycloalkyl), $C_{1-4}$alkyleneO(aryl), $C_{3-6}$alkynyl or $C_{1-4}$alkenylO($C_{3-6}$alkynyl); wherein said aryl, heterocycloalkyl and cycloalkyl are optionally substituted by 1, 2 or 3 substituents each independently selected from $C_{1-4}$alkyl, $C_{3-6}$cycloalkyl, $C_{1-4}$alkoxy, $C_{1-4}$haloalkyl, halo, CN, OH, $NR_{2a}R_{2b}$, $SO_2R_{2c}$ and $NHSO_2R_{2c}$;

$R_{2a}$ is selected from H and $C_{1-4}$alkyl;

$R_{2b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{2c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

each $R_3$ is independently halo, methyl, ethyl or n-propyl;

m is 0, 1, 2, 3 or 4;

wherein group (Ab) is:

(Ab)

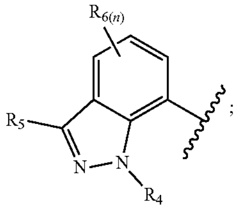

wherein:

$R_4$ is H, $C_{1-4}$alkyl or $C_{1-4}$alkylene(aryl); wherein said aryl is optionally substituted by 1, 2 or 3 substituents each independently selected from $C_{1-4}$alkyl, $C_{3-6}$cycloalkyl, $C_{1-4}$alkoxy, $C_{1-4}$haloalkyl, halo, CN, OH, $NR_{4a}R_{4b}$, $SO_2R_{4c}$ and $NHSO_2R_{4c}$;

$R_{4a}$ is selected from H and $C_{1-4}$alkyl;

$R_{4b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{4c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

$R_5$ is H or $C_{1-4}$alkyl;

each $R_6$ is independently $C_{1-4}$alkyl or halo;

n is 0, 1, 2 or 3;

wherein group (Ac) is:

$R_7$ (Ac);

wherein:

(Ac)

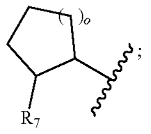

$R_7$ is $C_{1-4}$alkyl, $C_{1-4}$alkylene(OH) or $C_{1-4}$alkyleneO$C_{1-4}$alkyl;

o is 1 or 2;

wherein group (Ad) is:

(Ad)

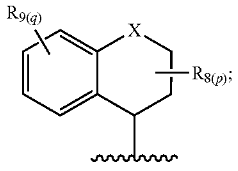

wherein:

X is a bond, O or $CH_2$;

each $R_3$ is independently halo, $C_{1-4}$alkyl, $C_{1-4}$alkoxy, O$C_{1-4}$haloalkyl, O$C_{1-4}$alkylene($C_{3-6}$cycloalkyl), O$C_{1-4}$alkylene(4-7 membered heterocycloalkyl) or OH; wherein said heterocycloalkyl and cycloalkyl are optionally substituted by 1, 2 or 3 substituents independently selected from $C_{1-4}$alkyl, $C_{3-6}$cycloalkyl, $C_{1-4}$alkoxy, $C_{1-4}$haloalkyl, halo, CN, OH, $NR_{8a}R_{8b}$, $SO_2R_{8c}$ and $NHSO_2R_{8c}$;

$R_{8a}$ is selected from H and $C_{1-4}$alkyl;

$R_{8b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{8c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

each $R_9$ is independently halo or $C_{1-4}$alkyl;

p is 0, 1 or 2;

q is 0, 1, 2, 3 or 4;

wherein B is group (Ba), (Bb) or (Bc):

wherein group (Ba) is:

(Ba)

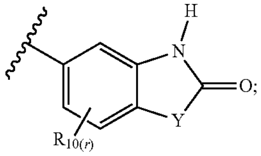

wherein:

Y is $C(R_{11})(R_{12})$, $N(R_{13})$, O or S;

each $R_{10}$ is independently halo or $C_{1-4}$alkyl;

r is 0, 1, 2 or 3;

$R_{11}$ is H or $C_{1-4}$alkyl;

$R_{12}$ is H or $C_{1-4}$alkyl; or $R_{11}$ and $R_{12}$ together with the carbon atom to which they are attached form a $C_{3-6}$cycloalkyl;

$R_{13}$ is H, $C_{1-4}$alkyl or $C_{3-6}$cycloalkyl;

wherein said cycloalkyl is optionally substituted by 1, 2 or 3 substituents independently selected from $C_{1-4}$alkyl, $C_{3-6}$cycloalkyl, $C_{1-4}$alkoxy, $C_{1-4}$haloalkyl, halo, CN, OH, $NR^{13a}R^{13b}SO_2R_{13c}$ and $NHSO_2R_{13c}$;

$R_{13a}$ is selected from H and $C_{1-4}$alkyl;

$R_{13b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{13c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

wherein group (Bb) is:

(Bb)

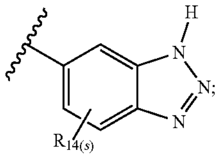

wherein:

each $R_{14}$ is independently halo or $C_{1-4}$alkyl;

s is 0, 1, 2 or 3;

wherein group (Bc) is:

(Bc)

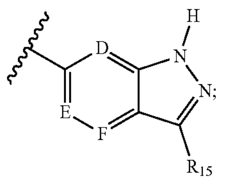

wherein:

$R_{15}$ is $C_{1-4}$alkyl, $C_{1-4}$alkoxy, $C_{3-6}$cycloalkyl, $C_{1-4}$haloalkyl, halo or CN; wherein said cycloalkyl is optionally substituted by 1, 2 or 3 substituents independently selected from $C_{1-4}$alkyl, $C_{3-6}$cycloalkyl, $C_{1-4}$alkoxy, $C_{1-4}$haloalkyl, halo, CN, OH, $NR_{15a}R_{15b}$, $SO_2R_{15c}$ and $NHSO_2R_{15c}$;

$R_{15a}$ is selected from H and $C_{1-4}$alkyl;

$R_{15b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{15c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

$R_{16}$ is H, halo or $C_{1-4}$alkyl; and

D, E and F are each independently $C(R_{16})$; or one of D, E and F is N, and the two remaining D, E and F groups are independently $C(R_{16})$;

or a pharmaceutically acceptable salt and/or solvate thereof.

Suitably, there is provided a compound of formula (I):

(I)

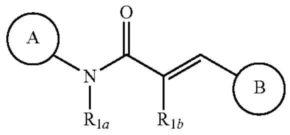

wherein:

$R_{1a}$ is H or methyl;

$R_{1b}$ is H or F;

A is group (Aa), (Ab), (Ac) or (Ad):

wherein group (Aa) is:

(Aa)

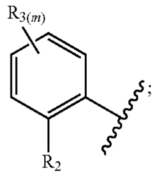

wherein:

$R_2$ is H, $C_{1-4}$alkyl, $C_{1-4}$alkylene(aryl), $C_{1-4}$alkylene (OH), $C_{1-4}$alkylene($C_{3-6}$cycloalkyl), $C_{1-4}$alkylene (4-7 membered heterocycloalkyl) such as $C_1$alkylene(4-7 membered heterocycloalkyl), $C_{1-4}$alkoxy, $OC_{1-4}$alkylene(aryl), $C_{1-4}$alkyleneO $C_{1-4}$alkyl, $C_{1-4}$alkyleneO$C_{3-6}$cycloalkyl, $C_{1-4}$alkyleneO(4-7 membered heterocycloalkyl), $C_{1-4}$alkyleneO(aryl), $C_{3-6}$alkynyl, or $C_{1-4}$alkyleneO($C_{3-6}$alkynyl); wherein said aryl, heterocycloalkyl and cycloalkyl may be optionally substituted by up to 3 substituents each independently selected from $C_{1-4}$alkyl, $C_{3-6}$cycloalkyl, $C_{1-4}$alkoxy, $C_{1-4}$haloalkyl, halo and CN;

each $R_3$ is independently halo, methyl, ethyl or n-propyl;

m is 0, 1, 2, 3 or 4;

wherein group (Ab) is:

(Ab)

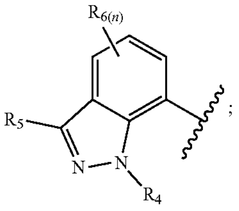

wherein:

$R_4$ is H, $C_{1-4}$alkyl or $C_{1-4}$alkylene(aryl); wherein said aryl may be optionally substituted by up to 3 substituents each independently selected from $C_{1-4}$alkyl, $C_{3-6}$cycloalkyl, $C_{1-4}$alkoxy, $C_{1-4}$haloalkyl, halo and CN;

$R_5$ is H or $C_{1-4}$alkyl;

each $R_6$ is independently $C_{1-4}$alkyl or halo;

n is 0, 1, 2 or 3;

wherein group (Ac) is:

(Ac)

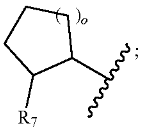

wherein:

$R_7$ is $C_{1-4}$alkyl, $C_{1-4}$alkylene(OH) or $C_{1-4}$alkylene $OC_{1-4}$alkyl;

o is 1 or 2;

wherein group (Ad) is:

(Ad)

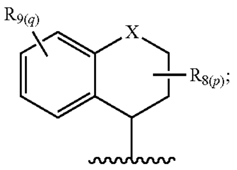

wherein:

X is a bond, O or $CH_2$;

each $R_3$ is independently halo, $C_{1-4}$alkyl, $C_{1-4}$alkoxy or OH;

each $R_9$ is independently halo or $C_{1-4}$alkyl;

p is 0, 1 or 2;

q is 0, 1, 2, 3 or 4;

wherein B is group (Ba), (Bb) or (Bc):

wherein group (Ba) is:

(Ba)

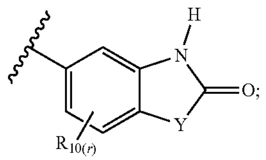

wherein:

Y is $C(R_{11})(R_{12})$, $N(R_{13})$, O or S;

each $R_{10}$ is independently halo or $C_{1-4}$alkyl;

r is 0, 1, 2 or 3;

$R_{11}$ is H or $C_{1-4}$alkyl;

$R_{12}$ is H or $C_{1-4}$alkyl; or $R_{11}$ and $R_{12}$ together with the carbon atom to which they are attached form a $C_{3-6}$cycloalkyl;

$R_{13}$ is H, $C_{1-4}$alkyl or $C_{3-6}$cycloalkyl;

wherein group (Bb) is:

(Bb)

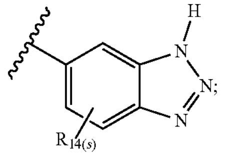

wherein:

each $R_{14}$ is independently halo or $C_{1-4}$alkyl;

s is 0, 1, 2 or 3;

wherein group (Bc) is:

(Bc)

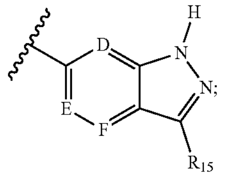

wherein:

$R_{15}$ is $C_{1-4}$alkyl, $C_{3-6}$cycloalkyl, $C_{1-4}$haloalkyl or CN;

$R_{16}$ is H, halo or $C_{1-4}$alkyl; and

D, E and F are each independently $C(R_{16})$; or one of D, E and F is N and the two remaining D, E and F groups are independently $C(R_{16})$;

or a pharmaceutically acceptable salt and/or solvate thereof.

In one embodiment, a compound of formula (I) is provided in the form of a pharmaceutically acceptable salt. In one embodiment, a compound of formula (I) is provided in the form of a solvate. In one embodiment, a compound of formula (I) is provided.

The invention further provides pharmaceutical compositions comprising a compound of formula (I), or a pharmaceutically acceptable salt and/or solvate thereof, and a pharmaceutically acceptable carrier or excipient.

The invention also provides a compound of formula (I), or pharmaceutically acceptable salt and/or solvate thereof, for use in the treatment or prophylaxis of a disease or disorder in which inhibition of mPTP provides a therapeutic or prophylactic effect.

The invention also provides a compound of formula (I), or a pharmaceutically acceptable salt and/or solvate thereof, for use in the manufacture of a medicament for the treatment or prophylaxis of a disease or disorder in which inhibition of mPTP provides a therapeutic or prophylactic effect.

The invention also provides a method of preventing or treating a disorder in which inhibition of mPTP provides a therapeutic or prophylactic effect in a subject.

Suitably the disease or disorder is selected from degenerative or neurodegenerative diseases, disorders of the central nervous system, ischemia and re-perfusion injury, metabolic diseases, inflammatory or autoimmune diseases, diseases of aging and renal diseases.

The invention also provides a compound of formula (I), or a pharmaceutically acceptable salt and/or solvate thereof, for use in the treatment or prophylaxis of a mitochondrial disease.

The invention also provides a compound of formula (I), or a pharmaceutically acceptable salt and/or solvate thereof, for use in the manufacture of a medicament for the treatment or prophylaxis of a mitochondrial disease.

The invention also provides a method of preventing or treating a mitochondrial disease in a subject, which comprises administering to a subject in need thereof an effective amount of a compound of formula (I), or a pharmaceutically acceptable salt and/or solvate thereof.

The invention also provides a compound of formula (I), or a pharmaceutically acceptable salt and/or solvate thereof, for use in the treatment or prophylaxis of a disease or disorder associated with TDP-43 proteinopathy such as TDP-43 associated neurodegeneration.

The invention also provides a compound of formula (I), or a pharmaceutically acceptable salt and/or solvate thereof, for use in the manufacture of a medicament for the treatment or prophylaxis of a disease or disorder associated with TDP-43 proteinopathy such as TDP-43 associated neurodegeneration.

The invention also provides a method of treating or preventing a disease or disorder associated with TDP-43 proteinopathy such as TDP-43 associated neurodegeneration, which comprises administering to a subject in need thereof an effective amount of a compound of formula (I), or a pharmaceutically acceptable salt and/or solvate thereof.

The invention also provides a compound of formula (I), or a pharmaceutically acceptable salt and/or solvate thereof, for use in the treatment or prophylaxis of a disease or disorder associated with fibrosis.

The invention also provides a compound of formula (I), or a pharmaceutically acceptable salt and/or solvate thereof, for use in the manufacture of a medicament for the treatment or prophylaxis of a disease or disorder associated with fibrosis.

The invention also provides a method of treating or preventing a disease or disorder associated with fibrosis, which comprises administering to a subject in need thereof an effective amount of a compound of formula (I), or a pharmaceutically acceptable salt and/or solvate thereof.

DETAILED DESCRIPTION OF THE INVENTION

The term "alkyl" as used herein, such as in $C_{1-4}$alkyl, whether alone or forming part of a larger group, is a straight or branched fully saturated hydrocarbon chain containing the specified number of carbon atoms. Examples of $C_{1-4}$alkyl groups include methyl, ethyl, n-propyl, iso-propyl, n-butyl, iso-butyl, tert-butyl and sec-butyl. Reference to "propyl" includes n-propyl and iso-propyl. Reference to "butyl" includes n-butyl, iso-butyl, tert-butyl and sec-butyl.

The term "alkylene" as used herein, such as $C_{1-4}$alkylene, whether alone or forming part of a larger group e.g. $C_{1-4}$alkylene(aryl), $C_{1-4}$alkylene(OH), $C_{1-4}$alkylene($C_{3-6}$cycloalkyl), $OC_{1-4}$alkylene($C_{3-6}$cycloalkyl), $C_{1-4}$alkylene(4-7 membered heterocycloalkyl), $OC_{1-4}$alkylene(4-7 membered heterocycloalkyl), $C_{1-4}$alkoxy, $OC_{1-4}$alkylene(aryl), $C_{1-4}$alkyleneO$C_{1-4}$alkyl, $C_{1-4}$alkyleneO$C_{3-6}$cycloalkyl, $C_{1-4}$alkyleneO(4-7 membered heterocycloalkyl), $C_{1-4}$alkyleneO (aryl) or $C_{1-4}$alkyleneO($C_{3-6}$alkynyl), e.g. $C_{1-4}$alkylene (aryl), $C_{1-4}$alkylene(OH), $C_{1-4}$alkylene($C_{3-6}$cycloalkyl), $C_{1-4}$alkylene(4-7 membered heterocycloalkyl), $C_{1-4}$alkoxy, $OC_{1-4}$alkylene(aryl), $C_{1-4}$alkyleneO$C_{1-4}$ alkyl, $C_{1-4}$alkyleneO$C_{3-6}$cycloalkyl, $C_{1-4}$alkyleneO(4-7 membered heterocycloalkyl), $C_{1-4}$alkyleneO(aryl) or $C_{1-4}$alkyleneO($C_{3-6}$alkynyl), is a bifunctional straight or branched fully saturated hydrocarbon group containing the specified number of carbon atoms. Examples of $C_{1-4}$alkylene groups include methylene (i.e. $—CH_2—$), ethylene (i.e. $—CH_2CH_2—$) n-propylene (i.e. $(—CH_2)_3—$) and n-butylene (i.e. $(—CH_2)_4—$). A branched example of a $C_{1-4}$alkylene group is i-propylene (i.e. $—CH(Me)CH_2—$).

The term $C_{1-4}$alkylene(OH) means an $C_{1-4}$alkyl group substituted by OH, such as $CH_2OH$.

The term "alkoxy" as used herein, such as in $C_{1-4}$alkoxy, refers to an alkyl group (e.g. a $C_{1-4}$alkyl group) as defined above, singularly bonded to an oxygen atom. Examples of $C_{1-4}$alkoxy groups include methoxy, ethoxy, 1-propoxy, 2-propoxy, 1-butoxy, 2-butoxy and 3-butoxy, especially methoxy.

The term 'halo' or 'halogen' as used herein, refers to fluorine, chlorine, bromine or iodine. Particular examples of halo are bromine, fluorine and chlorine, especially fluorine.

The term "haloalkyl" as used herein, such as in $C_{1-4}$haloalkyl, whether alone or forming part of a larger group such as $OC_{1-4}$haloalkyl, is a straight or branched alkyl group containing the specified number of carbon atoms, substituted by one or more halo atoms, for example fluoromethyl ($CH_2F$), di-fluoromethyl ($CHF_2$), tri-fluoromethyl ($CF_3$), 1-fluoroethyl ($CH_2FCH_2$) and 2-fluoroethyl ($CH_2CH_2F$).

The term "cycloalkyl" as used herein, such as in $C_{3-6}$cycloalkyl, whether alone or forming part of a larger group such as $C_{1-4}$alkylene($C_{3-6}$cycloalkyl) or $C_{1-4}$alkylene $OC_{3-6}$cycloalkyl is a fully saturated hydrocarbon ring containing the specified number of carbon atoms. Examples of $C_{3-6}$cycloalkyl groups include cyclopropyl, cyclobutyl, cyclopentyl and cyclohexyl, in particular cyclopropyl. Optionally, the cycloalkyl may be substituted as defined herein.

The term "heterocycloalkyl" as used herein, such as in 4-7 membered heterocycloalkyl, whether alone or forming part of a larger group such as $C_{1-4}$alkylene(4-7 membered heterocycloalkyl) and $C_{1-4}$alkyleneO(4-7 membered heterocycloalkyl), is a fully saturated hydrocarbon ring containing the specified number of carbon atoms, wherein at least one of the carbon atoms is replaced by a heteroatom such as N, S or O. Optionally, the heterocycloalkyl may be substituted as defined herein.

Examples of 4-7 membered heterocycloalkyl groups include those comprising one heteroatom such as containing one heteroatom (e.g. nitrogen) or containing two or more heteroatoms (such as two heteroatoms e.g. two nitrogen atoms or one nitrogen atom and one oxygen atom).

Examples of 4-7 membered heterocycloalkyl groups containing one nitrogen atom include azetidinyl, pyrrolidinyl, piperidinyl and azepanyl. Examples of 4-7 membered heterocycloalkyl groups containing two nitrogen atoms include diazetidinyl, imidazolidinyl, pyrazolidinyl, diazinanyl, and diazepanyl.

Other examples of 4-7 membered heterocycloalkyl groups include oxetanyl, thietanyl, dioxetanyl, dithietanyl, tetrahydrofuranyl, tetrahydrothiophenyl, oxazolidinyl, isoxazolidinyl, thiazolidinyl, isothiazolidinyl, tetrahydropyranyl, thianyl, morpholinyl, thiomorpholinyl, dioxanyl, dithianyl, triazinanyl, trioxanyl, trithianyl, oxepanyl, and thiepanyl.

The term "aryl" as used herein, whether alone or forming part of a larger group e.g. $C_{1-4}$alkylene(aryl), $OC_{1-4}$alkylene (aryl) or $C_{1-4}$alkyleneO(aryl), refers to a phenyl ring. Optionally, the aryl may be substituted as defined herein.

The term "alkynyl" as used herein, such as in $C_{3-6}$alkynyl, whether alone or forming part of a larger group such as $C_{1-4}$alkyleneO($C_{3-6}$alkynyl), is a straight or branched divalent hydrocarbon chain with a least one carbon-carbon triple bond. Examples of $C_{3-6}$alkynyl include ethynyl, 1-propynyl, 2-propynyl, 1-butynyl, 2-butynyl, pentynyl and hexynyl.

An example of $C_{1-4}$alkylene(aryl) is $CH_2Ph$ where Ph means phenyl. Examples of $C_{1-4}$alkyleneO$C_{1-4}$alkyl include $CH_2OMe$, $CH_2Oet$ and $CH_2Opr$. Examples of $C_{1-4}$alkyleneO$C_{3-6}$ cycloalkyl include $CH_2O—C_3$cycloalkyl and $CH_2O—C_4$cycloalkyl, for example $CH_2O$-cyclopropyl or $CH_2O$-cyclobutyl. Examples of $C_{1-4}$alkylene(4-7 membered heterocycloalkyl) include $CH_2$(4-membered heterocycloalkyl), for example $CH_2$-azetidinyl, $CH_2CH_2$-azetidinyl. Examples of $C_{1-4}$alkyleneO(4-7 membered heterocycloalkyl) include $C_{1-4}$alkylO$C_4$heterocycloalkyl, such as $CH_2O$-azetidinyl. An example of $C_{1-4}$alkyleneO($C_{3-6}$alkynyl) is $CH_2OCH_2C≡CH$.

Where substituents are indicated as being optionally substituted in formula (I) in the embodiments and preferences set out below, the optional substituent may be attached to an available carbon atom, which means a carbon atom which is attached to a hydrogen atom i.e. a C—H group or the optional substituent may be attached to an available nitrogen atom, which means a nitrogen atom which is attached to a hydrogen atom i.e. a N—H group. The optional substituent replaces the hydrogen atom attached to the carbon atom or the hydrogen atom attached to the nitrogen atom.

In one embodiment, A is group (Aa):

(Aa)

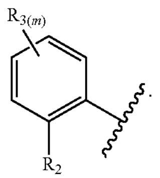

In one embodiment $R_2$ is $C_{1-4}$alkyl, such as methyl, ethyl, propyl or butyl, especially methyl; $C_{1-4}$alkylene(aryl), such as benzyl; $C_{1-4}$alkylene(OH), such as $CH_2OH$; $C_{1-4}$alkyleneO$C_{1-4}$alkyl, such as $CH_2OMe$, $CH_2OEt$ or $CH_2OPr$, especially $CH_2Ome$; $C_{1-4}$alkyleneO$C_{3-6}$cycloalkyl, such as $CH_2O—C_3$cycloalkyl or $CH_2O—C_4$cycloalkyl, for example $CH_2O$-cyclopropyl or $CH_2O$-cyclobutyl; $C_{1-4}$alkyleneO (aryl), such as $CH_2OPh$; $C_{1-4}$alkylene(4-7 membered heterocycloalkyl), such as $CH_2$(4-membered heterocycloalkyl), for example $CH_2$-azetidinyl, or $CH_2CH_2$(4-membered heterocycloalkyl) for example $CH_2CH_2$-azetidinyl; $C_{1-4}$alkyleneO(4-7 membered heterocycloalkyl) such as $C_{1-4}$alkylO$C_4$heterocycloalkyl, especially $CH_2O$-azetidinyl; or $C_{1-4}$alkyleneO($C_{3-6}$alkynyl), such as $CH_2OCH_2C{\equiv}CH$. Suitably, $R_2$ is methyl, $CH_2OH$ or $CH_2OMe$, in particular methyl.

The aryl, heterocycloalkyl and cycloalkyl groups present in $R_2$ may be optionally substituted by up to 3 substituents, such as 1, 2 or 3, such as 1 or 2, e.g. 1 substituent, each independently selected from $C_{1-4}$alkyl, such as methyl; $C_{3-6}$cycloalkyl, such as cyclopropyl; $C_{1-4}$alkoxy, such as OMe; $C_{1-4}$haloalkyl, such as $CF_3$; halo, such as chloro or fluoro; CN; OH; $NR_{2a}R_{2b}$; $SO_2R_{2c}$; and $NHSO_2R_{2c}$. Suitably, the aryl, heterocycloalkyl and cycloalkyl groups present in $R_2$ may be optionally substituted by up to 3 substituents, such as 1, 2 or 3, such as 1 or 2, e.g. 1 substituent, each independently selected from $C_{1-4}$alkyl, such as methyl; $C_{3-6}$cycloalkyl, such as cyclopropyl; $C_{1-4}$alkoxy, such as OMe; $C_{1-4}$haloalkyl, such as $CF_3$; halo, such as chloro or fluoro; and CN. Suitably, the aryl, heterocycloalkyl and cycloalkyl groups present in $R_2$ may be optionally substituted by up to 3 substituents, such as 1, 2 or 3, such as 1 or 2, e.g. 1 substituent, each independently selected from OH; $NR_{2a}R_{2b}$; $SO_2R_{2c}$; and $NHSO_2R_{2c}$.

In one embodiment $R_{2a}$ is H. In a second embodiment $R_{2a}$ is $C_{1-4}$alkyl, such as methyl, ethyl or propyl, especially methyl. In a third embodiment $R_{2a}$ is H or methyl.

In one embodiment $R_{2b}$ is H. In a second embodiment $R_{2b}$ is $C_{1-4}$alkyl, such as methyl, ethyl or propyl, especially methyl. In a third embodiment, $R_{2b}$ is $C_{3-6}$cycloalkyl, such as cyclopropyl, cyclobutyl and cyclopentyl, especially cyclopropyl. In a fourth embodiment, $R_{2b}$ is $C_{1-4}$alkoxy, such as OMe or OEt, especially OMe. In a fifth embodiment, $R_{2b}$ is $C_{1-4}$haloalkyl, such as $CF_3$. In a sixth embodiment, $R_{2b}$ is aryl, such as phenyl. In a seventh embodiment, $R_{2b}$ is 4-7 membered heterocycloalkyl, such as azetidinyl or oxetanyl. In an eighth embodiment $R_{2b}$ is H or methyl.

In one embodiment $R_{2c}$ is $C_{1-4}$alkyl, such as methyl, ethyl or propyl, especially methyl. In a second embodiment, $R_{2c}$ is $C_{3-6}$cycloalkyl, such as cyclopropyl, cyclobutyl and cyclopentyl, especially cyclopropyl. In a third embodiment, $R_{2c}$ is $C_{1-4}$alkoxy, such as OMe or OEt, especially OMe. In a fourth embodiment, $R_{2c}$ is $C_{1-4}$haloalkyl, such as $CF_3$. In a fifth embodiment, $R_{2c}$ is aryl, such as phenyl. In a sixth embodiment, $R_{2c}$ is 4-7 membered heterocycloalkyl, such as azetidinyl or oxetanyl. In a seventh embodiment $R_{2c}$ is methyl.

Suitably, the aryl is substituted by 1, 2 or 3 substituents, such as 1 or 2, e.g. 1 substituent, each independently selected from methyl, chloro and fluoro. In one embodiment, the aryl is not substituted.

Suitably, the heterocycloalkyl is substituted by 1, 2 or 3 substituents, such as 1 or 2, e.g. 1 substituent, each independently selected from $CH_2CH_2F$ (particularly as a substituent on a nitrogen atom) and fluoro (particularly as a substituent on a carbon atom). In one embodiment, the heterocycloalkyl is not substituted.

Suitably, when the heterocycloalkyl is azetidinyl, the nitrogen atom is in the 1-position or the 3-position (i.e. 1-azetidinyl or 3-azetidinyl) relative to the point of attachment to the remainder of the $R_2$ group, for example:

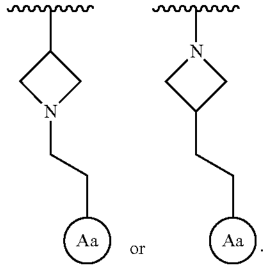

or 1-azetidinyl 3-azetidinyl

Suitably, when $R_2$ is $C_{1-4}$alkylene(4-7 membered heterocycloalkyl), such as $CH_2$-azetidinyl or $CH_2CH_2$-azetidinyl, the azetidinyl is 1-azetidinyl. Suitably, when $R_2$ is $C_{1-4}$alkyleneO(4-7 membered heterocycloalkyl), such as $CH_2O$-azetidinyl, the azetidinyl is 3-azetidinyl. For example:

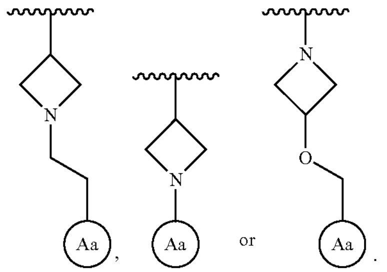

, or 1-azetidinyl 1-azetidinyl 3-azetidinyl

Suitably, when the heterocycloalkyl contains one or more nitrogen atoms, as required by valency the nitrogen atom(s) may be connected to a hydrogen atom to form an NH group. Alternatively the nitrogen atom(s) may be substituted (such as one nitrogen atom is substituted), for example by $C_{1-4}$alkyl, $C_{1-4}$haloalkyl, such as $CH_2CH_2F$, C(O)H, C(O)$C_{1-4}$alkyl, C(O)O$C_{1-4}$alkyl, such as C(O)OtBu, C(O)O$C_{1-4}$alkylene(aryl) such as C(O)Obz, C(O)NH$C_{1-4}$alkyl, C(O)NH$C_{1-4}$ alkylene(aryl) such as C(O)NHBz, an Fmoc group, C(O)$C_{1-4}$haloalkyl, C(O)O$C_{1-4}$haloalkyl or C(O)NH$C_{1-4}$haloalkyl. Suitably, when the heterocycloalkyl contains one or more S atoms, the S atom(s) is substituted (such as one S atom is substituted) by one or two oxygen atoms (i.e. S(O) or $S(O)_2$). Alternatively, any sulphur atom(s) in the heterocycloalkyl ring is not substituted.

When the one or more (such as one) nitrogen atoms is substituted by $C_{1-4}$alkyl, $C_{1-4}$haloalkyl, such as $CH_2CH_2F$, C(O)H, C(O)$C_{1-4}$alkyl, C(O)O$C_{1-4}$alkyl, such as C(O)OtBu, C(O)O$C_{1-4}$alkylene(aryl) such as C(O)OBz, C(O)NH$C_{1-4}$alkyl, C(O)NH$C_{1-4}$alkylene(aryl) such as C(O)NHBz, an Fmoc group, C(O)$C_{1-4}$haloalkyl, C(O)O$C_{1-4}$haloalkyl or C(O)NH$C_{1-4}$haloalkyl, these substituents may be present in addition to the optional substituents described above for heterocycloalkyl. The substituents on the nitrogen atom may be referred to or function as protecting groups, which can be added and removed by methods known to the person skilled in the art.

Suitably, the cycloalkyl is substituted by 1, 2 or 3 $C_{1-4}$alkyl substituents, such as 1 or 2 e.g. 1 $C_{1-4}$alkyl substituent, such as methyl, ethyl and propyl, especially methyl. In one embodiment, the cycloalkyl is not substituted.

Suitably unless $R_2$ is H, $C_{1-4}$alkyl or $C_{1-4}$alkylene O$C_{1-4}$alkyl, then m is 0. More suitably, unless $R_2$ is H, methyl or $CH_2OMe$, then m is 0.

When present, in one embodiment each $R_3$ is independently fluoro or methyl, in particular fluoro.

In one embodiment, m is 1 or 2.

In one preferred embodiment, m is 1 and $R_3$ is in the 3-position. In another preferred embodiment, m is 1 and $R_3$ is in the 6-position. In another preferred embodiment, m is 2, one $R_3$ is in the 3-position, and the other $R_3$ is in the 6-position. In one embodiment, m is 3, one $R_3$ is in the 3-position, one $R_3$ is in the 4-position, and one $R_3$ is in the 6-position. In one embodiment, m is 3, one $R_3$ is in the 3-position, one $R_3$ is in the 5-position, and one $R_3$ is in the 6-position.

Suitably, when $R_2$ is methyl, m is 1, and $R_3$ is chloro, $R_3$ is not in the 5-position. Suitably, when $R_2$ is methyl, m is 1 and $R_3$ is chloro, $R_3$ is in the 3-position, 4-position or 6-position. Suitably, when $R_2$ is H, m is 1 and $R_3$ is $C_{1-4}$alkyl, $R_3$ is not in the 3-position or the 5-position. Suitably, when $R_2$ is H, m is 1 and $R_3$ is $C_{1-4}$alkyl, $R_3$ is in the 4-position or the 6-position. Suitably, when m is 2, the two $R_3$ groups are not in the 3-position and the 5-position. Suitably, when m is 2, the two $R_3$ groups are in the 4-position and the 6-position.

References to substituent position are in respect of attachment to the amide moiety, for example:

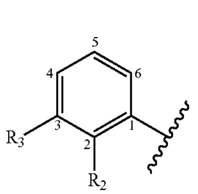

2,3-di-substituted

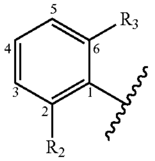

2,6-di-substituted

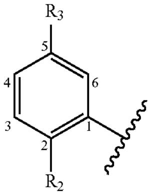

2,5-di-substituted

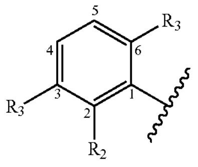

2,3,6-tri-substituted

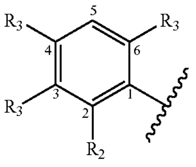

2,3,4-6-tetra-substituted

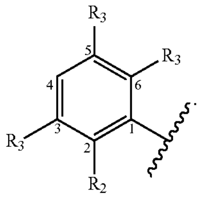

2,3,5,6-tetra-substituted

Examples of suitable substituents include 3-fluoro-2-methyl; 3-fluoro-2-$CH_2OCH_3$; 3-chloro-2-methyl-; 4,5-difluoro-2-methyl; 5-chloro-2-isopropyl; 5-fluoro-2-methyl; 2-isopropyl-6-methyl; 2,6-dimethyl; 2-methyl; 2-isopropyl; 4-fluoro-3-methyl; 3-fluoro-4-methyl; 3,4-difluoro-2,6-dimethyl; 3,5-difluoro-2,6-dimethyl; and 3-fluoro-2,6-dimethyl. In one embodiment, each $R_3$ is the same. In one embodiment, each $R_3$ is different.

In one embodiment, A is group (Ab):

(Ab)

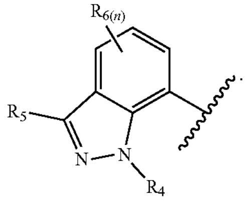

In one embodiment, $R_4$ is H. In a second embodiment, $R_4$ is $C_{1-4}$alkyl, such as methyl. In a third embodiment $R_4$ is $C_{1-4}$alkylene(aryl), such as benzyl. In one preferred embodiment, $R_4$ is H, methyl or benzyl, in particular methyl or benzyl. Suitably, the aryl present in $R_4$ is substituted by 1, 2 or 3 substituents, such as 1 or 2 e.g. 1 substituent, each independently selected from $C_{1-4}$alkyl, such as methyl; $C_{3-6}$cycloalkyl, such as cyclopropyl; $C_{1-4}$alkoxy, such as OMe; $C_{1-4}$haloalkyl, such as $CF_3$; halo, such as chloro or fluoro; CN; OH; $NR_{4a}R_{4b}$; $SO_2R_{4c}$; and $NHSO_2R_{4c}$. Suitably, the aryl present in $R_4$ is substituted by 1, 2 or 3 substituents, such as 1 or 2 e.g. 1 substituent, each independently selected from $C_{1-4}$alkyl, such as methyl; $C_{3-6}$cycloalkyl, such as cyclopropyl; $C_{1-4}$alkoxy, such as OMe; $C_{1-4}$haloalkyl, such as $CF_3$; halo, such as chloro or fluoro; and CN. Suitably, the aryl present in $R_4$ is substituted by 1, 2 or 3 substituents, such as 1 or 2 e.g. 1 substituent, each independently selected from OH; $NR_{4a}R_{4b}$; $SO_2R_{4c}$; and $NHSO_2R_{4c}$. Suitably, the aryl is substituted by 1, 2 or 3 substituents, such as 1 or 2 e.g. 1 substituent, each independently selected from methyl, chloro and fluoro. In one embodiment, the aryl is substituted by 1, 2 or 3, such as 1 or 2 e.g. 1 methyl groups. In one embodiment, the aryl is substituted by 1, 2 or 3, such as 1 or 2 e.g. 1 chloro groups. In one embodiment, the aryl is substituted by 1, 2 or 3, such as 1 or 2 e.g. 1 fluoro groups. Suitably, the aryl is not substituted.

In one embodiment $R_{4a}$ is H. In a second embodiment $R_{4a}$ is $C_{1-4}$alkyl, such as methyl, ethyl or propyl, especially methyl. In a third embodiment $R_{4a}$ is H or methyl.

In one embodiment $R_{4b}$ is H. In a second embodiment $R_{4b}$ is $C_{1-4}$alkyl, such as methyl, ethyl or propyl, especially methyl. In a third embodiment, $R_{4b}$ is $C_{3-6}$cycloalkyl, such as cyclopropyl, cyclobutyl and cyclopentyl, especially cyclopropyl. In a fourth embodiment, $R_{4b}$ is $C_{1-4}$alkoxy, such as OMe or OEt, especially OMe. In a fifth embodiment, $R_{4b}$ is $C_{1-4}$haloalkyl, such as $CF_3$. In a sixth embodiment, $R_{4b}$ is aryl, such as phenyl. In a seventh embodiment, $R_{4b}$ is 4-7 membered heterocycloalkyl, such as azetidinyl or oxetanyl. In an eighth embodiment, $R_{4b}$ is H or methyl.

In one embodiment $R_{4c}$ is $C_{1-4}$alkyl, such as methyl, ethyl or propyl, especially methyl. In a second embodiment, $R_{4c}$ is $C_{3-6}$cycloalkyl, such as cyclopropyl, cyclobutyl and cyclopentyl, especially cyclopropyl. In a third embodiment, $R_{4c}$ is $C_{1-4}$alkoxy, such as OMe or OEt, especially OMe. In a fourth embodiment, $R_{4c}$ is $C_{1-4}$haloalkyl, such as $CF_3$. In a fifth embodiment, $R_{4c}$ is aryl, such as phenyl. In a sixth embodiment, $R_{4c}$ is 4-7 membered heterocycloalkyl, such as azetidinyl or oxetanyl. In a seventh embodiment, $R_{4c}$ is methyl.

In one embodiment, $R^5$ is H.

When present, in one embodiment each $R_6$ is independently fluoro or methyl. Suitably, n may be 1, 2 or 3, such as 1 or 2 e.g. 1.

In one embodiment, n is 0.

In one embodiment, group A is group (Ac):

(Ac)

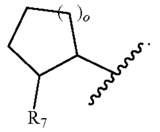

In one embodiment, $R_7$ is methyl, $CH_2OH$ or $CH_2OMe$.

In one embodiment, o is 2. Suitably, when o is 2, B is not group (Ba).

Suitably, the stereochemistry of $R_7$ is trans in respect of bond linking the (Ac) group to the amide moiety, for example having one of the two following stereochemical arrangements:

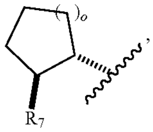

, or

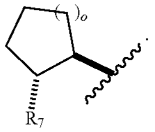

.

In one embodiment, A is group (Ad):

(Ad)

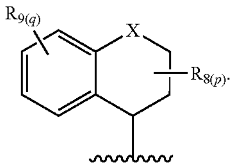

In one embodiment, X is a bond or O. Suitably, X is a bond. Alternatively, X is O. In a second embodiment, X is $CH_2$.

In one embodiment, $R_6$ is halo. In a second embodiment, $R_6$ is $C_{1-4}$alkyl. In a third embodiment, $R_3$ is $C_{1-4}$alkoxy. In a fourth embodiment, $R_3$ is OH.

When present, in one embodiment each $R_3$ is independently methyl, OMe or fluoro. In one embodiment, each $R_3$ is independently $OCH_2$-cyclopropyl, $OCH_2$-oxetanyl, $OCH_2CH_2F$, methyl, OMe, OEt or fluoro, for example $OCH_2CH_2F$, OMe or OEt, especially OMe. In another embodiment, each $R_3$ is independently $OCH_2$-cyclopropyl, $OCH_2$-oxetanyl, $OCH_2CH_2F$ or OEt, such as $OCH_2$-cyclopropyl, $OCH_2$-oxetanyl or $OCH_2CH_2F$.

Suitably, the cycloalkyl and heterocycloalkyl present in $R_3$ are each independently substituted by 1, 2 or 3 substituents, such as 1 or 2 e.g. 1 substituent, each independently selected from $C_{1-4}$ alkyl, such as methyl; $C_{3-6}$cycloalkyl, such as cyclopropyl; $C_{1-4}$alkoxy, such as OMe; $C_{1-4}$haloalkyl, such as $CF_3$; halo, such as chloro or fluoro; CN; OH; $NR_{8a}R_{8b}$; $SO_2R_{8c}$; and $NHSO_2R_{8c}$. Suitably, the cycloalkyl and heterocycloalkyl present in $R_3$ are each independently substituted by 1, 2 or 3 substituents, such as 1 or 2 e.g. 1 substituent, each independently selected from $C_{1-4}$alkyl, such as methyl; $C_{3-6}$cycloalkyl, such as cyclopropyl; $C_{1-4}$alkoxy, such as OMe; $C_{1-4}$haloalkyl, such as $CF_3$; halo, such as chloro or fluoro; and CN. Suitably, the cycloalkyl and heterocycloalkyl present in $R_3$ are each independently substituted by 1, 2 or 3 substituents, such as 1 or 2 e.g. 1 substituent, each independently selected from OH; $NR_{8a}R_{8b}$; $SO_2R_{8c}$; and $NHSO_2$Rao.

In one embodiment $R_{8a}$ is H. In a second embodiment $R_{8a}$ is $C_{1-4}$alkyl, such as methyl, ethyl or propyl, especially methyl. In a third embodiment $R_{8a}$ is H or methyl.

In one embodiment $R_{8b}$ is H. In a second embodiment $R_{8b}$ is $C_{1-4}$alkyl, such as methyl, ethyl or propyl, especially methyl. In a third embodiment, $R_{8b}$ is $C_{3-6}$cycloalkyl, such as cyclopropyl, cyclobutyl and cyclopentyl, especially cyclopropyl. In a fourth embodiment, $R_{8b}$ is $C_{1-4}$alkoxy, such as OMe or OEt, especially OMe. In a fifth embodiment, $R_{8b}$ is $C_{1-4}$haloalkyl, such as $CF_3$. In a sixth embodiment, $R_{8b}$ is aryl, such as phenyl. In a seventh embodiment, $R_{8b}$ is 4-7 membered heterocycloalkyl, such as azetidinyl or oxetanyl. In an eighth embodiment $R_{8b}$ is H or methyl.

In one embodiment $R_{8c}$ is $C_{1-4}$alkyl, such as methyl, ethyl or propyl, especially methyl. In a second embodiment, $R_{8c}$ is $C_{3-6}$cycloalkyl, such as cyclopropyl, cyclobutyl and cyclopentyl, especially cyclopropyl. In a third embodiment, $R_{8c}$ is $C_{1-4}$alkoxy, such as OMe or OEt, especially OMe. In a fourth embodiment, $R_{8c}$ is $C_{1-4}$haloalkyl, such as $CF_3$. In a fifth embodiment, $R_{8c}$ is aryl, such as phenyl. In a sixth embodiment, $R_{8c}$ is 4-7 membered heterocycloalkyl, such as azetidinyl or oxetanyl. In a seventh embodiment, $R_{8c}$ is methyl.

Suitably, the cycloalkyl present in $R_3$ (e.g. cyclopropyl) is substituted by 1, 2 or 3 substituents, such as 1 or 2 e.g. 1 substituent, each independently selected from fluoro and $C_{1-4}$alkyl, such as methyl, ethyl and propyl, especially methyl. In one embodiment, the cycloalkyl is not substituted.

Suitably, the heterocycloalkyl present in $R_3$ (e.g. oxetanyl) is substituted by 1, 2 or 3 substituents, such as 1 or 2 e.g. 1 substituent, each independently selected from fluoro and $C_{1-4}$alkyl, such as methyl, ethyl and propyl, especially methyl. In one embodiment, the heterocycloalkyl is not substituted.

Suitably, when the heterocycloalkyl is oxetanyl, the oxygen atom is in the 2- or 3-position (i.e. 2-oxetanyl or 3-oxetanyl) relative to the point of attachment to the remainder of the $R_3$ group, for example:

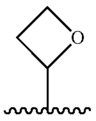

or

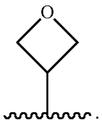

.

2-oxetanyl 3-oxetanyl

Suitably, when $R_3$ is $OC_{1-4}$alkylene(4-7 membered heterocycloalkyl), such as $OCH_2$-oxetanyl, the oxetanyl is 3-oxetanyl, for example:

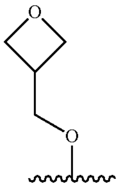

3-oxetanyl

When p is 1 or 2, $R_8$ may be in the 2- and/or 3 position. In one embodiment, p is 1 and $R_8$ is in the 2-position. In a second embodiment, p is 1 and $R_8$ is in the 3-position. In a third embodiment, p is 2, one $R_8$ is in the 2-position and one $R_8$ is in the 3-position. For example:

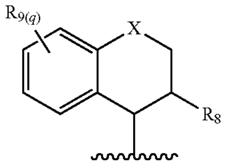
2-substituted

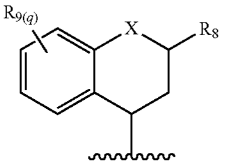
3-substituted

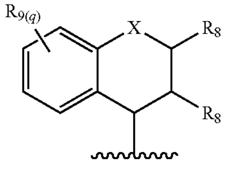
2,3-di-substituted

Examples of suitable $R_8$ substituents include 2-methyl, 2-methoxy, 2-ethoxy, 2-$OCH_2CH_2F$, 2-$OCH_2$-cyclopropyl and 2-$OCH_2$-oxetanyl such as 2-methyl and 2-methoxy.

In one embodiment, p is 0 or 1.

Suitably, when X is 0, p is 1 or 2. Suitably, when X is a bond and group B is (Ba), Y is $C(R_{11})(R_{12})$, $R_{11}$ and $R_{12}$ are both H, and p is 1 or 2. Suitably, when X is $CH_2$, B is not (Ba).

Suitably, when X is a bond and p is 0, the compound has the (R) stereochemical configuration. Suitably, when X is as defined above and p is 1, the stereochemistry of $R_8$ is trans in respect of the bond linking the (Ad) group to the amide substituent, for example having one of the following stereochemical arrangements:

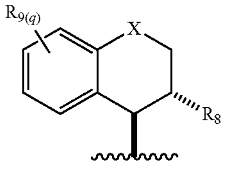
or
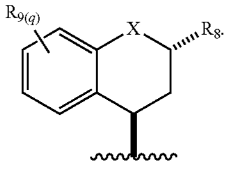

When present, in one embodiment each $R_9$ is independently fluoro.

Suitably, when q is 1, 2, 3 or 4, $R_9$ may be in the 5-, 6-, 7- and/or 8-position(s). In one embodiment, q is 1 and $R_9$ is in the 5-position. In a second embodiment, q is 1 and $R_9$ is in the 6-position. For example:

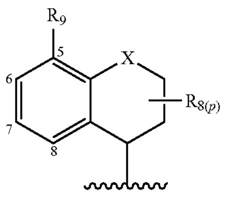
5-substituted

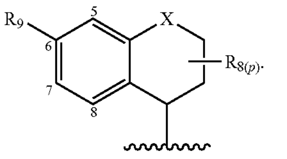
6-substituted

In embodiments wherein X is a bond, it will be understood that the substituent position numbering will change accordingly with the total number of atoms in the bicyclic ring system, for example:

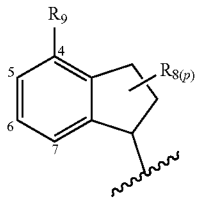
4-substituted

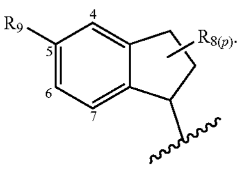
5-substituted

Suitable examples of $R_9$ substituents when X is a bond are 4-fluoro and 5-fluoro.

In one embodiment, q is 1 or 2.

In one embodiment, group B is (Ba):

(Ba)

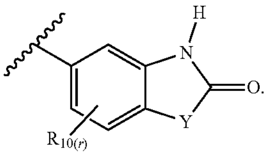

When Y is $C(R_{11})(R_{12})$, in one embodiment $R_{11}$ is H. In a second embodiment, $R_{11}$ is $C_{1-4}$alkyl, such as methyl.

When Y is $C(R_{11})(R_{12})$, in one embodiment $R_{12}$ is H. In a second embodiment, $R_{12}$ is $C_{1-4}$alkyl, such as methyl.

In a preferred embodiment, when Y is $C(R_{11})(R_{12})$, $R_{11}$ is H or methyl and $R_{12}$ is H. In a second preferred embodiment, $R_{11}$ and $R_{12}$ are both H. In a third embodiment, $R_{11}$ and $R_{12}$ together to the carbon atom to which they are attached form a cyclopropyl ring. Suitably, the cyclopropyl ring is substituted by 1, 2 or 3 $C_{1-4}$alkyl substituents, such as 1 or 2, e.g. 1 $C_{1-4}$alkyl substituent, such as methyl. In one embodiment, the cyclopropyl ring is not substituted.

Suitably, when Y is $C(R_{11})(R_{12})$, $R_{11}$ is methyl and $R_{12}$ is H, A is not group (Aa).

In one embodiment, Y is $N(R_{13})$. Suitably, $R_{13}$ is $C_{1-4}$alkyl, such as methyl, ethyl, propyl or butyl, especially methyl. In a second embodiment, $R_{13}$ is $C_{3-6}$cycloalkyl, such as cyclopropyl. Suitably, the $C_{3-6}$cycloalkyl present in $R_{13}$ e.g. cyclopropyl ring is substituted by 1, 2 or 3, such as 1 or 2 e.g. 1 substituents independently selected from $C_{1-4}$alkyl, $C_{3-6}$cycloalkyl, $C_{1-4}$alkoxy, $C_{1-4}$haloalkyl, halo, CN, OH, $NR_{13a}R_{13b}$, $SO_2R_{13c}$ and $NHSO_2R_{13c}$. Suitably, the $C_{3-6}$cycloalkyl present in $R_{13}$ e.g. cyclopropyl ring is substituted by 1, 2 or 3, such as 1 or 2 e.g. 1 substituents independently selected from $C_{1-4}$alkyl, $C_{3-6}$cycloalkyl, $C_{1-4}$alkoxy, $C_{1-4}$haloalkyl, halo and CN.

Suitably, the $C_{3-6}$cycloalkyl present in $R_{13}$ e.g. cyclopropyl ring is substituted by 1, 2 or 3, such as 1 or 2 e.g. 1 substituents independently selected from OH, $NR_{13a}R_{13b}$, $SO_2R_{13c}$ and $NHSO_2R_{13c}$. Suitably, the $C_{3-6}$cycloalkyl e.g. cyclopropyl ring is substituted by 1, 2 or 3 $C_{1-4}$alkyl substituents, such as 1 or 2 e.g. 1 $C_{1-4}$alkyl substituent, such as methyl. In one embodiment, the $C_{3-6}$cycloalkyl group e.g. cyclopropyl ring is not substituted.

In one embodiment $R_{13a}$ is H. In a second embodiment $R_{13a}$ is $C_{1-4}$alkyl, such as methyl, ethyl or propyl, especially methyl. In a third embodiment $R_{13a}$ is H or methyl.

In one embodiment $R_{13b}$ is H. In a second embodiment $R_{13b}$ is $C_{1-4}$alkyl, such as methyl, ethyl or propyl, especially methyl. In a third embodiment, $R_{13b}$ is $C_{3-6}$cycloalkyl, such as cyclopropyl, cyclobutyl and cyclopentyl, especially cyclopropyl. In a fourth embodiment, $R_{13b}$ is $C_{1-4}$alkoxy, such as OMe or OEt, especially OMe. In a fifth embodiment, $R_{13b}$ is $C_{1-4}$haloalkyl, such as $CF_3$. In a sixth embodiment, $R_{13b}$ is aryl, such as phenyl. In a seventh embodiment, $R_{13b}$ is 4-7 membered heterocycloalkyl, such as azetidinyl or oxetanyl. In an eighth embodiment, $R_{13b}$ is H or methyl.

In one embodiment $R_{13c}$ is $C_{1-4}$alkyl, such as methyl, ethyl or propyl, especially methyl. In a second embodiment, $R_{13c}$ is $C_{3-6}$cycloalkyl, such as cyclopropyl, cyclobutyl and cyclopentyl, especially cyclopropyl. In a third embodiment, $R_{13c}$ is $C_{1-4}$alkoxy, such as OMe or OEt, especially OMe. In a fourth embodiment, $R_{13c}$ is $C_{1-4}$haloalkyl, such as $CF_3$. In a fifth embodiment, $R_{13c}$ is aryl, such as phenyl. In a sixth embodiment, $R_{13c}$ is 4-7 membered heterocycloalkyl, such as azetidinyl or oxetanyl. In a seventh embodiment $R_{13c}$ is H or methyl.

In one embodiment, Y is O or S.

When present, in one embodiment each $R_{10}$ is independently fluoro, chloro or methyl.

In one embodiment, r is 0 or 1, especially 0.

When r is 1, 2 or 3, $R_{10}$ may be in the 7-, 5- and/or 4-position(s). In one embodiment, r is 1 and $R_{10}$ is in the 7-position. In a second embodiment, r is 1 and $R_{10}$ is in the 5-position. In one embodiment, r is 1 and $R_{10}$ is in the 4-position. For example:

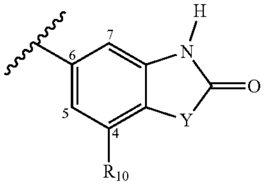

4-substituted

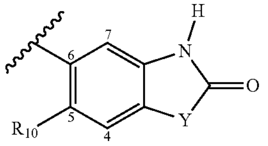

5-substituted

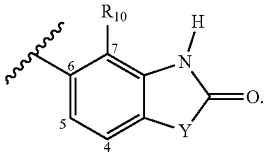

7-substituted

Examples of suitable $R_{10}$ substituents include 4-fluoro and 7-fluoro.

In one embodiment, group B is (Bb):

(Bb)

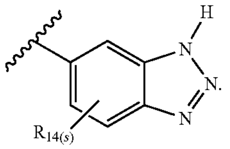

When present, in one embodiment each $R_{14}$ is independently fluoro or methyl.

In one embodiment, s is 0 or 1, especially 0.

Suitably, when s is 1, 2 or 3, $R_{14}$ may be in the 7-, 5- and/or 4-position(s). In one embodiment, s is 1 and $R_{14}$ is in the 5-position. In a second embodiment, s is 2, one $R_{14}$ is in the 7-position and one $R_{14}$ is in the 4-position, for example:

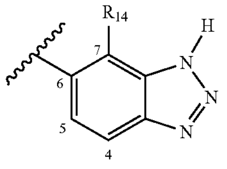

7-substituted

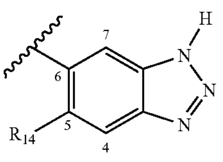

5-substituted

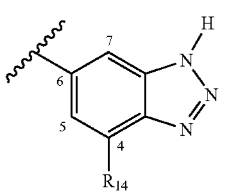

4-substituted

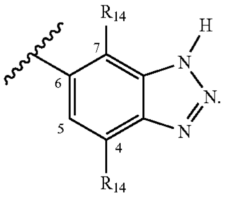

4,7-substituted

Suitably, $R_{14}$ is not in the 7-position. Suitably, $R_{14}$ is not in the 4-position.

An example of a suitable $R_{14}$ substituent is 5-fluoro.

In one embodiment, group B is (Bc):

(Bc)

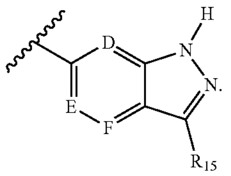

$R_{15}$ is $C_{1-4}$alkyl, $C_{1-4}$alkoxy, $C_{3-6}$cycloalkyl, $C_{1-4}$haloalkyl, halo or CN; wherein said cycloalkyl is optionally substituted by 1, 2 or 3 substituents independently selected from $C_{1-4}$alkyl, $C_{3-6}$cycloalkyl, $C_{1-4}$alkoxy, $C_{1-4}$haloalkyl, halo, CN, OH, $NR^{15a}R^{15b}$, $SO_2R^{15c}$ and $NHSO_2R^{15c}$.

In one embodiment, $R_{15}$ is methyl, ethyl, cyclopropyl, $CF_3$ or CN, for example methyl or CN, especially methyl. In a second embodiment, $R_{15}$ is methyl, ethyl, cyclopropyl, $CF_3$, CN, OMe, chloro or fluoro, for example methyl, CN, chloro or fluoro, especially chloro or fluoro. In a third embodiment, $R_{15}$ is OMe, chloro or fluoro. In a fourth embodiment, $R_{15}$ is methyl, CN, chloro or fluoro.

Suitably, the $C_{3-6}$cycloalkyl e.g. cyclopropyl ring present in $R_{15}$ is substituted by 1, 2 or 3, such as 1 or 2 e.g. 1 substituents independently selected from $C_{1-4}$alkyl, $C_{3-6}$cycloalkyl, $C_{1-4}$alkoxy, $C_{1-4}$haloalkyl, halo, CN, OH, $NR_{15a}R_{15b}$, $SO_2R_{15c}$ and $NHSO_2R_{15c}$. Suitably, the $C_{3-6}$cycloalkyl present in $R_{15}$ e.g. cyclopropyl ring is substituted by 1, 2 or 3, such as 1 or 2 e.g. 1 substituents independently selected from $C_{1-4}$alkyl, $C_{3-6}$cycloalkyl, $C_{1-4}$alkoxy, $C_{1-4}$haloalkyl, halo and CN. Suitably, the $C_{3-6}$cycloalkyl present in $R_{15}$ e.g. cyclopropyl ring is substituted by 1, 2 or 3, such as 1 or 2 e.g. 1 substituents independently selected from OH, $NR_{15a}R_{15b}$, $SO_2R_{15c}$ and $NHSO_2R_{15c}$. Suitably, the $C_{3-6}$cycloalkyl e.g. cyclopropyl ring is substituted by 1, 2 or 3 $C_{1-4}$alkyl substituents, such as 1 or 2 e.g. 1 $C_{1-4}$alkyl substituent, such as methyl. In one embodiment, the $C_{3-6}$cycloalkyl group e.g. cyclopropyl ring is not substituted.

In one embodiment $R_{15a}$ is H. In a second embodiment $R_{15a}$ is $C_{1-4}$alkyl, such as methyl, ethyl or propyl, especially methyl. In a third embodiment, $R_{15a}$ is H or methyl.

In one embodiment $R_{15b}$ is H. In a second embodiment $R_{15b}$ is $C_{1-4}$alkyl, such as methyl, ethyl or propyl, especially methyl. In a third embodiment, $R_{15b}$ is $C_{3-6}$cycloalkyl, such as cyclopropyl, cyclobutyl and cyclopentyl, especially cyclopropyl. In a fourth embodiment, $R_{15b}$ is $C_{1-4}$alkoxy, such as OMe or OEt, especially OMe. In a fifth embodiment, $R_{15b}$ is $C_{1-4}$haloalkyl, such as $CF_3$. In a sixth embodiment, $R_{15b}$ is aryl, such as phenyl. In a seventh embodiment, $R_{15b}$ is 4-7 membered heterocycloalkyl, such as azetidinyl or oxetanyl. In an eighth embodiment, $R_{15b}$ is H or methyl.

In one embodiment $R_{15c}$ is $C_{1-4}$alkyl, such as methyl, ethyl or propyl, especially methyl. In a second embodiment, $R_{15c}$ is $C_{3-6}$cycloalkyl, such as cyclopropyl, cyclobutyl and cyclopentyl, especially cyclopropyl. In a third embodiment, $R_{15c}$ is $C_{1-4}$alkoxy, such as OMe or OEt, especially OMe. In a fourth embodiment, $R_{15c}$ is $C_{1-4}$haloalkyl, such as $CF_3$. In a fifth embodiment, $R_{15c}$ is aryl, such as phenyl. In a sixth embodiment, $R_{15c}$ is 4-7 membered heterocycloalkyl, such as azetidinyl or oxetanyl. In a seventh embodiment, $R_{15c}$ is methyl.

In one embodiment, D, E and F are $C(R_{16})$. In a second embodiment, D is N, and E and F are $C(R_{16})$. In a third embodiment, E is N, and D and F are $C(R_{16})$. In a fourth embodiment, F is N, and D and E are $C(R_{16})$.

In one embodiment, $R_{16}$ is H. In a second embodiment, $R_{16}$ is halo, such as fluoro or chloro, especially chloro. In a third embodiment, $R_{16}$ is $C_{1-4}$alkyl, such as methyl. Suitably each $R_{16}$ is independently H, fluoro, chloro or methyl.

In a preferred embodiment of the invention, the compound of the invention has the formula (Ia'):

(Ia')

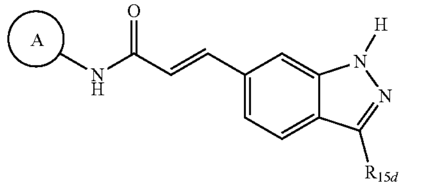

wherein:

A is group (Aa'), group (Ab'), group (Ad') or group (Ad");

$R_{15d}$ is methyl, ethyl, cyclopropyl, CN, $CF_3$, OMe, chloro or fluoro;

wherein group (Aa') is:

(Aa')

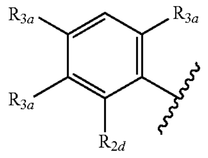

wherein:

$R_{2d}$ is H, methyl or $CH_2OMe$;

each $R_{3a}$ is independently H, fluoro or methyl; and wherein group (Ab') is:

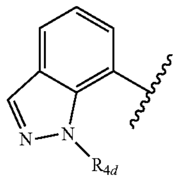

wherein:

$R_{4d}$ is methyl;

wherein group (Ad') is:

(Ad')

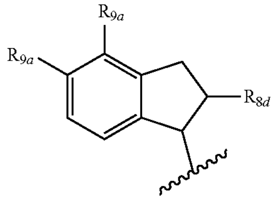

wherein:

$R_{8d}$ is H, methyl, $OCH_2$-cyclopropyl, $OCH_2$-oxetanyl, $OCH_2CH_2F$, OMe or OEt;

each $R_{9a}$ is independently H or fluoro;

wherein group (Ad") is:

(Ad")

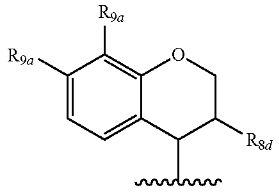

wherein:

$R_{8d}$ is methyl; and each $R_{8a}$ is independently H or fluoro;

or a pharmaceutically acceptable salt and/or solvate thereof.

In a preferred embodiment of the invention, the compound of the invention has the formula (Ia):

(Ia')

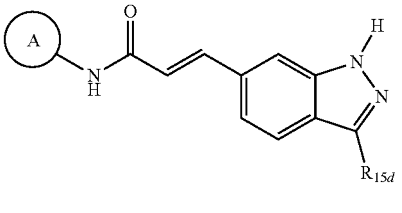

wherein:

A is group (Aa'), group (Ab') or group (Ad')

wherein group (Aa') is:

(Aa')

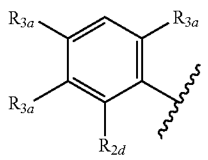

wherein:

$R_{2d}$ is H, methyl or $CH_2OMe$;

each $R_{8a}$ is independently H, fluoro or methyl; and $R_{15d}$ is methyl or CN;

wherein group (Ab') is:

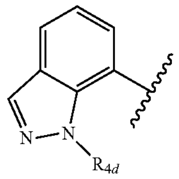

wherein:

$R_{4d}$ is methyl;

wherein group (Ad') is:

(Ad')

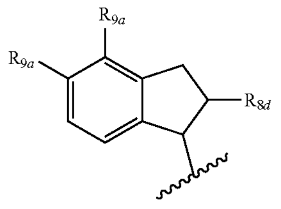

wherein:

$R_{8d}$ is H or methyl; and each $R_{8a}$ is independently H or fluoro;

or a pharmaceutically acceptable salt and/or solvate thereof.

In one preferred embodiment, A is group (Aa) and B is group (Ba). In a second preferred embodiment, A is group (Aa) and B is group (Bb). In a third preferred embodiment, A is group (Ad) and B is group (Bc).

In one embodiment, the compound of formula (I) is selected from the group consisting of:

(E)-3-(1H-benzo[d][1,2,3]triazol-6-yl)-N-(3-fluoro-2-methylphenyl)acrylamide;

(E)-N-(3-fluoro-2-methylphenyl)-3-(2-oxo-2,3-dihydrobenzo[d]thiazol-5-yl)acrylamide;

(E)-3-(3,3-dimethyl-2-oxoindolin-6-yl)-N-(3-fluoro-2-methylphenyl)acrylamide;

(E)-N-(3-fluoro-2-methylphenyl)-3-(2'-oxospiro[cyclopropane-1,3'-indolin]-6'-yl)acrylamide;

(E)-N-(3-fluoro-2-methylphenyl)-3-(7-fluoro-2-oxoindolin-6-yl)acrylamide;

(E)-N-(3-fluoro-2-methylphenyl)-3-(2-oxo-2,3-dihydrobenzo[d]oxazol-5-yl)acrylamide;

(E)-N-(3-fluoro-2-methylphenyl)-3-(1-methyl-2-oxo-2,3-dihydro-1H-benzo[d]imidazol-5-yl) acrylamide;

(E)-N-(3-fluoro-2-methylphenyl)-3-(3-methyl-2-oxoindolin-6-yl)acrylamide;

(E)-N-(3-chloro-2-methylphenyl)-3-(2-oxo-2,3-dihydrobenzo[d]oxazol-5-yl)acrylamide;

(E)-N-(3-fluoro-2-methylphenyl)-3-(2-oxoindolin-6-yl) acrylamide;

(E)-N-(2,3-dihydro-1H-inden-1-yl)-3-(2-oxo-2,3-dihydrobenzo[d]oxazol-5-yl)acrylamide;

(E)-3-(2-oxo-2,3-dihydrobenzo[d]oxazol-5-yl)-N-(o-tolyl) acrylamide;

(E)-N-(2-isopropylphenyl)-3-(2-oxo-2,3-dihydrobenzo[d]oxazol-5-yl)acrylamide;

(E)-N-(2-isopropyl-6-methylphenyl)-3-(2-oxo-2,3-dihydrobenzo[d]oxazol-5-yl)acrylamide;

(E)-N-(5-chloro-2-isopropylphenyl)-3-(2-oxo-2,3-dihydrobenzo[d]oxazol-5-yl)acrylamide;

(E)-N-(4,5-difluoro-2-methylphenyl)-3-(2-oxo-2,3-dihydrobenzo[d]oxazol-5-yl)acrylamide;

(E)-N-(5-fluoro-2-methylphenyl)-3-(2-oxo-2,3-dihydrobenzo[d]oxazol-5-yl)acrylamide;

(E)-N-(3-fluoro-2-methylphenyl)-3-(4-fluoro-2-oxoindolin-6-yl)acrylamide;

(E)-N-(2,6-dimethylphenyl)-3-(2-oxoindolin-6-yl)acrylamide;

(E)-N-(3-fluoro-2,6-dimethylphenyl)-3-(2-oxoindolin-6-yl) acrylamide;

(E)-N-(2-methyl-2,3-dihydro-1H-inden-1-yl)-3-(2-oxoindolin-6-yl)acrylamide;

(E)-3-(1-ethyl-2-oxo-2,3-dihydro-1H-benzo[d]imidazol-5-yl)-N-(3-fluoro-2-methylphenyl) acrylamide;

(E)-3-(1-cyclopropyl-2-oxo-2,3-dihydro-1H-benzo[d]imidazol-5-yl)-N-(3-fluoro-2-methylphenyl) acrylamide;

(E)-N-(2,3-dihydro-1H-inden-1-yl)-3-(1-methyl-2-oxo-2,3-dihydro-1H-benzo[d]imidazol-5-yl) acrylamide;

(E)-N-(2,3-dihydro-1H-inden-1-yl)-3-(3-methyl-1H-indazol-6-yl)acrylamide;

(E)-3-(3-cyano-1H-indazol-6-yl)-N-(2,3-dihydro-1H-inden-1-yl)acrylamide;

(E)-N-(2,3-dihydro-1H-inden-1-yl)-3-(5-fluoro-1H-benzo[d][1,2,3]triazol-6-yl)acrylamide;

(E)-N-(2,3-dihydro-1H-inden-1-yl)-3-(3-(trifluoromethyl)-1H-indazol-6-yl)acrylamide;

(E)-N-(2,6-dimethylphenyl)-3-(1-methyl-2-oxo-2,3-dihydro-1H-benzo[d]imidazol-5-yl)acrylamide;

(E)-N-(3-fluoro-2,6-dimethylphenyl)-3-(1-methyl-2-oxo-2,3-dihydro-1H-benzo[d]imidazol-5-yl)acrylamide;

(E)-N-(2,6-dimethylphenyl)-3-(3-methyl-1H-indazol-6-yl) acrylamide;

(E)-N-(2,3-dihydro-1H-inden-1-yl)-3-(3-ethyl-1H-indazol-6-yl)acrylamide;

(E)-3-(3-cyclopropyl-1H-indazol-6-yl)-N-(2,3-dihydro-1H-inden-1-yl)acrylamide;

(E)-N-(2,3-dihydro-1H-inden-1-yl)-3-(4-fluoro-3-methyl-1H-indazol-6-yl)acrylamide;

(E)-N-(3,5-difluoro-2,6-dimethylphenyl)-3-(2-oxoindolin-6-yl)acrylamide;

(E)-N-(3,4-difluoro-2,6-dimethylphenyl)-3-(2-oxoindolin-6-yl)acrylamide;

(E)-N-(3-fluoro-2-methylphenyl)-3-(3-methyl-1H-indazol-6-yl)acrylamide;

(E)-3-(3-methyl-1H-indazol-6-yl)-N-(2-methyl-2,3-dihydro-1H-inden-1-yl)acrylamide;

(E)-3-(3-methyl-1H-indazol-6-yl)-N-(1-methyl-1H-indazol-7-yl)acrylamide;

(E)-N-(5-fluoro-2,3-dihydro-1H-inden-1-yl)-3-(3-methyl-1H-indazol-6-yl)acrylamide;
(E)-N-(4-fluoro-3-methylphenyl)-3-(3-methyl-1H-indazol-6-yl)acrylamide;
(E)-N-(3-fluoro-4-methylphenyl)-3-(3-methyl-1H-indazol-6-yl)acrylamide;
Racemic-(E)-3-(3-methyl-1H-indazol-6-yl)-N-((1R,2R)-2-methylcyclohexyl)acrylamide;
(E)-3-(3-cyano-1H-indazol-6-yl)-N-(2-methyl-2,3-dihydro-1H-inden-1-yl)acrylamide;
(E)-N-(2-methyl-2,3-dihydro-1H-inden-1-yl)-3-(1-methyl-2-oxo-2,3-dihydro-1H-benzo[d]imidazol-5-yl)acrylamide;
(E)-N-(2-methyl-2,3-dihydro-1H-inden-1-yl)-3-(2-oxo-2,3-dihydrobenzo[d]oxazol-5-yl)acrylamide;
(Z)-2-fluoro-N-(3-fluoro-2-methylphenyl)-3-(2-oxoindolin-6-yl)acrylamide;
(E)-N-(3-chloro-2-methylphenyl)-N-methyl-3-(2-oxo-2,3-dihydrobenzo[d]oxazol-5-yl)acrylamide;
(E)-N-(2-methylcyclopentyl)-3-(2-oxo-2,3-dihydrobenzo[d]oxazol-5-yl)acrylamide;
(E)-N-(3-fluoro-2-(methoxymethyl)phenyl)-3-(3-methyl-1H-indazol-6-yl)acrylamide;
(E)-3-(3-cyano-1H-indazol-6-yl)-N-(3-fluoro-2-methylphenyl)acrylamide;
(E)-3-(3-methyl-1H-indazol-6-yl)-N-(3-methylchroman-4-yl)acrylamide;
(E)-N-(2-methyl-1,2,3,4-tetrahydronaphthalen-1-yl)-3-(3-methyl-1H-indazol-6-yl)acrylamide;
(E)-N-((1S,2S)-2-methoxy-2,3-dihydro-1H-inden-1-yl)-3-(3-methyl-1H-indazol-6-yl)acrylamide;
(R,E)-N-(2,3-dihydro-1H-inden-1-yl)-3-(3-methyl-1H-indazol-6-yl)acrylamide;
(E)-N-(chroman-4-yl)-3-(2-oxo-2,3-dihydrobenzo[d]oxazol-5-yl)acrylamide;
(E)-3-(2-oxo-2,3-dihydrobenzo[d]oxazol-5-yl)-N-(1,2,3,4-tetrahydronaphthalen-1-yl)acrylamide;
(E)-N-(2-methyl-1,2,3,4-tetrahydronaphthalen-1-yl)-3-(2-oxoindolin-6-yl)acrylamide;
(E)-N-(2,3-dihydro-1H-inden-1-yl)-3-(2-oxoindolin-6-yl)acrylamide;
(E)-N-(3,5-difluoro-2-methylphenyl)-3-(2-oxoindolin-6-yl)acrylamide;
(E)-N-(2,3-dihydro-1H-inden-1-yl)-3-(7-fluoro-1H-benzo[d][1,2,3]triazol-6-yl)acrylamide;
(E)-N-(2,3-dihydro-1H-inden-1-yl)-3-(4-fluoro-1H-benzo[d][1,2,3]triazol-6-yl)acrylamide;
(E)-N-(5-chloro-2-methylphenyl)-3-(2-oxo-2,3-dihydrobenzo[d]oxazol-5-yl)acrylamide; and
(E)-N-(2-methylcyclohexyl)-3-(2-oxoindolin-6-yl)acrylamide;

or a pharmaceutically acceptable salt and/or solvate of any one thereof.

In one embodiment, the compound of formula (I) is selected from the group consisting of:

(E)-3-(3-methyl-1H-indazol-6-yl)-N-(3-methylchroman-4-yl)acrylamide;
(E)-3-(3-methyl-1H-indazol-6-yl)-N-((3R,4S)-3-methylchroman-4-yl)acrylamide;
(E)-3-(3-methyl-1H-indazol-6-yl)-N-((3S,4R)-3-methylchroman-4-yl)acrylamide;
(E)-3-(3-methyl-1H-indazol-6-yl)-N-((3R,4R)-3-methylchroman-4-yl)acrylamide;
(E)-3-(3-methyl-1H-indazol-6-yl)-N-((3S,4S)-3-methylchroman-4-yl)acrylamide;
(E)-3-(3-methyl-1H-indazol-6-yl)-N-((1S,2S)-2-(oxetan-3-ylmethoxy)-2,3-dihydro-1H-inden-1-yl)acrylamide;
(E)-N-((1S,2S)-2-(cyclopropylmethoxy)-2,3-dihydro-1H-inden-1-yl)-3-(3-methyl-1H-indazol-6-yl)acrylamide;
(E)-N-((1S,2S)-2-(2-fluoroethoxy)-2,3-dihydro-1H-inden-1-yl)-3-(3-methyl-1H-indazol-6-yl)acrylamide;
(E)-N-((1S,2S)-2-ethoxy-2,3-dihydro-1H-inden-1-yl)-3-(3-methyl-1H-indazol-6-yl)acrylamide;
(E)-3-(3-cyclopropyl-1H-indazol-6-yl)-N-((1S,2S)-2-methoxy-2,3-dihydro-1H-inden-1-yl)acrylamide;
(E)-3-(3-methoxy-1H-indazol-6-yl)-N-((1S,2S)-2-methoxy-2,3-dihydro-1H-inden-1-yl)acrylamide;
(E)-3-(3-chloro-1H-indazol-6-yl)-N-((1S,2S)-2-methoxy-2,3-dihydro-1H-inden-1-yl)acrylamide;
(E)-3-(3-fluoro-1H-indazol-6-yl)-N-((1S,2S)-2-methoxy-2,3-dihydro-1H-inden-1-yl)acrylamide;
and
(E)-3-(3-cyano-1H-indazol-6-yl)-N-((1S,2S)-2-methoxy-2,3-dihydro-1H-inden-1-yl)acrylamide;

or a pharmaceutically acceptable salt and/or solvate of any one thereof.

The definition of the compounds of formula (I) is intended to include all tautomers of said compounds.

The compounds of the invention may be provided in the form of a pharmaceutically acceptable salt and/or solvate thereof. In particular, the compound of formula (I) may be provided in the form of a pharmaceutically acceptable salt and/or solvate, such as a pharmaceutically acceptable salt.

It will be appreciated that for use in medicine the salts of the compounds of formula (I) should be pharmaceutically acceptable. Non-pharmaceutically acceptable salts of the compounds of formula (I) may be of use in other contexts such as during preparation of the compounds of formula (I). Suitable pharmaceutically acceptable salts will be apparent to those skilled in the art. Pharmaceutically acceptable salts include those described by Berge et al. (1977). Such pharmaceutically acceptable salts include acid and base addition salts. Pharmaceutically acceptable acid additional salts may be formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain compounds of formula (I) may form acid or base addition salts with one or more equivalents of the acid or base. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exist as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^{2}H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 (15O), oxygen-17 (17O), oxygen-18 (18O), phosphorus-32 ($^{32}P$), sulphur-35 ($^{35}S$), chlorine-36 ($^{36}Cl$), chlorine-37 (37Cl), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Unnatural variant isotopic forms which incorporate deuterium i.e. $^{2}H$ or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in Positron Emission Topography (PET) studies for examining substrate receptor occupancy. In one embodiment, the compounds of the invention are provided in a natural isotopic form. In one embodiment, the compounds of the invention are provided in an unnatural variant isotopic form. In a specific embodiment, the unnatural variant isotopic form is a form in which deuterium (i.e. $^{2}H$ or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form. Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples, and modifications thereof. In the following schemes, reactive groups can be protected with protecting groups and deprotected according to established techniques well known to the skilled person.

Generic Routes

Generic routes by which compound examples of the invention may be conveniently prepared are summarised below. In the following description, the groups $R_{1a}$, $R_{1b}$, $R_2$, $R_3$, $R_{13}$, A and B are as defined above for the compound of formula (I), unless otherwise stated.

Scheme 1

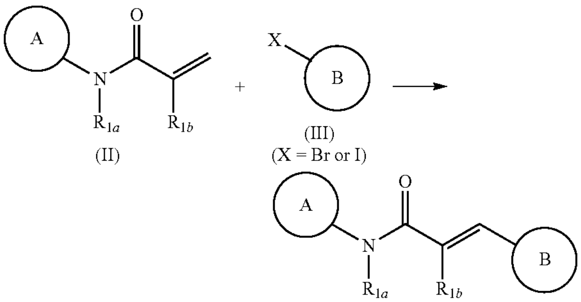

(II) (III) (X = Br or I) (I)

Compounds of formula (I) may be prepared by reacting a compound of formula (II) with a compound of formula (III) under palladium-catalyzed cross coupling conditions, using a palladium pre-catalyst, such as [1,1'-bis(diphenylphosphino)ferrocene]dichloropalladium(II), complex with dichloromethane ($Pd(dppf)Cl_2—CH_2Cl_2$), in the presence of a base, such as triethylamine, and a suitable solvent, such as dimethylformamide (DMF).

Scheme 2

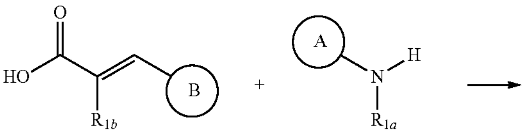

(IV) (V)

-continued

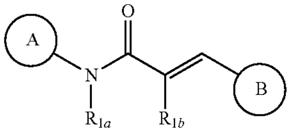

(I)

Alternatively, compounds of formula (I) may be prepared by reacting a compound of formula (IV) with a compound of formula (V) under amidation conditions, using an amide coupling reagent, such as 1-[bis(dimethylamino)methylene]-1H-1,2,3-triazolo[4,5-b]pyridinium 3-oxid hexafluorophosphate (HATU), in the presence of a base, such as N,N-diisopropylethylamine (DIPEA, also known as Hunig's base), in a suitable solvent, such as DMF.

Scheme 3

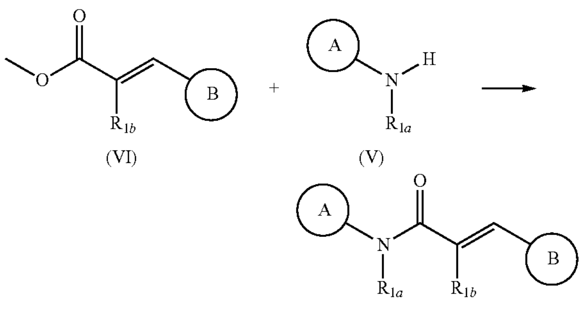

(VI) (V) (I)

Compounds of formula (I) may be also prepared by reacting a compound of formula (VI) with a compound of (V) under basic conditions, using a base such as lithium bis(trimethylsilyl)amide (LiHMDS), in a suitable solvent, such as tetrahydrofuran (THF).

Scheme 4

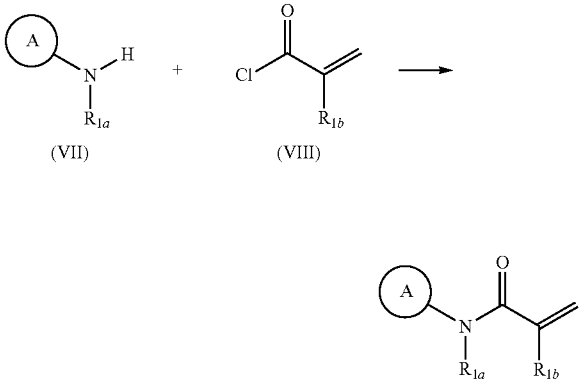

(VII) (VIII) (II)

Compounds of formula (II) are commercially available. Compounds of formula (II) may also be prepared by reacting a compound of formula (VII) with a compound of formula (VIII) in the presence of a base, such as N,N-diisopropylethylamine, in a suitable solvent, such as dichloromethane (DCM).

Scheme 5

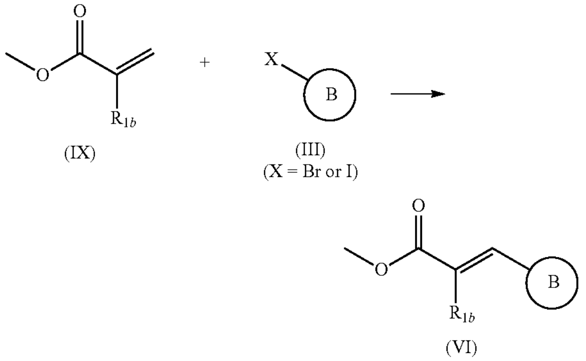

(IX) (III) (X = Br or I) (VI)

Compounds of formula (VI) may be obtained by reacting a compound of formula (IX) with a compound of formula (III) under palladium-catalyzed cross coupling conditions, using a palladium-precatalyst, such as [1,1'-bis(diphenylphosphino)ferrocene]dichloropalladium(II), complex with dichloromethane ($Pd(dppf)Cl_2$—$CH_2Cl_2$), in the presence of a base, such as triethylamine, and a suitable solvent, such as dimethylformamide (DMF).

Scheme 6

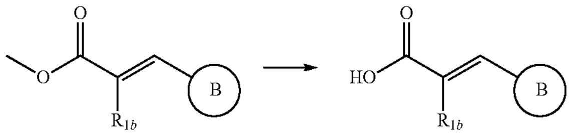

(VI) (IV)

Compounds of formula (IV) may be obtained by reacting a compound of formula (VI) under hydrolysis conditions, using a base, such as sodium hydroxide (NaOH), in a suitable solvent system, such as a mixture of methanol and water.

Scheme 7

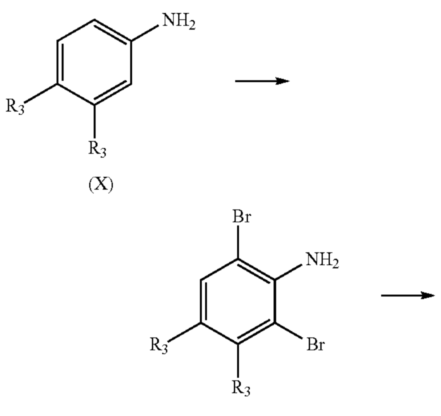

(X) (XI)

-continued

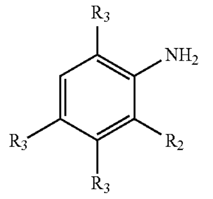

(VII)

Compounds of formula (VII), wherein $R_{1a}$ is H, A is group (Aa), $R_2$ is $C_{1-4}$alkyl, m is 3 and $R_3$ is $C_{1-4}$alkyl or halo, may be prepared in two steps. Firstly, reacting a compound of formula (X) with a brominating agent, such as N-bromosuccinimide (NBS), in a solvent, such as acetonitrile, affords di-brominated compounds of formula (X). The compound of formula (VII) may be further reacted under palladium-catalyzed cross coupling conditions, using a palladium-precatalyst, such as [1,1'-bis(diphenylphosphino)ferrocene] dichloropalladium(II), complex with dichloromethane (Pd(dppf)$Cl_2$—$CH_2Cl_2$), an organoboron compound, such as trimethyl-1,3,5,2,4,6-trioxatriborinane, a base, such as caesium carbonate ($Cs_2CO_3$), and a suitable solvent, such as 1,4-dioxane, to give a compound of formula (VII).

Scheme 8

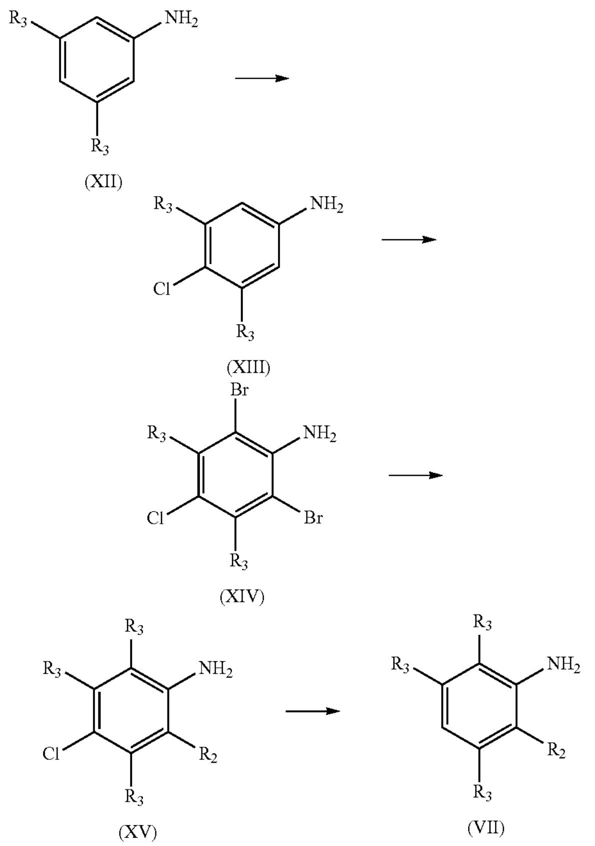

(XII) (XIII) (XIV) (XV) (VII)

Compounds of formula (VII), wherein $R_{1a}$ is H, A is group (Aa), $R_2$ is $C_{1-4}$alkyl, m is 3 and $R_3$ is $C_{1-4}$alkyl or halo, may be prepared in four steps. Firstly, reacting a compound of formula (XII) with a chlorinating agent, such as N-chlorosuccinimide (NCS), in a solvent, such as acetonitrile, affords a compound of formula (XIII). Further reacting a compound of formula (XIII) with a brominating agent, such as N-bromosuccinimide (NBS), in a solvent, such as acetonitrile, affords tri-halogenated compounds of formula (XIV). The compound of formula (XIV) may be further reacted under palladium-catalyzed cross coupling conditions, using a palladium-precatalyst, such as [1,1'-bis(diphenylphosphino)ferrocene]dichloropalladium(II), complex with dichloromethane (Pd(dppf)$Cl_2$—$CH_2Cl_2$), an organoboron compound, such as trimethyl-1,3,5,2,4,6-trioxatriborinane, a base, such as caesium carbonate ($Cs_2CO_3$), and a suitable solvent, such as 1,4-dioxane, to give a compound of formula (XV). The compound of formula may be reacted under reductive dehalogenation conditions, using a hydrogen atmosphere, such as hydrogen at 30 atm, a palladium catalyst, such as palladium on carbon (Pd/C), an acid, such as hydrochloric acid, and a solvent, such as ethanol (EtOH), to afford the compound of formula (VII).

Scheme 9

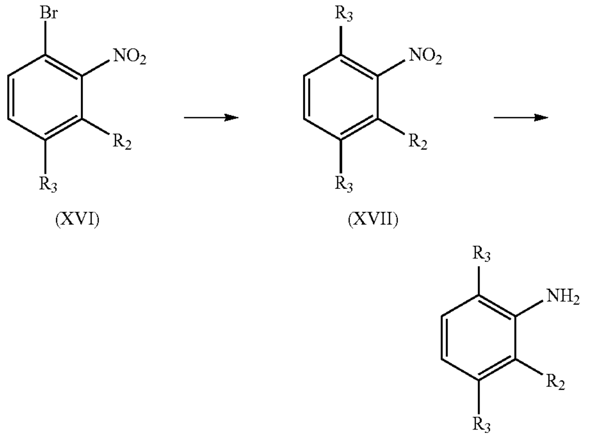

(XVI) (XVII) (VII)

Compounds of formula (VII), wherein $R_{1a}$ is H, A is group (Aa), $R_2$ is $C_{1-4}$alkyl, m is 2 and $R_3$ is $C_{1-4}$alkyl or halo, may be prepared in two steps. Nitro compounds of formula (XVI) may be reacted under under palladium-catalyzed cross coupling conditions, using a palladium-precatalyst, such as [1,1'-bis(diphenylphosphino)ferrocene]dichloropalladium (II), complex with dichloromethane (Pd(dppf)$Cl_2$—$CH_2Cl_2$), an organoboron compound, such as trimethyl-1,3,5,2,4,6-trioxatriborinane, a base, such as caesium carbonate ($Cs_2CO_3$), and a suitable solvent system, such as a mixture of water 1,4-dioxane, to give a compound of formula (XVII). The compound of formula (XVII) may be further reacted with a metal, such as iron, in the presence of an acid, such as acetic acid, to give the compound of formula (VII).

Scheme 10

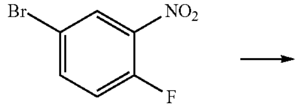

(XVIII)

-continued

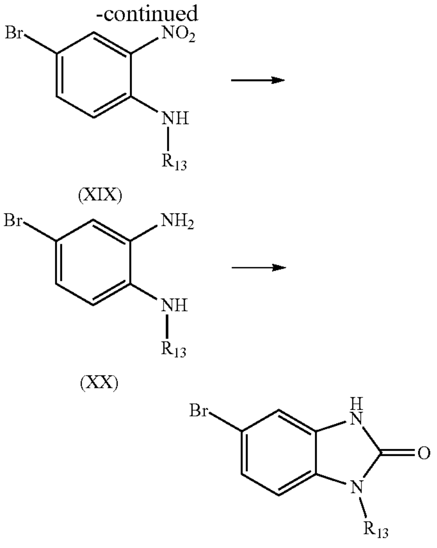

(XIX)

(XX)

(III)

Compounds of formula (III), wherein B is group (Ba), Y is $N(R_{13})$ and r is 0, may be prepared in three steps. Firstly, a compound of formula (XVIII) may be reacted with an amine in a suitable solvent, such as ethanol, to give a compound of formula (XIX). Subsequently, the compound of formula (XIX) may be subjected to reduction conditions using a metal, such as zinc, and an inorganic salt, such as ammonium chloride ($NH_4Cl$), in a suitable solvent, such as acetone, to afford a compound of formula (XX). Finally, the compound of formula (XX) may be reacted with a carbonylating agent, such as triphosgene, in a suitable solvent, such as dichloromethane (DCM), to afford the compound of formula (III).

Scheme 11

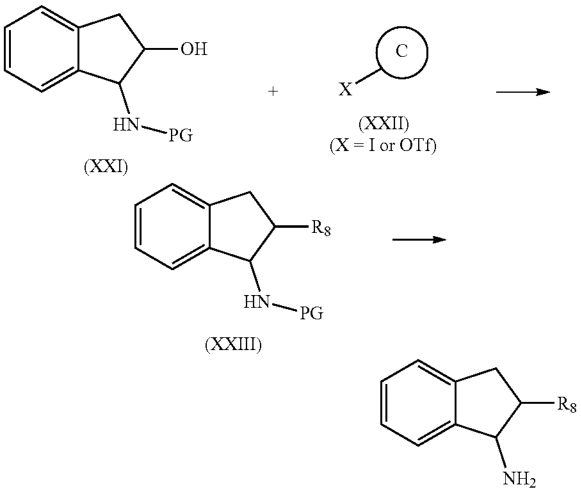

(XXI)

(XXII)
(X = I or OTf)

(XXIII)

(V)

Compounds of formula (V) wherein A is group (Ad), X is a bond, q is 0, p is 1 and $R_3$ is $OC_{1-4}$ haloalkyl, $OC_1$-alkylene (4-7 membered heterocycloalkyl) or $C_{1-4}$ alkoxy may be prepared by reacting a compound of formula (XXI), wherein PG is a nitrogen protecting group, such as tert-butoxycarbonyl (BOC), with a compound of formula (XXII), wherein C is $C_{1-4}$alkyl, $C_{1-4}$haloalkyl or $C_{1-4}$alkylene(4-7 membered heterocycloalkyl), in the presence of a base e.g. NaH in a suitable solvent e.g. THF, to afford compounds of formula (XXIII). Deprotection of the compounds of formula (XXIII) e.g. with aqueous acid, such as 2 M HCl, in a suitable solvent, such as methanol affords compounds of formula (V).

Scheme 12

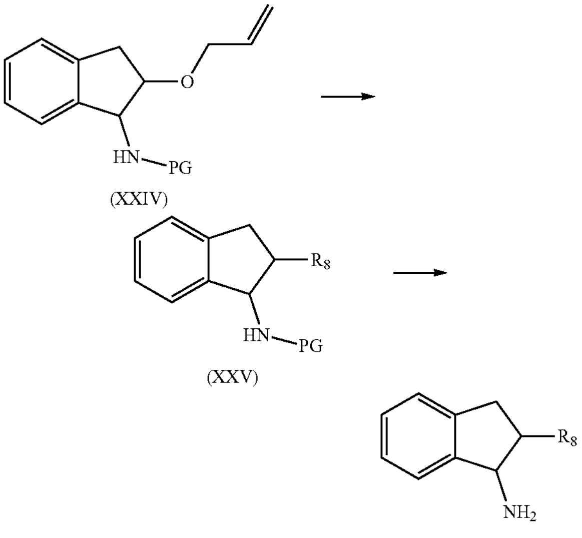

(XXIV)

(XXV)

(V)

Compounds of formula (V) wherein A is group (Ad), X is a bond, q is 0, p is 1 and $R_3$ is $OC_{1-4}$ alkylene($C_{3-6}$cycloalkyl) may be prepared by treating a compound of formula (XXIV), wherein PG is a nitrogen protecting group, such as tert-butoxycarbonyl (BOC), with a suitable reagent e.g. di-iodomethane, in the presence of an organometallic reagent e.g. $ZnEt_2$ in a suitable solvent, such as dichloromethane, to afford compounds of formula (XXV). Deprotection of the compounds of formula (XXV) e.g. with aqueous acid, such as 2 M HCl, in a suitable solvent, such as methanol affords compounds of formula (V).

Therefore, in one embodiment the invention provides a process for preparing a compound of formula (I) or a pharmaceutically acceptable salt and/or solvate thereof, which comprises reacting a compound of formula (II):

(II)

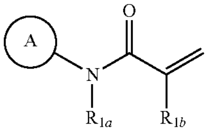

wherein A, $R_{1a}$ and $R_{1b}$ are as defined for the compound of formula (I); or salt thereof; with a compound of formula (III):

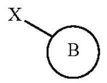

(III)

wherein X is halo, such as bromo or iodo, and B is as defined for the compound of formula (I); or a salt thereof.

The invention also provides a process for preparing a compound of formula (I) or a pharmaceutically acceptable salt and/or solvate thereof, which comprises reacting a compound of formula (IV):

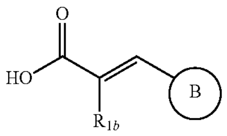

(IV)

wherein $R_{1b}$ and B are as defined for the compound of formula (I); or a salt thereof; with a compound of formula (V):

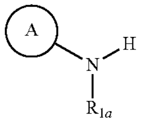

(V)

wherein A and $R_{1a}$ are as defined for the compound of formula (I); or a salt thereof.

The invention also provides a process for preparing a compound of formula (I) or a pharmaceutically acceptable salt and/or solvate thereof, which comprises reacting a compound of formula (VI):

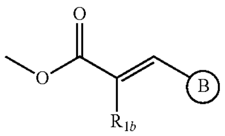

(VI)

wherein $R_{1b}$ and B are as defined for the compound of formula (I); or a salt thereof; with a compound of formula (V):

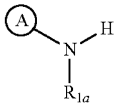

(V)

wherein A and $R_{1a}$ are as defined for the compound of formula (I); or a salt thereof.

Therapeutic Methods

Compounds of formula (I) of the present invention have utility as inhibitors of mPTP.

Therefore, the invention provides a compound of formula (I), or a pharmaceutically acceptable salt and/or solvate thereof, for use a pharmaceutical, in particular in the treatment or prophylaxis of a disease or disorder in which inhibition of mPTP provides a therapeutic or prophylactic effect, for example those diseases and disorders mentioned herein below.

The invention also provides a compound of formula (I), or a pharmaceutically acceptable salt and/or solvate thereof, for use a pharmaceutical, in particular in the treatment of a disease or disorder in which inhibition of mPTP provides a therapeutic effect, for example those diseases and disorders mentioned herein below.

The invention also provides a compound of formula (I), or a pharmaceutically acceptable salt and/or solvate thereof, for use a pharmaceutical, in particular in the prophylaxis of a disease or disorder in which inhibition of mPTP provides a prophylactic effect, for example those diseases and disorders mentioned herein below.

The invention also provides a compound of formula (I), or a pharmaceutically acceptable salt and/or solvate thereof, for use in the manufacture of a medicament for the treatment or prophylaxis of a disease or disorder in which inhibition of mPTP provides a therapeutic or prophylactic effect, for example those diseases and disorders mentioned herein below.

The invention also provides a compound of formula (I), or a pharmaceutically acceptable salt and/or solvate thereof, for use in the manufacture of a medicament for the treatment of a disease or disorder in which inhibition of mPTP provides a therapeutic effect, for example those diseases and disorders mentioned herein below.

The invention also provides a compound of formula (I), or a pharmaceutically acceptable salt and/or solvate thereof, for use in the manufacture of a medicament for the prophylaxis of a disease or disorder in which inhibition of mPTP provides a prophylactic effect, for example those diseases and disorders mentioned herein below.

The invention also provides a method of preventing or treating a disease or disorder in which inhibition of mPTP provides a therapeutic or prophylactic effect in a subject, which comprises administering to a subject in need thereof an effective amount of a compound of formula (I), or a pharmaceutically acceptable salt and/or solvate thereof, for example those diseases and disorders mentioned herein below.

The invention also provides a method of treating a disease or disorder in which inhibition of mPTP provides a therapeutic effect in a subject, which comprises administering to a subject in need thereof an effective amount of a compound of formula (I), or a pharmaceutically acceptable salt and/or solvate thereof, for example those diseases and disorders mentioned herein below.

The invention also provides a method of preventing a disease or disorder in which inhibition of mPTP provides a prophylactic effect in a subject, which comprises administering to a subject in need thereof an effective amount of a compound of formula (I), or a pharmaceutically acceptable salt and/or solvate thereof, for example those diseases and disorders mentioned herein below.

The term 'treatment' or 'treating' as used herein includes the control, mitigation, reduction, or modulation of the disease state or its symptoms.

The term 'prophylaxis' or 'preventing' is used herein to mean preventing symptoms of a disease or disorder in a subject or preventing recurrence of symptoms of a disease or disorder in an afflicted subject and is not limited to complete prevention of an affliction.

In one embodiment, the disease or disorder is selected from degenerative or neurodegenerative diseases, disorders of the central nervous system, ischemia or re-perfusion injury, metabolic diseases, inflammatory or autoimmune diseases, diseases of aging and renal diseases.

In one particular embodiment, the disease or disorder is a degenerative or neurodegenerative disease, such as Parkinson's disease, dementia with Lewy bodies, Alzheimer's disease, amyotrophic lateral sclerosis, multiple sclerosis, frontal temporal dementia, chemotherapy induced neuropathy, Huntington's disease, spinocerebellar ataxias, progressive supranuclear palsy, hereditary spastic paraplegia, Duchenne muscular dystrophy, congenital muscular dystrophy, traumatic brain injury and Friedreich's ataxia. In one preferred embodiment, the disease or disorder is Parkinson's disease. In one preferred embodiment, the disease or disorder is Alzheimer's disease. In one preferred embodiment, the disease or disorder is amyotrophic lateral sclerosis.

In another particular embodiment, the disease or disorder is a disease of the central nervous system, such as AIDS dementia complex, depressive disorders, schizophrenia and epilepsy.

In another embodiment, the disease or disorder is ischemia or re-perfusion injury, such as acute myocardial infarction, stroke, kidney ischemia reperfusion injury, and organ damage during transplantation.

In another embodiment, the disease or disorder is a metabolic disease, such as hepatic steatosis, diabetes, diabetic retinopathy, cognitive decline and other diabetes associated conditions, obesity and feeding behaviours, and non-alcoholic fatty liver disease.

In another embodiment, the disease or disorder is an inflammatory or autoimmune disease, such as acute pancreatitis, systemic lupus, organ failure in sepsis and hepatitis.

In another embodiment, the disease or disorder is a disease of aging, such as bone repair, bone weakness in aging in osteoporosis and sarcopenia.

In another embodiment, the disease or disorder is a renal disease, such as chronic kidney disease associated with APOL1 genetic variants and chronic kidney disease.

The compounds of formula (I) are expected to be useful in the treatment or prophylaxis of a mitochondrial disease.

Therefore, the invention provides a compound of formula (I), or a pharmaceutically acceptable salt and/or solvate thereof, for use in the treatment or prophylaxis of a mitochondrial disease, for example those diseases and disorders mentioned herein below.

The invention also provides a compound of formula (I), or a pharmaceutically acceptable salt and/or solvate thereof, for use in the treatment of a mitochondrial disease, for example those diseases and disorders mentioned herein below.

The invention also provides a compound of formula (I), or a pharmaceutically acceptable salt and/or solvate thereof, for use in the prophylaxis of a mitochondrial disease, for example those diseases and disorders mentioned herein below.

The invention also provides a compound of formula (I), or a pharmaceutically acceptable salt and/or solvate thereof, for use in the manufacture of a medicament for the treatment or prophylaxis of a mitochondrial disease, for example those diseases and disorders mentioned herein below.

The invention also provides a compound of formula (I), or a pharmaceutically acceptable salt and/or solvate thereof, for use in the manufacture of a medicament for the treatment of a mitochondrial disease, for example those diseases and disorders mentioned herein below.

The invention also provides a compound of formula (I), or a pharmaceutically acceptable salt and/or solvate thereof, for use in the manufacture of a medicament for the prophylaxis of a mitochondrial disease, for example those diseases and disorders mentioned herein below.

The invention also provides a method of treating or preventing a mitochondrial disease in a subject, which comprises administering to a subject in need thereof an effective amount of a compound of formula (I), or a pharmaceutically acceptable salt and/or solvate thereof, for example those diseases and disorders mentioned herein below.

The invention also provides a method of treating a mitochondrial disease in a subject, which comprises administering to a subject in need thereof an effective amount of a compound of formula (I), or a pharmaceutically acceptable salt and/or solvate thereof, for example those diseases and disorders mentioned herein below.

The invention also provides a method of preventing a mitochondrial disease in a subject, which comprises administering to a subject in need thereof an effective amount of a compound of formula (I), or a pharmaceutically acceptable salt and/or solvate thereof, for example those diseases and disorders mentioned herein below.

Suitably, the mitochondrial disease is selected from Reye syndrome, Leber's hereditary optic neuropathy and associated disorders and disorders, such as those diseases and disorders disclosed in CA2884607A1 (Stealth Peptides International Inc.)

The compounds of formula (I) are expected to be useful in the treatment or prophylaxis of a disease or disorder associated with TDP-43 proteinopathy such as TDP-43 associated neurodegeneration.

Therefore, the invention provides a compound of formula (I), or a pharmaceutically acceptable salt and/or solvate thereof, for use in the treatment or prophylaxis of a disease or disorder associated with TDP-43 proteinopathy such as TDP-43 associated neurodegeneration, for example those diseases and disorders mentioned herein below.

The invention also provides a compound of formula (I), or a pharmaceutically acceptable salt and/or solvate thereof, for use in the treatment of a disease or disorder associated with TDP-43 proteinopathy such as TDP-43 associated neurodegeneration, for example those diseases and disorders mentioned herein below.

The invention also provides a compound of formula (I), or a pharmaceutically acceptable salt and/or solvate thereof, for use in the prophylaxis of a disease or disorder associated with TDP-43 proteinopathy such as TDP-43 associated neurodegeneration, for example those diseases and disorders mentioned herein below.

The invention also provides a compound of formula (I), or a pharmaceutically acceptable salt and/or solvate thereof, for use in the manufacture of a medicament for the treatment or prophylaxis of a disease or disorder associated with TDP-43 proteinopathy such as TDP-43 associated neurodegeneration, for example those diseases and disorders mentioned herein below.

The invention also provides a compound of formula (I), or a pharmaceutically acceptable salt and/or solvate thereof, for use in the manufacture of a medicament for the treatment of a disease or disorder associated with TDP-43 proteinopathy such as TDP-43 associated neurodegeneration, for example those diseases and disorders mentioned herein below.

The invention also provides a compound of formula (I), or a pharmaceutically acceptable salt and/or solvate thereof, for use in the manufacture of a medicament for the prophylaxis of a disease or disorder associated with TDP-43 proteinopathy such as TDP-43 associated neurodegeneration, for example those diseases and disorders mentioned herein below.

The invention also provides a method of treating or preventing a disease or disorder associated with TDP-43 proteinopathy such as TDP-43 associated neurodegeneration, which comprises administering to a subject in need thereof an effective amount of a compound of formula (I), or a pharmaceutically acceptable salt and/or solvate thereof, for example those diseases and disorders mentioned herein below.

The invention also provides a method of treating a disease or disorder associated with TDP-43 proteinopathy such as TDP-43 associated neurodegeneration, which comprises administering to a subject in need thereof an effective amount of a compound of formula (I), or a pharmaceutically acceptable salt and/or solvate thereof, for example those diseases and disorders mentioned herein below.

The invention also provides a method of preventing a disease or disorder associated with TDP-43 proteinopathy such as TDP-43 associated neurodegeneration, which comprises administering to a subject in need thereof an effective amount of a compound of formula (I), or a pharmaceutically acceptable salt and/or solvate thereof, for example those diseases and disorders mentioned herein below.

Suitably, the disease or disorder associated with TDP-43 proteinopathy such as TDP-43 associated neurodegeneration is selected from Amyotrophic Lateral Sclerosis, Frontotemporal dementia, Facial onset sensory and motor neuronopathy, Primary lateral sclerosis, Progressive muscular atrophy, Inclusion body myopathy associated with early-onset Paget disease of the bone and Frontotemporal lobar degeneration dementia, Perry disease, Chronic traumatic encephalopathy, Severe traumatic brain injury, Alzheimer's disease, Hippocampal sclerosis dementia, Limbic-predominant age-related TDP-43 encephalopathy, and Cerebral age-related TDP-43 with sclerosis.

The invention also provides a compound of formula (I), or a pharmaceutically acceptable salt and/or solvate thereof, for use in the treatment or prophylaxis of a disease or disorder associated with fibrosis.

The invention also provides a compound of formula (I), or a pharmaceutically acceptable salt and/or solvate thereof, for use in the treatment of a disease or disorder associated with fibrosis.

The invention also provides a compound of formula (I), or a pharmaceutically acceptable salt and/or solvate thereof, for use in the prophylaxis of a disease or disorder associated with fibrosis.

The invention also provides a compound of formula (I), or a pharmaceutically acceptable salt and/or solvate thereof, for use in the manufacture of a medicament for the treatment or prophylaxis of a disease or disorder associated with fibrosis.

The invention also provides a compound of formula (I), or a pharmaceutically acceptable salt and/or solvate thereof, for use in the manufacture of a medicament for the treatment of a disease or disorder associated with fibrosis.

The invention also provides a compound of formula (I), or a pharmaceutically acceptable salt and/or solvate thereof, for use in the manufacture of a medicament for the prophylaxis of a disease or disorder associated with fibrosis.

The invention also provides a method of treating or preventing a disease or disorder associated with fibrosis, which comprises administering to a subject in need thereof an effective amount of a compound of formula (I), or a pharmaceutically acceptable salt and/or solvate thereof.

The invention also provides a method of treating a disease or disorder associated with fibrosis, which comprises administering to a subject in need thereof an effective amount of a compound of formula (I), or a pharmaceutically acceptable salt and/or solvate thereof.

The invention also provides a method of preventing a disease or disorder associated with fibrosis, which comprises administering to a subject in need thereof an effective amount of a compound of formula (I), or a pharmaceutically acceptable salt and/or solvate thereof.

Suitably, the disease or disorder associated with fibrosis is selected from chronic kidney disease, idiopathic pulmonary fibrosis, non-alcoholic steatohepatitis, primary biliary cholangitis and systemic sclerosis.

Suitably the subject is a mammal, in particular the subject is a human.

Pharmaceutical Compositions

For use in therapy the compounds of the invention are usually administered as a pharmaceutical composition. The invention also provides a pharmaceutical composition comprising a compound of formula (I), or a pharmaceutically acceptable salt and/or solvate (e.g. salt) thereof, and a pharmaceutically acceptable carrier or excipient.

In one embodiment, there is provided a pharmaceutical composition comprising a compound of formula (I), or a pharmaceutically acceptable salt and/or solvate (e.g. salt) thereof, for use in the treatment or prophylaxis of a disease or disorder as described herein. In one embodiment, there is provided a pharmaceutical composition comprising a compound of formula (I), or a pharmaceutically acceptable salt and/or solvate (e.g. salt) thereof, for use in the treatment of a disease or disorder as described herein. In one embodiment, there is provided a pharmaceutical composition comprising a compound of formula (I), or a pharmaceutically acceptable salt and/or solvate (e.g. salt) thereof, for use in the prophylaxis of a disease or disorder as described herein.

In a further embodiment, there is provided a method for the treatment or prophylaxis of a disease or disorder as described herein, which comprises administering to a subject in need thereof an effective amount of a pharmaceutical composition comprising a compound of formula (I) or a pharmaceutically acceptable salt and/or solvate (e.g. salt) thereof. In a further embodiment, there is provided a method for the treatment of a disease or disorder as described herein, which comprises administering to a subject in need thereof an effective amount of a pharmaceutical composition comprising a compound of formula (I) or a pharmaceutically acceptable salt and/or solvate (e.g. salt) thereof. In a further embodiment, there is provided a method for the prophylaxis of a disease or disorder as described herein, which comprises administering to a subject in need thereof an effective amount of a pharmaceutical composition comprising a compound of formula (I) or a pharmaceutically acceptable salt and/or solvate (e.g. salt) thereof. Pharmaceutical compositions of the invention may take the form of a pharmaceutical formulation as described below.

The invention also provides the use of a pharmaceutical composition comprising a compound of formula (I), or a pharmaceutically acceptable salt and/or solvate thereof (e.g. salt) thereof, in the manufacture of a medicament for the treatment or prophylaxis of a disease or disorder as described herein. The invention also provides the use of a pharmaceutical composition comprising a compound of formula (I), or a pharmaceutically acceptable salt and/or solvate thereof (e.g. salt) thereof, in the manufacture of a medicament for the treatment of a disease or disorder as described herein. The invention also provides the use of a pharmaceutical composition comprising a compound of formula (I), or a pharmaceutically acceptable salt and/or solvate thereof (e.g. salt) thereof, in the manufacture of a medicament for the prophylaxis of a disease or disorder as described herein.

The amount of active ingredient which is required to achieve a therapeutic effect will, of course, vary with the particular compound, the route of administration, the subject under treatment or prophylaxis, including the type, species, age, weight, sex, and medical condition of the subject and the renal and hepatic function of the subject, and the particular disorder or disease being treated or prevented, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, suitably 0.01 mg per kg of body weight per day (mg/kg/day) to 10 mg/kg/day, and most suitably 0.1 to 5.0 mg/kg/day, for adult humans. For oral administration, the compositions are suitably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, suitably from about 1 mg to about 100 mg of active ingredient. Intravenously, the most suitable doses will range from about 0.1 to about 10 mg/kg/minute during a constant rate infusion. Advantageously, compounds of the invention may be administered in a single daily dose, or the total daily dosage may be administered in divided doses of two, three or four times daily. Furthermore, suitably compounds of the invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The pharmaceutical formulations according to the invention include those suitable for oral, parenteral (including subcutaneous, intradermal, intramuscular, intravenous [bolus or infusion], and intraarticular), intranasal (also known as nasal administration), inhalation (including fine particle dusts or mists which may be generated by means of various types of metered dose pressurized aerosols, nebulizers or insufflators) insufflation, rectal, intraperitoneal, topical (including dermal, buccal, sublingual, and intraocular) and intrathecal administration, although the most suitable route may depend upon, for example, the condition and disorder of the recipient.

Suitable pharmaceutical formulations according to the invention are those suitable for oral, intrathecal and parenteral administration; and more suitably are those suitable for oral or intrathecal administration.

In one suitable embodiment a compound according to formula (I) is administered by intrathecal administration. Such a method of administration involves injection of the compound of the invention into the spinal canal, or into the subarachnoid space so that it reaches the cerebrospinal fluid. This is advantageous for the administration of compounds which may not be able to pass the blood brain barrier via other routes of administration, such as oral administration.

Suitable pharmaceutical formulations may be administered intrathecally by continuous infusion such as with a catheter, or a pump, or intrathecally by a single bolus injection or by intermittent bolus injection. To be administered intrathecally, the pharmaceutical composition may be administered continuously or intermittently. The intermittent administration may be, for example, every thirty minutes, every hour, every several hours, every 24 hours, every couple of days (for example every 48 or 72 hours) or any combination thereof.

When the pharmaceutical formulation of the invention is administered continuously, implantable delivery devices, such as an implantable pump may be employed. Examples of such delivery devices include devices which can be implanted subcutaneously in the body or in the cranium, and provides an access port through which the pharmaceutical formulation may be delivered to the nerves or brain.

Intrathecal dosages of the present invention, when used for the indicated effects, will typically be less than 1 mg, such as less than 500 μg, for example less than 250 μg per kg of body weight when administered in a single dose or intermittently for adult humans. When administered continuously, the intrathecal dosages of the present invention will typically be less than 250 μg per kg body weight per hour, such as less than 125 μg per kg body weight per hour for adult humans.

In another suitable embodiment a compound according to formula (I) is administered by intranasal, inhalation (including fine particle dusts or mists which may be generated by means of various types of metered dose pressurized aerosols, nebulizers or insufflators) or insufflation administration. Such a method of administration allows for low doses of the compound of the invention to be administered, which can lead to a reduction in side-effects. For example, a daily dose of 10 to 0.01 μg, suitably 1 to 0.01 μg, and more suitably in the region of as low as 0.1 μg (100 ng) of compound of the invention may be used.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The compounds of formula (I) can, for example, be administered in a form suitable for immediate release or extended release. Immediate release or extended release can be achieved by the use of suitable pharmaceutical compositions comprising a compound of the present invention, or, particularly in the case of extended release, by the use of devices such as subcutaneous implants or osmotic pumps. The compounds of the invention may also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating a compound of the present invention with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of formula (I) can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for intranasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Suitable unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of formula (I) are expected to display one or more of the following advantageous properties:

- inhibitory activity of mPTP as demonstrated in the assay of Biological Example 1 (preferably with a $pIC_{50}$ value of 6.0 and above); and
- low inhibition of CYP2D6 as demonstrated in the assays of Biological Example 2.

In addition to the properties described above, certain compounds of formula (I) may also display one or more of the following advantageous properties:

- improved solubility and/or improved intrinsic clearance ($CL_{int}$) resulting in e.g. improved oral bioavailability and/or improved systemic exposure as demonstrated in the assays of Biological Examples 3 and 4.

The invention is further exemplified by the following non-limiting examples.

EXAMPLES

The invention is illustrated by the compounds described below. The following examples describe the laboratory synthesis of specific compounds of the invention and are not meant to limit the scope of the invention in any way with respect to compounds or processes. It is understood that, although specific reagents, solvents, temperatures and time periods are used, there are many possible equivalent alternatives that can be used to produce similar results. The invention is meant to include such equivalents.

General Experimental Details

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities, ranging from for example 85% to 99%. Calculations of number of moles and yield are in some cases adjusted for this.

Purity of final compounds was confirmed by HPLC/MS analysis and determined to be at least ≥90%, and in the significant majority of cases 95%. Analytical LCMS was conducted using the instrumentation shown in Table 1. $^{1}H$ NMR were recorded at 300K in a Bruker 300 MHz instruments (ADVANCE Ill and ADVANCE Ill HD). Flash prep HPLC was conducted using the following columns: XBridge Prep C18 OBD Column, 5 um, 19×150 mm; Welch Xtimate C18, 21.2×250 mm, 5 um; SunFire Prep C18 OBD 19×150 mm×5 um. SFC purification was conducted using the following columns; (a) CHIRALPAK AS-H, 3*25 cm, 5 um (b) SFC-YMC Cellulose-SB, 4.6×100 mm, 3 um.

TABLE 1

Analytical LC-MS conditions

| Instrument ID | Column | Mobile Phase | Flow Rate |
|---|---|---|---|
| LCMS01 | Halo-C18, 30*3.0 mm, 2.0 μm | A: $H_2O$/0.05% TFA; B: ACN | 1.5 mL/min |
| LCMS02 | Cortecs C18+, 50*3.0 mm, 2.7 μm | A: $H_2O$/0.05% TFA; B: ACN/0.05% TFA | 1.5 mL/min |
| LCMS03 | Halo-C18, 30*3.0 mm, 2.0 μm | A: $H_2O$/0.1% TFA; B: ACN/0.05% FA | 1.5 mL/min |
| LCMS04 | Kinetex XB-C18, 50*3.0 mm, 2.6 μm | A: $H_2O$/0.01% TFA; B: ACN/0.01% FA | 1.5 mL/min |
| LCMS05 | Poroshell HPH-C18, 50*3.0 mm, 2.7 μm | A: $H_2O$/5 mM $NH_4HCO_3$; B: MeOH | 1.0 mL/min |
| LCMS06 | Xbridge C18, 50*3.0 mm, 3.5 μm | A: $H_2O$/5 mM $NH_4HCO_3$ + 0.05% $NH_3$•$H_2O$; B: 5% $H_2O$ in ACN | 1.2 mL/min |
| LCMS07 | Poroshell HPH-C18, 50*3.0 mm, 2.7 μm | A: $H_2O$/0.05% $NH_3$•$H_2O$; B: ACN | 1.2 mL/min |
| LCMS08 | Halo C18, 50*3.0 mm, 2.7 μm | A: $H_2O$/0.05% TFA; B: ACN | 1.5 mL/min |
| LCMS09 | Poroshell HPH-C18, 50*3.0 mm, 2.7 μm | A: $H_2O$/0.05% $NH_3$•$H_2O$; B: ACN | 1.2 mL/min |

Abbreviations $CH_3CN$ Acetonitrile
$Cs_2CO_3$ Cesium Carbonate
DCM Dichloromethane
DIPEA Diisopropylethylamine DMF Dimethylformamide
Et Ethyl
$Et_3N$ Triethylamine
EtOAc Ethyl acetate
EtOH Ethyl alcohol
HATU 1-[Bis(dimethylamino)methylene]-1H-1,2,3-triazolo[4,5-b]pyridinium 3-oxide hexafluorophosphate
heps hepatocytes
HCl Hydrochloric acid
$K_2CO_3$ Potassium Carbonate
$K_3PO_4$ Potassium Phosphate
LiHMDS Lithium bis(trimethylsilyl)amide
Me Methyl
MeOH Methanol
$NaHCO_3$ Sodium bicarbonate
NaOAc Sodium acetate
NaOH Sodium hydroxide
NBS N-Bromosuccinimide
NCS N-Chlorosuccinimide
$NH_4Cl$ Ammonium chloride
PE Petroleum ether
$Pd(OAc)_2$ Palladium(II) Acetate
$Pd(dppf)Cl_2·CH_2Cl_2$ Bis(diphenylphosphino)ferrocene]dichloropalladium(II), complex with dichloromethane
$Pd(dppf)Cl_2$ Bis(diphenylphosphino)ferrocene]dichloropalladium(II)
RT room temperature
o/n overnight (16 h)
TFA Trifluoroacetic acid
THF Tetrahydrofuran
THP Tetrahydropyranyl
$T_3P$ Propanephosphonic anhydride
uL microlitre
uM micromolar Preparation of Comparative Example 1

Comparative Example 1: (E)-N-(2-methyl-3-fluorophenyl)-3-(1H-indazol-6-yl)acrylamide

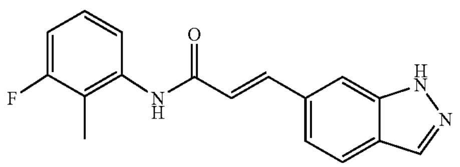 [SMILES: Cc1c(F)cccc1NC(=O)/C=C/c1ccc2cn[nH]c2c1]

Comparative Example 1 was prepared according to methods described in Chen et al. (Assay and Drug Development Technologies, 2018, 16, 445-455). Comparative Example 1 may also be prepared using analogous synthetic methods to those described herein for Examples 1 to 64.

Preparation of Examples 1 to 74

Intermediate 1: N-(3-fluoro-2-methylphenyl)acrylamide

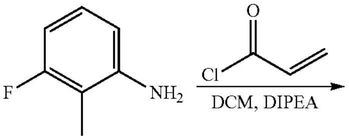

-continued

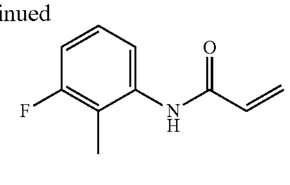

To a stirred solution of 3-fluoro-2-methyl aniline (1.0 g, 8.0 mmol, 1.0 eq.) and DIPEA (3.1 g, 23.9 mmol, 3.0 eq.) in DCM (40 mL) was added acryloyl chloride (0.71 mL, 8.8 mmol, 1.1 eq.) dropwise at 0° C. under nitrogen. The resulting mixture was stirred at 25° C. under an inert atmosphere of nitrogen for 3 h. The resulting mixture was washed with 2×30 mL of water and the organic layer was concentrated. The residue was purified by silica gel chromatography eluting with EtOAc/petroleum ether (1:5). This resulted in 1.04 g (73%) of N-(3-fluoro-2-methylphenyl) acrylamide as a white solid. LC-MS (ES, m/z): $[M+H]^+=180$ Intermediate 2: N-(3-chloro-2-methylphenyl)acrylamide

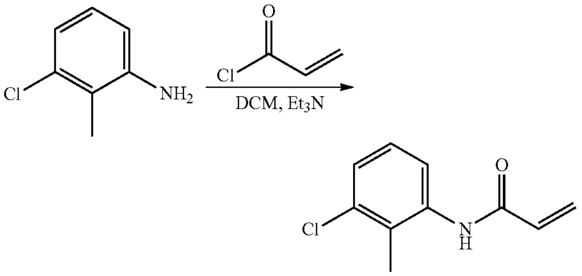

Into a 50-mL 3-necked round-bottom flask purged and maintained with an inert atmosphere of nitrogen, was placed 3-chloro-2-methyl-aniline (300 mg, 2.12 mmol, 1.0 eq.), DCM (15 mL), $Et_3N$ (1 mL, 7.19 mmol, 3.0 eq.). This was followed by the addition of acryloyl chloride (260 mg, 2.9 mmol, 1.2 eq.) dropwise with stirring at 25° C. The resulting solution was stirred for 5 h at 25° C. The resulting mixture was washed with 2×10 ml of water and the organic layer was concentrated. The residue was purified by silica gel chromatography eluting with EtOAc/PE (1:5). This resulted in 300 mg (74%) of N-(3-chloro-2-methylphenyl)acrylamide as a light yellow solid. LC-MS (ES, m/z): $[M+H]^+=196$ Example 1: (E)-3-(1H-benzo[d][1,2,3]triazol-6-yl)-N-(3-fluoro-2-methylphenyl)acrylamide

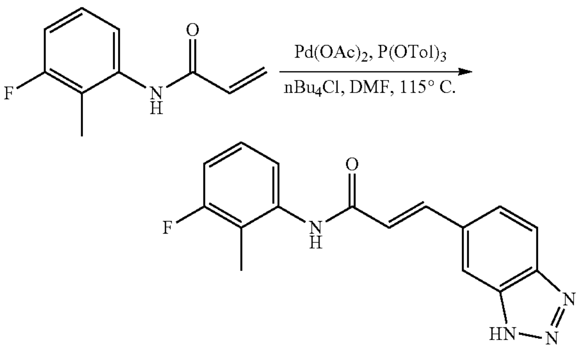

To a microwave vial with N-(3-fluoro-2-methylphenyl) acrylamide (Intermediate 1, 100 mg, 0.56 mmol, 1.0 eq.), 5-bromo-3H-1,2,3-benzotriazole (110 mg, 0.56 mmol, 1.0 equiv), $Pd(OAc)_2$ (19 mg, 0.084 mmol, 0.15 equiv), tris(2-methylphenyl)phosphane (34 mg, 0.112 mmol, 0.20 equiv) and tetrabutylammonium chloride (155 mg, 0.558 mmol, 1.0 equiv) was added DMF (1.5 mL). The resulting solution was stirred for 12 h at 115° C. The resulting mixture was diluted with 20 mL EtOAc washed with 2×10 mL of 1 M aq. $K_2CO_3$ and the organic layer was concentrated and dried over anhydrous sodium sulfate and concentrated. The residue was applied onto a silica gel column. The resulting crude product was purified by Flash-Prep-HPLC. This resulted in 9 mg (5%) of (E)-3-(1H-benzo[d][1,2,3]triazol-6-yl)-N-(3-fluoro-2-methylphenyl) acrylamide as a pale grey solid. LC-MS (ES, m/z): $[M+H]^+=297$;

$^1H$ NMR (400 MHz, DMSO-$d_6$, ppm): δ 9.65 (s, 1H), 8.15 (s, 1H), 7.96-7.92 (m, 1H), 7.79 (d, J=16.0 Hz, 1H), 7.71-7.66 (m, 1H), 7.49 (s, 1H) 7.27-7.20 (m, 1H), 7.10-6.96 (m, 2H), 2.18 (s, 3H).

Intermediate 3: (E)-3-(3-methyl-1H-indazol-6-yl) acrylic acid

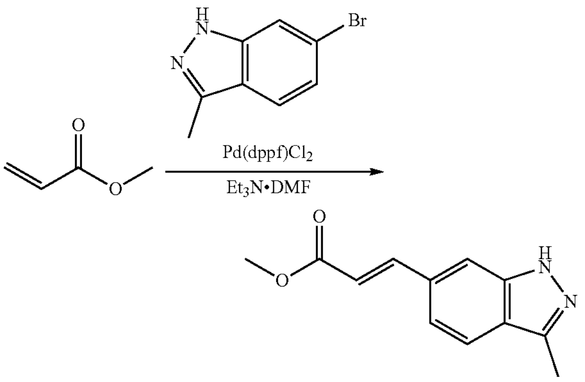

Step 1: Into a 250-mL 3-necked round-bottom flask, was placed 6-bromo-3-methyl-1H-indazole (2.50 g, 11.84 mmol, 1.00 equiv), methyl acrylate (1.53 g, 17.76 mmol, 1.50 equiv), $Et_3N$ (3.60 g, 35.53 mmol, 3.00 equiv), $Pd(dppf)Cl_2$ (0.87 g, 1.18 mmol, 0.10 equiv), DMF (100.00 mL). The resulting solution was stirred for 10 hr at 120° C. The mixture was concentrated and the residue was applied onto a silica gel column with THF/PE (1/1). This resulted in 0.9 g (35% yield) of methyl (2E)-3-(3-methyl-1H-indazol-6-yl) prop-2-enoate as a light yellow solid.

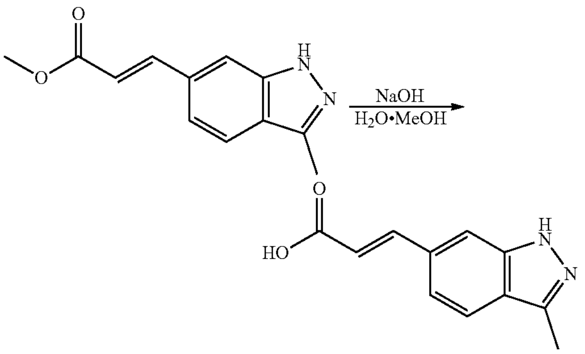

Step 2: Into a 40-mL vial, was placed methyl (2E)-3-(3-methyl-1H-indazol-6-yl)prop-2-enoate (890.00 mg, 4.12 mmol, 1.00 equiv), NaOH (329.24 mg, 8.23 mmol, 2.00 equiv) in $H_2O$(10.00 mL) and MeOH (10.00 mL). The resulting solution was stirred for 2 hr at 20° C. The pH value of the solution was adjusted to 3 with HCl (1 mol/L). The solids were collected by filtration. This resulted in 500 mg (60% yield) of (E)-3-(3-methyl-1H-indazol-6-yl)acrylic acid as a off-white solid.

Example 2: (E)-N-(3-fluoro-2-methylphenyl)-3-(2-oxo-2,3-dihydrobenzo[d]thiazol-5-yl)acrylamide

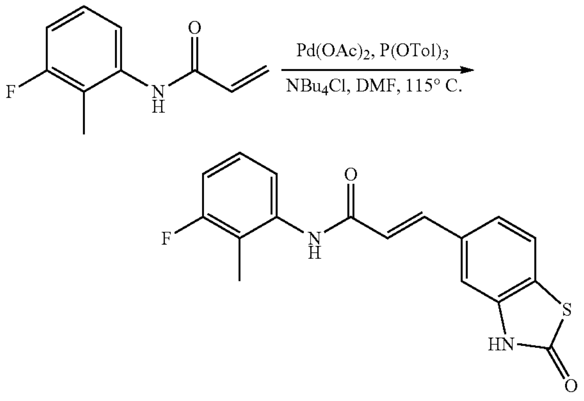

To a microwave vial with N-(3-fluoro-2-methylphenyl) acrylamide (Intermediate 1, 180 mg, 1.0 mmol, 1.0 equiv), 5-bromo-3H-1,3-benzothiazol-2-one (231 mg, 1.0 mmol, 1.0 equiv), $Pd(OAc)_2$ (34 mg, 0.151 mmol, 0.15 equiv), tris(2-methylphenyl)phosphane (62 mg, 0.201 mmol, 0.20 equiv) and tetrabutylammonium chloride (279 mg, 1.0 mmol, 1.0 equiv) was added DMF (2.8 mL). The resulting solution was stirred for 12 h at 115° C. The resulting mixture was diluted with 30 mL EtOAc washed with 2×15 mL of 1 M aq. $K_2CO_3$ and the organic layer was concentrated and dried over anhydrous sodium sulfate and concentrated. The residue was applied onto a silica gel column. The resulting crude product was purified by Flash-Prep-HPLC. This resulted in 6 mg (2%) of (E)-N-(3-fluoro-2-methylphenyl)-3-(2-oxo-2,3-dihydrobenzo[d]thiazol-5-yl)acrylamide as a white solid. LC-MS (ES, m/z): $[M+H]^+$=329

$^1$H NMR (400 MHz, DMSO-$d_6$, ppm): δ 12.12 (s, 1H), 9.66 (s, 1H), 7.66-7.56 (m, 2H), 7.48 (d, J=8.0 Hz, 1H), 7.39-7.30 (m, 2H), 7.29-7.21 (m, 1H) 7.06-6.92 (m, 2H), 2.17 (s, 3H).

Example 3: (E)-3-(3,3-dimethyl-2-oxoindolin-6-yl)-N-(3-fluoro-2-methylphenyl)acrylamide

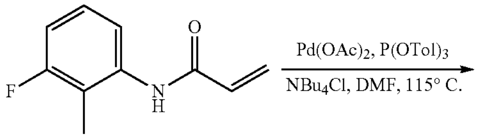

-continued

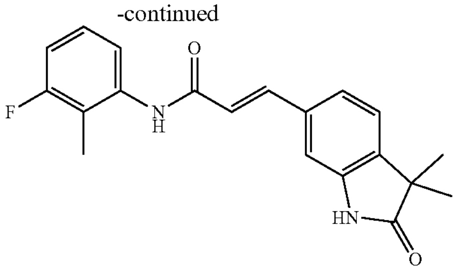

To a microwave vial with N-(3-fluoro-2-methylphenyl) acrylamide (Intermediate 1, 185 mg, 1.03 mmol, 1.0 equiv), 6-bromo-3,3-dimethyl-1H-indol-2-one (240 mg, 1.03 mmol, 1.0 equiv), $Pd(OAc)_2$ (35 mg, 0.155 mmol, 0.15 equiv), tris(2-methylphenyl)phosphane (63 mg, 0.206 mmol, 0.20 equiv) and tetrabutylammonium chloride (286 mg, 1.03 mmol, 1.0 equiv) was added DMF (2.9 mL). The resulting solution was stirred for 12 h at 115° C. The resulting mixture was diluted with 30 mL EtOAc washed with 2×15 mL of 1 M aq. $K_2CO_3$ and the organic layer was concentrated and dried over anhydrous sodium sulfate and concentrated. The residue was applied onto a silica gel column. The resulting crude product was purified by Flash-Prep-HPLC. This resulted in 76 mg (22%) of (E)-3-(3,3-dimethyl-2-oxoindolin-6-yl)-N-(3-fluoro-2-methylphenyl)acrylamide as a white solid. LC-MS (ES, m/z): $[M+H]^+$=339

$^1$H NMR (400 MHz, DMSO-$d_6$, ppm): δ 10.54 (s, 1H), 9.63 (s, 1H), 7.75 (d, J=15.7 Hz, 1H), 7.48 (d, J=8.1 Hz, 1H), 7.37 (d, J=7.6 Hz, 1H) 7.28-7.17 (m, 2H), 7.09 (d, J=1.5 Hz, 1H), 7.05-6.97 (m, 1H), 6.93 (d, J=15.7 Hz, 1H), 2.16 (s, 3H), 1.27 (s, 6H).

Example 4: (E)-N-(3-fluoro-2-methylphenyl)-3-(2'-oxospiro[cyclopropane-1,3'-indolin]-6'-yl)acrylamide

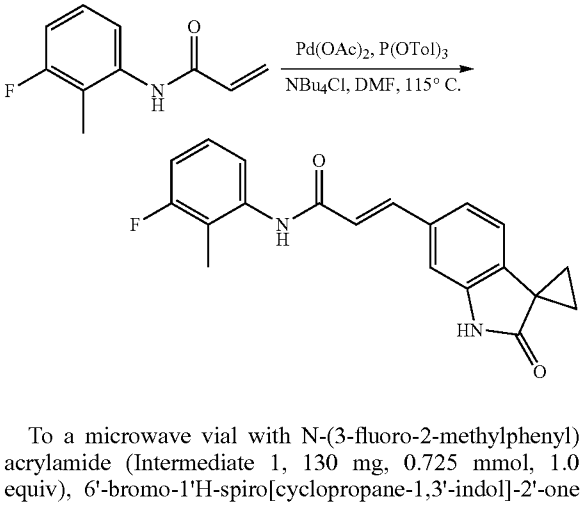

To a microwave vial with N-(3-fluoro-2-methylphenyl) acrylamide (Intermediate 1, 130 mg, 0.725 mmol, 1.0 equiv), 6'-bromo-1'H-spiro[cyclopropane-1,3'-indol]-2'-one (172 mg, 0.725 mmol, 1.0 equiv), $Pd(OAc)_2$ (24 mg, 0.109 mmol, 0.15 equiv) tris(2-methylphenyl)phosphane (44 mg, 0.145 mmol, 0.20 equiv) and tetrabutylammonium chloride (278 mg, 0.725 mmol, 1.0 equiv) was added DMF (2 mL). The resulting solution was stirred for 12 h at 115° C. The resulting mixture was diluted with 30 mL EtOAc washed with 2×15 mL of 1 M aq. $K_2CO_3$ and the organic layer was concentrated and dried over anhydrous sodium sulfate and concentrated. The residue was applied onto a silica gel column. The resulting crude product was purified by Flash-Prep-HPLC. This resulted in 10 mg (4%) of (E)-N-(3-fluoro-2-methylphenyl)-3-(2'-oxospiro[cyclopropane-1,3'-indolin]-6'-yl)acrylamide as a white solid.

LC-MS (ES, m/z): $[M+H]^+$=337

$^1$H NMR (400 MHz, DMSO-$d_6$, ppm): δ 10.77 (s, 1H), 9.62 (s, 1H), 7.57 (d, J=15.7 Hz, 1H), 7.49 (d, J=8.1 Hz, 1H), 7.29-7.18 (m, 2H), 7.16 (s, 1H), 7.06 (d, J=7.7 Hz, 1H), 7.01 (t, J=9.0 Hz, 1H), 6.95 (d, J=15.7 Hz, 1H), 2.17 (d, J=2.0 Hz, 3H), 1.66-1.60 (m, 2H), 1.55-1.50 (m, 2H).

Example 5: (E)-N-(3-fluoro-2-methylphenyl)-3-(7-fluoro-2-oxoindolin-6-yl)acrylamide

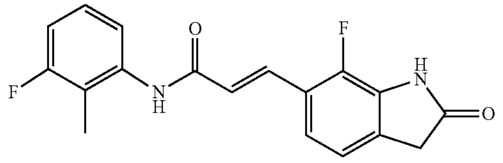 [SMILES: Cc1c(F)cccc1NC(=O)/C=C/c1ccc2c(c1F)NC(=O)C2]

Prepared according to the methodology described above using Intermediate 1 and 6-bromo-7-fluoro-1,3-dihydro-2H-Indol-2-one. LC-MS (ES, m/z): 327 $[M-H]^+$ $^1$H NMR (300 MHz, DMSO-$d_6$, ppm): δ 10.59 (s, 1H), 9.72 (s, 1H), 7.64 (d, J=15.9 Hz, 1H), 7.45-7.19 (m, 3H), 7.04-6.98 (m, 3H), 3.56 (s, 2H), 2.16 (s, 3H).

Example 6: (E)-N-(3-fluoro-2-methylphenyl)-3-(2-oxo-2,3-dihydrobenzo[d]oxazol-5-yl)acrylamide

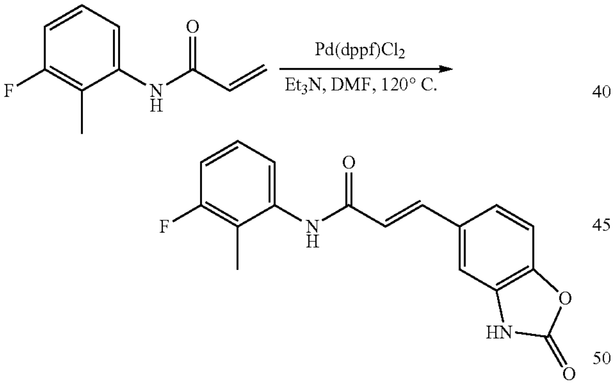

Into a 8-mL sealed tube purged and maintained with an inert atmosphere of nitrogen, was placed N-(3-fluoro-2-methylphenyl)acrylamide (Intermediate 1, (50 mg, 0.28 mmol, 1.0 equiv), DMF (4 mL), 5-bromo-2-benzoxazolinone, (66 mg, 0.31 mmol, 1.10 equiv), $Et_3N$ (0.12 mL, 0.84 mmol, 3.0 equiv), and $Pd(dppf)Cl_2 \cdot CH_2Cl_2$ (11 mg, 0.014 mmol, 0.05 equiv). The resulting solution was stirred for 12 h at 120° C. The reaction was then quenched by the addition of 3 mL of water. The resulting solution was extracted with 5 mL of DCM and the organic layer was dried over anhydrous sodium sulfate and concentrated. The crude product was purified by Flash-Prep-HPLC. This resulted in 21 mg (24%) of (E)-N-(3-fluoro-2-methylphenyl)-3-(2-oxo-2,3-dihydrobenzo[d]oxazol-5-yl)acrylamide as a white solid. LC MS (ES, m/z): $[M+H]^+$=313

$^1$H NMR (300 MHz, DMSO-$d_6$, ppm): δ 11.89 (brs, 1H), 9.59 (s, 1H), 7.62 (d, J=15.6 Hz, 1H), 7.48 (d, J=8.1 Hz, 1H), 7.44-7.31 (m, 3H), 7.26-7.19 (m, 1H), 7.07-6.95 (m, 2H), 2.16 (s, 3H).

Example 7: (E)-N-(3-fluoro-2-methylphenyl)-3-(1-methyl-2-oxo-2,3-dihydro-1H-benzo[d]imidazol-5-yl)acrylamide

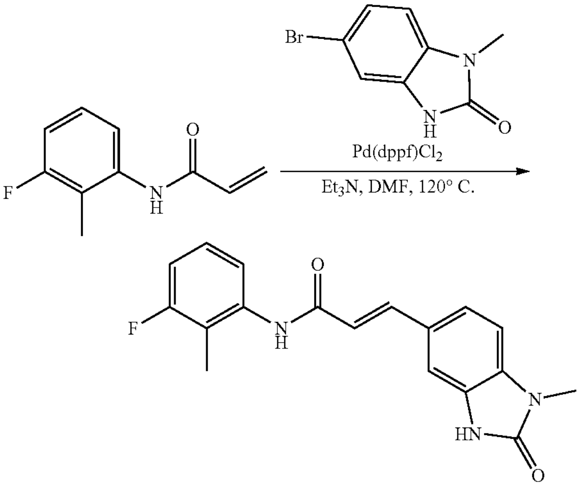

Into a 8-mL vial purged and maintained with an inert atmosphere of nitrogen, was placed N-(3-fluoro-2-methylphenyl)acrylamide (Intermediate 1, 90 mg, 0.50 mmol, 1.0 equiv), DMF (5 mL), 5-bromo-1-methyl-3H-1,3-benzodiazol-2-one (137 mg, 0.60 mmol, 1.20 equiv), $Et_3N$ (0.21 mL, 1.51 mmol, 3.0 equiv), and $Pd(dppf)Cl_2 \cdot CH_2Cl_2$ (20 mg, 0.025 mmol, 0.05 equiv). The resulting solution was stirred for 12 h at 120° C. and cooled to 25° C. The mixture was purified by Prep-HPLC. This resulted in 7 mg (4%) of (E)-N-(3-fluoro-2-methylphenyl)-3-(1-methyl-2-oxo-2,3-dihydro-1H-benzo[d]imidazol-5-yl)acrylamide as an off-white solid. LC MS (ES, m/z): $[M+H]^+$=326

$^1$H NMR (300 MHz, DMSO-$d_6$, ppm): δ 11.03 (s, 1H), 9.51 (s, 1H), 7.60 (d, J=15.6 Hz, 1H), 7.49 (d, J=8.1 Hz, 1H), 7.33 (dd, J=8.1, 1.5 Hz, 1H), 7.29-7.16 (m, 3H), 7.0-6.98 (m, 1H), 6.88 (d, J=15.6 Hz, 1H), 2.16 (s, 3H).

Example 8: (E)-N-(3-fluoro-2-methylphenyl)-3-(3-methyl-2-oxoindolin-6-yl)acrylamide

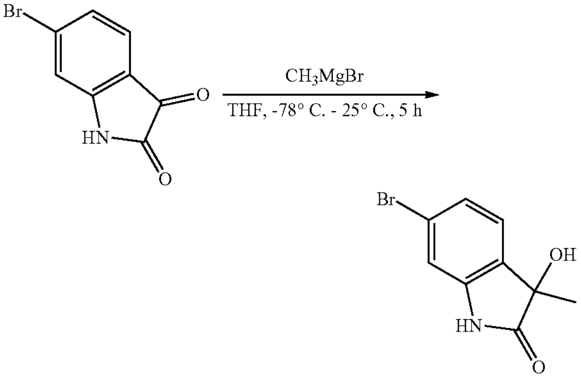

Step 1: Into a 100-mL 3-necked round-bottom flask purged and maintained with an inert atmosphere of nitrogen, was placed 6-bromo-1H-indole-2,3-dione (3.5 g, 15.48 mmol, 1.0 eq), THF (70 mL). The 3M Methylmagnesium bromide (5.2 mL, 15.48 mmol, 1.0 eq) was added dropwise at −78° C. over 0.5 h. The resulting solution was allowed to react, with stirring, for an additional 5 h at −78° C. and then warmed to 25° C. The reaction was then quenched by the addition of 10 mL of 0.2 M HCl. The resulting solution was extracted with 2×50 mL of EtOAc, and the organic was dried over anhydrous sodium sulfate and concentrated. The residue was applied onto a silica gel column with EtOAc/PE (35/65). This resulted in 3 g (80%) of 6-bromo-3-hydroxy-3-methyl-1H-indol-2-one as an off-white solid. LC-MS (ES, m/z): [M−H]$^+$=240

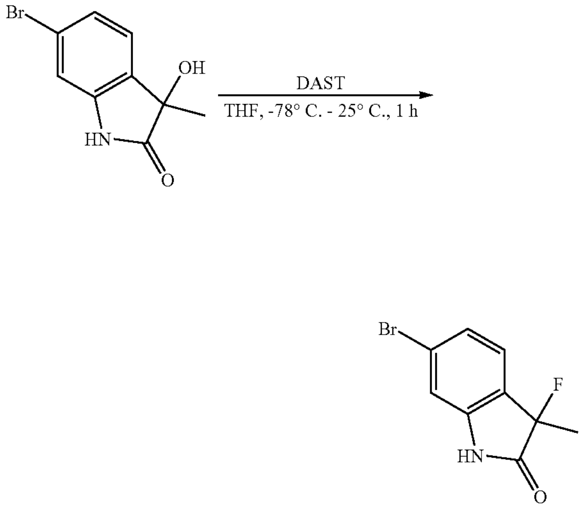

Step 2: Into a 100-mL 3-necked round-bottom flask purged and maintained with an inert atmosphere of nitrogen, was placed 6-bromo-3-hydroxy-3-methyl-1H-indol-2-one (2.0 g, 8.26 mmol, 1.0 eq) and THF (30 mL). This was followed by the addition of diethylaminosulfur trifluoride (DAST)(2.0 g, 12.39 mmol, 1.50 eq) at −78° C. The resulting solution was stirred for 1 h from −78° C. and warmed to 25° C. The reaction was then quenched by the addition of 10 mL of Sat. $NaHCO_3$. The resulting solution was extracted with 2×50 mL of EtOAc, and the organic layer was dried over anhydrous sodium sulfate and concentrated. The residue was applied onto a silica gel column with EtOAc/PE (25/75). This resulted in 1.65 g (82%) of 6-bromo-3-fluoro-3-methyl-1H-indol-2-one as a white solid. LC-MS (ES, m/z): [M−H]$^+$=242

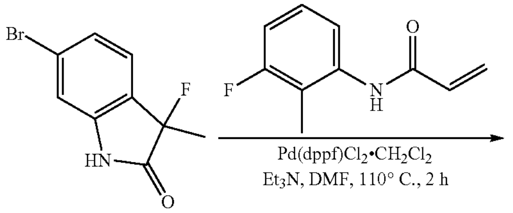

-continued

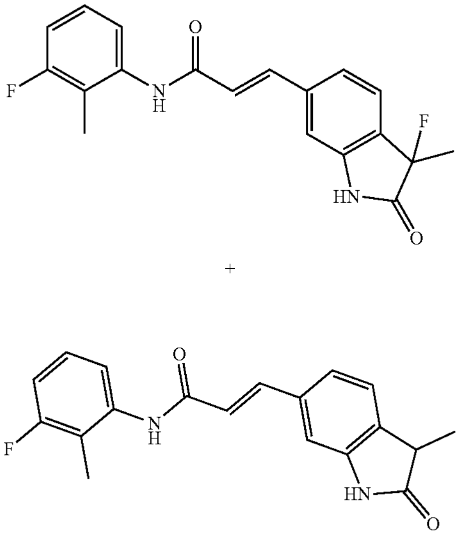

Step 3: Into a 8-mL sealed tube purged and maintained with an inert atmosphere of nitrogen, was placed 6-bromo-3-fluoro-3-methyl-1H-indol-2-one (200 mg, 0.82 mmol, 1.0 eq), N-(3-fluoro-2-methylphenyl)acrylamide (Intermediate 1, 147 mg, 0.82 mmol, 1.0 eq), $Pd(dppf)Cl_2 \cdot CH_2Cl_2$ (13 mg, 0.02 mmol, 0.02 eq), DMF (4 mL), $Et_3N$ (0.23 mL, 1.64 mmol, 2.0 eq). The resulting solution was stirred for 2 h at 110° C. The solids were filtered out. The filtrate was concentrated. The crude product was purified by Flash-Prep-HPLC. This resulted in 13 mg (4.5%) of (E)-N-(3-fluoro-2-methylphenyl)-3-(3-fluoro-3-methyl-2-oxoindolin-6-yl) acrylamide and 12 mg (4%) of (E)-N-(3-fluoro-2-methylphenyl)-3-(3-methyl-2-oxoindolin-6-yl)acrylamide.

(E)-N-(3-fluoro-2-methylphenyl)-3-(3-fluoro-3-methyl-2-oxoindolin-6-yl)acrylamide LC-MS (ES, m/z): [M+H]$^+$=343

$^1$H NMR (300 MHz, DMSO-$d_6$, ppm): δ 10.87 (s, 1H), 9.68 (s, 1H), 7.60-7.46 (m, 3H), 7.34-7.19 (m, 2H), 7.12 (s, 1H), 7.04-6.97 (m, 2H), 2.16 (s, 3H), 1.70 (d, J=22.5 Hz, 3H).

E)-N-(3-fluoro-2-methylphenyl)-3-(3-methyl-2-oxoindolin-6-yl)acrylamide LC-MS (ES, m/z): [M+H]$^+$=325

$^1$H NMR (300 MHz, DMSO-$d_6$, ppm): δ 10.53 (s, 1H), 9.62 (s, 1H), 7.58-7.46 (m, 2H), 7.34-7.21 (m, 3H), 7.06-6.90 (m, 3H), 3.48-3.45 (m, 1H), 2.16 (s, 3H), 1.34 (d, J=7.8 Hz, 3H).

Example 9: (E)-N-(3-chloro-2-methylphenyl)-3-(2-oxo-2,3-dihydrobenzo[d]oxazol-5-yl) acrylamide

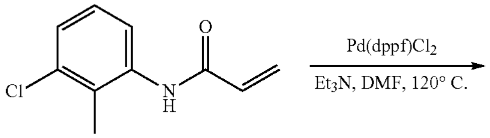

-continued

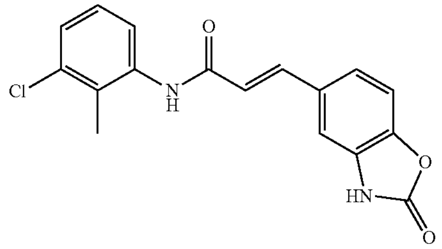

Into a 8-mL sealed tube purged and maintained with an inert atmosphere of nitrogen, was placed N-(3-chloro-2-methylphenyl)prop-2-enamide (Intermediate 2, 55 mg, 0.28 mmol, 1.0 equiv), DMF (4 mL), 2-benzoxazolinone, 5-bromo-(66 mg, 0.31 mmol, 1.10 equiv), $Et_3N$ (0.12 mL, 0.84 mmol, 3.0 equiv) and $Pd(dppf)Cl_2 \cdot CH_2Cl_2$ (11 mg, 0.014 mmol, 0.05 equiv). The resulting solution was stirred for 12 h at 120° C. The reaction was then quenched by the addition of 3 mL of water. The resulting solution was extracted with 5 mL of DCM and the organic layer was dried over anhydrous sodium sulfate and concentrated. The crude product was purified by Flash-Prep-HPLC. This resulted in 21 mg (24%) of (E)-N-(3-chloro-2-methylphenyl)-3-(2-oxo-2,3-dihydrobenzo[d]oxazol-5-yl)acrylamide as a white solid. LC MS (ES, m/z): $[M+H]^+$=329

$^1H$ NMR (300 MHz, DMSO-$d_6$, ppm): δ 11.83 (s, 1H), 9.68 (s, 1H), 7.61 (d, J=15.6 Hz, 1H), 7.53-7.51 (m, 1H), 7.43-7.30 (m, 5H), 6.91 (d, J=15.6 Hz, 1H), 2.28 (s, 3H).

Example 10: (E)-N-(3-fluoro-2-methylphenyl)-3-(2-oxoindolin-6-yl)acrylamide

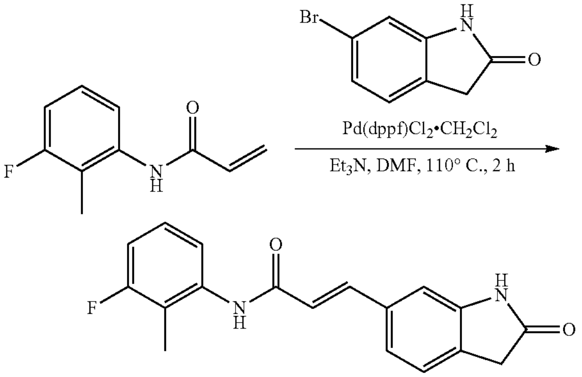

Into a 40-mL sealed tube purged and maintained with an inert atmosphere of nitrogen, was placed N-3-fluoro-2-methylphenyl)prop-2-enamide (Intermediate 1, (500 mg, 2.79 mmol, 1.0 eq), 6-bromo-1,3-dihydroindol-2-one (592 mg, 2.79 mmol, 1.0 eq), DMF (20 mL), $Et_3N$ (1.2 mL, 8.37 mmol, 3.0 eq) and $Pd(dppf)Cl_2$ (41 mg, 0.05 mmol, 0.02 eq). The reaction mixture was stirred for 2 h at 110° C. The resulting mixture was concentrated. The crude product was purified by Flash-Prep-HPLC. This resulted in 102 mg (11%) of (E)-N-(3-fluoro-2-methylphenyl)-3-(2-oxoindolin-6-yl)acrylamide as a white solid. LC-MS (ES, m/z): $[M-H]^+$ =309

$^1H$ NMR (300 MHz, DMSO-$d_6$, ppm): δ 10.57 (s, 1H), 9.62 (s, 1H), 7.55 (d, J=15.9 Hz, 1H), 7.48-7.45 (m, 1H), 7.29-7.18 (m, 3H), 7.05-6.89 (m, 3H), 3.52 (s, 2H), 2.26 (s, 3H).

Example 11: (E)-N-(2,3-dihydro-1H-inden-1-yl)-3-(2-oxo-2,3-dihydrobenzo[d]oxazol-5-yl)acrylamide

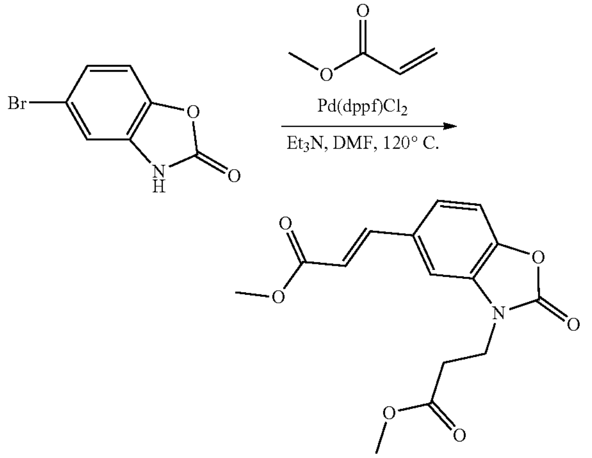

Step 1: Into a 500-mL sealed tube, was placed 5-bromobenzo[d]oxazol-2(3H)-one 1.0 g, 46.96 mmol, 1.0 equiv), methyl acrylate (12.1 g, 140.8 mmol, 3.0 equiv), $Et_3N$ (19.6 mL, 140.8 mmol, 3.0 equiv), $Pd(dppf)Cl_2$ (350 mg, 4.7 mmol, 0.01 equiv) in DMF (200 mL). The resulting solution was stirred for 2 h at 120° C. The resulting solution was concentrated. The residue was applied onto a silica gel column eluting with THF/hexane (20/80). This resulted in 11 g (82%) of methyl (E)-3-(3-(3-methoxy-3-oxopropyl)-2-oxo-2,3-dihydrobenzo[d]oxazol-5-yl)acrylate as a yellow solid.

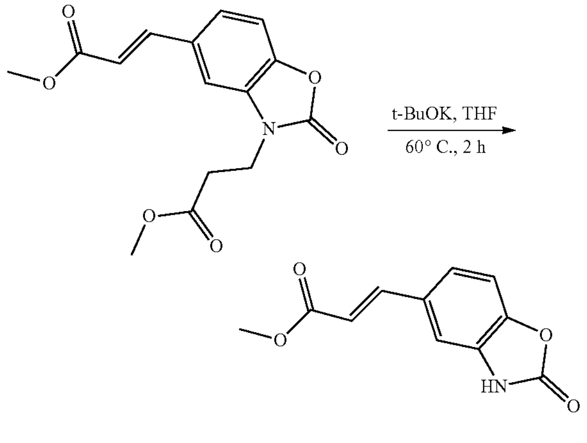

Step 2: Into a 500 mL 3-necked round-bottom flask purged and maintained with an inert atmosphere of nitrogen, was placed THF (300 mL), methyl (E)-3-(3-(3-methoxy-3-oxopropyl)-2-oxo-2,3-dihydrobenzo[d]oxazol-5-yl)acrylate (11.0 g, 36.1 mmol, 1.0 equiv), t-BuOK (13.2 g, 108.2 mmol, 3.0 equiv). The resulting solution was stirred for 2 h at 60° C. The reaction was then quenched by the addition of 600 mL of Satd. $NH_4Cl$. The resulting solution was extracted with 2×300 mL of EtOAc. The organic layer was washed with 2×400 ml of Water. The organic layer was dried over anhydrous sodium sulfate and concentrated. The resulting solution was concentrated. The residue was applied onto a silica gel column with EtOAc/hexane (40/60). This resulted in 5.5 g (69%) of methyl (E)-3-(2-oxo-2,3-dihydrobenzo[d]oxazol-5-yl)acrylate as a light-red solid.

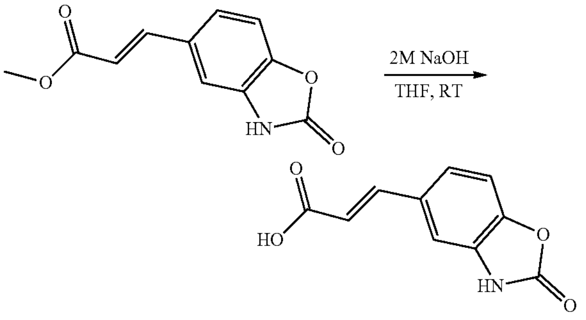

Step 3: Into a 100 mL 3-necked round-bottom flask purged, was placed THF (20 mL), methyl (E)-3-(2-oxo-2,3-dihydrobenzo[d]oxazol-5-yl)acrylate (2.5 g, 11.4 mmol, 1.0 equiv), 2 M NaOH (17.1 mL, 34.2 mmol, 3.0 equiv). The resulting solution was stirred for 2 h at 25° C. The reaction mixture was concentrated under low temperature (<30° C.). The residue was dissolved into water (30 mL), and the pH was adjusted to 2-3 with 2 M HCl. The solid was collected. This resulted in 2.5 g (65%) of (E)-3-(2-oxo-2,3-dihydrobenzo[d]oxazol-5-yl)acrylic acid as an off-white solid.

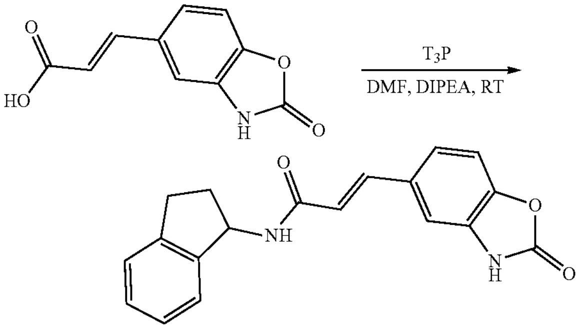

Step 4: In each vial was added (E)-3-(2-oxo-2,3-dihydrobenzo[d]oxazol-5-yl)acrylic acid (30 mg, 0.146 mmol, 1.0 equiv) in DMF (2 mL). Then $T_3P$ (70 mg, 0.22 mmol, 1.50 equiv) and DIPEA (28 mg, 0.22 mmol, 1.50 equiv), 1-indanamine (0.161 mmol, 1.1 equiv) were added. The reaction mixture was stirred for 2 h at room temperature. The reaction mixture was quenched by water and extracted with EtOAc, the organic layer was concentrated under vacuum to afford crude product. The crude product was then purified by Prep-HPLC directly. The collected fraction was lyophilized to get the final compounds. LC-MS (ES, m/z): 321 $[M+H]^+$ $^1H$ NMR: (300 MHz, DMSO-$d_6$, ppm): δ 11.77 (s, 1H), 8.44 (d, J=8.4 Hz, 1H), 7.51 (d, J=15.6 Hz, 1H), 7.34-7.18 (m, 7H), 6.65 (d, J=15.9 Hz, 1H), 5.42-5.33 (m, 1H), 2.96-2.81 (m, 2H), 2.48-2.42 (m, 1H), 1.85-1.81 (m, 1H).

General Procedure A:

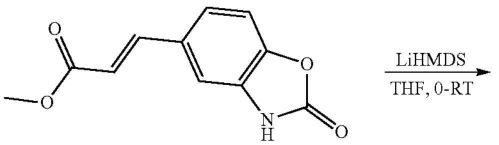

-continued

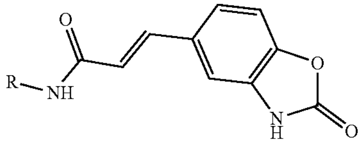

To each vial was added methyl (E)-3-(2-oxo-2,3-dihydrobenzo[d]oxazol-5-yl)acrylate (Example 11, Step 2, 30 mg, 0.14 mmol, 1.0 equiv) in THF (2 mL). The amine (0.18 mmol, 1.30 equiv) was added and the reaction mixture was cooled to 0° C. Then 1M LiHMDS (0.68 mL, 0.68 mmol, 5.0 equiv) was added. The reaction mixture was stirred for 1 h at 25° C. The reaction mixture was quenched by water and extracted with EtOAc, the organic was concentrated under vacuum to afford crude product which was then purified by Prep-HPLC. The collected fraction was lyophilized to get the final compounds.

Example 12: (E)-3-(2-oxo-2,3-dihydrobenzo[d]oxazol-5-yl)-N-(o-tolyl)acrylamide

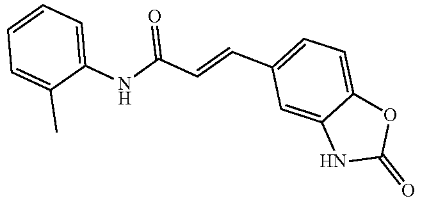 [SMILES: Cc1ccccc1NC(=O)/C=C/c1ccc2oc(=O)[nH]c2c1]

Synthesised using general procedure A using 2-methyl aniline and (E)-3-(2-oxo-2,3-dihydrobenzo[d]oxazol-5-yl) acrylate to give (E)-3-(2-oxo-2,3-dihydrobenzo[d]oxazol-5-yl)-N-(o-tolyl)acrylamide as a solid. LC-MS (ES, m/z): 295 $[M+H]^+$ $^1H$ NMR: (300 MHz, DMSO-d6, ppm): δ 9.40 (brs, 1H), 7.63-7.57 (m, 2H), 7.38-7.32 (m, 3H), 7.25-6.91 (m, 4H), 2.26 (s, 3H).

Example 13: (E)-N-(2-isopropylphenyl)-3-(2-oxo-2,3-dihydrobenzo[d]oxazol-5-yl) acrylamide

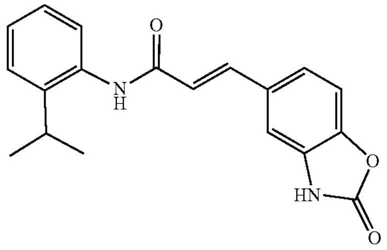 [SMILES: CC(C)c1ccccc1NC(=O)/C=C/c1ccc2oc(=O)[nH]c2c1]

Synthesised using general procedure A using 2-isopropyl aniline and (E)-3-(2-oxo-2,3-dihydrobenzo[d]oxazol-5-yl) acrylate to give (E)-N-(2-isopropylphenyl)-3-(2-oxo-2,3-dihydrobenzo[d]oxazol-5-yl)acrylamide as a solid. LC-MS (ES, m/z): $323[M+H]^+$ $^1H$ NMR (300 MHz, DMSO-$d_6$, ppm): δ 11.83 (brs, 1H), 9.48 (brs, 1H), 7.59 (d, J=15.6 Hz, 1H), 7.40-7.34 (m, 5H), 7.24-7.18 (m, 2H), 6.93 (d, J=15.3 Hz, 1H), 3.23-0.319 (m, 1H), 1.17 (d, J=6.6 Hz, 6H)

Example 14: (E)-N-(2-isopropyl-6-methylphenyl)-3-(2-oxo-2,3-dihydrobenzo[d]oxazol-5-yl) acrylamide

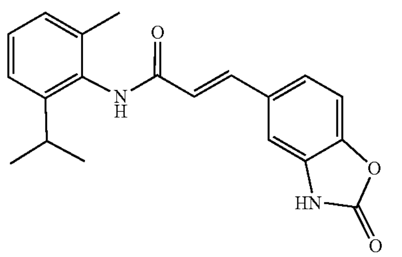 [SMILES: Cc1cccc(C(C)C)c1NC(=O)/C=C/c1ccc2oc(=O)[nH]c2c1]

Synthesised using general procedure A using 2-isopropyl-6-methyl aniline and (E)-3-(2-oxo-2,3-dihydrobenzo[d]oxazol-5-yl)acrylate to give (E)-N-(2-isopropyl-6-methylphenyl)-3-(2-oxo-2,3-dihydrobenzo[d]oxazol-5-yl)acrylamide as a solid. LC-MS (ES, m/z): 337[M+H]$^+$ $^1$H NMR (300 MHz, DMSO-$d_6$, ppm): δ 11.82 (brs, 1H), 9.43 (brs, 1H), 7.57 (d, J=15.6 Hz, 1H), 7.40-7.33 (m, 3H), 7.27-7.09 (m, 3H), 6.85 (d, J=15.6 Hz, 1H), 3.15-.3.06 (m, 1H), 2.18 (s, 3H), 1.173 (d, J=6.9 Hz, 6H)

Example 15: (E)-N-(5-chloro-2-isopropylphenyl)-3-(2-oxo-2,3-dihydrobenzo[d]oxazol-5-yl) acrylamide

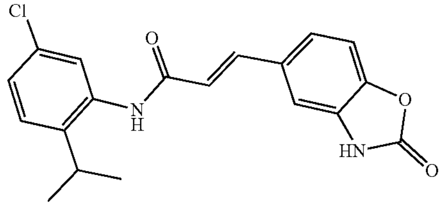 [SMILES: CC(C)c1ccc(Cl)cc1NC(=O)/C=C/c1ccc2oc(=O)[nH]c2c1]

Synthesised using general procedure A using 5-chloro-2-isopropyl aniline and (E)-3-(2-oxo-2,3-dihydrobenzo[d]oxazol-5-yl)acrylate to give (E)-N-(5-chloro-2-isopropylphenyl)-3-(2-oxo-2,3-dihydrobenzo[d]oxazol-5-yl) acrylamide as a solid. LC-MS (ES, m/z): 357[M+H]$^+$ $^1$H NMR (300 MHz, DMSO-$d_6$, ppm): δ 11.79 (brs, 1H), 9.56 (brs, 1H), 7.64-7.58 (m, 2H), 7.37-7.23 (m, 5H), 6.95 (d, J=15.6 Hz, 1H), 3.25-.3.20 (m, 1H), 1.16 (d, J=6.9 Hz, 6H).

Example 16: (E)-N-(4,5-difluoro-2-methylphenyl)-3-(2-oxo-2,3-dihydrobenzo[d]oxazol-5-yl) acrylamide

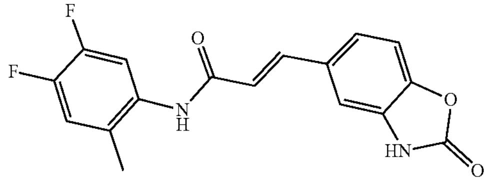 [SMILES: Cc1cc(F)c(F)cc1NC(=O)/C=C/c1ccc2oc(=O)[nH]c2c1]

Synthesised using general procedure A using 4,5-difluoro-2-methyl aniline and (E)-3-(2-oxo-2,3-dihydrobenzo[d]oxazol-5-yl)acrylate to give (E)-N-(4,5-difluoro-2-methylphenyl)-3-(2-oxo-2,3-dihydrobenzo[d]oxazol-5-yl)acrylamide as a solid. LC-MS (ES, m/z): 331[M+H]$^+$, 373 [M+$CH_3CN$]$^+$.

Example 17: (E)-N-(5-fluoro-2-methylphenyl)-3-(2-oxo-2,3-dihydrobenzo[d]oxazol-5-yl) acrylamide

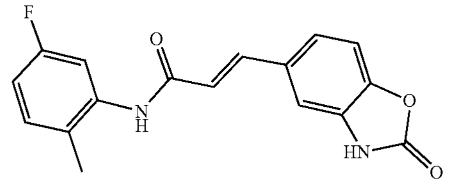 [SMILES: Cc1ccc(F)cc1NC(=O)/C=C/c1ccc2oc(=O)[nH]c2c1]

Synthesised using general procedure A using 5-fluoro-2-methyl aniline and (E)-3-(2-oxo-2,3-dihydrobenzo[d]oxazol-5-yl)acrylate to give (E)-N-(5-fluoro-2-methylphenyl)-3-(2-oxo-2,3-dihydrobenzo[d]oxazol-5-yl)acrylamide as a solid. LC-MS (ES, m/z): 311[M+H]$^+$ Example 18: (E)-N-(3-fluoro-2-methylphenyl)-3-(4-fluoro-2-oxoindolin-6-yl)acrylamide

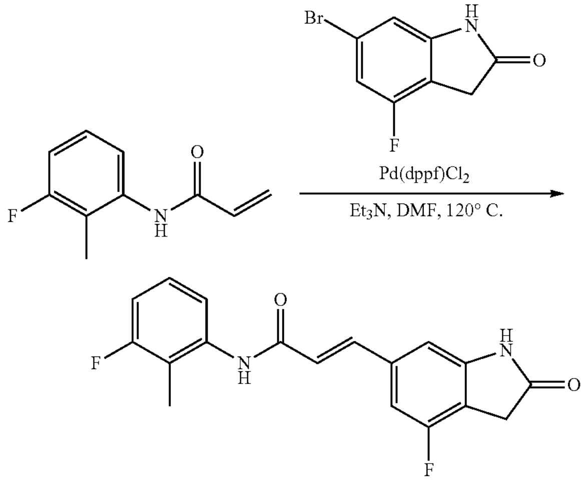

Into a 8-mL sealed tube purged and maintained with an inert atmosphere of nitrogen, was placed N-(3-fluoro-2-methylphenyl)acrylamide (60.0 mg, 0.34 mmol, 1.0 eq), 6-bromo-4-fluoroindolin-2-one (78 mg, 0.34 mmol, 1.0 eq), $Et_3N$ (0.14 mL, 1.0 mmol, 3.0 eq), DMF (4.0 mL), Pd(dppf)$Cl_2$ (25.2 mg, 0.034 mmol, 0.10 eq). The resulting solution was stirred for 2 h at 120° C. The crude mixture was purified by Flash-Prep-HPLC. This resulted in 11.8 mg (11%) of (E)-N-(3-fluoro-2-methylphenyl)-3-(4-fluoro-2-oxoindolin-6-yl)acrylamide as an off-white solid.

LC-MS (ES, m/z): [M+H]$^+$=329

$^1$H NMR (300 MHz, DMSO-$d_6$, ppm): δ 10.80 (brs, 1H), 9.66 (s, 1H), 7.55 (d, J=15.9 Hz, 1H), 7.47 (d, J=8.4 Hz, 1H), 7.24-7.22 (m, 1H), 7.10-6.93 (m, 4H), 3.60 (s, 2H), 2.15 (s, 3H)

Example 19: (E)-N-(2,6-dimethylphenyl)-3-(2-oxoindolin-6-yl)acrylamide

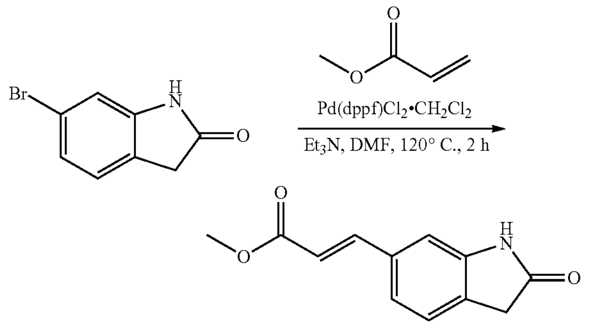

Step 1: Into a 500-mL 3-necked round-bottom flask purged and maintained with an inert atmosphere of nitrogen, was placed 6-bromo-1,3-dihydroindol-2-one (20.0 g, 94.32 mmol, 1.0 equiv), DMF (350 mL), methyl acrylate (6.50 g, 75.50 mmol, 0.80 equiv), $Et_3N$ (26.3 mL, 188.64 mmol, 2.0 equiv), $Pd(dppf)Cl_2 \cdot CH_2Cl_2$ (0.77 g, 0.94 mmol, 0.01 equiv). The resulting solution was stirred for 2 hr at 120° C. The reaction mixture was cooled to RT. The mixture was applied onto a silica gel column with THF/PE (2/1). This resulted in 7.4 g (36%) of methyl (2E)-3-(2-oxo-1,3-dihydroindol-6-yl)prop-2-enoate as a light yellow solid.

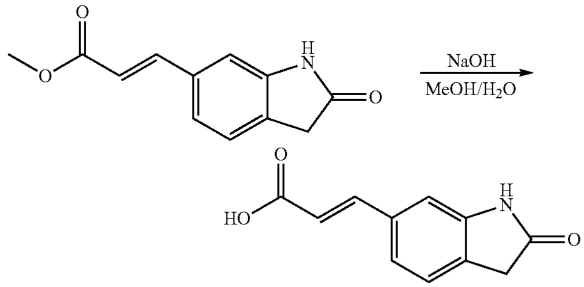

Step 2: Into a 250-mL round-bottom flask, was placed methyl (2E)-3-(2-oxo-1,3-dihydroindol-6-yl)prop-2-enoate (3.0 g, 13.81 mmol, 1.0 equiv), MeOH/$H_2O$(80/40 mL), NaOH (1.7 g, 41.43 mmol, 3.0 equiv). The resulting solution was stirred for 12 h at 25° C. The resulting mixture was concentrated. The resulting solution was diluted with 40 mL of water. The resulting solution was extracted with 2×50 mL of DCM. The pH value of the aqueous phase was adjusted to 5 with 2M HCl. The solids were collected by filtration. This resulted in 1.8 g (64%) of (2E)-3-(2-oxo-1,3-dihydroindol-6-yl)prop-2-enoic acid as a light yellow solid.

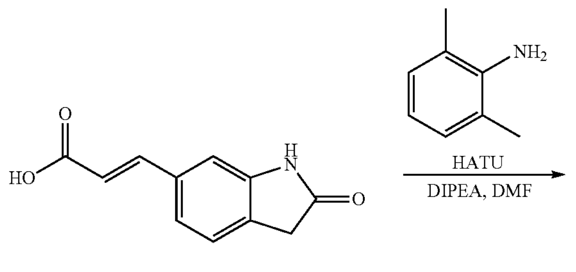

-continued

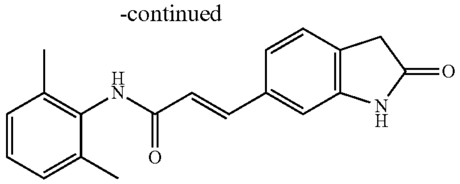

Step 3: Into a 8-mL vial purged and maintained with an inert atmosphere of nitrogen was added (E)-3-(2-oxoindolin-6-yl)acrylic acid (60.0 mg, 0.30 mmol, 1.0 equiv) in DMF (4.0 mL). Then HATU (167.6 mg, 0.44 mmol, 1.50 equiv) and DIPEA (56.8 mg, 0.44 mmol, 1.50 equiv), 2,6-dimethylbenzenamine (39.5 mg, 0.33 mmol, 1.10 equiv) were added. The reaction mixture was stirred for 2 h at room temperature. The crude mixture was then purified by Prep-HPLC. This resulted in 12 mg (13%) of (E)-N-(2,6-dimethylphenyl)-3-(2-oxoindolin-6-yl)acrylamide as a white solid. LC-MS (ES, m/z): $[M+H]^+$=307

$^1$HNMR (300 MHz, DMSO-$d_6$, ppm) δ 10.53 (brs, 1H), 9.47 (brs, 1H), 7.51 (d, J=15.9 Hz, 1H), 7.29-7.18 (m, 2H), 7.10-7.05 (m, 4H), 6.83 (d, J=15.9 Hz, 1H), 3.52 (s, 2H), 2.18 (s, 6H).

Example 20: (E)-N-(3-fluoro-2,6-dimethylphenyl)-3-(2-oxoindolin-6-yl)acrylamide

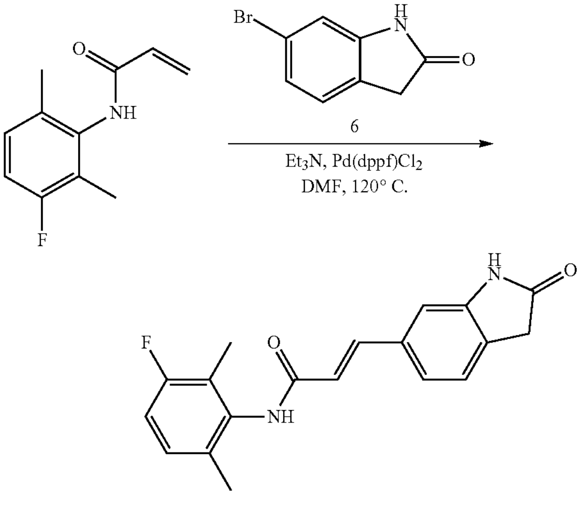

Into a 8-mL round-bottom flask, was placed 6-bromoindolin-2-one (100 mg, 0.47 mmol, 1.0 equiv), N-(3-fluoro-2,6-dimethylphenyl)prop-2-enamide (Prepared according to the procedure described for Intermediate 1 from 2,6-dimethyl-3-fluoroaniline and acryloyl chloride; 90.7 mg, 0.47 mmol, 1.0 equiv), $Pd(dppf)Cl_2$ (34.4 mg, 0.047 mmol, 0.10 equiv), $Et_3N$ (0.2 mL, 1.41 mmol, 3.0 equiv), DMF (4.0 mL). The resulting solution was stirred for 2 hr at 120° C. in an oil bath. The mixture was applied onto a silica gel column with PE/THF (1/1). This resulted in 11 mg (7%) of (E)-N-(3-fluoro-2,6-dimethylphenyl)-3-(2-oxoindolin-6-yl) acrylamide as a solid.

LC-MS (ES, m/z): $[M+H]^+$=325

$^1$H NMR (300 MHz, DMSO-$d_6$, ppm): δ 10.55 (s, 1H), 9.63 (s, 1H), 7.55 (d, J=15.6 Hz, 1H), 7.29-7.03 (m, 5H), 6.84 (d, J=15.9 Hz, 1H), 3.53 (s, 2H), 2.14 (s, 3H), 2.07 (s, 3H).

Example 21: (E)-N-(2-methyl-2,3-dihydro-1H-inden-1-yl)-3-(2-oxoindolin-6-yl)acrylamide

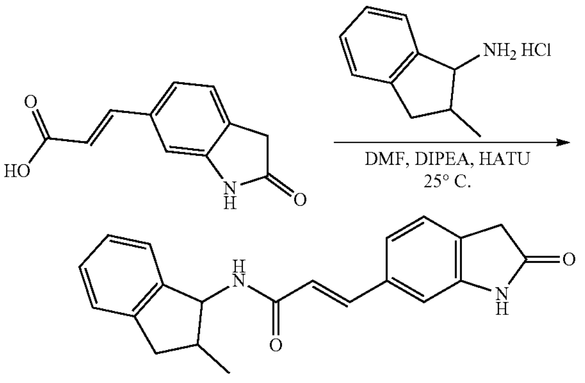

Into a 8-mL vial, was placed (E)-3-(2-oxoindolin-6-yl) acrylic acid (50.0 mg, 0.25 mmol, 1.0 equiv), 2-methyl-2,3-dihydro-1H-inden-1-amine hydrochloride (45.20 mg, 0.25 mmol, 1.0 equiv), HATU (141.38 mg, 0.37 mmol, 1.50 equiv) and DIPEA (95.41 mg, 0.74 mmol, 3.0 equiv) in DMF (2.0 mL). The resulting solution was stirred for 2 h at 20° C. The mixture was purified by Flash-Prep-HPLC. This resulted in 27 mg (33%) of ((E)-N-(2-methyl-2,3-dihydro-1H-inden-1-yl)-3-(2-oxoindolin-6-yl)acrylamide as an off-white solid. LC-MS (ES, m/z): $[M+H]^+=333$ $^1H$ NMR (300 MHz, DMSO-$d_6$, ppm) δ 10.51 (brs, 1H), 8.45-8.20 (m, 1H), 7.50-7.45 (m, 1H), 7.26-7.13 (m, 6H), 7.05-6.96 (m, 1H), 6.68-6.63 (m, 1H), 5.45-5.0 (m, 1H), 3.51 (s, 2H), 3.10-3.0 (m, 1H), 2.70-2.20 (m, 2H), 1.20-0.90 (m, 3H).

Example 22: (E)-3-(1-ethyl-2-oxo-2,3-dihydro-1H-benzo[d]imidazol-5-yl)-N-(3-fluoro-2-methylphenyl) acrylamide

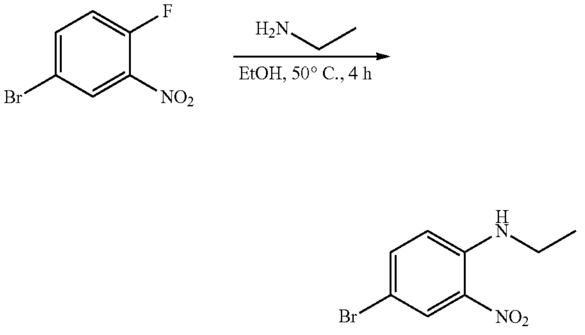

Step 1: Into a 100-mL sealed tube, was placed 4-bromo-1-fluoro-2-nitrobenzene (2.0 g, 9.09 mmol, 1.0 eq), EtOH (8.0 mL, 1.0 eq), ethylamine (22.73 mL, 45.45 mmol, 5.0 eq, 2 M in ethanol). The resulting solution was stirred for 4 h at 50° C. The resulting mixture was concentrated. The residue was diluted with 15 mL of $H_2O$ and stirred 15 min. The solids were collected by filtration. This resulted in 2.2 g (98%) of 4-bromo-N-ethyl-2-nitroaniline as a red solid. LC-MS (ES, m/z): $[M+H]^+=245$

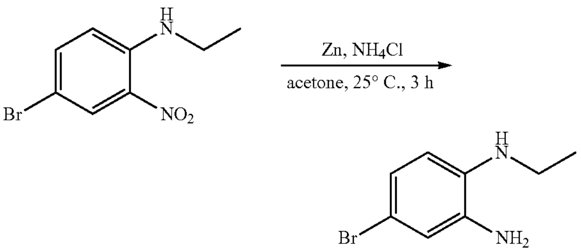

Step 2: Into a 50-mL round-bottom flask, was placed 4-bromo-N-ethyl-2-nitroaniline (2.0 g, 8.16 mmol, 1.0 eq), acetone (16.0 mL), $H_2O$(2.0 mL), $NH_4Cl$ (4.37 g, 81.61 mmol, 10.0 eq), Zn (2.67 g, 40.80 mmol, 5.0 eq). The resulting solution was stirred for 3 h at room temperature. The solids were filtered out. The filtrate was concentrated. The residue was diluted with 20 mL of $H_2O$ and stirred 15 min. The solids were collected by filtration. This resulted in 1.1 g (63%) of 4-bromo-$N^1$-ethylbenzene-1,2-diamine as a light yellow solid. LC-MS (ES, m/z): $[M+H]^+=215$

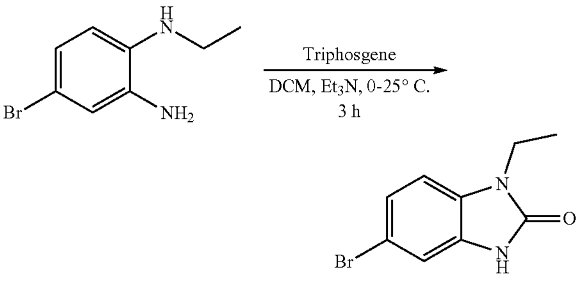

Step 3: Into a 50-mL 3-necked round-bottom flask purged and maintained with an inert atmosphere of nitrogen, was placed 4-bromo-$N^1$-ethylbenzene-1,2-diamine (400.0 mg, 1.86 mmol, 1.0 eq), DCM (8.0 mL), Triphosgene (441.5 mg, 1.48 mmol, 0.80 eq). This was followed by the addition of $Et_3N$ (0.8 mL, 5.58 mmol, 3.0 eq) at 0° C. The resulting solution was stirred for 3 h at room temperature. The reaction was then quenched by the addition of 5 mL of water. The organic phase was separated and dried over anhydrous sodium sulfate and concentrated. The residue was applied onto a silica gel column with (THF/PE=18/82). This resulted in 210 mg (47%) of 5-bromo-1-ethyl-3H-1,3-benzodiazol-2-one as a light brown solid.

LC-MS (ES, m/z): $[M+H]^+=240$

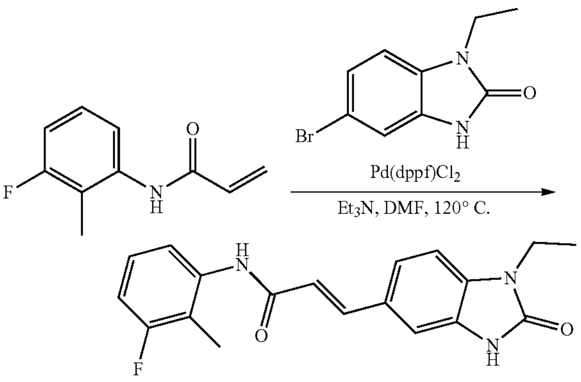

Step 4: Into a 8-mL sealed tube purged and maintained with an inert atmosphere of nitrogen, was placed N-(3-fluoro-2-methylphenyl)acrylamide (120.0 mg, 0.67 mmol, 1.0 eq), 5-bromo-1-ethyl-3H-1,3-benzodiazol-2-one (161.5 mg, 0.67 mmol, 1.0 eq), $Et_3N$ (0.28 mL, 2.01 mmol, 3.0 eq), DMF (5.0 mL), $Pd(dppf)Cl_2$ (9.8 mg, 0.01 mmol, 0.02 eq). The resulting solution was stirred for 2 h at 120° C. The crude mixture was purified by Flash-Prep-HPLC. This resulted in 25 mg (11%) of (E)-3-(1-ethyl-2-oxo-2,3-dihydro-1H-benzo[d]imidazol-5-yl)-N-(3-fluoro-2-methylphenyl)acrylamide as an off-white solid. LC-MS (ES, m/z): $[M+H]^+$=340

$^1H$ NMR (300 MHz, DMSO-$d_6$, ppm): δ 11.05 (brs, 1H), 9.52 (s, 1H), 7.62-7.48 (m, 2H), 7.33-7.19 (m, 4H), 7.11-6.85 (m, 2H), 3.88-3.81 (m, 2H), 2.27 (s, 3H), 1.31-1.19 (m, 3H).

Example 23: (E)-3-(1-cyclopropyl-2-oxo-2,3-dihydro-1H-benzo[d]imidazol-5-yl)-N-(3-fluoro-2-methylphenyl)acrylamide

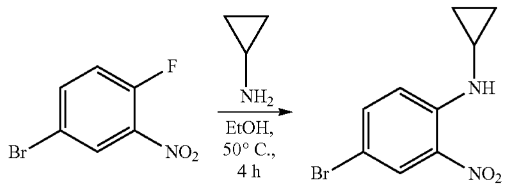

Step 1: Into a 40-mL sealed tube, was placed 4-bromo-1-fluoro-2-nitrobenzene (2.0 g, 9.09 mmol, 1.0 eq), aminocyclopropane (2.60 g, 45.45 mmol, 5.0 eq), EtOH (20.0 mL). The resulting solution was stirred for 4 h at 50° C. The resulting mixture was concentrated. The residue compound was diluted with 15 mL of $H_2O$ and stirred 15 min. The solids were collected by filtration. The solid was dried in an oven under reduced pressure. This resulted in 2.4 g (96%) of 4-bromo-N-cyclopropyl-2-nitroaniline as a red solid. LC-MS (ES, m/z): $[M+H]^+$=257

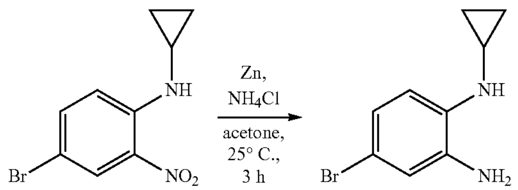 [SMILES: O=[N+]([O-])c1cc(Br)ccc1NC1CC1 ; Nc1cc(Br)ccc1NC1CC1]

Step 2: Into a 40-mL sealed tube, was placed 4-bromo-N-cyclopropyl-2-nitroaniline (2.0 g, 7.8 mmol, 1.0 eq), acetone (16.0 mL), $H_2O$(2.0 mL), Zn (2.54 g, 38.89 mmol, 5.0 eq), $NH_4Cl$ (4.16 g, 77.8 mmol, 10.0 eq). The resulting solution was stirred for 3 h at 25° C. The solids were filtered out. The filtrate was concentrated. The residue was diluted with 20 mL of $H_2O$ and stirred 15 min. The solids were collected by filtration. This resulted in 1 g (56%) of 4-bromo-$N^1$-cyclopropylbenzene-1,2-diamine as a light brown solid.

LC-MS (ES, m/z): $[M+H]^+$=227

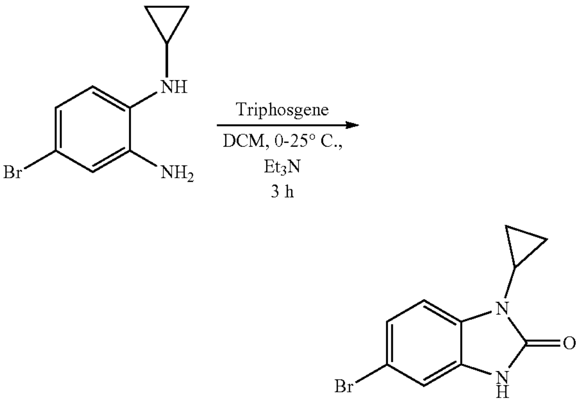

Step 3: Into a 50-mL 3-necked round-bottom flask purged and maintained with an inert atmosphere of nitrogen, was placed 4-bromo-$N^1$-cyclopropylbenzene-1,2-diamine (300.0 mg, 1.32 mmol, 1.0 eq), Triphosgene (313.60 mg, 1.06 mmol, 0.80 eq), DCM (6.0 mL). This was followed by the addition of $Et_3N$ (0.6 mL, 3.96 mmol, 3.0 eq) at 0° C. The resulting solution was stirred for 3 h at room temperature. The reaction was then quenched by the addition of 5 mL of water. The organic phase was separated and dried over anhydrous sodium sulfate and concentrated. This resulted in 180 mg (53%) of 5-bromo-1-cyclopropyl-3H-1,3-benzodiazol-2-one as a light brown solid. LC-MS (ES, m/z): $[M+H]^+$=253

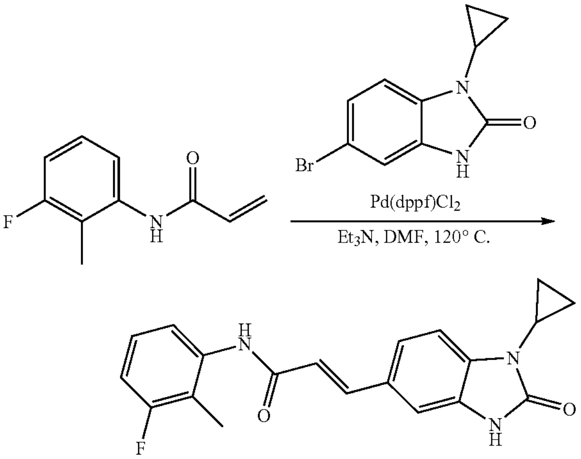

Step 4: Into a 8-mL sealed tube purged and maintained with an inert atmosphere of nitrogen, was placed N-(3-fluoro-2-methylphenyl)acrylamide (120.0 mg, 0.67 mmol, 1.0 eq), 5-bromo-1-cyclopropyl-3H-1,3-benzodiazol-2-one (169.5 mg, 0.67 mmol, 1.0 eq), $Et_3N$ (0.2 mL, 1.34 mmol, 2.0 eq), DMF (5.0 mL), $Pd(dppf)Cl_2$ (9.80 mg, 0.013 mmol, 0.02 equiv). The resulting solution was stirred for 2 h at 120° C. The solids were filtered out. The crude mixture was purified by Flash-Prep-HPLC. This resulted in 21 mg (9%) of (E)-3-(1-cyclopropyl-2-oxo-2,3-dihydro-1H-benzo[d]imidazol-5-yl)-N-(3-fluoro-2-methylphenyl)acrylamide as an off-white solid.

LC-MS (ES, m/z): $[M+H]^+$=352

$^1$H-NMR (300 MHz, DMSO-$d_6$, ppm): δ 10.96 (brs, 1H), 9.54 (brs, 1H), 7.61-7.47 (m, 2H), 7.33-7.18 (m, 4H), 7.02-6.85 (m, 2H), 2.95-2.87 (m, 1H), 2.28 (s, 3H), 1.04-0.88 (m, 4H).

Example 24: (E)-N-(2,3-dihydro-1H-inden-1-yl)-3-(1-methyl-2-oxo-2,3-dihydro-1H-benzo[d]imidazol-5-yl)acrylamide

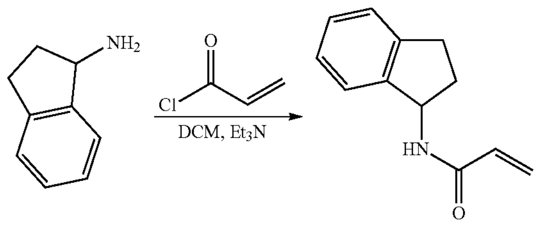

Step 1: Into a 500-mL 3-necked round-bottom flask, acryloyl chloride (6.80 g, 75.08 mmol, 1.0 equiv), was added to indanamine (10.0 g, 75.08 mmol, 1.0 equiv) and $Et_3N$ (20.9 mL, 150.16 mmol, 2.0 equiv) in DCM (200.0 mL) at 0° C. The resulting solution was stirred for 15 h at 25° C. The reaction was then quenched by the addition of 100 mL of water/ice. The resulting solution was extracted with 2×100 mL of dichloromethane and the organic layer was dried over anhydrous sodium sulfate and concentrated. The residue was applied onto a silica gel column with EtOAc/PE (10/1, resulting in 7.3 g (52%) of N-(2,3-dihydro-1H-inden-1-yl)prop-2-enamide as a white solid. LC-MS (ES, m/z): $[M+H]^+$=188

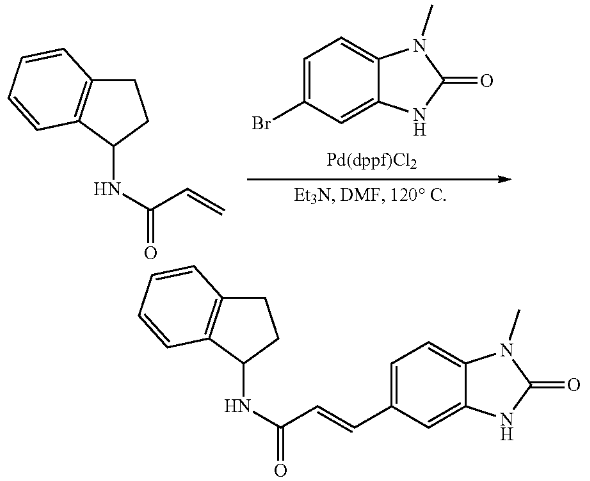

Into a 8-mL vial, was placed N-(2,3-dihydro-1H-inden-1-yl)prop-2-enamide (100.0 mg, 0.53 mmol, 1.0 equiv), 5-bromo-1-methyl-3H-1,3-benzodiazol-2-one (121.27 mg, 0.53 mmol, 1.0 equiv), $Pd(dppf)Cl_2$ (39.08 mg, 0.05 mmol, 0.10 equiv) and $Et_3N$ (0.22 mL, 1.60 mmol, 3.0 equiv) in DMF (4.0 mL, 25.844 mmol). The resulting solution was stirred for 15 h at 120° C. in an oil bath. The reaction mixture was cooled. The crude mixture was purified by Flash-Prep-HPLC. This resulted in 7.8 mg (4%) of (E)-N-(2,3-dihydro-1H-inden-1-yl)-3-(1-methyl-2-oxo-2,3-dihydro-1H-benzo[d]imidazol-5-yl)acrylamide as a white solid. LC-MS (ES, m/z): $[M+H]^+$=334

$^1$H-NMR (300 MHz, DMSO-$d_6$, ppm): δ 10.98 (brs, 1H), 8.37 (d, J=8.4 Hz, 1H), 7.50 (d, J=15.9 Hz, 1H), 7.34-7.03 (m, 7H), 6.56 (d, J=15.6 Hz, 1H), 5.42-5.39 (m, 1H), 3.29 (s, 3H), 3.02-2.77 (m, 2H), 2.47-2.37 (m, 1H), 1.93-1.72 (m, 1H).

Example 25: (E)-N-(2,3-dihydro-1H-inden-1-yl)-3-(3-methyl-1H-indazol-6-yl)acrylamide

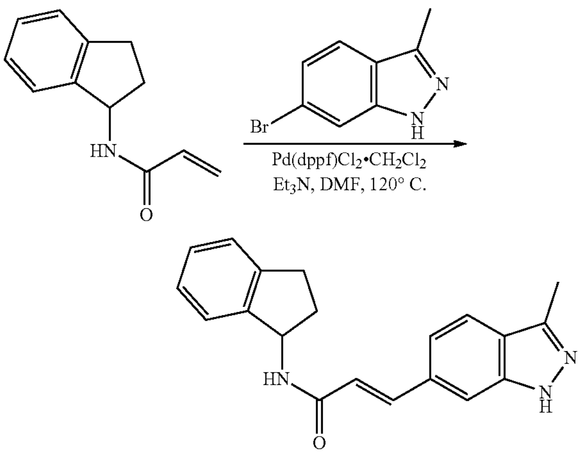

Into a 8-mL sealed tube purged and maintained with an inert atmosphere of nitrogen, was placed N-(2,3-dihydro-1H-inden-1-yl)prop-2-enamide (Example 24, Step 1, 100.0 mg, 0.53 mmol, 1.0 equiv), 6-bromo-3-methyl-1H-indazole (135.27 mg, 0.64 mmol, 1.20 equiv), $Pd(dppf)Cl_2·CH_2Cl_2$ (87.23 mg, 0.11 mmol, 0.20 equiv), DMF (4.0 mL), $Et_3N$ (0.22 mL, 1.60 mmol, 3.0 equiv). The resulting solution was stirred overnight at 120° C. The reaction mixture was cooled to room temperature. The crude mixture was purified by Prep-HPLC. This resulted in 64 mg (38%) of (E)-N-(2,3-dihydro-1H-inden-1-yl)-3-(3-methyl-1H-indazol-6-yl)acrylamide as a off-white solid. LC-MS (ES, m/z): $[M+H]^+$=318

$^1$H NMR (300 MHz, DMSO-$d_6$, ppm): δ 12.77 (brs, 1H), 8.46 (d, J=8.4 Hz, 1H), 7.73-7.60 (m, 3H), 7.31-7.17 (m, 5H), 6.74 (d, J=15.9 Hz, 1H), 5.46-5.38 (m, 1H), 3.02-2.93 (m, 1H), 2.89-2.79 (m, 1H), 2.51 (s, 3H), 2.48-2.41 (m, 1H), 1.90-1.77 (m, 1H).

Example 26: (E)-3-(3-cyano-1H-indazol-6-yl)-N-(2,3-dihydro-1H-inden-1-yl)acrylamide

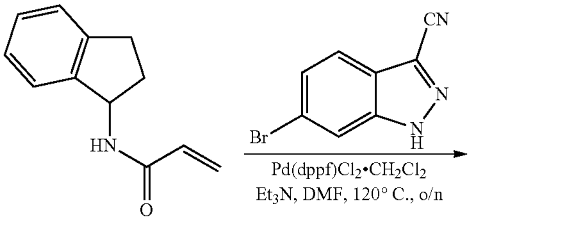

-continued

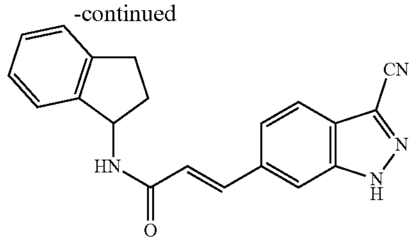

Into a 8-mL sealed tube purged and maintained with an inert atmosphere of nitrogen, was placed N-(2,3-dihydro-1H-inden-1-yl)prop-2-enamide (Example 24, Step 1, 100.0 mg, 0.53 mmol, 1.0 equiv), 6-bromo-1H-indazole-3-carbonitrile (142.30 mg, 0.64 mmol, 1.20 equiv), Pd(dppf)$Cl_2 \cdot CH_2Cl_2$ (43.61 mg, 0.05 mmol, 0.10 equiv), DMF (4 mL), $Et_3N$ (0.22 mL, 1.60 mmol, 3.0 equiv). The resulting solution was stirred overnight at 120° C. The reaction mixture was cooled to room temperature. The crude mixture was purified by Prep-HPLC. This resulted in 24 mg (14%) of (E)-3-(3-cyano-1H-indazol-6-yl)-N-(2,3-dihydro-1H-inden-1-yl)acrylamide as an off-white solid. LC-MS (ES, m/z): $[M+H]^+$=329

$^1$H-NMR (300 MHz, DMSO-$d_6$, ppm): δ 14.33 (brs, 1H), 8.55 (d, J=8.1 Hz, 1H), 7.93-7.91 (m, 2H), 7.70 (d, J=15.9 Hz, 1H), 7.62-7.59 (m, 1H), 7.30-7.17 (m, 4H), 6.84 (d, J=15.6 Hz, 1H), 5.47-5.39 (m, 1H), 3.03-2.94 (m, 1H), 2.90-2.80 (m, 1H), 2.47-2.42 (m, 1H), 1.91-1.76 (m, 1H).

Example 27: (E)-N-(2,3-dihydro-1H-inden-1-yl)-3-(5-fluoro-1H-benzo[d][1,2,3]triazol-6-yl) acrylamide

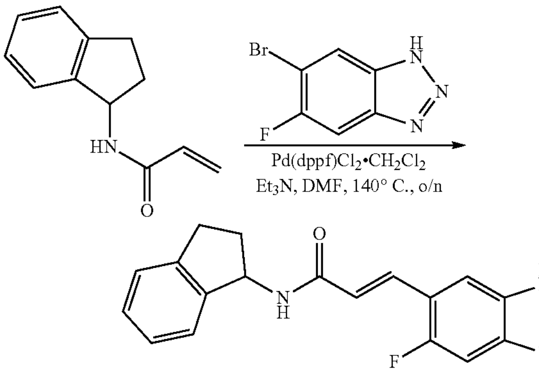

Into a 8-mL sealed tube purged and maintained with an inert atmosphere of nitrogen, was placed N-(2,3-dihydro-1H-inden-1-yl)prop-2-enamide (Example 24, Step 1, 100.0 mg, 0.53 mmol, 1.0 equiv), 5-bromo-6-fluoro-3H-1,2,3-benzotriazole (138.44 mg, 0.64 mmol, 1.20 equiv), Pd(dppf)$Cl_2 \cdot CH_2Cl_2$ (43.61 mg, 0.05 mmol, 0.10 equiv), DMF (4.0 mL), $Et_3N$ (0.22 mL, 1.60 mmol, 3.0 equiv). The resulting solution was stirred overnight at 140° C. The reaction mixture was cooled to room temperature. The crude mixture was purified by Prep-HPLC. This resulted in 6.3 mg (4%) of (E)-N-(2,3-dihydro-1H-inden-1-yl)-3-(5-fluoro-1H-benzo [d][1,2,3]triazol-6-yl) acrylamide as a off-white solid. LC-MS (ES, m/z): $[M+H]^+$=323

$^1$H NMR (300 MHz, DMSO-$d_6$, ppm): δ 8.63 (d, J=8.1 Hz, 1H), 8.27 (d, J=6.6 Hz, 1H), 7.82 (d, J=10.8 Hz, 1H), 7.68 (d, J=16.2 Hz, 1H), 7.29-7.18 (m, 4H), 6.88 (d, J=15.9 Hz, 1H), 5.47-5.40 (m, 1H), 3.01-2.94 (m, 1H), 2.90-2.79 (m, 1H), 2.49-2.44 (m, 1H), 1.92-1.79 (m, 1H).

Example 28: (E)-N-(2,3-dihydro-1H-inden-1-yl)-3-(3-(trifluoromethyl)-1H-indazol-6-yl) acrylamide

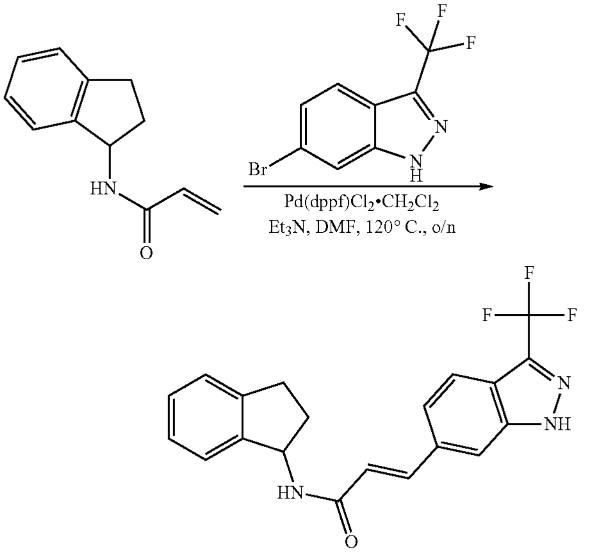

Into a 8-mL sealed tube purged and maintained with an inert atmosphere of nitrogen, was placed N-(2,3-dihydro-1H-inden-1-yl)prop-2-enamide (Example 24, Step 1, 100.0 mg, 0.53 mmol, 1.0 equiv), 6-bromo-3-(trifluoromethyl)-1H-indazole (169.9 mg, 0.64 mmol, 1.20 equiv), Pd(dppf)$Cl_2 \cdot CH_2Cl_2$ (43.61 mg, 0.05 mmol, 0.10 equiv), DMF (4.0 mL), $Et_3N$ (0.22 mL, 1.60 mmol, 3.0 equiv). The resulting solution was stirred overnight at 120° C. The reaction mixture was cooled to room temperature. The crude mixture was purified by Prep-HPLC. This resulted in 80 mg (40%) of (E)-N-(2,3-dihydro-1H-inden-1-yl)-3-(3-(trifluoromethyl)-1H-indazol-6-yl) acrylamide as an off-white solid. LC-MS (ES, m/z): $[M+H]^+$=372

$^1$H NMR (300 MHz, DMSO-$d_6$, ppm): δ 14.16 (brs, 1H), 8.55 (d, J=8.1 Hz, 1H), 7.89-7.83 (m, 2H), 7.70 (d, J=15.9 Hz, 1H), 7.58-7.54 (m, 1H), 7.30-7.17 (m, 4H), 6.83 (d, J=15.6 Hz, 1H), 5.47-5.39 (m, 1H), 3.03-2.94 (m, 1H), 2.90-2.80 (m, 1H), 2.47-2.42 (m, 1H), 1.91-1.78 (m, 1H).

Example 29: (E)-N-(2,6-dimethylphenyl)-3-(1-methyl-2-oxo-2,3-dihydro-1H-benzo[d]imidazol-5-yl)acrylamide

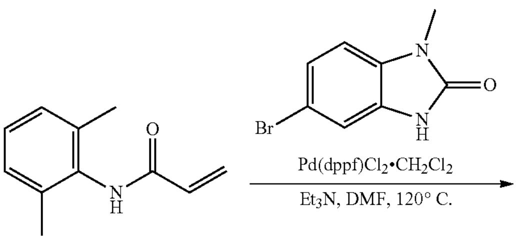

-continued

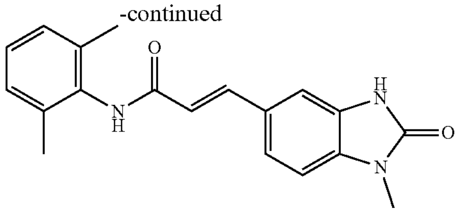

Into a 8-mL vial purged and maintained with an inert atmosphere of nitrogen, was placed N-(2,6-dimethylphenyl) prop-2-enamide ((Prepared as for Intermediate 1 from acroyl chloride and 2,6-dimethylaniline) 50.0 mg, 0.29 mmol, 1.0 equiv), DMF (4.0 mL), 5-bromo-1-methyl-3H-1,3-benzodiazol-2-one (71.3 mg, 0.31 mmol, 1.10 equiv), $Et_3N$ (0.12 mL, 0.86 mmol, 3.0 equiv), $Pd(dppf)Cl_2 \cdot CH_2Cl_2$ (11.65 mg, 0.014 mmol, 0.05 equiv). The resulting solution was stirred for 5 h at 120° C. The reaction mixture was cooled to RT. The crude mixture was applied onto a silica gel column with EtOAc/PE (1/1). This resulted in 20 mg (22%) of (E)-N-(2,6-dimethylphenyl)-3-(1-methyl-2-oxo-2,3-dihydro-1H-benzo[d]imidazol-5-yl)acrylamide as an off-white solid.

LC-MS (ES, m/z): $[M+H]^+=322$ $^1H$ NMR (300 MHz, DMSO-$d_6$, ppm): 11.02 (s, 1H), 9.38 (s, 1H), 7.56 (d, J=15.6 Hz, 1H), 7.33-7.31 (m, 1H), 7.24 (s, 1H), 7.16-7.09 (m, 4H), 6.78 (d, J=15.6 Hz, 1H), 3.32 (s, 1H), 2.17 (s, 6H).

Example 30: (E)-N-(3-fluoro-2,6-dimethylphenyl)-3-(1-methyl-2-oxo-2,3-dihydro-1H-benzo[d]imidazol-5-yl)acrylamide

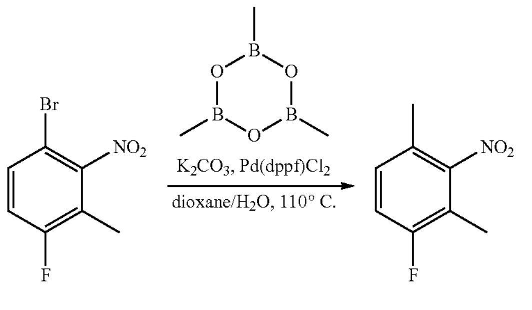

Step 1: Into a 40-mL vial, was placed 1-bromo-4-fluoro-3-methyl-2-nitrobenzene (500.0 mg, 2.14 mmol, 1.0 equiv), trimethyl-1,3,5,2,4,6-trioxatriborinane (268.20 mg, 2.13 mmol, 1.0 equiv), $K_2CO_3$ (590.6 mg, 4.27 mmol, 2.0 equiv) and $Pd(dppf)Cl_2$ (156.3 mg, 0.21 mmol, 0.10 equiv) in dioxane (10.0 mL) and $H_2O$(2.0 mL). The resulting solution was stirred for 1 h at 110° C. in an oil bath. The crude mixture was applied onto a silica gel column with EtOAc/PE (1/10). This resulted in 250 mg (69%) of 1-fluoro-2,4-dimethyl-3-nitrobenzene as a solid.

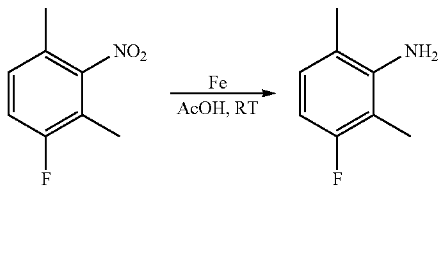

Step 2: Into a 40-mL vial, was placed 1-bromo-4-fluoro-3-methyl-2-nitrobenzene (0.50 g, 2.14 mmol, 1.0 equiv) in AcOH (10.0 mL) was added Fe (596.6 mg, 10.68 mmol, 5.0 equiv), The resulting solution was stirred for 1 h at RT. The solids were filtered out. The resulting solution was diluted with 20 mL water and extracted with 40 mL of EtOAc. The organic layer was dried and concentrated. This resulted in 250 mg (84%) of 3-fluoro-2,6-dimethylaniline as a solid.

LC-MS (ES, m/z): $[M+H]^+=140$

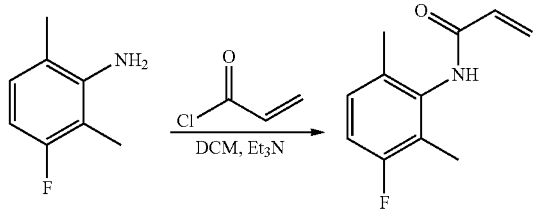

Step 3: Into a 8-mL vial, was placed 6-bromo-3-fluoro-2-methylaniline (100.0 mg, 0.49 mmol, 1.0 equiv) and $Et_3N$ (0.2 mL, 1.47 mmol, 3.0 equiv) in DCM (4 mL) was added acryloyl chloride (53.2 mg, 0.59 mmol, 1.20 equiv), The resulting solution was stirred for 1 h at 0° C. The resulting mixture was concentrated under vacuum. The residue was purified with flash chromatography (PE/EA=10/1). This resulted in 120 mg (126.72%) of N-(3-fluoro-2,6-dimethylphenyl)prop-2-enamide as a white solid. LC-MS (ES, m/z): $[M+H]^+=194$

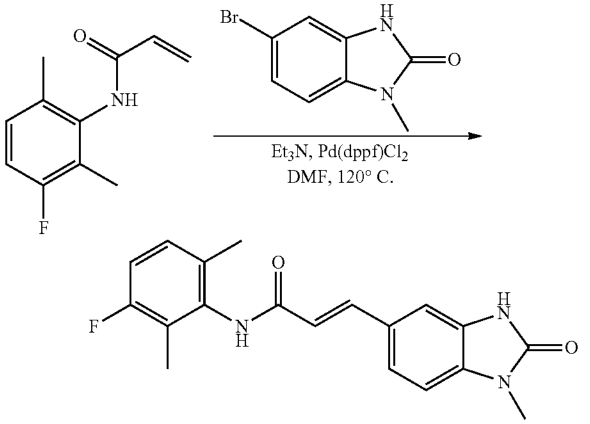

Step 4: Into a 8-mL round-bottom flask, was placed 5-bromo-1-methyl-3H-1,3-benzodiazol-2-one (100 mg, 0.44 mmol, 1.0 equiv), N-(3-fluoro-2,6-dimethylphenyl) prop-2-enamide (85.1 mg, 0.44 mmol, 1.0 equiv), $Pd(dppf)Cl_2$ (32.2 mg, 0.044 mmol, 0.10 equiv), $Et_3N$ (0.18 mL, 1.32 mmol, 3.0 equiv), DMF (4.0 mL). The resulting solution was stirred for 2 h at 120° C. in an oil bath. The mixture was applied onto a silica gel column with PE/THF (1/1). This resulted in 45 mg (30%) of (E)-N-(3-fluoro-2,6-dimethylphenyl)-3-(1-methyl-2-oxo-2,3-dihydro-1H-benzo[d]imidazol-5-yl)acrylamide as a solid. LC-MS (ES, m/z): $[M+H]^+=340$ $^1H$ NMR (300 MHz, DMSO-$d_6$, ppm): δ 11.04 (s, 1H), 9.53 (s, 1H), 7.58 (d, J=15.3 Hz, 1H), 7.33 (d, J=8.4 Hz, 1H), 7.24 (s, 1H), 7.17-7.01 (m, 3H), 6.79 (d, J=15.6 Hz, 1H), 3.31 (s, 3H), 2.15 (s, 3H), 2.07 (s, 3H).

Example 31: (E)-N-(2,6-dimethylphenyl)-3-(3-methyl-1H-indazol-6-yl)acrylamide

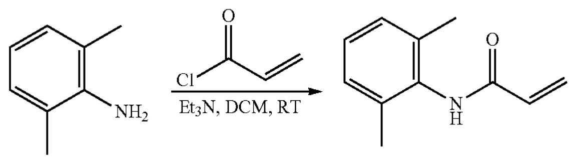

Into a 50-mL 3-necked round-bottom flask purged and maintained with an inert atmosphere of nitrogen, was placed 2,6-dimethylaniline (160.0 mg, 1.32 mmol, 1.0 equiv), DCM (10.0 mL), $Et_3N$ (0.55 mL, 3.96 mmol, 3.0 equiv). This was followed by the addition of acryloyl chloride (143.40 mg, 1.58 mmol, 1.20 equiv) dropwise with stirring at 0° C. The resulting solution was stirred for 3 h at 25° C. The reaction was then quenched by the addition of 15 mL of water. The resulting solution was extracted with 2×10 mL of dichloromethane and the organic layer was dried over anhydrous sodium sulfate and concentrated. The residue was applied onto a silica gel column with EtOAc/PE (1/3). This resulted in 150 mg (65%) of N-(2,6-dimethylphenyl)prop-2-enamide as a white solid. LC-MS (ES, m/z): $[M+H]^+=176$

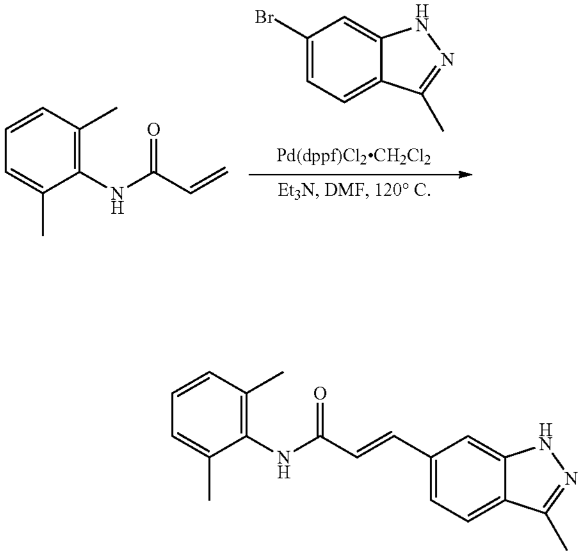

Into a 8-mL vial purged and maintained with an inert atmosphere of nitrogen, was placed N-(2,6-dimethylphenyl) prop-2-enamide (50.0 mg, 0.29 mmol, 1.0 equiv), DMF (5.0 mL), 6-bromo-3-methyl-1H-indazole (66.3 mg, 0.31 mmol, 1.10 equiv), $Et_3N$ (0.12 mL, 0.86 mmol, 3.0 equiv) and $Pd(dppf)Cl_2·CH_2Cl_2$ (11.7 mg, 0.014 mmol, 0.05 equiv). The resulting solution was stirred for 5 h at 120° C. The reaction mixture was cooled to 25° C. The crude mixture was purified by Flash-Prep-HPLC. This resulted in 30 mg (34%) of (E)-N-(2,6-dimethylphenyl)-3-(3-methyl-1H-indazol-6-yl)acrylamide as an off-white solid. LC-MS (ES, m/z): $[M+H]^+=306$ $^1H$ NMR (300 MHz, DMSO-$d_6$, ppm): 12.81 (s, 1H), 9.49 (s, 1H), 7.77-7.67 (m, 3H), 7.40 (d, J=8.4 Hz, 1H), 7.11 (s, 3H), 6.97 (d, J=15.6 Hz, 1H), 2.51 (s, 3H), 2.19 (s, 6H).

Example 32: (E)-N-(2,3-dihydro-1H-inden-1-yl)-3-(3-ethyl-1H-indazol-6-yl)acrylamide

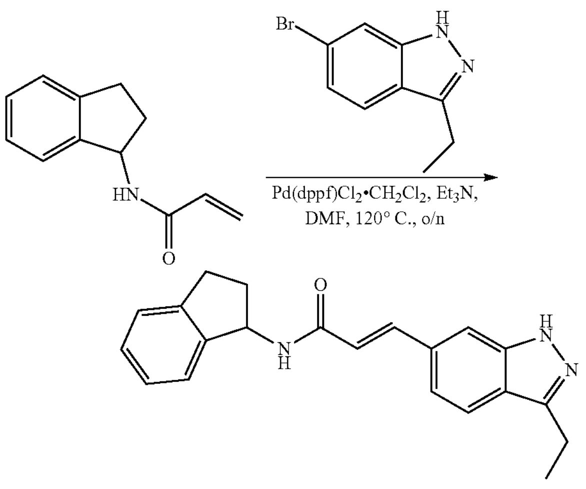

Into a 8-mL sealed tube purged and maintained with an inert atmosphere of nitrogen, was placed N-(Example 24, Step 1, 2,3-dihydro-1H-inden-1-yl)prop-2-enamide (100.0 mg, 0.53 mmol, 1.0 equiv), 6-bromo-3-ethyl-1H-indazole (144.3 mg, 0.64 mmol, 1.20 equiv), $Pd(dppf)Cl_2·CH_2Cl_2$ (43.6 mg, 0.05 mmol, 0.10 equiv), DMF (4.0 mL) and $Et_3N$ (0.22 mL, 1.60 mmol, 3.0 equiv). The resulting solution was stirred overnight at 120° C. The reaction mixture was cooled to room temperature. The crude product was purified by Prep-HPLC. This resulted in 86 mg (49%) of (E)-N-(2,3-dihydro-1H-inden-1-yl)-3-(3-ethyl-1H-indazol-6-yl)acrylamide as a off-white solid. LC MS (ES, m/z): $[M+H]^+=332$ $^1H$ NMR (300 MHz, DMSO-$d_6$, ppm): δ 12.77 (brs, 1H), 8.47 (d, J=8.1 Hz, 1H), 7.75 (d, J=8.4 Hz, 1H), 7.63-7.61 (m, 2H), 7.31-7.17 (m, 5H), 6.75 (d, J=15.9 Hz, 1H), 5.45-5.39 (m, 1H), 3.03-2.79 (m, 4H), 2.47-2.41 (m, 1H), 1.90-1.78 (m, 1H), 1.34-1.29 (m, 3H).

Example 33: (E)-3-(3-cyclopropyl-1H-indazol-6-yl)-N-(2,3-dihydro-1H-inden-1-yl)acrylamide

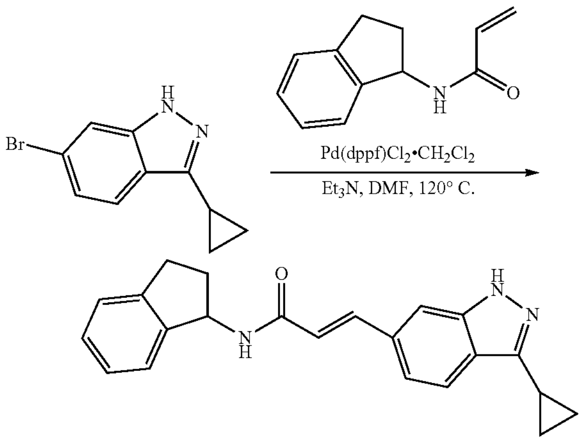

Into a 8-mL vial, was placed N-(2,3-dihydro-1H-inden-1-yl)prop-2-enamide (Example 24, Step 1, 100.0 mg, 0.53 mmol, 1.0 equiv), 6-bromo-3-cyclopropyl-1H-indazole (126.6 mg, 0.53 mmol, 1.0 equiv), Pd(dppf)$Cl_2$ (39.1 mg, 0.05 mmol, 0.10 equiv), $Et_3N$ (0.22 mL, 1.60 mmol, 3.0 equiv), DMF (4 mL). The resulting solution was stirred for 2 h at 120° C. in an oil bath. The reaction mixture was cooled. The mixture was applied onto a silica gel column with PE/THF (1/1). This resulted in 15 mg (8%) of (E)-3-(3-cyclopropyl-1H-indazol-6-yl)-N-(2,3-dihydro-1H-inden-1-yl)acrylamide as a solid. LC MS (ES, m/z): $[M+H]^+$=344

$^1$H NMR (300 MHz, DMSO-$d_6$, ppm): δ 12.70 (s, 1H), 8.48 (d, J=8.4 Hz, 1H), 7.78 (d, J=8.4 Hz, 1H), 7.63 (m, 2H), 7.37-7.16 (m, 5H), 6.74 (d, J=15.6 Hz, 1H), 5.49-5.37 (m, 1H), 3.10-2.75 (m, 2H), 2.48-2.39 (m, 1H), 2.33-2.20 (m, 1H), 1.91-1.77 (m, 1H), 1.06-0.89 (m, 4H).

Example 34: (E)-N-(2,3-dihydro-1H-inden-1-yl)-3-(4-fluoro-3-methyl-1H-indazol-6-yl)acrylamide

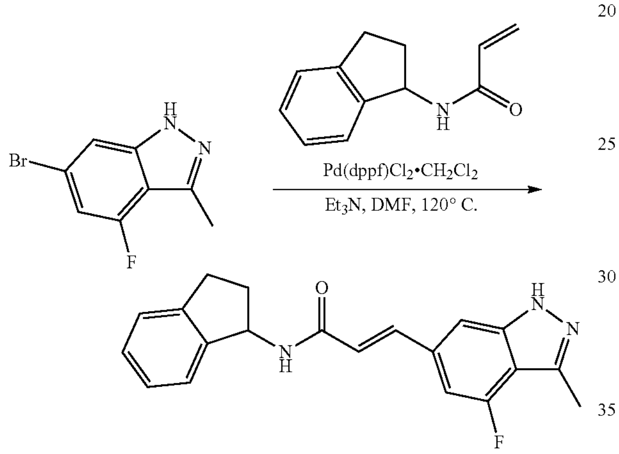

Into a 8-mL vial, was placed 6-bromo-4-fluoro-3-methyl-1H-indazole (Example 24, Step 1, 100.0 mg, 0.44 mmol, 1.0 equiv), N-(2,3-dihydro-1H-inden-1-yl)prop-2-enamide (81.8 mg, 0.44 mmol, 1.0 equiv), Pd(dppf)$Cl_2$ (31.9 mg, 0.04 mmol, 0.10 equiv), $Et_3N$ (0.18 mL, 1.31 mmol, 3.0 equiv), DMF (4.0 mL). The resulting solution was stirred for 2 h at 120° C. in an oil bath. The reaction mixture was cooled. The residue was applied onto a silica gel column with PE/THF (1/1). This resulted in 17 mg (12%) of (E)-N-(2,3-dihydro-1H-inden-1-yl)-3-(4-fluoro-3-methyl-1H-indazol-6-yl)acrylamide as a solid. LC MS (ES, m/z): $[M+H]^+$=336

$^1$H-NMR (300 MHz, DMSO-$d_6$, ppm) δ 13.09 (s, 1H), 8.47 (d, J=8.1 Hz, 1H), 7.61 (d, J=15.6 Hz, 1H), 7.48 (s, 1H), 7.35-7.15 (m, 4H), 7.01 (d, J=12.0 Hz, 1H), 6.73 (d, J=15.6 Hz, 1H), 5.49-5.36 (m, 1H), 3.06-2.76 (m, 2H), 2.56 (s, 3H), 2.47-2.38 (m, 1H), 1.92-1.76 (m, 1H).

Example 35: (E)-N-(3,5-difluoro-2,6-dimethylphenyl)-3-(2-oxoindolin-6-yl)acrylamide

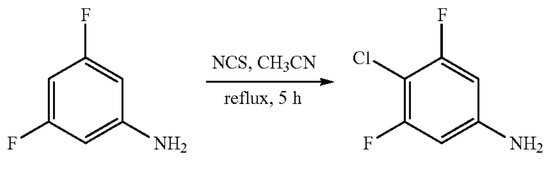 [SMILES: Nc1cc(F)cc(F)c1 ; Nc1cc(F)c(Cl)c(F)c1]

Step 1: Into a 100-mL 3-necked round-bottom flask purged and maintained with an inert atmosphere of nitrogen, was placed 3,5-difluoroaniline (1.0 g, 7.8 mmol, 1.0 equiv), $CH_3CN$ (30 mL), NCS (1.1 g, 8.16 mmol, 1.05 equiv). The resulting solution was stirred for 5 h at 80° C. The reaction mixture was cooled to room temperature. The resulting mixture was concentrated. The residue was applied onto a silica gel column with THF:PE (1:4-1:1). This resulted in 500 mg (39%) of 4-chloro-3,5-difluoroaniline as a grey solid.

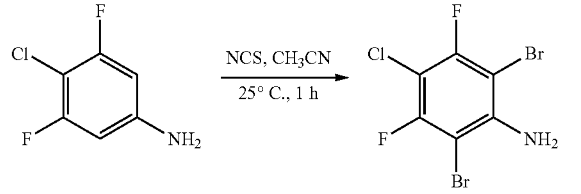 [SMILES: Nc1cc(F)c(Cl)c(F)c1 ; Nc1c(Br)c(F)c(Cl)c(F)c1Br]

Step 2: Into a 50-mL 3-necked round-bottom flask purged and maintained with an inert atmosphere of nitrogen, was placed 4-bromo-3,5-difluoroaniline (500.0 mg, 2.40 mmol, 1.0 equiv), $CH_3CN$ (20.0 mL), NBS (1.3 g, 7.21 mmol, 3.0 equiv). The resulting solution was stirred for 1 h at room temperature. The resulting mixture was concentrated. The residue was applied onto a silica gel column with THF:PE (1:5-1:3). This resulted in 700 mg (91%) of 2,6-dibromo-4-chloro-3,5-difluoroaniline as a yellow solid.

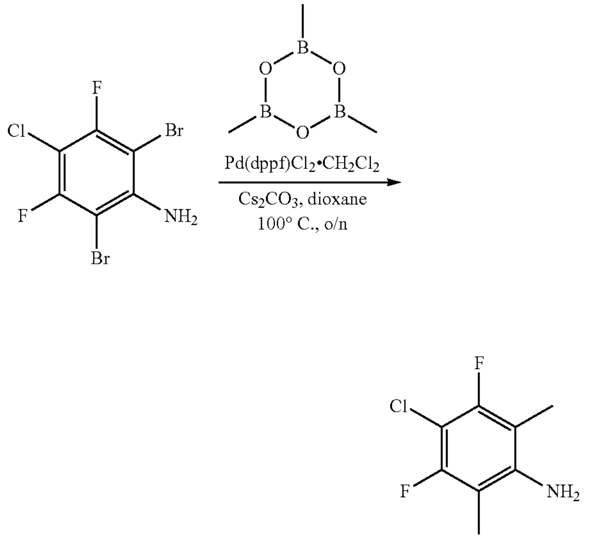

Step 3: Into a 250-mL round-bottom flask purged and maintained with an inert atmosphere of nitrogen, was placed 2,6-dibromo-4-chloro-3,5-difluoroaniline (3.0 g, 9.36 mmol, 1.0 equiv), Pd(dppf)$Cl_2$·$CH_2Cl_2$ (0.76 g, 0.94 mmol, 0.10 equiv), dioxane (60.0 mL), $Cs_2CO_3$ (12.20 g, 37.46 mmol, 4.0 equiv), trimethyl-1,3,5,2,4,6-trioxatriborinane (8.23 g, 32.77 mmol, 3.50 equiv, 50%).

The resulting solution was stirred overnight at 100° C. The reaction mixture was cooled to room temperature. The resulting mixture was concentrated. The crude mixture was purified by Prep-HPLC. This resulted in 600 mg (33%) of 4-chloro-3,5-difluoro-2,6-dimethylaniline as an off-white solid.

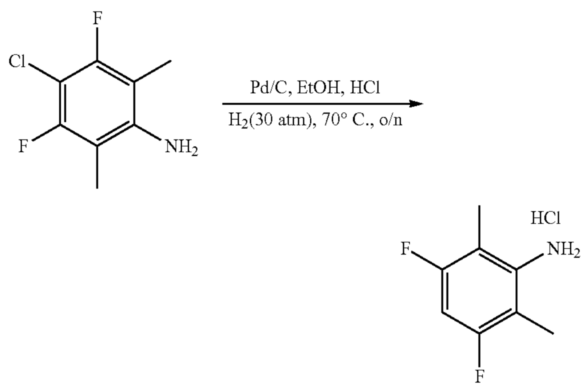

Step 4: Into a 100-mL pressure tank reactor, was placed 4-chloro-3,5-difluoro-2,6-dimethylaniline (280.0 mg, 1.46 mmol, 1.0 equiv), EtOH (20.0 mL), HCl (1.0 mL), Pd/C (77.76 mg). The flask was evacuated and flushed three times with nitrogen, followed by flushing with hydrogen. The resulting solution was stirred overnight at 70° C. under an atmosphere of hydrogen (30 atm). The reaction mixture was cooled to room temperature. The solids were filtered out and the resulting mixture was concentrated. This resulted in 220 mg (crude) of 3,5-difluoro-2,6-dimethylaniline hydrochloride as an off-white solid.

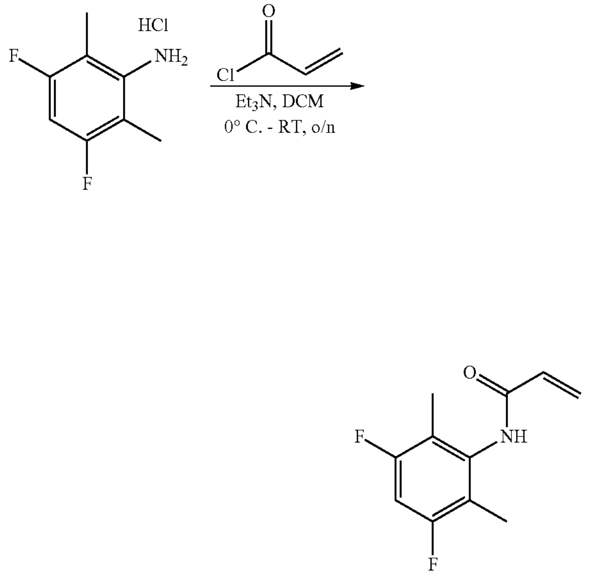

Step 5: Into a 100-mL 3-necked round-bottom flask purged and maintained with an inert atmosphere of nitrogen, was placed 3,5-difluoro-2,6-dimethylaniline hydrochloride (220.0 mg, 1.14 mmol, 1.0 equiv), DCM (20.0 mL), $Et_3N$ (0.48 mL, 3.41 mmol, 3.0 equiv). This was followed by the addition of acryloyl chloride (123.4 mg, 1.36 mmol, 1.20 equiv) dropwise with stirring at 0° C. The resulting solution was stirred overnight at room temperature. The resulting mixture was concentrated. The residue was applied onto a silica gel column with THF:PE (1:5-1:3). This resulted in 160 mg (67%) of N-(3,5-difluoro-2,6-dimethylphenyl)prop-2-enamide as a off-white solid.

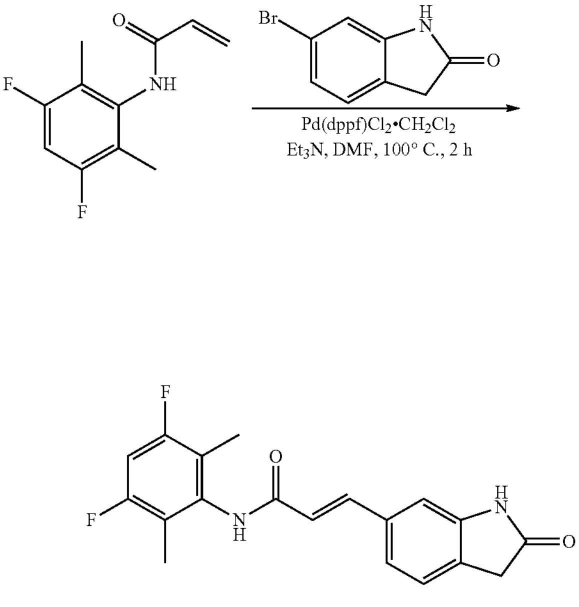

Step 6: Into a 8-mL sealed tube purged and maintained with an inert atmosphere of nitrogen, was placed N-(3,5-difluoro-2,6-dimethylphenyl)prop-2-enamide (160.0 mg, 0.76 mmol, 1.0 equiv), 6-bromo-1,3-dihydroindol-2-one (192.8 mg, 0.91 mmol, 1.20 equiv), $Pd(dppf)Cl_2 \cdot CH_2Cl_2$ (61.7 mg, 0.076 mmol, 0.10 equiv), DMF (5.0 mL), $Et_3N$ (0.32 mL, 2.27 mmol, 3.0 equiv). The resulting solution was stirred for 2 h at 100° C. The reaction mixture was cooled to room temperature. The crude mixture was purified by Prep-HPLC. This resulted in 14.8 mg (6%) of (E)-N-(3,5-difluoro-2,6-dimethylphenyl)-3-(2-oxoindolin-6-yl)acrylamide as a solid.

LC MS (ES, m/z): $[M+H]^+$=343

$^1H$ NMR (300 MHz, DMSO-$d_6$, ppm): δ 10.56 (s, 1H), 9.77 (s, 1H), 7.56 (d, J=15.6 Hz, 1H), 7.29-7.06 (m, 4H), 6.85 (d, J=15.9 Hz, 1H), 3.53 (s, 2H), 2.05 (s, 6H).

Example 36: (E)-N-(3,4-difluoro-2,6-dimethylphenyl)-3-(2-oxoindolin-6-yl)acrylamide

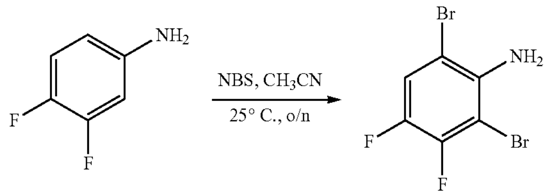 [SMILES: Nc1ccc(F)c(F)c1 ; Nc1c(Br)cc(F)c(F)c1Br]

Step 1: Into a 100-mL 3-necked round-bottom flask purged and maintained with an inert atmosphere of nitrogen, was placed benzenamine, 3,4-difluoro-(1.0 g, 7.75 mmol, 1.0 equiv), $CH_3CN$ (30.0 mL), NBS (2.9 g, 16.27 mmol, 2.10 equiv). The resulting solution was stirred overnight at room temperature. The resulting mixture was concentrated. The residue was applied onto a silica gel column with THF:PE (1:5-1:3). This resulted in 1.4 g (63%) of 2,6-dibromo-3,4-difluoroaniline as a dark brown solid.

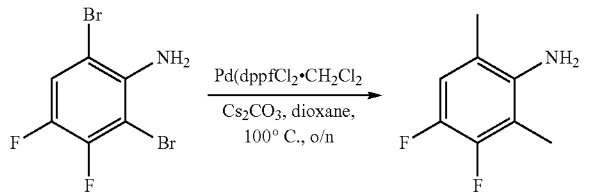

Step 2: Into a 100-mL round-bottom flask purged and maintained with an inert atmosphere of nitrogen, was placed 2,6-dibromo-3,4-difluoroaniline (1.20 g, 4.18 mmol, 1.0 equiv), Pd(dppf)$Cl_2$·$CH_2Cl_2$ (340.7 mg, 0.42 mmol, 0.10 equiv), $Cs_2CO_3$ (4.8 g, 14.64 mmol, 3.50 equiv), dioxane (50.0 mL), trimethyl-1,3,5,2,4,6-trioxatriborinane (3.2 g, 12.55 mmol, 3.0 equiv, 50%).

The resulting solution was stirred overnight at 100° C. The reaction mixture was cooled to room temperature. The resulting mixture was concentrated. The crude mixture was purified by Prep-HPLC. This resulted in 350 mg (53%) of 3,4-difluoro-2,6-dimethylaniline as a off-white solid.

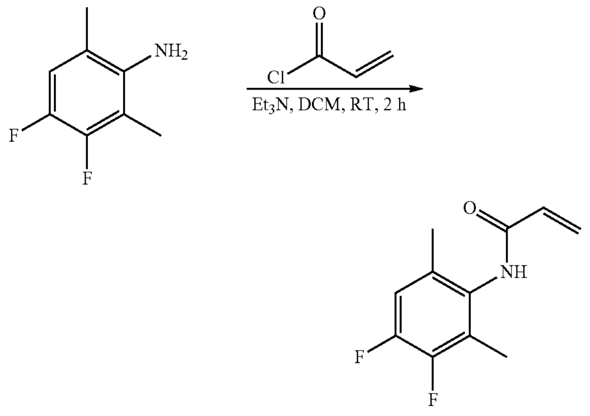

Step 3: Into a 100-mL 3-necked round-bottom flask purged and maintained with an inert atmosphere of nitrogen, was placed 3,4-difluoro-2,6-dimethylaniline (210.0 mg, 1.34 mmol, 1.0 equiv), DCM (20 mL), $Et_3N$ (0.28 mL, 2.0 mmol, 1.50 equiv). This was followed by the addition of acryloyl chloride (145.13 mg, 1.60 mmol, 1.20 equiv) dropwise with stirring at 0° C. The resulting solution was stirred for 2 hr at room temperature. The resulting mixture was concentrated. The residue was applied onto a silica gel column with THF:PE (1:5-1:3). This resulted in 180 mg (64%) of N-(3,4-difluoro-2,6-dimethylphenyl)prop-2-enamide as a off-white solid.

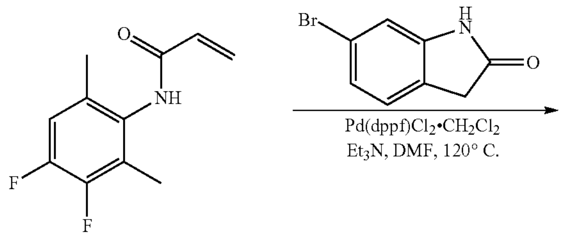

-continued

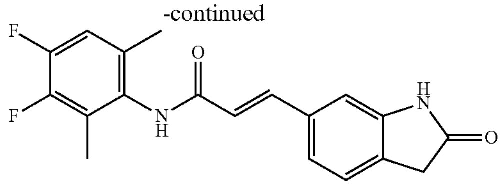

Step 4: Into a 8-mL sealed tube purged and maintained with an inert atmosphere of nitrogen, was placed N-(3,4-difluoro-2,6-dimethylphenyl)prop-2-enamide (100.0 mg, 0.47 mmol, 1.0 equiv), 6-bromo-1,3-dihydroindol-2-one (120.47 mg, 0.57 mmol, 1.20 equiv), Pd(dppf)$Cl_2$·$CH_2Cl_2$ (38.57 mg, 0.05 mmol, 0.10 equiv), DMF (4.0 mL), $Et_3N$ (0.2 mL, 1.42 mmol, 3.0 equiv). The resulting solution was stirred overnight at 120° C. The reaction mixture was cooled to room temperature. The crude mixture was purified by Prep-HPLC. This resulted in 11.3 mg (7%) of (E)-N-(3,4-difluoro-2,6-dimethylphenyl)-3-(2-oxoindolin-6-yl)acrylamide as an off-white solid.

LCMS (ES, m/z): $[M+H]^+$=343

$^1$H NMR (300 MHz, DMSO-$d_6$, ppm): δ 10.55 (s, 1H), 9.63 (s, 1H), 7.53 (d, J=15.9 Hz, 1H), 7.29-7.18 (m, 3H), 7.06 (s, 1H), 6.82 (d, J=15.9 Hz, 1H), 3.53 (s, 2H), 2.05 (s, 3H), 2.10 (s, 3H).

Example 37: (E)-N-(3-fluoro-2-methylphenyl)-3-(3-methyl-1H-indazol-6-yl)acrylamide

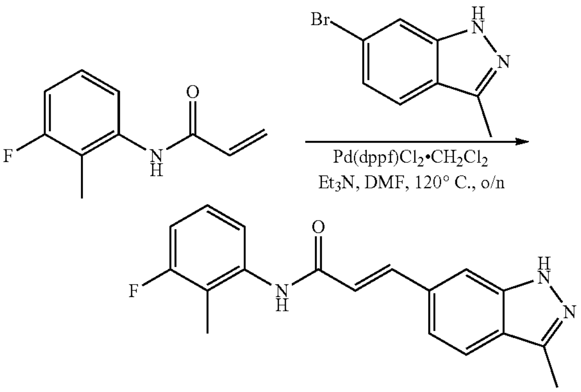

Into a 8-mL sealed tube purged and maintained with an inert atmosphere of nitrogen, was placed N-(3-fluoro-2-methylphenyl)acrylamide (Intermediate 1, 110.0 mg, 0.61 mmol, 1.0 equiv), 6-bromo-3-methyl-1H-indazole (155.47 mg, 0.74 mmol, 1.20 equiv), Pd(dppf)$Cl_2$·$CH_2Cl_2$ (100.01 mg, 0.12 mmol, 0.20 equiv), DMF (4.0 mL), $Et_3N$ (0.26 mL, 1.84 mmol, 3.0 equiv). The resulting solution was stirred overnight at 120° C. The reaction mixture was cooled to room temperature. The crude mixture was purified by Prep-HPLC. This resulted in 26 mg (14%) of (E)-N-(3-fluoro-2-methylphenyl)-3-(3-methyl-1H-indazol-6-yl)acrylamide as an off-white solid.

LC MS (ES, m/z): $[M+H]^+$=310

$^1$H NMR 300 MHz, DMSO-$d_6$, ppm): δ 12.83 (brs, 1H), 9.62 (brs, 1H), 7.78-7.69 (m, 3H), 7.49 (d, J=7.8 Hz, 1H), 7.39 (d, J=8.4 Hz, 1H), 7.27-7.20 (m, 1H), 7.09-6.98 (m, 2H), 2.51 (s, 3H), 2.17 (s, 3H).

Example 38: (E)-3-(3-methyl-1H-indazol-6-yl)-N-(2-methyl-2,3-dihydro-1H-inden-1-yl)acrylamide

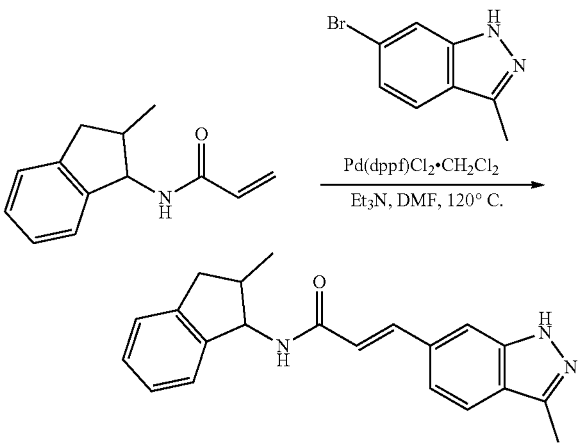

Into a 8-mL vial, was placed 6-bromo-3-methyl-1H-indazole (40.0 mg, 0.19 mmol, 1.0 equiv), N-(2-methyl-2,3-dihydro-1H-inden-1-yl)prop-2-enamide (Prepared according to Example 24, Step 1 using 2-methylindanamine, 38.14 mg, 0.19 mmol, 1.0 equiv), Pd(dppf)$Cl_2$ (13.87 mg, 0.02 mmol, 0.10 equiv) and $Et_3N$ (0.8 mL, 0.57 mmol, 3.0 equiv) in DMF (2.0 mL). The resulting solution was stirred for 2 hr at 120° C. in an oil bath. The reaction solution was cooled to RT. The crude mixture was purified by Flash-Prep-HPLC. This resulted in 29 mg (44%) of (E)-3-(3-methyl-1H-indazol-6-yl)-N-(2-methyl-2,3-dihydro-1H-inden-1-yl)acrylamide as a off-white solid.

LC MS (ES, m/z): $[M+H]^+$=332

$^1$H-NMR (300 MHz, DMSO-$d_6$, ppm) δ 12.78 (brs, 1H), 8.45-8.21 (m, 1H), 7.82-7.57 (m, 3H), 7.42-7.11 (m, 5H), 6.88-6.74 (m, 1H), 5.40-5.0 (m, 1H), 3.12-2.95 (m, 1H), 2.75-2.58 (m, 2H), 2.49 (s, 3H), 2.38-2.24 (m, 1H), 1.24-0.88 (m, 3H).

Example 39: (E)-3-(3-methyl-1H-indazol-6-yl)-N-(1-methyl-1H-indazol-7-yl)acrylamide

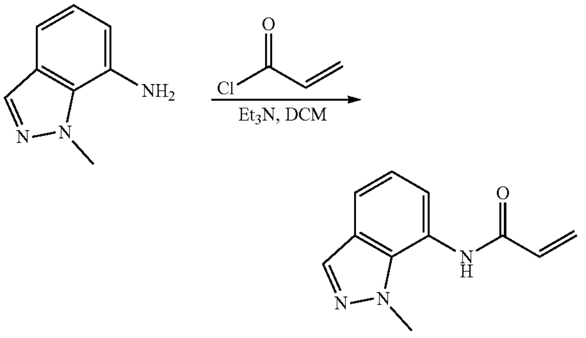

Step 1: Into a 50-mL 3-necked round-bottom as purge an maintained with an inert atmosphere of nitrogen, was placed 1-methylindazol-7-amine (400.0 mg, 2.71 mmol, 1.0 eq), DCM (10.0 mL), $Et_3N$ (0.6 mL, 4.07 mmol, 1.50 eq). This was followed by the addition of acryloyl chloride (246 mg, 2.71 mmol, 1.0 eq) at −30° C. The resulting solution was stirred for 10 min at −30° C. The reaction was then quenched by the addition of 8 mL of water. The organic layer was separated and dried over anhydrous sodium sulfate and concentrated. The residue was applied onto a silica gel column with EtOAc/PE (15:85). This resulted in 120 mg (21%) of N-(1-methylindazol-7-yl)prop-2-enamide as an off-white solid. LC MS (ES, m/z): $[M+H]^+$=202

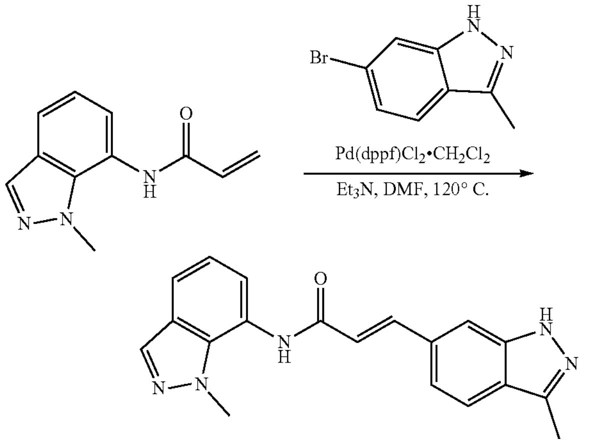

Step 2: Into a 8-mL sealed tube purged and maintained with an inert atmosphere of nitrogen, was placed N-(1-methylindazol-7-yl)prop-2-enamide (100.0 mg, 0.49 mmol, 1.0 eq), 6-bromo-3-methyl-1H-indazole (104.8 mg, 0.49 mmol, 1.0 eq), DMF (4.0 mL), $Et_3N$ (0.14 mL, 0.99 mmol, 2.0 eq), Pd(dppf)$Cl_2$·$CH_2Cl_2$ (41 mg, 0.05 mmol, 0.10 eq). The resulting solution was stirred for 2 h at 120° C. The crude mixture was purified by Flash-Prep-HPLC. This resulted in 33 mg (20%) of (E)-3-(3-methyl-1H-indazol-6-yl)-N-(1-methyl-1H-indazol-7-yl)acrylamide as an off-white solid.

LC MS (ES, m/z): $[M+H]^+$=332

$^1$H NMR (300 MHz, DMSO-$d_6$, ppm): 12.83 (brs, 1H), 10.14 (brs, 1H), 8.07 (s, 1H), 7.81-7.67 (m, 4H), 7.44-7.41 (m, 1H), 7.25-7.11 (m, 2H), 7.01 (d, J=15.9 Hz, 1H), 4.12 (s, 3H), 2.50 (s, 3H).

Example 40: (E)-N-(5-fluoro-2,3-dihydro-1H-inden-1-yl)-3-(3-methyl-1H-indazol-6-yl)acrylamide

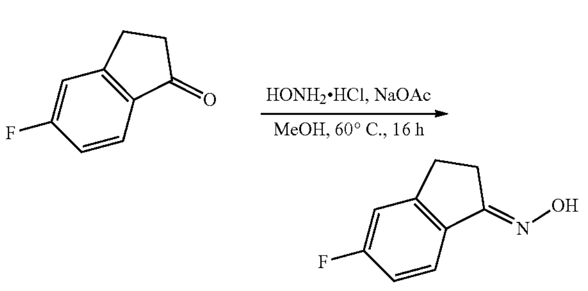

Step 1: Into a 40-mL sealed tube, was placed 5-fluoro-2,3-dihydroinden-1-one (800.0 mg, 5.33 mmol, 1.0 eq), NaOAc (874.14 mg, 10.66 mmol, 2.0 eq), MeOH (15.0 mL), Hydroxylamine hydrochloride (1.10 g, 15.98 mmol, 3.0 eq). The resulting solution was stirred for 16 h at 60° C. The resulting mixture was concentrated. The crude product was diluted with of EtOAc (30.0 mL) and $H_2O$(15.0 mL). The organic phase was washed with 20 ml of $H_2O$. The organic layer was concentrated. This resulted in 810 mg (92%) of N-[5-fluoro-2,3-dihydroinden-1-ylidene]hydroxylamine as an off-white solid. LC MS (ES, m/z): $[M+H]^+$=166

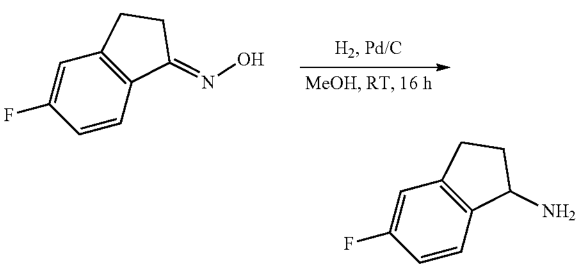

Step 2: Into a 50-mL round-bottom flask, was placed N-[5-fluoro-2,3-dihydroinden-1-ylidene]hydroxylamine (810.0 mg, 4.90 mmol, 1.0 eq), MeOH (20.0 mL). This was followed by the addition of Pd/C (104.38 mg) under $H_2$. The resulting solution was stirred for 16 h at room temperature. The solid was filtered out and washed with 10 mL MeOH. The combined solution was concentrated. This resulted in 530 mg (71%) of 5-fluoro-2,3-dihydro-1H-inden-1-amine as an off-white solid. LC MS (ES, m/z): $[M+H]^+$=152

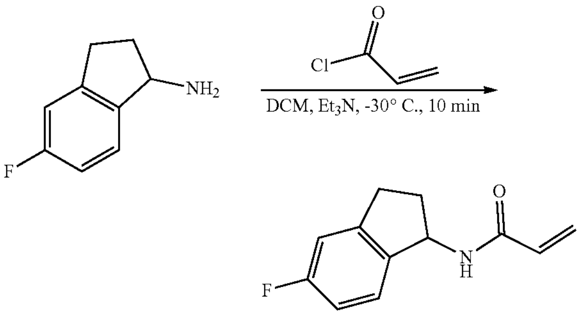

Step 3: Into a 25-mL 3-necked round-bottom flask purged and maintained with an inert atmosphere of nitrogen, was placed 5-fluoro-2,3-dihydro-1H-inden-1-amine (210.0 mg, 1.38 mmol, 1.0 eq), DCM (5.0 mL), $Et_3N$ (0.4 mL, 2.77 mmol, 2.0 eq). This was followed by the addition of acryloyl chloride (188.58 mg, 2.08 mmol, 1.50 eq) at −30° C. The resulting solution was stirred for 10 min at −30° C. The reaction was then quenched by the addition of 5 mL of water. The organic layer was separated and concentrated. The residue was applied onto a silica gel column with EtOAc/PE (80:20). This resulted in 200 mg (70%) of N-(5-fluoro-2,3-dihydro-1H-inden-1-yl)prop-2-enamide as an off-white solid. LC MS (ES, m/z): $[M+H]^+$=206

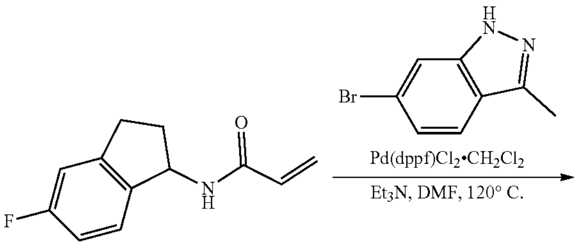

-continued

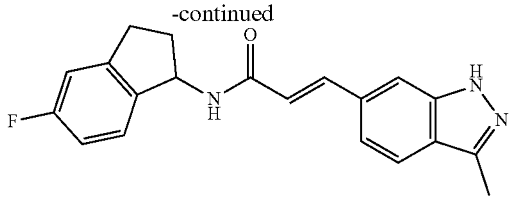

Step 4: Into a 8-mL sealed tube purged and maintained with an inert atmosphere of nitrogen, was placed N-(5-fluoro-2,3-dihydro-1H-inden-1-yl)acrylamide (100.0 mg, 0.48 mmol, 1.0 eq), 6-bromo-3-methyl-1H-indazole (102.8 mg, 0.48 mmol, 1.0 eq), $Et_3N$ (0.14 mL, 0.97 mmol, 2.0 eq), DMF (5.0 mL), $Pd(dppf)Cl_2 \cdot CH_2Cl_2$ (39.69 mg, 0.05 mmol, 0.10 eq). The resulting solution was stirred for 2 h at 120° C. The reaction solution was cooled to RT. The crude mixture was purified by Flash-Prep-HPLC. This resulted in 34 mg (20%) of (E)-N-(5-fluoro-2,3-dihydro-1H-inden-1-yl)-3-(3-methyl-1H-indazol-6-yl)acrylamide as a white solid. LC MS (ES, m/z): $[M+H]^+$=336

$^1H$ NMR (300 MHz, DMSO-$d_6$, ppm): 12.78 (s, 1H), 8.48 (d, J=8.1 Hz, 1H), 7.74-7.61 (m, 3H), 7.32-7.24 (m, 2H), 7.13-7.09 (m, 2H), 6.73 (d, J=15.9 Hz, 1H), 5.40-5.37 (m, 1H), 3.16-2.73 (m, 2H), 2.52 (s, 3H), 2.50-1.83 (m, 2H).

Example 41: (E)-N-(4-fluoro-3-methylphenyl)-3-(3-methyl-1H-indazol-6-yl)acrylamide

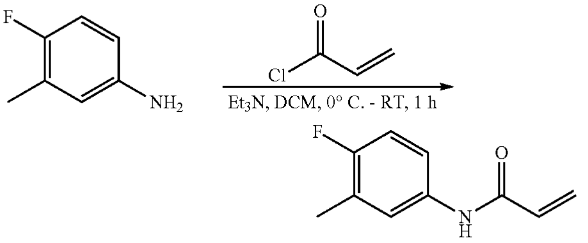

Step 1: Into a 100-mL 3-necked round-bottom flask purged and maintained with an inert atmosphere of nitrogen, was placed 4-fluoro-3-methylaniline (600.0 mg, 4.79 mmol, 1.0 equiv), DCM (20.0 mL), $Et_3N$ (2.0 mL, 14.38 mmol, 3.0 equiv). This was followed by the addition of acryloyl chloride (520.73 mg, 5.75 mmol, 1.20 equiv) dropwise with stirring at 0° C. The resulting solution was stirred for 1 h at room temperature. The resulting mixture was concentrated. The residue was applied onto a silica gel column with THF:PE (1:5-1:3). This resulted in 400 mg (56%) of N-(4-fluoro-3-methylphenyl)prop-2-enamide as a light yellow solid.

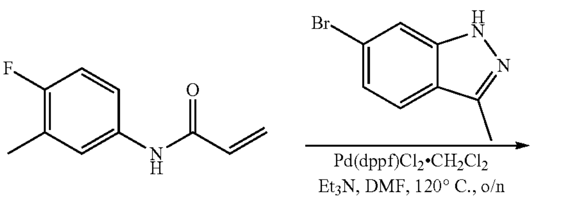

-continued

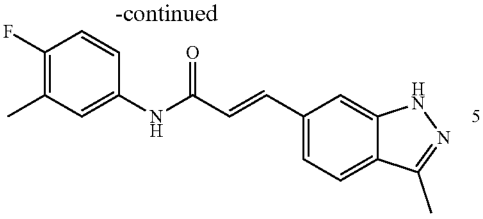

Step 2: Into a 8-mL sealed tube purged and maintained with an inert atmosphere of nitrogen, was placed N-(4-fluoro-3-methylphenyl)prop-2-enamide (110.0 mg, 0.61 mmol, 1.0 equiv), 6-bromo-3-methyl-1H-indazole (155.47 mg, 0.74 mmol, 1.20 equiv), $Pd(dppf)Cl_2 \cdot CH_2Cl_2$ (100.01 mg, 0.12 mmol, 0.20 equiv), DMF (4.0 mL), $Et_3N$ (0.26 mL, 1.84 mmol, 3.0 equiv). The resulting solution was stirred overnight at 120° C. The reaction mixture was cooled to room temperature. The crude mixture was purified by Prep-HPLC. This resulted in 20.4 mg (11%) of (E)-N-(4-fluoro-3-methylphenyl)-3-(3-methyl-1H-indazol-6-yl)acrylamide as a off-white solid.

LC MS (ES, m/z): $[M+H]^+$=310

$^1$H NMR (300 MHz, DMSO-$d_6$, ppm): δ 12.82 (brs, 1H), 10.16 (brs, 1H), 7.77-7.67 (m, 3H), 7.62-7.59 (m, 1H), 7.56-7.51 (m, 1H), 7.36 (d, J=8.4 Hz, 1H), 7.14-7.08 (m, 1H), 6.88 (d, J=15.6 Hz, 1H), 2.51 (s, 3H), 2.24 (s, 3H).

Example 42: (E)-N-(3-fluoro-4-methylphenyl)-3-(3-methyl-1H-indazol-6-yl)acrylamide

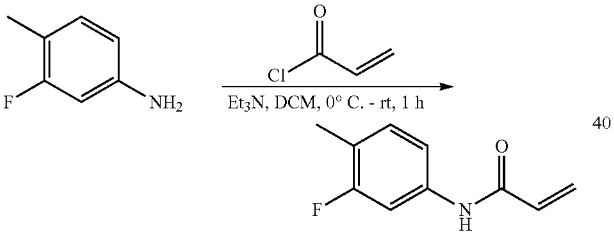

Step 1: Into a 100-mL 3-necked round-bottom flask purged and maintained with an inert atmosphere of nitrogen, was placed 3-fluoro-4-methylaniline (550.0 mg, 4.40 mmol, 1.0 equiv), DCM (20.0 mL), $Et_3N$ (1.2 mL, 8.79 mmol, 2.0 equiv). This was followed by the addition of acryloyl chloride (477.34 mg, 5.27 mmol, 1.20 equiv) dropwise with stirring at 0° C. The resulting solution was stirred for 1 h at room temperature. The resulting mixture was concentrated. The residue was applied onto a silica gel column with THF:PE (1:5-1:3). This resulted in 450 mg (57%) of N-(3-fluoro-4-methylphenyl)prop-2-enamide as a off-white solid.

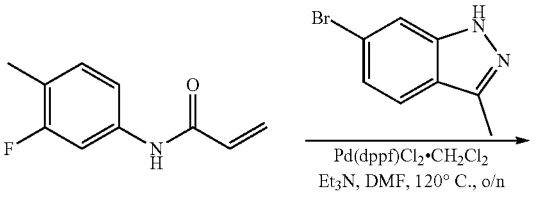

-continued

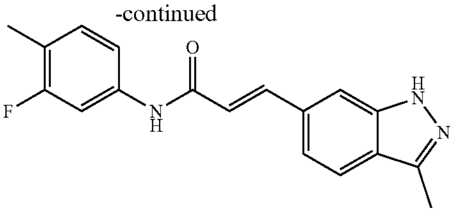

Step 2: Into a 8-mL sealed tube purged and maintained with an inert atmosphere of nitrogen, was placed N-(3-fluoro-4-methylphenyl)prop-2-enamide (110.0 mg, 0.61 mmol, 1.0 equiv), 6-bromo-3-methyl-1H-indazole (155.5 mg, 0.74 mmol, 1.20 equiv), $Pd(dppf)Cl_2 \cdot CH_2Cl_2$ (100.0 mg, 0.12 mmol, 0.20 equiv), DMF (4.0 mL), $Et_3N$ (0.26 mL, 1.84 mmol, 3.0 equiv). The resulting solution was stirred overnight at 120° C. The reaction mixture was cooled to room temperature. The crude mixture was purified by Prep-HPLC. This resulted in 35.8 mg (19%) of (E)-N-(3-fluoro-4-methylphenyl)-3-(3-methyl-1H-indazol-6-yl)acrylamide as a off-white solid.

LC MS (ES, m/z): $[M+H]^+$=310

$^1$H NMR (300 MHz, DMSO-$d_6$, ppm): δ 12.83 (brs, 1H), 10.30 (brs, 1H), 7.77-7.67 (m, 4H), 7.39-7.35 (m, 1H), 7.30-7.20 (m, 2H), 6.87 (d, J=15.6 Hz, 1H), 2.51 (s, 3H), 2.20 (s, 3H).

Example 43: Racemic-(E)-3-(3-methyl-1H-indazol-6-yl)-N-((1R,2R)-2-methylcyclohexyl)acrylamide

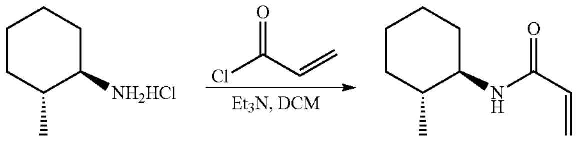

Step 1: Into a 25-mL 3-necked round-bottom flask purged and maintained with an inert atmosphere of nitrogen, was placed Racemic-trans-(1R,2R)-2-methylcyclohexan-1-amine hydrochloride (300.0 mg, 2.0 mmol, 1.0 eq), DCM (6.0 mL), $Et_3N$ (0.84 mL, 6.01 mmol, 3.0 eq). This was followed by the addition of acryloyl chloride (181.43 mg, 2.0 mmol, 1.0 eq) at 0° C. The resulting solution was stirred for 40 min at room temperature. The reaction was then quenched by the addition of 5 mL of water. The resulting solution was diluted with 10 mL of DCM. The resulting mixture was washed with 10 ml of brine. The organic layer was dried over anhydrous sodium sulfate and concentrated. The residue was applied onto a silica gel column with ethyl acetate/petroleum ether (22:78). This resulted in 200 mg (60%) of N-[(1R,2R)-2-methylcyclohexyl]prop-2-enamide as an off-white solid.

LC-MS (ES, m/z): $[M+H]^+$=168

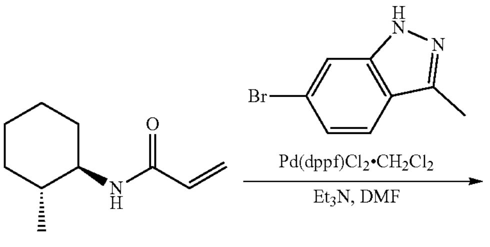

-continued

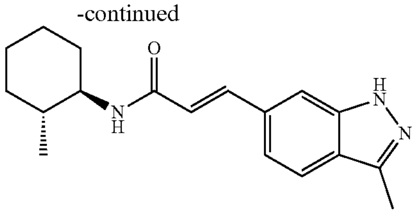

Step 2: Into a 8-mL sealed tube purged and maintained with an inert atmosphere of nitrogen, was placed DMF (4.0 mL), N-[(1R,2R)-2-methylcyclohexyl]prop-2-enamide (100.0 mg, 0.60 mmol, 1.0 eq), 6-bromo-3-methyl-1H-indazole (126. mg, 0.60 mmol, 1.0 eq), $Et_3N$ (0.25 mL, 1.79 mmol, 3.0 eq), $Pd(dppf)Cl_2 \cdot CH_2Cl_2$ (48.71 mg, 0.06 mmol, 0.10 eq). The resulting solution was stirred for 2 h at 120° C. The crude mixture was purified by Flash-Prep-HPLC. This resulted in 41 mg (23%) of Racemic (E)-3-(3-methyl-1H-indazol-6-yl)-N-((1R,2R)-2-methylcyclohexyl)acrylamide as an off-white solid. LC MS (ES, m/z): $[M+H]^+=298$ $^1H$ NMR (300 MHz, $CD_3OD-d_4$, ppm): 7.75-7.60 (m, 3H), 7.43-7.40 (m, 1H), 6.70 (d, J=15.6 Hz, 1H), 3.54-3.50 (m, 1H), 2.57 (s, 3H), 1.96-1.71 (m, 4H), 1.48-1.37 (m, 5H), 1.30 (d, J=9.3 Hz, 3H).

Example 44: (E)-3-(3-cyano-1H-indazol-6-yl)-N-(2-methyl-2,3-dihydro-1H-inden-1-yl)acrylamide

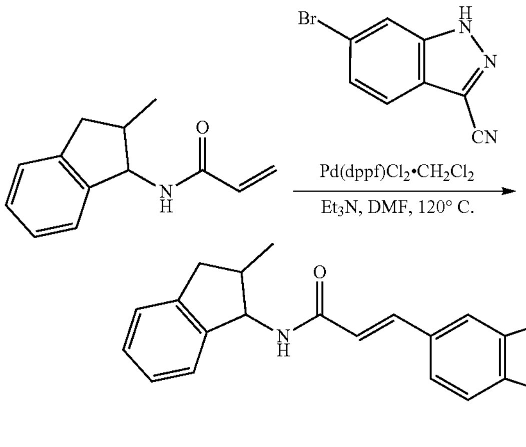

Into a 8-mL vial, was placed 6-bromo-1H-indazole-3-carbonitrile (40.0 mg, 0.18 mmol, 1.0 equiv), N-(2-methyl-2,3-dihydro-1H-inden-1-yl)prop-2-enamide (Prepared according to Example 24, Step 1 using 2-methylindanamine, 36.26 mg, 0.18 mmol, 1.0 equiv), $Pd(dppf)Cl_2$ (13.18 mg, 0.018 mmol, 0.10 equiv) and $Et_3N$ (0.075 mL, 0.54 mmol, 3.0 equiv) in DMF (2.0 mL) The resulting solution was stirred for 2 h at 120° C. in an oil bath. The mixture was cooled to RT. The crude mixture was purified by Flash-Prep-HPLC. This resulted in 16 mg (26%) of (E)-3-(3-cyano-1H-indazol-6-yl)-N-(2-methyl-2,3-dihydro-1H-inden-1-yl) acrylamide as a off-white solid. LC MS (ES, m/z): $[M+H]^+=343$ $^1H$ NMR (300 MHz, DMSO-$d_6$, ppm) δ 8.59-8.30 (m, 1H), 8.05-7.87 (m, 2H), 7.77-7.55 (m, 2H), 7.34-7.08 (m, 4H), 6.97-6.79 (m, 1H), 5.50-4.98 (m, 1H), 3.06-2.95 (m, 1H), 2.84-2.62 (m, 1H), 2.39-2.19 (m, 1H), 1.25-0.88 (m, 3H).

Example 45: (E)-N-(2-methyl-2,3-dihydro-1H-inden-1-yl)-3-(1-methyl-2-oxo-2,3-dihydro-1H-benzo[d]imidazol-5-yl)acrylamide

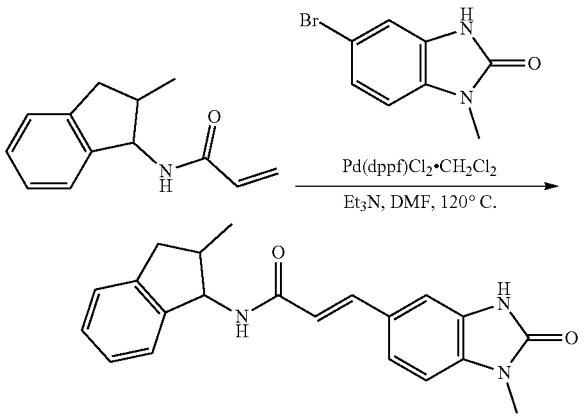

Into a 8-mL vial, was placed 5-bromo-1-methyl-3H-1,3-benzodiazol-2-one (50.0 mg, 0.22 mmol, 1.0 equiv), N-(2-methyl-2,3-dihydro-1H-inden-1-yl)prop-2-enamide (Prepared according to Example 24, Step 1 using 2-methylindanamine 44.3 mg, 0.22 mmol, 1.0 equiv), $Pd(dppf)Cl_2$ (16.1 mg, 0.022 mmol, 0.10 equiv) and $Et_3N$ (0.092 mL, 0.66 mmol, 3.0 equiv) in DMF (2.0 mL). The resulting solution was stirred for 2 h at 120° C. in an oil bath. The reaction solution was cooled to RT. The crude mixture was purified by Flash-Prep-HPLC. This resulted in 29 mg (38%) of (E)-N-(2-methyl-2,3-dihydro-1H-inden-1-yl)-3-(1-methyl-2-oxo-2,3-dihydro-1H-benzo[d]imidazol-5-yl) acrylamide as a off-white solid. LC MS (ES, m/z): $[M+H]^+=348$ $^1H$ NMR (300 MHz, DMSO-$d_6$, ppm) δ 10.99 (s, 1H), 8.32-8.12 (m, 1H), 7.54-7.46 (m, 1H), 7.28-7.10 (m, 7H), 6.69-6.57 (m, 1H), 5.40-5.02 (m, 1H), 3.30 (s, 3H), 3.07-3.0 (m, 1H), 2.69-2.50 (m, 1H), 2.27-2.20 (m, 1H), 1.21-0.90 (m, 3H).

Example 46: (E)-N-(2-methyl-2,3-dihydro-1H-inden-1-yl)-3-(2-oxo-2,3-dihydrobenzo[d]oxazol-5-yl) acrylamide

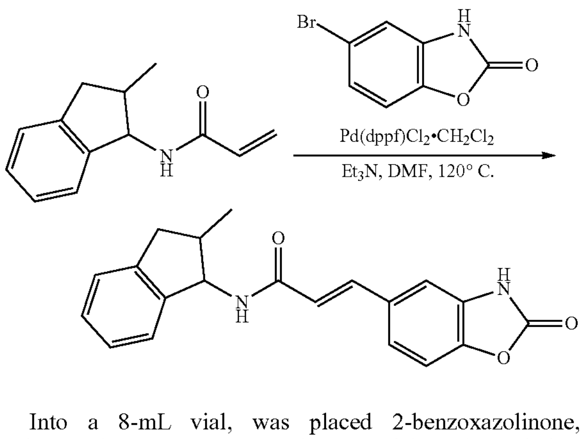

Into a 8-mL vial, was placed 2-benzoxazolinone, 5-bromo-(50.0 mg, 0.23 mmol, 1.0 equiv), N-(2-methyl-2,3-dihydro-1H-inden-1-yl)prop-2-enamide (Prepared according to Example 24, Step 1 using 2-methylindanamine 47.0 mg, 0.23 mmol, 1.0 equiv), Pd(dppf)$Cl_2$ (17.1 mg, 0.023 mmol, 0.10 equiv) and $Et_3N$ (0.098 mL, 0.70 mmol, 3.0 equiv) in DMF (2.0 mL). The resulting solution was stirred for 2 hr at 120° C. in an oil bath. The reaction solution was cooled to RT. The crude mixture was purified by Flash-Prep-HPLC. This resulted in 29 mg (37%) of (E)-N-(2-methyl-2,3-dihydro-1H-inden-1-yl)-3-(2-oxo-2,3-dihydrobenzo[d]oxazol-5-yl)acrylamide as a off-white solid. LCMS (ES, m/z): $[M+H]^+$=335

$^1$H NMR (300 MHz, DMSO-$d_6$, ppm) δ 11.76 (brs, 1H), 8.40-8.19 (m, 1H), 7.56-7.48 (m, 1H), 7.33-7.12 (m, 6H), 6.74-6.63 (m, 1H), 5.39-4.99 (m, 1H), 3.10-2.94 (m, 1H), 2.69-2.20 (m, 2H), 1.21-0.91 (m, 3H).

Example 47: (Z)-2-fluoro-N-(3-fluoro-2-methylphenyl)-3-(2-oxoindolin-6-yl)acrylamide

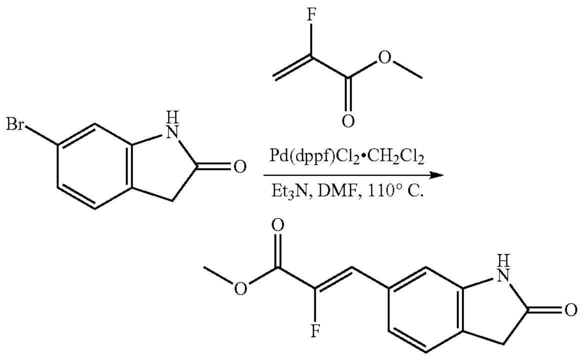

Step 1: Into a 40-mL sealed tube purged and maintained with an inert atmosphere of nitrogen, was placed DMF (20.0 mL), 6-bromo-1,3-dihydroindol-2-one (1.0 g, 4.72 mmol, 1.0 eq), methyl 2-fluoroacrylate (0.59 g, 5.66 mmol, 1.20 eq), Pd(dppf)$Cl_2$·$CH_2Cl_2$ (77.0 mg, 0.094 mmol, 0.02 eq), $Et_3N$ (1.3 mL, 9.43 mmol, 2.0 eq). The resulting solution was stirred for 2 h at 110° C. The resulting mixture was concentrated. The residue was applied onto a silica gel column with (25/75). This resulted in 420 mg (37%) of methyl 2-fluoro-3-(2-oxo-1,3-dihydroindol-6-yl)prop-2-enoate as a yellow solid. LC-MS-PH-NRG0255-1 (ES, m/z): $[M-H]^+$=234

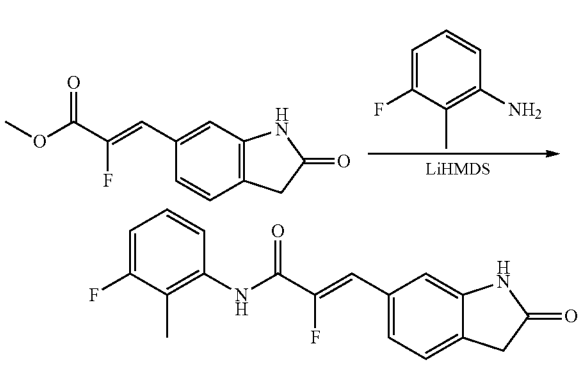

Step 2: Into a 8-mL sealed tube, was placed methyl 2-fluoro-3-(2-oxo-1,3-dihydroindol-6-yl)prop-2-enoate (150.0 mg, 0.64 mmol, 1.0 eq), 3-fluoro-2-methyl-aniline (239.42 mg, 1.91 mmol, 3.0 eq), THF (3.0 mL). This was followed by the addition of LiHMDS (1.92 mL, 1.92 mmol, 3.0 eq) at 0° C. The resulting solution was stirred for 30 min at room temperature. The reaction was then quenched by the addition of 15 mL of $H_2O$. The resulting solution was extracted with 2×10 mL of EtOAc. The combined organic phase was dried over anhydrous sodium sulfate and concentrated. The crude product was purified by Flash-Prep-HPLC. This resulted in 28 mg (13%) of (Z)-2-fluoro-N-(3-fluoro-2-methylphenyl)-3-(2-oxoindolin-6-yl)acrylamide as a white solid. LC MS (ES, m/z): $[M+H]^+$=329

$^1$H NMR (300 MHz, DMSO-$d_6$, ppm): δ 10.50 (s, 1H), 10.16 (s, 1H), 7.31-6.93 (m, 7H), 3.53 (s, 2H), 2.12 (s, 3H).

Example 48: (E)-N-(3-chloro-2-methylphenyl)-N-methyl-3-(2-oxo-2,3-dihydrobenzo[d]oxazol-5-yl)acrylamide

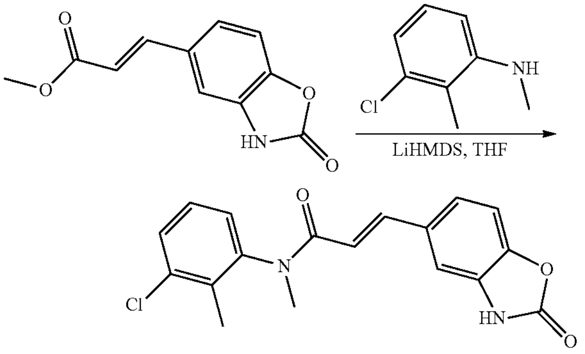

Into a 8-mL sealed tube purged and maintained with an inert atmosphere of nitrogen, was placed (E)-methyl 3-(2-oxo-2,3-dihydrobenzo[d]oxazol-5-yl)acrylate (Prepared according to Example 11, Step 2, 30.0 mg, 0.14 mmol, 1.0 equiv) in THF (2.0 mL). Then 3-chloro-N,2-dimethylbenzenamine (27.60 mg, 0.18 mmol, 1.30 equiv) was added. The reaction mixture was cooled to 0° C. Then 1M LiHMDS (0.68 mL, 0.68 mmol, 5.0 equiv) was added. The reaction mixture was stirred 1 h at RT. The reaction mixture was quenched by 1 mL water and extracted with 2×5 mL EtOAc, the organic was concentrated under vacuum to afford crude product. The crude product was then purified by Prep-HPLC. This resulted in 9.6 mg (21%) of (E)-N-(3-chloro-2-methylphenyl)-N-methyl-3-(2-oxo-2,3-dihydrobenzo[d]oxazol-5-yl)acrylamide as a white solid. LC-MS (ES, m/z): $[M+H]^+$=343

Example 49: (E)-N-(2-methylcyclopentyl)-3-(2-oxo-2,3-dihydrobenzo[d]oxazol-5-yl)acrylamide

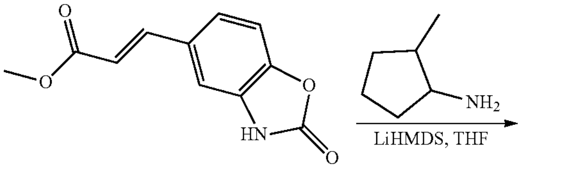

-continued

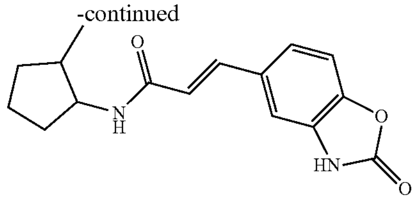

Into a 8-mL sealed tube purged and maintained with an inert atmosphere of nitrogen, was placed (E)-methyl 3-(2-oxo-2,3-dihydrobenzo[d]oxazol-5-yl)acrylate (Prepared according to Example 11, Step 2, 30.0 mg, 0.14 mmol, 1.0 equiv) in THF (2.0 mL). Then 2-methylcyclopentanamine (17.6 mg, 0.18 mmol, 1.30 equiv) was added. The reaction mixture was cooled to 0° C. Then 1M LiHMDS (0.68 mL, 0.68 mmol, 5.0 equiv) was added. The reaction mixture was stirred 1 h at RT. The reaction mixture was quenched by 1 mL water and extracted with 2×5 mL EtOAc, the organic was concentrated under vacuum to afford crude product. The crude product was then purified by Prep-HPLC. This resulted in 19 mg (48%) of (E)-N-(2-methylcyclopentyl)-3-(2-oxo-2,3-dihydrobenzo[d]oxazol-5-yl)acrylamide as a white solid.

LC-MS (ES, m/z): $[M+H]^+=287$

Example 50: (E)-N-(3-fluoro-2-(methoxymethyl) phenyl)-3-(3-methyl-1H-indazol-6-yl)acrylamide

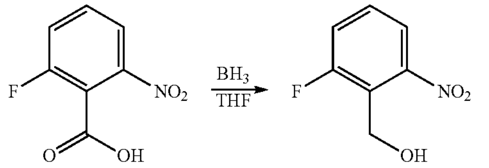

Step 1: Into a 250-mL round-bottom flask purged and maintained with an inert atmosphere of nitrogen, was placed THF (50.0 mL), 2-fluoro-6-nitrobenzoic acid (2.0 g, 10.80 mmol, 1.0 eq). This was followed by the addition of borane (32.41 mL, 32.41 mmol, 3.0 eq, 1 M/THF) at 0° C. The resulting solution was stirred for 10 h at 50° C. The reaction was then quenched by the addition of 20 mL of 3 M HCl. The resulting solution was diluted with 50 mL of EtOAc. The organic layer was washed with 2×30 ml of brine. The solution was dried over sodium sulfate and evaporated under reduced pressure. This resulted in 1.3 g (70%) of (2-fluoro-6-nitrophenyl)methanol as a light brown solid.

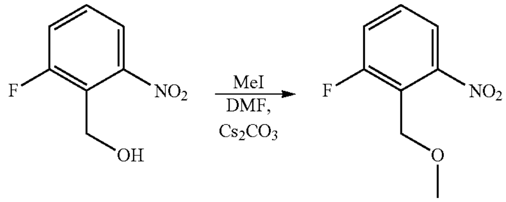

Step 2: Into a 40-mL sealed tube, was placed (2-fluoro-6-nitrophenyl)methanol (1.30 g, 7.59 mmol, 1.0 eq), DMF (20.0 mL), methyl iodide (5.39 g, 37.98 mmol, 5.0 eq). This was followed by the addition of $Cs_2CO_3$ (3.71 g, 11.39 mmol, 1.50 eq) at 0° C. The resulting solution was stirred for 5 h at 50° C. The solids were filtered out. The filtrate solution was diluted with 100 mL of EtOAc. The resulting mixture was washed with 3×50 ml of $H_2O$ and 50 mL of brine. The organic layer was dried over sodium sulfate and evaporated. The crude product was purified by Flash-Prep-HPLC. This resulted in 0.91 g (64%) of 1-fluoro-2-(methoxymethyl)-3-nitrobenzene as yellow oil.

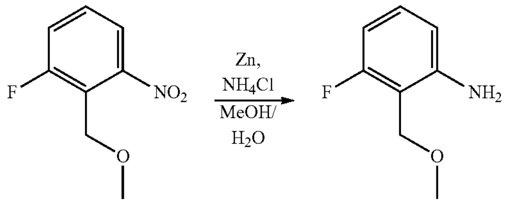

Step 3: Into a 40-mL sealed tube, was placed 1-fluoro-2-(methoxymethyl)-3-nitrobenzene (0.70 g, 3.78 mmol, 1.0 eq), MeOH (20.0 mL), $H_2O$(3.0 mL), $NH_4Cl$ (1.21 g, 22.68 mmol, 6.0 eq). This was followed by the addition of Zn (1.24 g, 18.90 mmol, 5.0 eq) at 10° C. The resulting solution was stirred for 1 h at 25° C. The solids were filtered out. The resulting solution was diluted with 20 mL of DCM. The mixture was dried over anhydrous sodium sulfate and concentrated (low temp). This resulted in 0.21 g (35%) of 3-fluoro-2-(methoxymethyl)aniline as light brown oil (the amine was unstable and was used in next step directly and quickly). LC-MS (ES, m/z): $[M+H]^+=156$

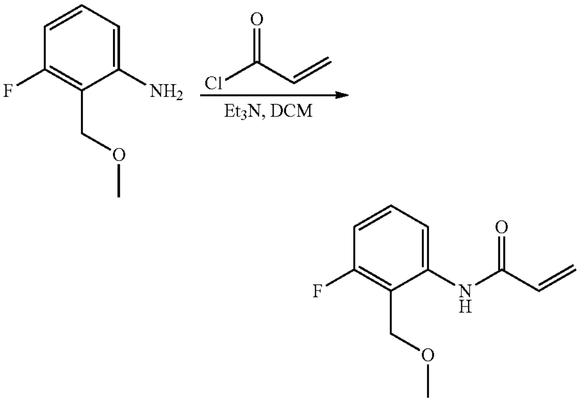

Step 4: Into a 8-mL sealed tube, was placed 3-fluoro-2-(methoxymethyl)aniline (200.0 mg, 1.28 mmol, 1.0 eq), DCM (4.0 mL), $Et_3N$ (0.36 mL, 2.57 mmol, 2.0 eq). This was followed by the addition of acryloyl chloride (116.6 mg, 1.28 mmol, 1.0 eq) at 0° C. The resulting solution was stirred for 0.5 h at 0° C. The reaction was then quenched by the addition of 2 mL of water. The resulting mixture was washed with 2 ml of brine. The organic layer was dried over sodium sulfate and concentrated. This resulted in 160 mg (59%) of N-[3-fluoro-2-(methoxymethyl)phenyl]prop-2-enamide as an off-white solid. LC-MS (ES, m/z): $[M+H]^+=210$

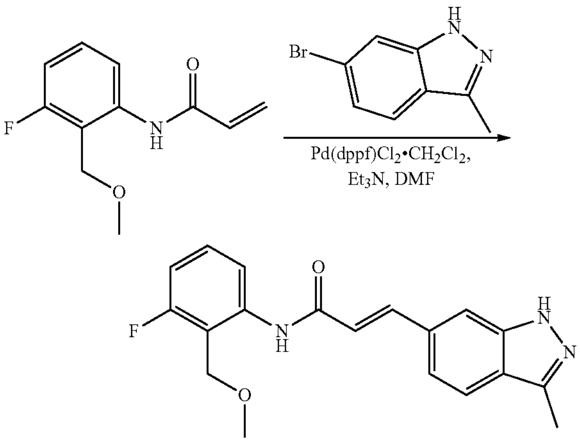

Step 5: Into a 8-mL sealed tube purged and maintained with an inert atmosphere of nitrogen was placed N-[3-fluoro-2-(methoxymethyl)phenyl]prop-2-enamide (100.0 mg, 0.47 mmol, 1.0 eq), DMF (4.0 mL), 6-bromo-3-methyl-1H-indazole (100.88 mg, 0.47 mmol, 1.0 eq), $Et_3N$ (0.2 mL, 1.43 mmol, 3.0 eq), $Pd(dppf)Cl_2{\cdot}CH_2Cl_2$ (38.94 mg, 0.048 mmol, 0.10 eq). The resulting solution was stirred for 2 h at 120° C. The crude mixture was purified by Flash-Prep-HPLC. This resulted in 71 mg (43%) of (E)-N-(3-fluoro-2-(methoxymethyl)phenyl)-3-(3-methyl-1H-indazol-6-yl) acrylamide as a white solid. LC-MS (ES, m/z): $[M+H]^+$=340

$^1$H NMR (300 MHz, DMSO-$d_6$, ppm): δ 12.84 (s, 1H), 9.55 (s, 1H), 7.78-7.69 (m, 4H), 7.44-7.38 (m, 2H), 7.11-7.02 (m, 2H), 4.56 (s, 2H), 3.32 (s, 3H), 2.51 (s, 3H).

Example 51: (E)-3-(3-cyano-1H-indazol-6-yl)-N-(3-fluoro-2-methylphenyl)acrylamide

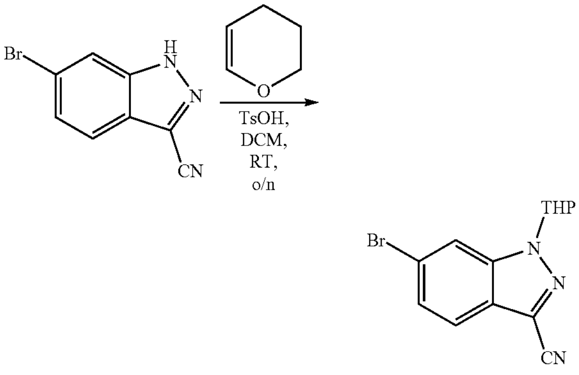

Step 1: Into a 40-mL sealed tube purged and maintained with an inert atmosphere of nitrogen, was placed 6-bromo-1H-indazole-3-carbonitrile (220.0 mg, 0.99 mmol, 1.0 equiv), dihydropyran (416.7 mg, 4.95 mmol, 5.0 equiv), DCM (10.0 mL), TsOH (34.1 mg, 0.20 mmol, 0.20 equiv). The resulting solution was stirred overnight at room temperature. The resulting mixture was concentrated. The residue was applied onto a silica gel column with THF:PE (1:20-1:8). This resulted in 300 mg (99%) of 6-bromo-1-(oxan-2-yl) indazole-3-carbonitrile as a off-white solid.

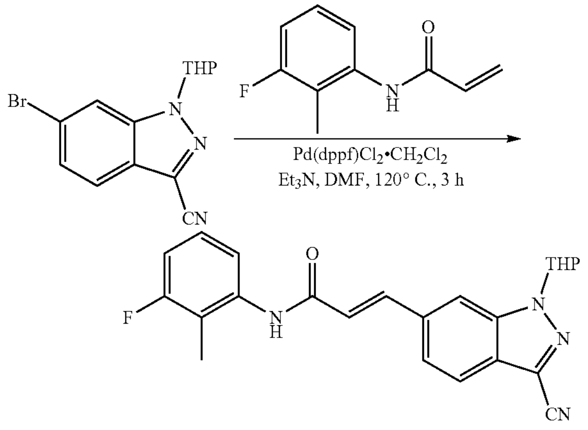

Step 2: Into a 8-mL sealed tube purged and maintained with an inert atmosphere of nitrogen, was placed N-(3-fluoro-2-methylphenyl)acrylamide (150.0 mg, 0.84 mmol, 1.0 equiv), 6-bromo-1-(oxan-2-yl) indazole-3-carbonitrile (307.5 mg, 1.0 mmol, 1.20 equiv), $Pd(dppf)Cl_2{\cdot}CH_2Cl_2$ (68.2 mg, 0.08 mmol, 0.10 equiv), DMF (4.0 mL), $Et_3N$ (0.35 mL, 2.51 mmol, 3.0 equiv). The resulting solution was stirred for 3 h at 120° C. The reaction mixture was cooled to room temperature. The mixture was applied onto a silica gel column with THF:PE (1:4-1:1). This resulted in 150 mg (44%) of (2E)-3-[3-cyano-1-(oxan-2-yl) indazol-6-yl]-N-(3-fluoro-2-methylphenyl)acrylamideas a light brown solid.

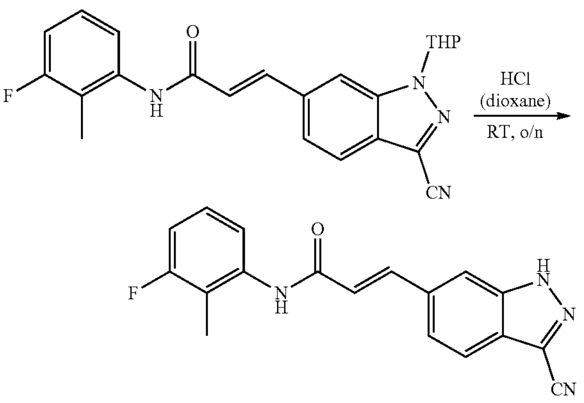

Step 3: Into a 40-mL sealed tube, was placed (2E)-3-[3-cyano-1-(oxan-2-yl) indazol-6-yl]-N-(3-fluoro-2-methylphenyl)acrylamide (150.0 mg, 0.37 mmol, 1.0 equiv), 4M HCl/dioxane (10 mL). The resulting solution was stirred overnight at room temperature. The resulting mixture was concentrated. The crude product was purified by Prep-HPLC. This resulted in 12.5 mg (11%) of (E)-3-(3-cyano-1H-indazol-6-yl)-N-(3-fluoro-2-methylphenyl)acrylamide as a off-white solid.

LC-MS (ES, m/z): $[M+H]^+$=321

$^1$H NMR (300 MHz, DMSO-$d_6$, ppm): δ 14.55 (brs, 1H), 9.68 (s, 1H), 8.0-7.95 (m, 2H), 7.80 (d, J=15.9 Hz, 1H), 7.68 (d, J=9.0 Hz, 1H), 7.49 (d, J=9.6 Hz, 1H), 7.28-7.20 (m, 1H), 7.15 (d, J=15.9 Hz, 1H), 7.05-6.99 (m, 1H), 2.17 (s, 3H).

Example 52: (E)-3-(3-methyl-1H-indazol-6-yl)-N-(3-methylchroman-4-yl)acrylamide

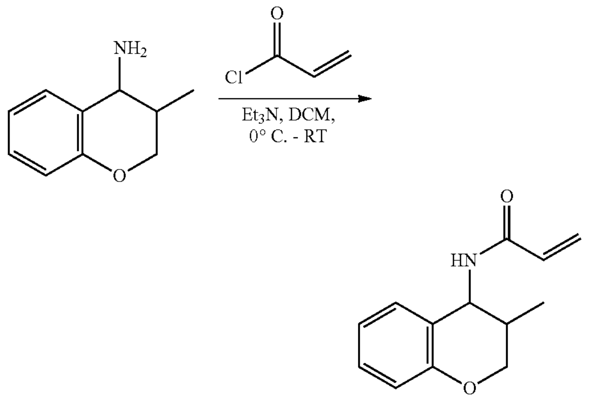

Step 1: Into a 25-mL 3-necked round-bottom flask purged and maintained with an inert atmosphere of nitrogen, was placed 3-methyl-3,4-dihydro-2H-1-benzopyran-4-amine (110.0 mg, 0.67 mmol, 1.0 equiv), DCM (10.0 mL), $Et_3N$ (0.19 mL, 1.35 mmol, 2.0 equiv). This was followed by the addition of acryloyl chloride (67.10 mg, 0.74 mmol, 1.10 equiv) dropwise with stirring at 0° C. The resulting solution was stirred for 2 h at room temperature. The reaction was then quenched by the addition of 10 mL of water. The resulting solution was extracted with 2×15 mL of dichloromethane dried over anhydrous sodium sulfate and concentrated. The residue was applied onto a silica gel column with EtOAc/PE (1/5). This resulted in 110 mg (75%) of N-(3-methyl-3,4-dihydro-2H-1-benzopyran-4-yl)prop-2-enamide as a light yellow solid.

LC-MS (ES, m/z): $[M+H]^+$=218

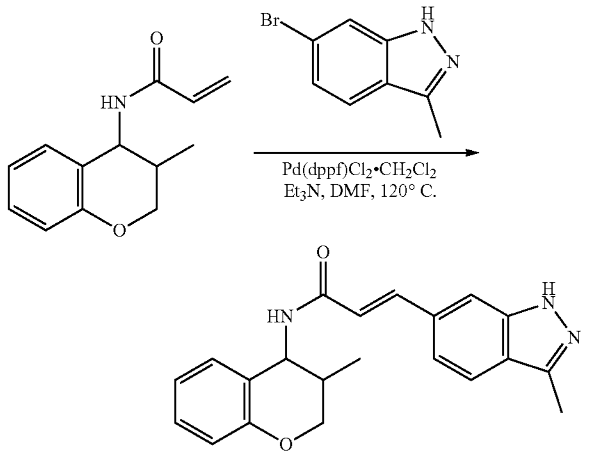

Step 2: Into a 8-mL vial purged and maintained with an inert atmosphere of nitrogen, was placed N-(3-methyl-3,4-dihydro-2H-1-benzopyran-4-yl)prop-2-enamide (120.0 mg, 0.55 mmol, 1.0 equiv), DMF (5.0 mL), 6-bromo-3-methyl-1H-indazole (116.6 mg, 0.55 mmol, 1.0 equiv), $Et_3N$ (0.23 mL, 1.66 mmol, 3.0 equiv), $Pd(dppf)Cl_2 \cdot CH_2Cl_2$ (22.50 mg, 0.028 mmol, 0.05 equiv). The resulting solution was stirred for 5 h at 120° C. The reaction mixture was cooled to room temperature. The residue was applied onto a silica gel column with EtOAc (1/3). This resulted in 55 mg (29%) of (E)-3-(3-methyl-1H-indazol-6-yl)-N-(3-methylchroman-4-yl)acrylamide as a off-white solid. LC-MS (ES, m/z): $[M+H]^+$=348

$^1H$ NMR (300 MHz, DMSO-$d_6$, ppm): 12.80 (brs, 1H), 8.52-8.33 (m, 1H), 7.74-7.62 (m, 3H), 7.33-7.28 (m, 1H), 7.18-7.13 (m, 2H), 6.92-6.73 (m, 3H), 5.24-4.81 (m, 1H), 4.24-4.10 (m, 1H), 3.98-3.88 (m, 1H), 2.50-2.49 (m, 3H), 2.28-2.04 (m, 1H), 0.98-0.90 (m, 3H).

Example 53: (E)-N-(2-methyl-1,2,3,4-tetrahydronaphthalen-1-yl)-3-(3-methyl-1H-indazol-6-yl)acrylamide

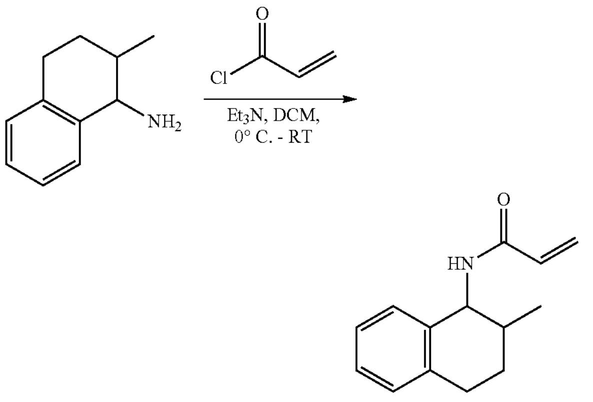

Step 1: Into a 25-mL 3-necked round-bottom flask purged and maintained with an inert atmosphere of nitrogen, was placed 2-methyl-1,2,3,4-tetrahydronaphthalen-1-amine (160.0 mg, 0.99 mmol, 1.0 equiv), DCM (10.0 mL), $Et_3N$ (0.28 mL, 1.98 mmol, 2.0 equiv). This was followed by the addition of acryloyl chloride (98.79 mg, 1.09 mmol, 1.10 equiv) dropwise with stirring at 0° C. The resulting solution was stirred for 2 h at room temperature. The reaction was then quenched by the addition of 5 mL of water. The resulting solution was extracted with 2×10 mL of DCM and the organic layer was dried over anhydrous sodium sulfate and concentrated. The residue was applied onto a silica gel column with EtOAc/PE (1/5). This resulted in 140 mg (66%) of N-(2-methyl-1,2,3,4-tetrahydronaphthalen-1-yl)prop-2-enamide as a light yellow solid.

LC-MS (ES, m/z): $[M+H]^+$=216

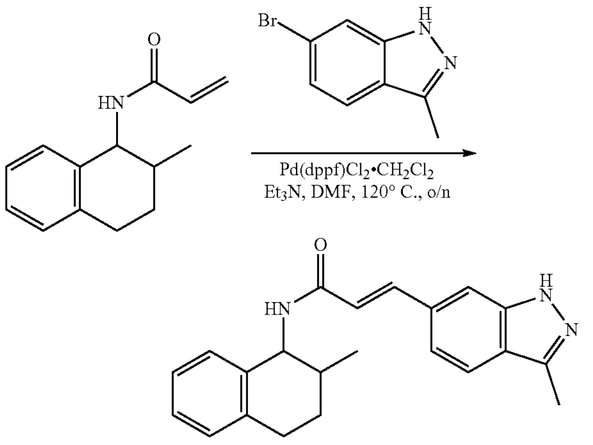

Step 2: Into a 8-mL vial purged and maintained with an inert atmosphere of nitrogen, was placed N-(2-methyl-1,2,3,4-tetrahydronaphthalen-1-yl)prop-2-enamide (140.0 mg, 0.65 mmol, 1.0 equiv), DMF (5.0 mL), 6-bromo-3-methyl-1H-indazole (137.3 mg, 0.65 mmol, 1.0 equiv), $Et_3N$ (0.27 mL, 1.95 mmol, 3.0 equiv), $Pd(dppf)Cl_2 \cdot CH_2Cl_2$ (26.5 mg, 0.033 mmol, 0.05 equiv). The resulting solution was stirred for 5 h at 120° C. The reaction mixture was cooled to room temperature. The crude mixture was purified by Prep-HPLC. This resulted in 30 mg (13%) of (E)-N-(2-methyl-1,2,3,4-tetrahydronaphthalen-1-yl)-3-(3-methyl-1H-indazol-6-yl) acrylamide as a off-white solid. LC-MS (ES, m/z): $[M+H]^+=346$ $^1H$ NMR (300 MHz, DMSO-d6, ppm): 12.77 (brs, 1H), 8.39-8.15 (m, 1H), 7.74-7.59 (m, 3H), 7.34-7.11 (m, 5H), 6.84-6.76 (m, 1H), 5.23-4.76 (m, 1H), 2.84-2.77 (m, 2H), 2.51-2.48 (m, 3H), 2.08-1.98 (m, 1H), 1.97-1.52 (m, 2H), 1.10-0.90 (m, 3H).

Example 54: (E)-N-((1S,2S)-2-methoxy-2,3-dihydro-1H-inden-1-yl)-3-(3-methyl-1H-indazol-6-yl) acrylamide

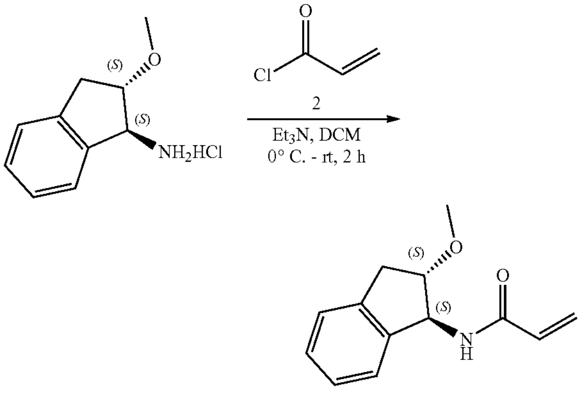

Step 1: Into a 100-mL 3-necked round-bottom flask purged and maintained with an inert atmosphere of nitrogen, was placed (1S,2S)-2-methoxy-2,3-dihydro-1H-inden-1-amine hydrochloride (300.0 mg, 1.50 mmol, 1.0 equiv), DCM (20.0 mL), $Et_3N$ (0.31 mL, 2.25 mmol, 1.50 equiv). This was followed by the addition of acryloyl chloride (163.2 mg, 1.80 mmol, 1.20 equiv) dropwise with stirring at 0° C. The resulting solution was stirred for 2 h at room temperature. The resulting mixture was concentrated. The residue was applied onto a silica gel column with THF:PE (1:5-1:3). This resulted in 200 mg (61%) of N-[(1S,2S)-2-methoxy-2,3-dihydro-1H-inden-1-yl]prop-2-enamide as a off-white solid.

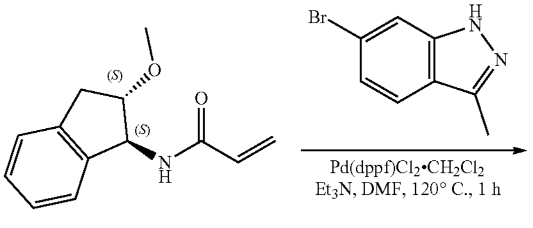

-continued

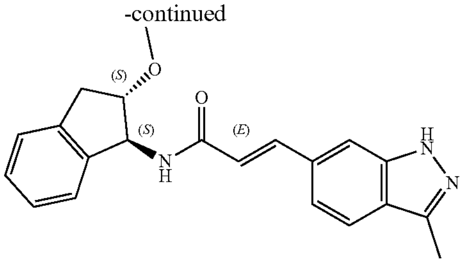

Step 2: Into a 8-mL sealed tube purged and maintained with an inert atmosphere of nitrogen, was placed N-[(1S,2S)-2-methoxy-2,3-dihydro-1H-inden-1-yl]prop-2-enamide (140.0 mg, 0.64 mmol, 1.0 equiv), 6-bromo-3-methyl-1H-indazole (163.2 mg, 0.77 mmol, 1.20 equiv), Pd(dppf) $Cl_2 \cdot CH_2Cl_2$ (52.5 mg, 0.064 mmol, 0.10 equiv), DMF (4 mL), $Et_3N$ (0.27 mL, 1.93 mmol, 3.0 equiv). The resulting solution was stirred for 1 h at 120° C. The reaction mixture was cooled to room temperature. The crude mixture was purified by Flash-Prep-HPLC. This resulted in 28.6 mg (13%) of (E)-N-((1S,2S)-2-methoxy-2,3-dihydro-1H-inden-1-yl)-3-(3-methyl-1H-indazol-6-yl)acrylamide as an off-white solid. LC-MS (ES, m/z): $[M+H]^+=348$ $^1H$ NMR (300 MHz, DMSO-$d_6$, ppm): δ 12.78 (brs, 1H), 8.58 (d, J=8.7 Hz, 1H), 7.74-7.62 (m, 3H), 7.33-7.18 (m, 5H), 6.75 (d, J=15.6 Hz, 1H), 5.34-5.30 (m, 1H), 4.07-4.01 (m, 1H), 3.38 (s, 3H), 3.35-3.27 (m, 1H), 2.84-2.76 (m, 1H), 2.49 (s, 3H).

Example 55: (R,E)-N-(2,3-dihydro-1H-inden-1-yl)-3-(3-methyl-1H-indazol-6-yl)acrylamide

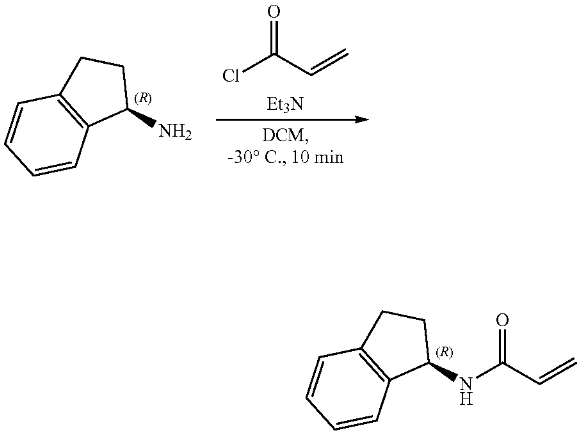

Step 1: Into a 8-mL sealed tube, was placed (1R)-2,3-dihydro-1H-inden-1-amine (100.0 mg, 0.75 mmol, 1.0 equiv), DCM (5.0 mL), $Et_3N$ (0.21 mL, 1.50 mmol, 2.0 equiv). This was followed by the addition of acryloyl chloride (81.54 mg, 0.90 mmol, 1.20 equiv) at −30° C. The resulting solution was stirred for 10 min at −30° C. The reaction was then quenched by the addition of 5 mL of water. The organic phase was dried over $Na_2SO_4$ and concentrated. The residue was applied onto a silica gel column with ethyl acetate/petroleum ether (15:75). This resulted in 93 mg (66%) of N-[(1R)-2,3-dihydro-1H-inden-1-yl]prop-2-enamide as a white solid. LC-MS-PH-NRG0457-1 (ES, m/z): $[M+H]^+=188$

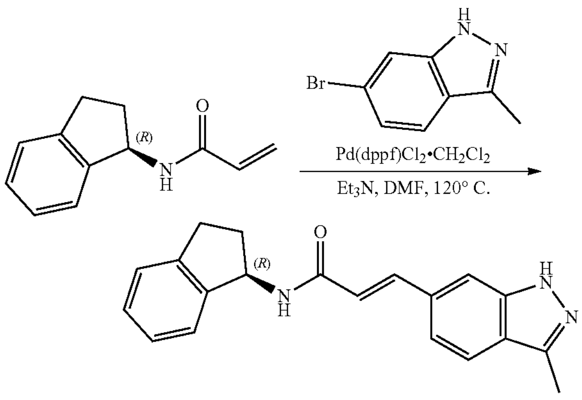

Step 2: Into a 8-mL sealed tube purged and maintained with an inert atmosphere of nitrogen, was placed N-[(1R)-2,3-dihydro-1H-inden-1-yl]prop-2-enamide (60.0 mg, 0.32 mmol, 1.0 equiv), 6-bromo-3-methyl-1H-indazole (67.63 mg, 0.32 mmol, 1.0 equiv), DMF (2.0 mL), $Et_3N$ (0.09 mL, 0.64 mmol, 2.0 equiv), $Pd(dppf)Cl_2{\cdot}CH_2Cl_2$ (5.2 mg, 0.06 mmol, 0.02 equiv). The resulting solution was stirred for 2 h at 120° C. The crude mixture was purified by Flash-Prep-HPLC. This resulted in 41 mg (40%) of (R,E)-N-(2,3-dihydro-1H-inden-1-yl)-3-(3-methyl-1H-indazol-6-yl)acrylamide as a white solid. LC-MS (ES, m/z): $[M+H]^+$=318

$^1$H NMR (300 MHz, DMSO-$d_6$, ppm): 12.78 (s, 1H), 8.47 (d, J=8.4 Hz, 1H), 7.73-7.62 (m, 3H), 7.32-7.17 (m, 5H), 6.74 (d, J=15.9 Hz, 1H), 5.47-5.39 (m, 1H), 3.03-2.79 (m, 2H), 2.51-2.41 (m, 4H), 1.90-1.81 (m, 1H).

Example 56: (E)-N-(chroman-4-yl)-3-(2-oxo-2,3-dihydrobenzo[d]oxazol-5-yl)acrylamide

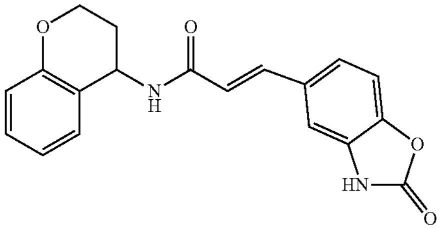 [SMILES: O=C(/C=C/c1ccc2oc(=O)[nH]c2c1)NC1CCOc2ccccc21]

Prepared according to Example 11, Step 4 using (E)-3-(2-oxo-2,3-dihydrobenzo[d]oxazol-5-yl)acrylic acid and chroman-4-amine to give (E)-N-(chroman-4-yl)-3-(2-oxo-2,3-dihydrobenzo[d]oxazol-5-yl)acrylamide as a white solid. LC-MS (ES, m/z): $[M+H]^+$=337

Example 57: (E)-3-(2-oxo-2,3-dihydrobenzo[d]oxazol-5-yl)-N-(1,2,3,4-tetrahydronaphthalen-1-yl)acrylamide

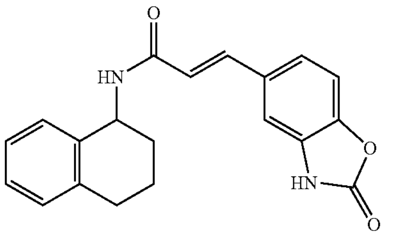 [SMILES: O=C(/C=C/c1ccc2oc(=O)[nH]c2c1)NC1CCCc2ccccc21]

Prepared according to Example 11, Step 4 using (E)-3-(2-oxo-2,3-dihydrobenzo[d]oxazol-5-yl)acrylic acid and 1,2,3,4-tetrahydronaphthalen-1-amine to give (E)-3-(2-oxo-2,3-dihydrobenzo[d]oxazol-5-yl)-N-(1,2,3,4-tetrahydronaphthalen-1-yl)acrylamide as a white solid.

LC-MS (ES, m/z): $[M+H]^+$=335

Example 58: (E)-N-(2-methyl-1,2,3,4-tetrahydronaphthalen-1-yl)-3-(2-oxoindolin-6-yl)acrylamide

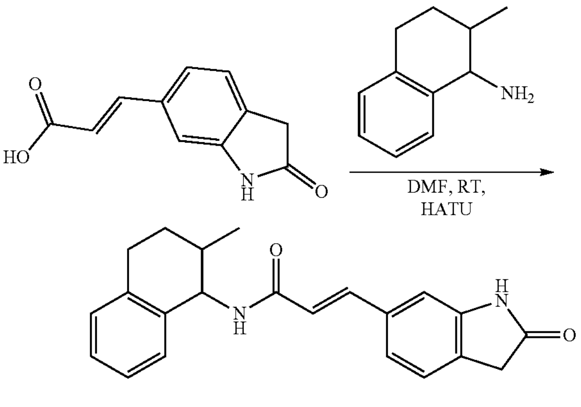

Into a 8-mL vial, was placed (E)-3-(2-oxoindolin-6-yl) acrylic acid (50.0 mg, 0.25 mmol, 1.00 equiv), 2-methyl-1,2,3,4-tetrahydronaphthalen-1-amine (40.3 mg, 0.25 mmol, 1.00 equiv), HATU (141.4 mg, 0.37 mmol, 1.50 equiv) and DIPEA (95.4 mg, 0.74 mmol, 3.00 equiv) in DMF (2.00 mL). The resulting solution was stirred for 2 h at 20° C. The mixture was purified by Flash-Prep-HPLC. This resulted in 19 mg (22%) of (E)-N-(2-methyl-1,2,3,4-tetrahydronaphthalen-1-yl)-3-(2-oxoindolin-6-yl)acrylamide as a off-white solid. LC-MS (ES, m/z): $[M+H]^+$=347

$^1$H NMR (300 MHz, DMSO-d6, ppm) δ 10.51 (brs, 1H), 8.40-8.20 (m, 1H), 7.50-7.45 (m, 1H), 7.27-7.14 (m, 6H), 7.05-6.96 (m, 1H), 6.68-6.63 (m, 1H), 5.45-5.00 (m, 1H), 3.51 (s, 2H), 3.10-3.00 (m, 1H), 2.70-2.20 (m, 4H), 1.20-0.91 (m, 3H).

Example 59: (E)-N-(2,3-dihydro-1H-inden-1-yl)-3-(2-oxoindolin-6-yl)acrylamide

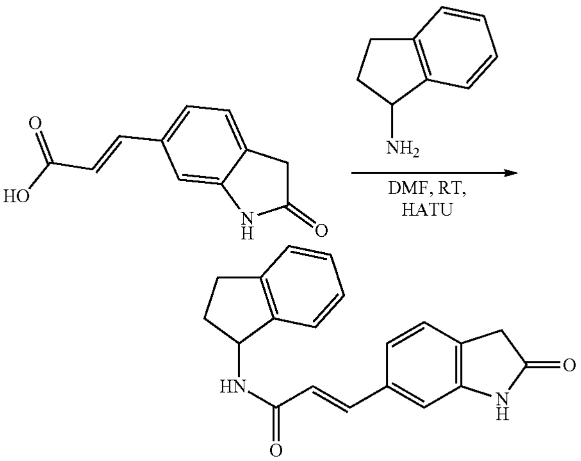

Into a 8-mL vial, was placed (E)-3-(2-oxoindolin-6-yl) acrylic acid (50.0 mg, 0.25 mmol, 1.00 equiv), 2,3-dihydro-1H-inden-1-amine (33.3 mg, 0.25 mmol, 1.00 equiv), HATU (141.4 mg, 0.37 mmol, 1.50 equiv) and DIPEA (95.4 mg, 0.74 mmol, 3.00 equiv) in DMF (2.00 mL). The resulting solution was stirred for 2 h at 20° C. The mixture was purified by Flash-Prep-HPLC. This resulted in 15 mg (19%) of (E)-N-(2,3-dihydro-1H-inden-1-yl)-3-(2-oxoindolin-6-yl)acrylamide as a off-white solid. LC-MS (ES, m/z): $[M+H]^+=319$ $^1H$ NMR (300 MHz, DMSO-d6, ppm) δ 10.50 (brs, 1H), 8.46 (d, J=8.1 Hz, 1H), 7.45 (d, J=15.6 Hz, 1H), 7.29-7.12 (m, 6H), 6.98 (s, 1H), 6.62 (d, J=15.9 Hz, 1H), 5.45-5.37 (m, 1H), 3.51 (s, 2H), 3.02-2.79 (m, 2H), 2.50-2.40 (m, 1H), 1.89-1.82 (m, 1H).

Example 60: (E)-N-(3,5-difluoro-2-methylphenyl)-3-(2-oxoindolin-6-yl)acrylamide

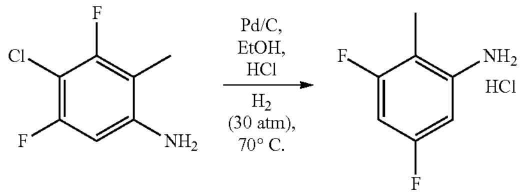

Step 1: Into a 100-mL pressure tank reactor, was placed 4-chloro-3,5-difluoro-2-methylaniline (160.00 mg, 0.90 mmol, 1.00 equiv), EtOH (30.00 mL), 4M HCl/EtOH (1.00 mL), Pd/C (47.94 mg). The flask was evacuated and flushed three times with nitrogen, followed by flushing with hydrogen. The resulting solution was stirred overnight at 70° C. under an atmosphere of hydrogen (30 atm). The reaction mixture was cooled to room temperature. The solids were filtered out. The resulting mixture was concentrated. This resulted in 120 mg (crude) of 3,5-3,5-difluoro-2-methylaniline hydrochloride.

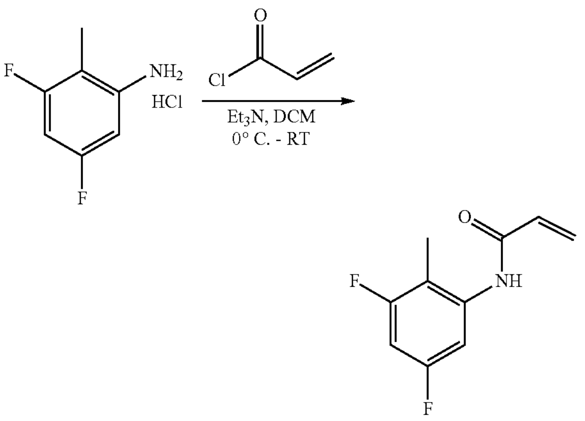

Step 2: Into a 100-mL 3-necked round-bottom flask purged and maintained with an inert atmosphere of nitrogen, was placed 3,5-difluoro-2-methylaniline hydrochloride (120.00 mg, 0.67 mmol, 1.00 equiv), DCM (20 mL), $Et_3N$ (0.28 mL, 2.01 mmol, 3.00 equiv). This was followed by the addition of acryloyl chloride (90.7 mg, 1.00 mmol, 1.50 equiv) dropwise with stirring at 0° C. The resulting solution was stirred overnight at room temperature. The resulting mixture was concentrated. The residue was applied onto a silica gel column with THF:PE (1:5-1:3). This resulted in 120 mg (91%) of N-(3,5-difluoro-2-methylphenyl)prop-2-enamide as a off-white solid.

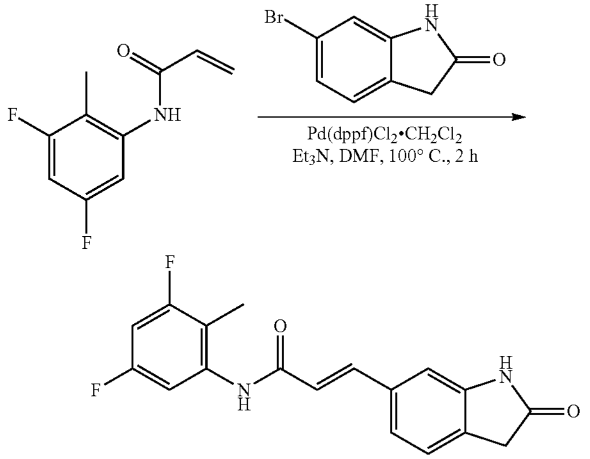

Step 3: Into a 8-mL sealed tube purged and maintained with an inert atmosphere of nitrogen, was placed N-(3,5-difluoro-2-methylphenyl)prop-2-enamide (120.00 mg, 0.61 mmol, 1.00 equiv), 6-bromo-1,3-dihydroindol-2-one (154.9 mg, 0.73 mmol, 1.20 equiv), $Pd(dppf)Cl_2 \cdot CH_2Cl_2$ (49.6 mg, 0.06 mmol, 0.10 equiv), DMF (4.00 mL), $Et_3N$ (0.25 mL, 1.83 mmol, 3.00 equiv). The resulting solution was stirred for 2 h at 100° C. The reaction mixture was cooled to room temperature. The crude mixture was purified by Prep-HPLC. This resulted in 11.3 mg (6%) of (E)-N-(2,3-dihydro-1H-inden-1-yl)-3-(2-oxoindolin-6-yl)acrylamide as a off-white solid.

LC-MS (ES, m/z): $[M+H]^+=329$ $^1H$ NMR (300 MHz, DMSO-$d_6$, ppm): δ 10.57 (s, 1H), 9.88 (s, 1H), 7.95-7.90 (m, 1H), 7.54 (d, J=15.6 Hz, 1H), 7.31-7.17 (m, 3H), 7.04 (s, 1H), 6.96 (d, J=15.3 Hz, 1H), 3.52 (s, 2H), 2.22 (s, 3H).

Example 61: (E)-N-(2,3-dihydro-1H-inden-1-yl)-3-(7-fluoro-1H-benzo[d][1,2,3]triazol-6-yl)acrylamide

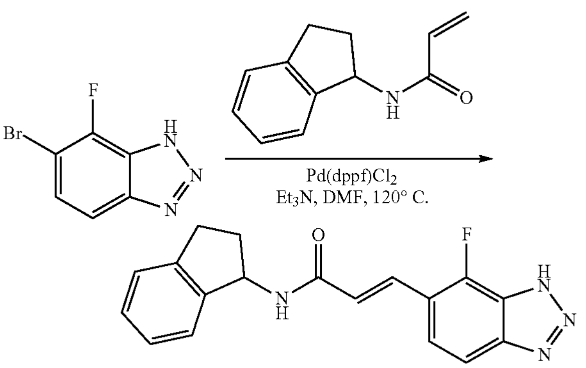

Into a 8-mL round-bottom flask, was placed 5-bromo-4-fluoro-3H-1,2,3-benzotriazole (50.0 mg, 0.23 mmol, 1.00 equiv), N-(2,3-dihydro-1H-inden-1-yl)prop-2-enamide (43.3 mg, 0.23 mmol, 1.00 equiv), Pd(dppf)$Cl_2$ (16.9 mg, 0.023 mmol, 0.10 equiv), $Et_3N$ (0.096 mL, 0.70 mmol, 3.00 equiv), DMF (3.00 mL). The resulting solution was stirred for 2 h at 120° C. in an oil bath. The reaction mixture was cooled. The residue was applied onto a silica gel column with PE/THF (1/1). This resulted in 19 mg (25%) of (E)-N-(2,3-dihydro-1H-inden-1-yl)-3-(7-fluoro-1H-benzo[d][1,2,3]triazol-6-yl)acrylamide as a solid. LC-MS (ES, m/z): $[M+H]^+$=323

$^1$H NMR (300 MHz, DMSO-$d_6$, ppm): δ 8.63 (d, J=8.1 Hz, 1H), 7.93-7.63 (m, 3H), 7.32-7.15 (m, 4H), 6.85 (d, J=15.9 Hz, 1H), 5.47-5.35 (m, 1H), 3.06-2.81 (m, 2H), 2.47-2.39 (m, 1H), 1.90-1.78 (m, 1H).

Example 62: (E)-N-(2,3-dihydro-1H-inden-1-yl)-3-(4-fluoro-1H-benzo[d][1,2,3]triazol-6-yl)acrylamide

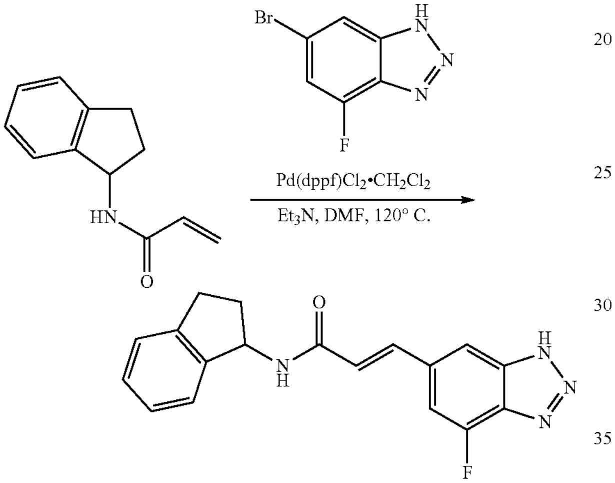

Into a 8-mL round-bottom flask, was placed 6-bromo-4-fluoro-1H-1,2,3-benzotriazole (40.00 mg, 0.18 mmol, 1.00 equiv), N-(2,3-dihydro-1H-inden-1-yl)prop-2-enamide (34.7 mg, 0.18 mmol, 1.00 equiv), Pd(dppf)$Cl_2$ (13.6 mg, 0.019 mmol, 0.10 equiv) and $Et_3N$ (0.077 mL, 0.55 mmol, 3.00 equiv) in DMF (2.00 mL). The resulting solution was stirred for 1 h at 120° C. in an oil bath. The reaction mixture was cooled. The mixture was applied onto a silica gel column with PE/THF (1/1). This resulted in 17.8 mg (30%) of (E)-N-(2,3-dihydro-1H-inden-1-yl)-3-(4-fluoro-1H-benzo[d][1,2,3]triazol-6-yl)acrylamide as a white solid. LC MS (ES, m/z): $[M+H]^+$=323

$^1$H NMR (300 MHz, DMSO-$d_6$, ppm): δ 8.51 (d, J=8.1 Hz, 1H), 7.90 (s, 1H), 7.68 (d, J=15.6 Hz, 1H), 7.41 (d, J=12.0 Hz, 1H), 7.28-7.15 (m, 4H), 6.77 (d, J=15.6 Hz, 1H), 5.47-5.34 (m, 1H), 3.03-2.81 (m, 2H), 2.44-2.35 (m, 1H), 1.93-1.78 (m, 1H).

Example 63: (E)-N-(5-chloro-2-methylphenyl)-3-(2-oxo-2,3-dihydrobenzo[d]oxazol-5-yl)acrylamide

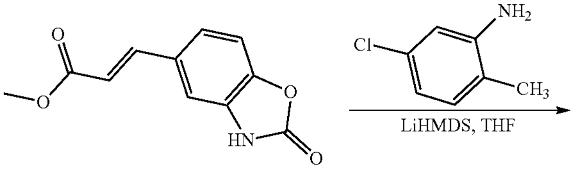

-continued

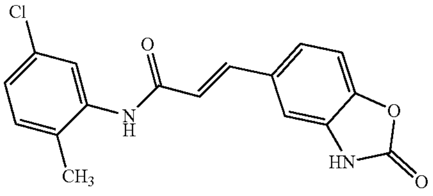

Into a 8-mL sealed tube purged and maintained with an inert atmosphere of nitrogen, was placed (E)-methyl 3-(2-oxo-2,3-dihydrobenzo[d]oxazol-5-yl)acrylate (30.0 mg, 0.14 mmol, 1.00 equiv) in THF (2.00 mL). Then 5-chloro-2-methylbenzenamine (25.4 mg, 0.18 mmol, 1.30 equiv) was added. The reaction mixture was cooled to 0° C. Then 1M LiHMDS (0.68 mL, 0.68 mmol, 5.00 equiv) was added. The reaction mixture was stirred 1 h at RT. The reaction mixture was quenched by 1 mL water and extracted with 2×5 mL ETOAc, the organic was concentrated under vacuum to afford crude product. The crude product was then purified by Prep-HPLC. This resulted in 5 mg (11%) of (E)-N-(5-chloro-2-methylphenyl)-3-(2-oxo-2,3-dihydrobenzo[d]oxazol-5-yl)acrylamide as a white solid. LC-MS (ES, m/z): $[M+H]^+$=329

$^1$H NMR (300 MHz, DMSO-$d_6$, ppm) δ 9.42 (s, 1H), 7.85 (s, 1H), 7.60 (d, J=15.9 Hz, 1H), 7.36-7.11 (m, 5H), 6.97 (d, J=15.6 Hz, 1H), 2.26 (s, 3H).

Example 64: (E)-N-(2-methylcyclohexyl)-3-(2-oxoindolin-6-yl)acrylamide

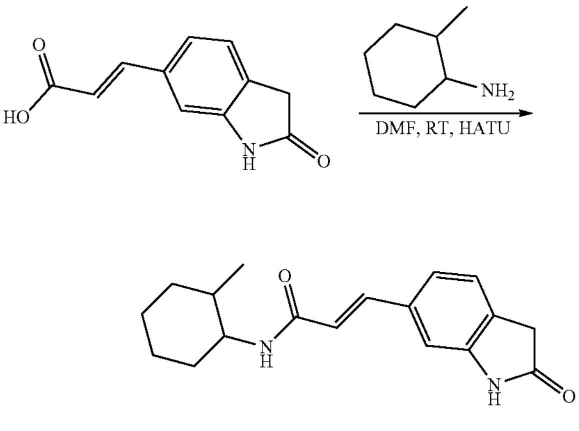

Into a 8-mL vial, was placed (E)-3-(2-oxoindolin-6-yl) acrylic acid (50.00 mg, 0.25 mmol, 1.00 equiv), 2-methyl-cyclohexanamine (28.25 mg, 0.25 mmol, 1.00 equiv), HATU (141.38 mg, 0.37 mmol, 1.50 equiv) and DIPEA (95.41 mg, 0.74 mmol, 3.00 equiv) in DMF (2.00 mL). The resulting solution was stirred for 2 h at 20° C. The mixture was purified by Flash-Prep-HPLC. This resulted in 8.3 mg (11%) of (E)-N-(2-methylcyclohexyl)-3-(2-oxoindolin-6-yl) acrylamide as a off-white solid. LC-MS (ES, m/z): $[M+H]^+$=299

Example 65: (E)-3-(3-methyl-1H-indazol-6-yl)-N-(3-methylchroman-4-yl)acrylamide

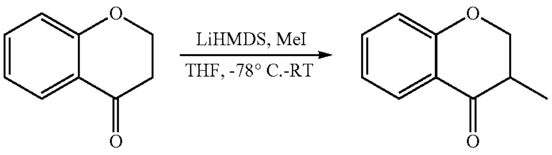

Step 1: Into a 500-mL 3-necked round-bottom flask purged and maintained with an inert atmosphere of nitrogen, was placed 2,3-dihydro-1-benzopyran-4-one (15.00 g, 101.24 mmol, 1.00 equiv) and THF (200 mL). This was followed by the addition of LiHMDS (1 M in THF, 1.20 equiv) dropwise with stirring at −78° C. The resulting solution was stirred for 40 min at −78° C. To this was added a solution of MeI (17.24 g, 121.49 mmol, 1.20 equiv) in THF (10 mL) dropwise with stirring at −78° C. The resulting solution was allowed to react, with stirring, for an additional 40 min at −78° C. Then stirred for an additional 1 h at 25° C. The reaction was then quenched by the addition of 150 mL of $NH_4Cl$. The resulting solution was extracted with 2×150 mL of ethyl acetate and the organic layer was dried over anhydrous sodium sulfate and concentrated. The residue was applied onto a silica gel column with ethyl acetate/petroleum ether (1/10). This resulted in 5 g (30% yield) of 3-methyl-2,3-dihydro-1-benzopyran-4-one as a light yellow oil.

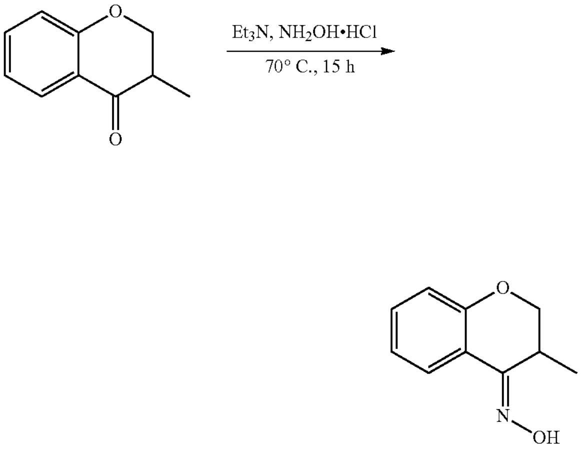

Step 2: Into a 40-mL vial purged and maintained with an inert atmosphere of nitrogen, was placed 3-methyl-2,3-dihydro-1-benzopyran-4-one (1.10 g, 6.78 mmol, 1.00 equiv), MeOH (20.00 mL), $NH_2OH·HCl$ (1.41 g, 20.35 mmol, 3.00 equiv), $Et_3N$ (2.06 g, 20.35 mmol, 3.00 equiv). The resulting solution was stirred for 15 h at 70° C. The resulting mixture was concentrated. The resulting solution was diluted with 10 mL of water. The resulting solution was extracted with 2×10 mL of ethyl acetate and the organic layer was dried over anhydrous sodium sulfate. The resulting mixture was concentrated. This resulted in 1 g (83% yield) of N-[(4E)-3-methyl-2,3-dihydro-1-benzopyran-4-ylidene]hydroxylamine as a white solid.

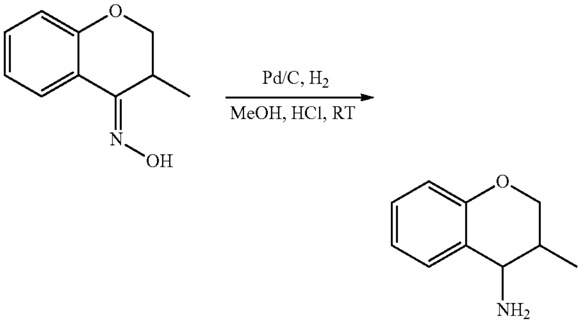

Step 3: Into a 100-mL 1-necked round-bottom flask purged and maintained with an inert atmosphere of $H_2$, was placed N-[(4E)-3-methyl-2,3-dihydro-1-benzopyran-4-ylidene]hydroxylamine (0.70 g, 3.95 mmol, 1.00 equiv), MeOH (20.00 mL), Pd/C (0.06 g). The resulting solution was stirred for 12 h at 40° C. The solids were filtered out. The resulting mixture was concentrated. This resulted in 530 mg (82% yield) of 3-methyl-3,4-dihydro-2H-1-benzopyran-4-amine as light yellow oil.

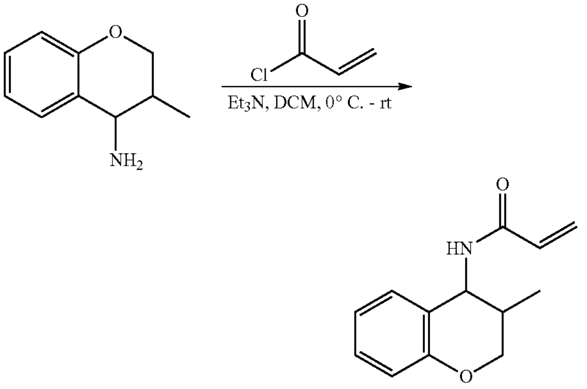

Step 4: Into a 40-mL vial, was placed 3-methyl-3,4-dihydro-2H-1-benzopyran-4-amine (300.00 mg, 1.838 mmol, 1.00 equiv), DCM (10.00 mL), $Et_3N$ (371.98 mg, 3.676 mmol, 2.00 equiv). This was followed by the addition of a solution of acryloyl chloride (182.99 mg, 2.022 mmol, 1.10 equiv) in DCM (2 mL) dropwise with stirring at 0° C. The resulting solution was stirred for 5 h at 0° C. The reaction was then quenched by the addition of 8 mL of water. The resulting solution was extracted with 2×15 mL of dichloromethane and the organic layer was dried over anhydrous sodium sulfate and concentrated. The residue was applied onto a silica gel column with ethyl acetate/petroleum ether (1/2). This resulted in 280 mg (70% yield) of N-(3-methyl-3,4-dihydro-2H-1-benzopyran-4-yl)prop-2-enamide as an off-white solid.

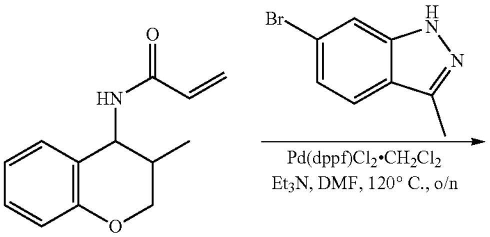

-continued

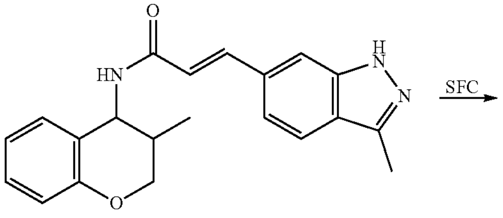

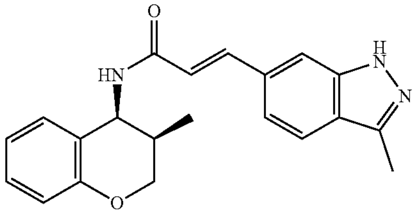

65a

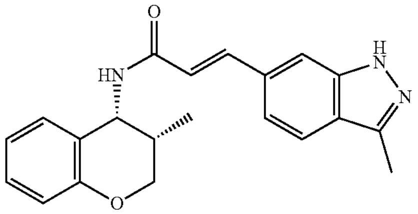

65b

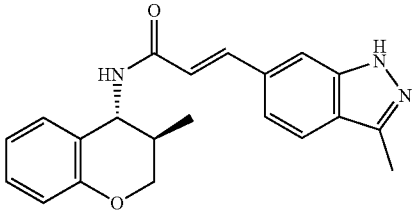

65c

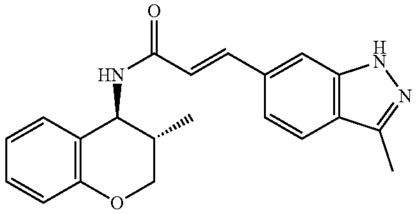

65d

Step 5: Into a 20-mL vial purged and maintained with an inert atmosphere of nitrogen, was placed N-(3-methyl-3,4-dihydro-2H-1-benzopyran-4-yl)prop-2-enamide (150.00 mg, 0.690 mmol, 1.00 equiv), DMF (6.00 mL), 6-bromo-3-methyl-1H-indazole (145.72 mg, 0.690 mmol, 1.00 equiv), $Et_3N$ (174.65 mg, 1.725 mmol, 2.50 equiv), Pd(dppf)$Cl_2 \cdot CH_2Cl_2$ (33.74 mg, 0.041 mmol, 0.06 equiv). The resulting solution was stirred overnight at 120° C. The reaction mixture was cooled to room temperature. The residue was applied onto a silica gel column with ethyl acetate/petroleum ether (1/1). This resulted in 110 mg racemic mixture of cis/trans isomers as a light yellow solid. The mixture was purified by Chiral-Prep-HPLC to give the 4 separated stereoisomers, including (E)-3-(3-methyl-1H-indazol-6-yl)-N-((3R,4R)-3-methylchroman-4-yl)acrylamide (Example 65c). The cis-trans isomers were assigned using NOESY NMR. The stereochemistry of each enantiomeric pair has been assigned arbitrarily.

Example 65a: (E)-3-(3-methyl-1H-indazol-6-yl)-N-((3R,4S)-3-methylchroman-4-yl)acrylamide LC-MS (ES, m/z): $[M+H]^+$=348

$^1$H-NMR (300 MHz, DMSO-$d_6$, ppm): δ 12.77 (s, 1H), 8.33 (d, J=6.6 Hz, 1H), 7.73-7.61 (m, 3H), 7.30-7.16 (m, 3H), 6.91-6.77 (m, 3H), 5.23-5.20 (m, 1H), 4.13 (d, J=8.1 Hz, 1H), Example 65b: (E)-3-(3-methyl-1H-indazol-6-yl)-N-((3S,4R)-3-methylchroman-4-yl)acrylamide LC-MS1 (ES, m/z): $[M+H]^+$=348

$^1$H-NMR (300 MHz, DMSO-$d_6$, ppm): δ 12.77 (s, 1H), 8.33 (d, J=6.9 Hz, 1H), 7.73-7.61 (m, 3H), 7.30-7.16 (m, 3H), 6.91-6.77 (m, 3H), 5.23-5.20 (m, 1H), 4.13 (d, J=8.1 Hz, 1H), 3.94-3.89 (m, 1H), 2.55-2.50 (m, 3H), 2.29-2.33 (m, 1H), 0.91 (d, J=4.5 Hz, 3H).

Example 65c: (E)-3-(3-methyl-1H-indazol-6-yl)-N-((3R,4R)-3-methylchroman-4-yl)acrylamide LC-MS (ES, m/z): $[M+H]^+$=348

$^1$H-NMR (300 MHz, DMSO-$d_6$, ppm): δ 12.77 (s, 1H), 8.49 (d, J=6.3 Hz, 1H), 7.73-7.62 (m, 3H), 7.32-7.30 (m, 1H), 7.18-7.13 (m, 2H), 6.91-6.87 (m, 1H), 6.81-6.74 (m, 2H), 4.86-4.82 (m, 1H), 4.23-4.21 (m, 1H), 3.97-3.95 (m, 1H), 2.55-2.50 (m, 3H), 2.08-2.05 (m, 1H), 0.97 (d, J=5.1 Hz, 3H).

Example 65d: (E)-3-(3-methyl-1H-indazol-6-yl)-N-((3S,4S)-3-methylchroman-4-yl)acrylamide LC-MS (ES, m/z): $[M+H]^+$=348

$^1$H-NMR (300 MHz, DMSO-$d_6$, ppm): δ 12.77 (s, 1H), 8.49 (d, J=6.3 Hz, 1H), 7.73-7.62 (m, 3H), 7.32-7.30 (m, 1H), 7.18-7.13 (m, 2H), 6.91-6.87 (m, 1H), 6.81-6.74 (m, 2H), 4.86-4.82 (m, 1H), 4.23-4.21 (m, 1H), 3.97-3.95 (m, 1H), 2.55-2.50 (m, 3H), 2.08-2.05 (m, 1H), 0.97 (d, J=5.1 Hz, 3H).

Example 66: (E)-3-(3-methyl-1H-indazol-6-yl)-N-((1S,2S)-2-(oxetan-3-ylmethoxy)-2,3-dihydro-1H-inden-1-yl)acrylamide

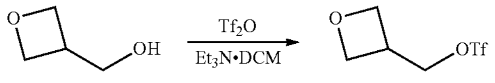 [SMILES: "Tf2O" ; OCC1COC1 ; O=S(=O)(OCC1COC1)C(F)(F)F]

Step 1: Into a 100-mL 3-necked round-bottom flask, was placed oxetan-3-ylmethanol (2.00 g, 22.70 mmol, 1.00 equiv), triflic anhydride (9.61 g, 34.050 mmol, 1.50 equiv), $Et_3N$ (4.59 g, 45.40 mmol, 2.00 equiv), DCM (50.00 mL). The resulting solution was stirred for 10 hr at 20° C. The resulting mixture was washed with 2×50 ml of $NaCO_3$ aq. and 1×50 mL of NaCl aq. The organic layer was dried over anhydrous sodium sulfate and concentrated and used for next step without purification.

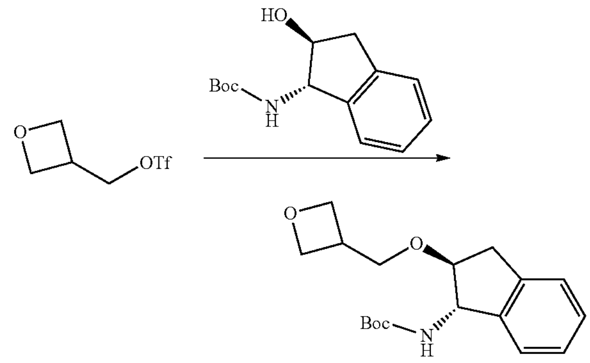

Step 2: Into a 100-mL 3-necked round-bottom flask, was placed tert-butyl N-[(1S,2S)-2-hydroxy-2,3-dihydro-1H-inden-1-yl]carbamate (1.00 g, 4.01 mmol, 1.00 equiv), oxetan-3-ylmethyl trifluoromethanesulfonate (0.88 g, 4.01 mmol, 1.00 equiv), NaH (0.14 g, 6.01 mmol, 1.50 equiv) in THF (20.00 mL). The resulting solution was stirred for 10 hr at 20° C. The reaction was then quenched by the addition of 5 mL of water. The resulting solution was extracted with 2×20 mL of ethyl acetate and the organic layers combined. The organic layer was concentrated and the residue was applied onto a silica gel column with ethyl acetate/petroleum ether (1/1). This resulted in 150 mg of tert-butyl N-[(1S,2S)-2-(oxetan-3-ylmethoxy)-2,3-dihydro-1H-inden-1-yl]carbamate as a solid.

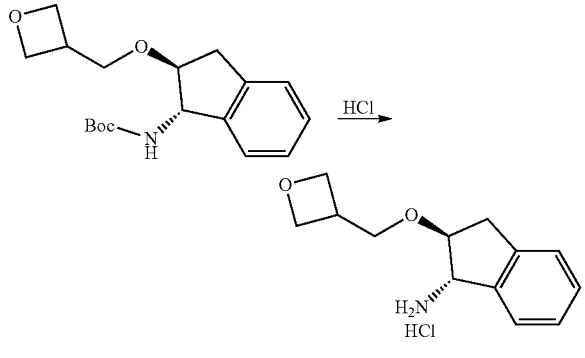

Step 3: Into a 8-mL vial, was placed tert-butyl N-[(1S, 2S)-2-(oxetan-3-ylmethoxy)-2,3-dihydro-1H-inden-1-yl] carbamate (140.00 mg, 0.438 mmol, 1.00 equiv) in 2M HCl(g) in MeOH (2.00 mL) and MeOH (2.00 mL). The resulting solution was stirred for 2 hr at 10° C. The resulting mixture was concentrated. This resulted in 35 mg of (1S, 2S)-2-(oxetan-3-ylmethoxy)-2,3-dihydro-1H-inden-1-amine as a solid.

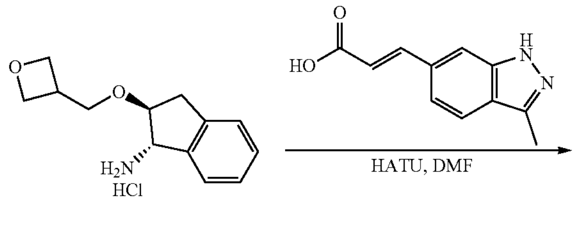

-continued

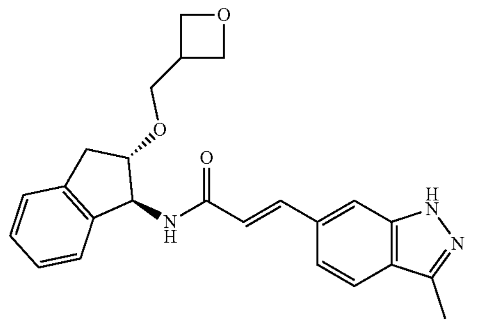

Step 4: Into a 8-mL vial, was placed (1S,2S)-2-(oxetan-3-ylmethoxy)-2,3-dihydro-1H-inden-1-amine (25.00 mg, 0.114 mmol, 1.00 equiv), (E)-3-(3-methyl-1H-indazol-6-yl) acrylic acid (Intermediate 3, 22.83 mg, 0.114 mmol, 1.00 equiv), HATU (65.02 mg, 0.171 mmol, 1.50 equiv) and $Et_3N$ (34.61 mg, 0.342 mmol, 3.00 equiv) in DMF (3.00 mL). The resulting solution was stirred for 2 hr at 20° C. The crude mixture was purified by Prep-HPLC. This resulted in 15 mg of (E)-3-(3-methyl-1H-indazol-6-yl)-N-((1S,2S)-2-(oxetan-3-ylmethoxy)-2,3-dihydro-1H-inden-1-yl)acrylamide as an off-white solid. LC-MS (ES, m/z): $[M+H]^+$=404

$^1$H-NMR (300 MHz, DMSO-$d_6$, ppm) δ 12.78 (s, 1H), 8.58 (d, J=8.4 Hz, 1H), 7.74-7.63 (m, 3H), 7.33-7.22 (m, 5H), 6.75 (d, J=15.9 Hz, 1H), 5.34-5.29 (m, 1H), 4.65-4.60 (m, 2H), 4.32-4.28 (m, 2H), 4.17-4.14 (m, 1H), 3.89-3.86 (m, 1H), 3.84-3.74 (m, 1H), 3.36-3.34 (m, 1H), 3.32-3.31 (m, 1H), 2.86-2.78 (m, 1H), 2.50 (s, 3H).

Example 67: (E)-N-((1S,2S)-2-(cyclopropylmethoxy)-2,3-dihydro-1H-inden-1-yl)-3-(3-methyl-1H-indazol-6-yl)acrylamide

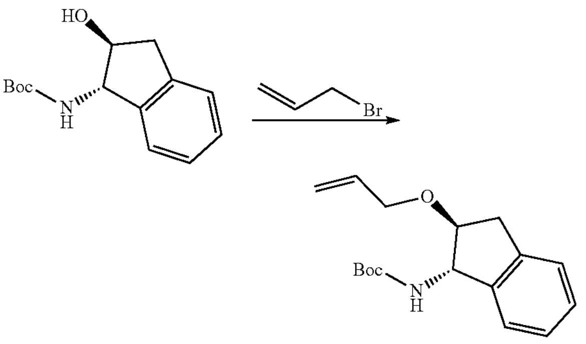

Step 1: Into a 8-mL vial, was placed tert-butyl N-(2-hydroxy-octahydro-1H-inden-1-yl)carbamate (200.00 mg, 0.783 mmol, 1.00 equiv), allyl bromide (94.75 mg, 0.783 mmol, 1.00 equiv) and NaH (5.00 mg, 0.783 mmol, 60%) in THF (3.00 mL). The resulting solution was stirred for 10 hr at 20° C. The reaction was then quenched by the addition of 0.5 mL of water. The mixture was concentrated and the residue was applied onto a silica gel column with ethyl acetate/petroleum ether (1/1). This resulted in 150 mg (66% yield) of tert-butyl N-[(1S,2S)-2-(prop-2-en-1-yloxy)-2,3-dihydro-1H-inden-1-yl]carbamate as a light yellow solid.

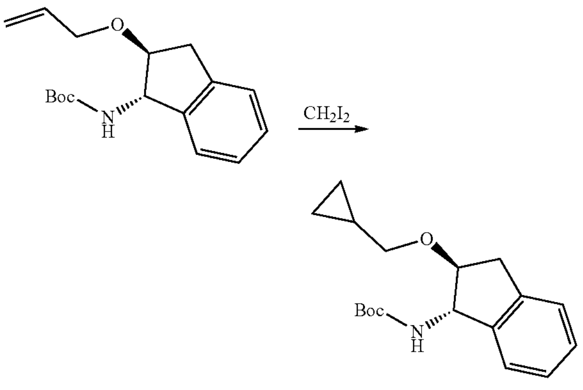

Step 2: Into a 40-mL vial, was placed tert-butyl N-[2-(prop-2-en-1-yloxy)-octahydro-1H-inden-1-yl]carbamate (140.00 mg, 0.474 mmol, 1.00 equiv), 1M $ZnEt_2$ (4.74 mL, 4.739 mmol, 10.00 equiv), $CH_2I_2$(1015.41 mg, 3.791 mmol, 8.00 equiv) and TFA (432.28 mg, 3.791 mmol, 8.00 equiv) in DCM (5.00 mL). The resulting solution was stirred for 10 hr at 20° C. The mixture was concentrated and the residue was applied onto a silica gel column with ethyl acetate/petroleum ether (10/1). This resulted in 70 mg (48% yield) of tert-butyl N-[(1S,2S)-2-(cyclopropylmethoxy)-2,3-dihydro-1H-inden-1-yl]carbamate as a solid.

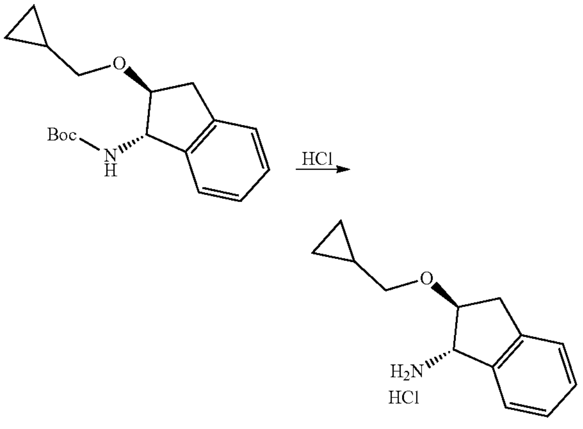

Step 3: Into a 8-mL vial, was placed tert-butyl N-[2-(cyclopropylmethoxy)-octahydro-1H-inden-1-yl]carbamate (50.00 mg, 1.00 equiv). in 2M HCl(g) in MeOH (3.00 mL) and MeOH (3.00 mL). The resulting solution was stirred for 2 hr at 20° C. The resulting mixture was concentrated. This resulted in 30 mg of (1S,2S)-2-(cyclopropylmethoxy)-2,3-dihydro-1H-inden-1-amine as an off-white solid.

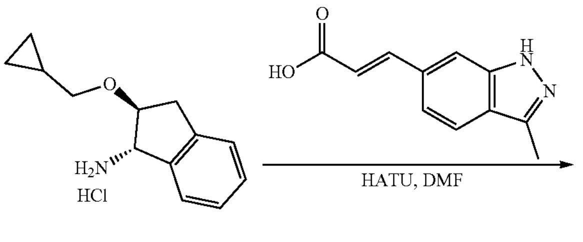

-continued

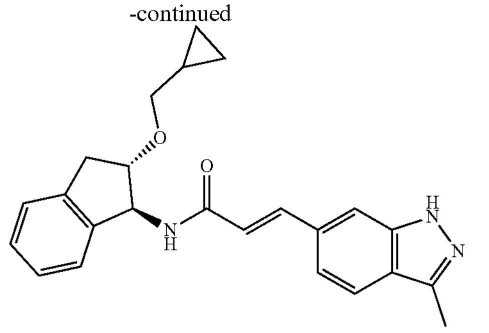

Step 4: Into a 8-mL vial, was placed (1S,2S)-2-(cyclopropylmethoxy)-2,3-dihydro-1H-inden-1-amine (20.00 mg, 0.098 mmol, 1.00 equiv), (E)-3-(3-methyl-1H-indazol-6-yl) acrylic acid (19.70 mg, 0.098 mmol, 1.00 equiv), HATU (56.11 mg, 0.148 mmol, 1.50 equiv) and $Et_3N$ (29.87 mg, 0.295 mmol, 3.00 equiv) in DMF (2.00 mL). The resulting solution was stirred for 2 hr at 20° C. The mixture was purified by Flash-Prep-HPLC. This resulted in 20 mg (52% yield) of (E)-N-((1S,2S)-2-(cyclopropylmethoxy)-2,3-dihydro-1H-inden-1-yl)-3-(3-methyl-1H-indazol-6-yl)acrylamide as an off-white solid. LC-MS (ES, m/z): $[M+H]^+$=388 $^1$H-NMR (300 MHz, DMSO-$d_6$, ppm) δ 8.57 (d, J=8.7 Hz, 1H), 7.74-7.62 (m, 3H), 7.31 (d, J=7.8 Hz, 1H), 7.25-7.19 (m, 4H), 6.74 (d, J=15.6 Hz, 1H), 5.31-5.27 (m, 1H), 4.19-4.12 (m, 1H), 3.48-3.44 (m, 1H), 3.38-3.32 (m, 2H), 2.84-2.73 (m, 1H), 1.04-1.00 (m, 1H), 0.53-0.42 (m, 2H), 0.24-0.12 (m, 2H)

Example 68: (E)-N-((1S,2S)-2-(2-fluoroethoxy)-2,3-dihydro-1H-inden-1-yl)-3-(3-methyl-1H-indazol-6-yl)acrylamide

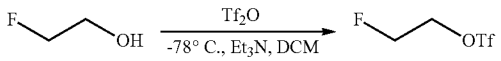

Step 1: Into a 100-mL 3-necked round-bottom flask, was placed 2-fluoroethanol (3.20 g, 49.95 mmol, 1.00 equiv), triflic anhydride (14.09 g, 49.95 mmol, 1.00 equiv) and $Et_3N$ (10.11 g, 99.91 mmol, 2.00 equiv) in DCM (60.00 mL). The resulting solution was stirred for 10 hr at −78° C. in a liquid nitrogen bath. The resulting mixture was washed with 2×50 ml of $NaCO_3$ aq. and 1×50 mL of NaCl aq. The organic layer was dried over anhydrous sodium sulfate and concentrated, the resulted in 9.7 g was used for the next step without purification.

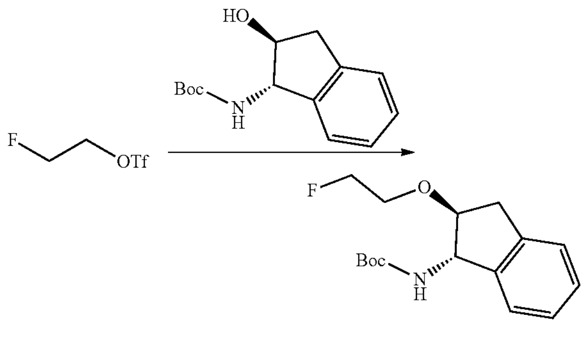

Step 2: Into a 20-mL vial, was placed tert-butyl N-[(1S,2S)-2-hydroxy-2,3-dihydro-1H-inden-1-yl]carbamate (400.00 mg, 1.60 mmol, 1.00 equiv), 2-fluoroethyl trifluoromethanesulfonate (629.32 mg, 3.21 mmol, 2.00 equiv), NaH (77.01 mg, 3.21 mmol, 2.00 equiv) in THF (10.00 mL). The resulting solution was stirred for 10 hr at 20° C. The reaction was then quenched by the addition of 5 mL of water. The resulting solution was extracted with 2×20 mL of ethyl acetate and the organic layers combined. The organic layer was concentrated and the residue was applied onto a silica gel column with ethyl acetate/petroleum ether (1/1). This resulted in 300 mg (63% yield) of tert-butyl N-[(1S,2S)-2-(2-fluoroethoxy)-2,3-dihydro-1H-inden-1-yl]carbamate as a light yellow solid.

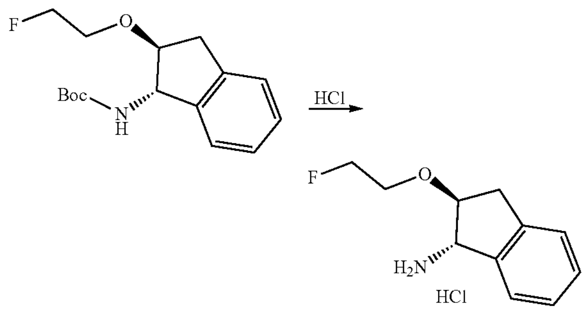

Step 3: Into a 20-mL vial, was placed tert-butyl N-[(1S,2S)-2-(2-fluoroethoxy)-2,3-dihydro-1H-inden-1-yl]carbamate (300.00 mg) in 2M HCl(g) in MeOH (5.00 mL) and MeOH (5.00 mL) was stirred for 10 hr at 20° C. The resulting mixture was concentrated. This resulted in 120 mg of (1S,2S)-2-(2-fluoroethoxy)-2,3-dihydro-1H-inden-1-amine as a light yellow solid.

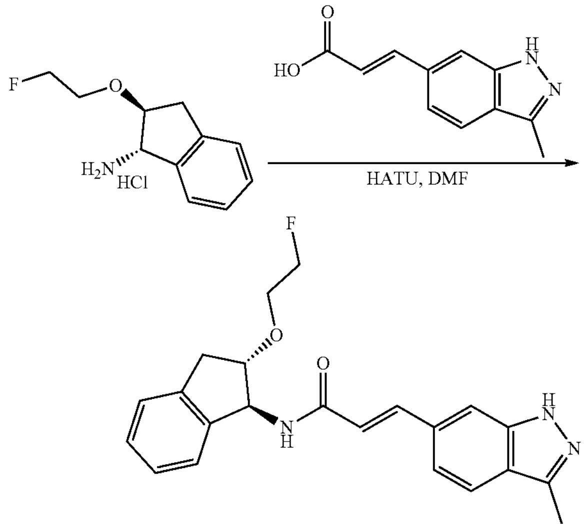 [SMILES: N[C@H]1c2ccccc2C[C@@H]1OCCF ; Cl ; Cc1n[nH]c2cc(/C=C/C(=O)O)ccc12 ; Cc1n[nH]c2cc(/C=C/C(=O)N[C@H]3c4ccccc4C[C@@H]3OCCF)ccc12]

Step 4: Into a 8-mL vial, was placed (1S,2S)-2-(2-fluoroethoxy)-2,3-dihydro-1H-inden-1-amine (40.00 mg, 0.205 mmol, 1.00 equiv), ((E)-3-(3-methyl-1H-indazol-6-yl) acrylic acid (Intermediate 3, 41.03 mg, 0.205 mmol, 1.00 equiv), HATU (116.85 mg, 0.307 mmol, 1.50 equiv), DIPEA (79.44 mg, 0.615 mmol, 3.00 equiv), DMF (2.00 mL). The resulting solution was stirred for 10 hr at 20° C. The mixture was purified by Flash-Prep-HPLC. This resulted in 21 mg of (E)-N-((1S,2S)-2-(2-fluoroethoxy)-2,3-dihydro-1H-inden-1-yl)-3-(3-methyl-1H-indazol-6-yl)acrylamide as an off-white solid. LC-MS (ES, m/z): $[M+H]^+$=380

$^1$H-NMR1(300 MHz, DMSO-$d_6$, ppm) 612.78 (s, 1H), 8.58 (d, J=8.1 Hz, 1H), 7.74-7.62 (m, 3H), 7.33-7.22 (m, 5H), 6.75 (d, J=15.6 Hz, 1H), 5.34-5.29 (m, 1H), 4.65-4.62 (m, 1H), 4.49-4.46 (m, 1H), 4.20-4.16 (m, 1H), 3.97-3.71 (m, 2H), 3.37-3.35 (m, 1H), 2.88-2.80 (m, 1H), 2.50 (s, 3H)

Example 69: (E)-N-((1S,2S)-2-ethoxy-2,3-dihydro-1H-inden-1-yl)-3-(3-methyl-1H-indazol-6-yl)acrylamide

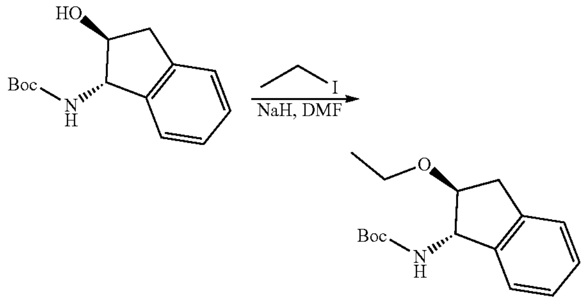

Step 1: Into a 20-mL vial, was placed tert-butyl N-[(1S,2S)-2-hydroxy-2,3-dihydro-1H-inden-1-yl]carbamate (400.00 mg, 1.604 mmol, 1.00 equiv), ethyl iodide (500.47 mg, 3.209 mmol, 2.00 equiv) and NaH (128.36 mg, 3.209 mmol, 2.00 equiv, 60%) in THF (10.00 mL). The resulting solution was stirred for 10 hr at 20° C. The mixture was quenched with 5 ml $H_2O$ and extracted with 30 mL of ethyl acetate. The organic layers combined and dried over anhydrous sodium sulfate and concentrated. The residue was applied onto a silica gel column with ethyl acetate/petroleum ether (1/1). This resulted in 200 mg (45% yield) of tert-butyl N-[(1S,2S)-2-ethoxy-2,3-dihydro-1H-inden-1-yl]carbamate as a light yellow solid.

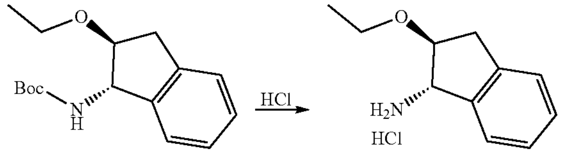 [SMILES: CCO[C@H]1Cc2ccccc2[C@@H]1NC(=O)OC(C)(C)C ; Cl ; CCO[C@H]1Cc2ccccc2[C@@H]1N ; Cl]

Step 2: Into a 20-mL vial, was placed tert-butyl N-[(1S,2S)-2-ethoxy-2,3-dihydro-1H-inden-1-yl]carbamate (170.00 mg) in 2M HCl(g) in MeOH (5.00 mL) and MeOH (5.00 mL) was stirred for 10 hr at 20° C. The resulting mixture was concentrated. This resulted in 80 mg of (1S,2S)-2-ethoxy-2,3-dihydro-1H-inden-1-amine as a light yellow solid.

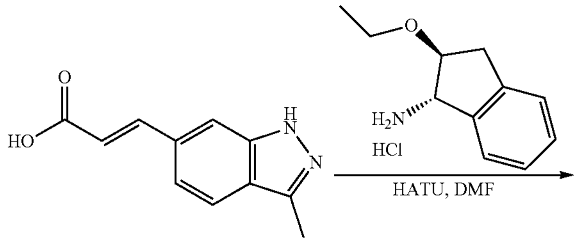

-continued

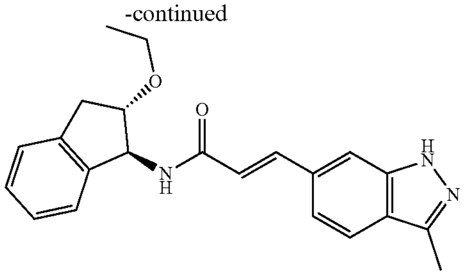

Step 3: Into a 8-mL vial, was placed (1S,2S)-2-ethoxy-2,3-dihydro-1H-inden-1-amine (40.00 mg, 0.226 mmol, 1.00 equiv), (E)-3-(3-methyl-1H-indazol-6-yl)acrylic acid (Intermediate 3, 45.19 mg, 0.226 mmol, 1.00 equiv), HATU (128.71 mg, 0.339 mmol, 1.50 equiv) and DIPEA (87.50 mg, 0.677 mmol, 3.00 equiv) in DMF (2.00 mL). The resulting solution was stirred for 2 hr at 20° C. The mixture was purified by Prep-HPLC. This resulted in 25 mg of (E)-N-((1S,2S)-2-ethoxy-2,3-dihydro-1H-inden-1-yl)-3-(3-methyl-1H-indazol-6-yl)acrylamide as a off-white solid.

LC-MS (ES, m/z): $[M+H]^+$=362

$^1$H-NMR (300 MHz, DMSO-$d_6$, ppm) δ 8.57 (d, J=8.4 Hz, 1H), 7.74-7.63 (m, 3H), 7.33-7.17 (m, 5H), 6.75 (d, J=15.6 Hz, 1H), 5.32-5.28 (m, 1H), 4.14-4.10 (m, 1H), 3.69-3.55 (m, 2H), 3.34-3.26 (m, 1H). 2.83-2.73 (m, 1H), 2.78-2.76 (m, 3H). 1.16-1.12 (m, 3H)

Example 70: (E)-3-(3-cyclopropyl-1H-indazol-6-yl)-N-((1S,2S)-2-methoxy-2,3-dihydro-1H-inden-1-yl) acrylamide

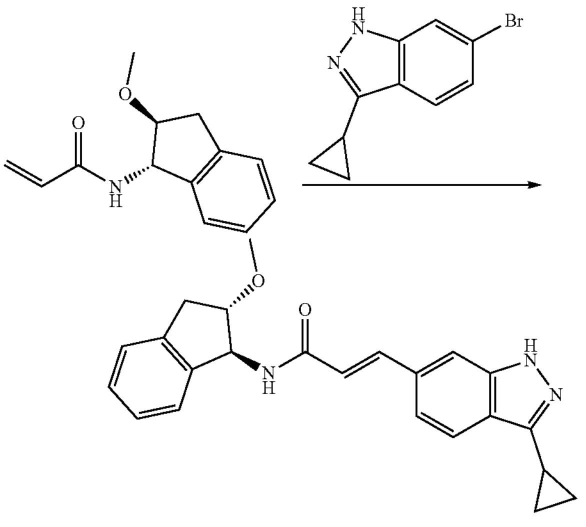

Into a 8-mL vial, was placed N-[(1S,2S)-2-methoxy-2,3-dihydro-1H-inden-1-yl]prop-2-enamide (see Example 54, Step 1, 60.00 mg, 0.276 mmol, 1.00 equiv), 6-bromo-3-cyclopropyl-1H-indazole (65.48 mg, 0.276 mmol, 1.00 equiv), $Pd(dppf)Cl_2$ (20.21 mg, 0.028 mmol, 0.10 equiv), $Et_3N$ (83.83 mg, 0.828 mmol, 3.00 equiv) in DMF (2.00 mL). The resulting solution was stirred for 3 hr at 120° C. The mixture was purified by Prep-HPLC. This resulted in 31 mg of (E)-3-(3-cyclopropyl-1H-indazol-6-yl)-N-((1S,2S)-2-methoxy-2,3-dihydro-1H-inden-1-yl)acrylamide as an off-white solid. LC-MS (ES, m/z): $[M+H]^+$=374

$^1$H-NMR-(300 MHz, DMSO-$d_6$, ppm) δ 8.61-8.58 (d, J=8.7 Hz, 1H), 7.87-7.78 (d, J=8.7 Hz, 1H), 7.68-7.62 (m, 2H), 7.32-7.20 (m, 5H), 6.77-6.72 (d, J=15.9 Hz, 1H), 5.34-5.32 (m, 1H), 4.08-4.07 (m, 1H), 3.38 (s, 3H). 3.35-3.27 (m, 1H), 2.84-2.77 (m, 1H). 2.29-2.24 (m, 1H), 1.01-0.94 (m, 4H).

Example 71: (E)-3-(3-methoxy-1H-indazol-6-yl)-N-((1S,2S)-2-methoxy-2,3-dihydro-1H-inden-1-yl) acrylamide

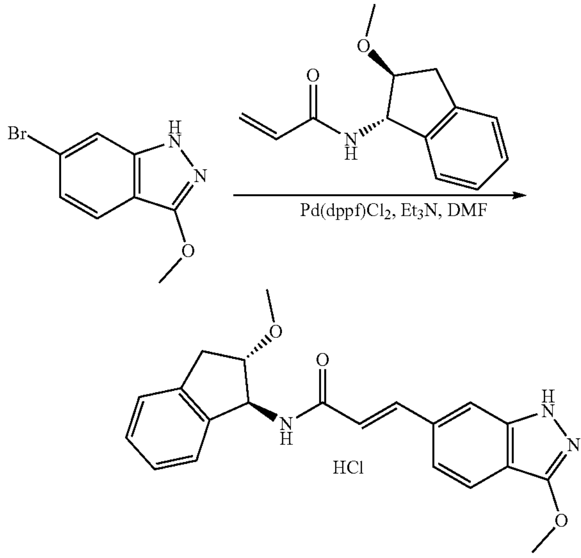

Into a 8-mL vial, was placed N-[(1S,2S)-2-methoxy-2,3-dihydro-1H-inden-1-yl]prop-2-enamide (see Example 54, Step 1, 60.00 mg, 0.276 mmol, 1.00 equiv), 6-bromo-3-methoxy-1H-indazole (62.70 mg, 0.276 mmol, 1.00 equiv), $Pd(dppf)Cl_2$ (20.21 mg, 0.028 mmol, 0.10 equiv), $Et_3N$ (83.83 mg, 0.828 mmol, 3.00 equiv) in DMF (2.00 mL). The resulting solution was stirred for 3 hr at 120° C. The mixture was purified by Prep-HPLC. This resulted in 33 mg of (E)-3-(3-methoxy-1H-indazol-6-yl)-N-((1S,2S)-2-methoxy-2,3-dihydro-1H-inden-1-yl)acrylamide as an off-white solid. The compounds was converted to the HCl. LC-MS (ES, m/z): $[M+H]^+$=364

$^1$H-NMR (300 MHz, DMSO-$d_6$, ppm) δ 12.09 (s, 1H), 8.59 (d, J=8.4 Hz, 1H), 7.67-7.54 (m, 3H), 7.26-7.17 (m, 5H), 6.74 (d, J=15.9 Hz, 1H), 5.34-5.30 (m, 1H), 4.07-4.01 (m, 4H), 3.38 (s, 3H), 3.37-3.29 (m, 1H), 2.84-2.78 (m, 1H)

Example 72: (E)-3-(3-chloro-1H-indazol-6-yl)-N-((1S,2S)-2-methoxy-2,3-dihydro-1H-inden-1-yl) acrylamide

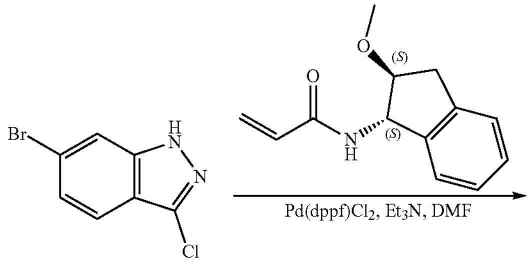

-continued

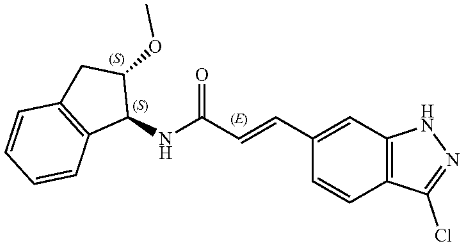

Into a 8-mL vial, was placed N-[(1S,2S)-2-methoxy-2,3-dihydro-1H-inden-1-yl]prop-2-enamide (60.00 mg, 0.276 mmol, 1.00 equiv), 6-bromo-3-chloro-1H-indazole (63.92 mg, 0.276 mmol, 1.00 equiv), Pd(dppf)$Cl_2$ (20.21 mg, 0.028 mmol, 0.10 equiv), $Et_3N$ (83.83 mg, 0.828 mmol, 3.00 equiv) in DMF (4.00 mL). The resulting solution was stirred for 3 hr at 120° C. The mixture was purified by Prep-HPLC. This resulted in 32 mg of (E)-3-(3-chloro-1H-indazol-6-yl)-N-((1S,2S)-2-methoxy-2,3-dihydro-1H-inden-1-yl)acrylamide as an off-white solid. LC-MS (ES, m/z): $[M+H]^+$=368

$^1$H-NMR (300 MHz, DMSO-$d_6$, ppm) δ13.45 (s, 1H), 8.62 (d, J=8.7 Hz, 1H), 7.75-7.67 (m, 3H), 7.46 (d, J=9.6 Hz, 1H), 7.28-7.17 (m, 4H), 6.80 (d, J=15.9 Hz, 1H), 5.35-5.30 (m, 1H), 4.08-4.01 (m, 1H), 3.38 (s, 3H), 3.35-3.27 (m, 1H), 2.84-2.77 (m, 1H)

Example 73: (E)-3-(3-fluoro-1H-indazol-6-yl)-N-((1S,2S)-2-methoxy-2,3-dihydro-1H-inden-1-yl) acrylamide

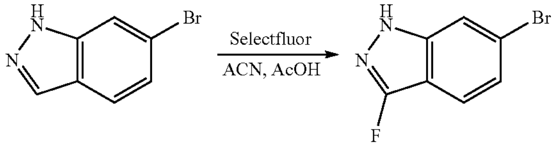 [SMILES: Brc1ccc2cn[nH]c2c1 ; Fc1n[nH]c2cc(Br)ccc12]

Step 1: Into a 40-mL vial, was placed 6-bromo-1H-indazole (500.00 mg, 2.54 mmol, 1.00 equiv), Selectfluor (1797.95 mg, 5.075 mmol, 2.00 equiv) in $CH_3CN$ (10.00 mL) and AcOH (1.00 mL). The resulting solution was stirred for 15 hr at 95° C. The mixture was applied onto a silica gel column with ethyl acetate/petroleum ether (1/1). This resulted in 110 mg (20% yield) of 6-bromo-3-fluoro-1H-indazole as a light yellow solid.

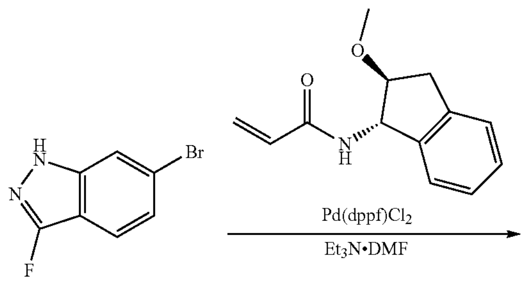

-continued

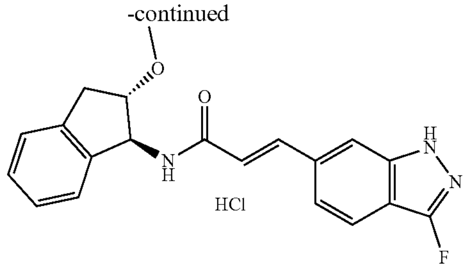

Step 2: Into a 8-mL vial, was placed N-[(1S,2S)-2-methoxy-2,3-dihydro-1H-inden-1-yl]prop-2-enamide (see Example 54, Step 1, 60.00 mg, 0.276 mmol, 1.00 equiv), 6-bromo-3-fluoro-1H-indazole (59.38 mg, 0.276 mmol, 1.00 equiv), Pd(dppf)$Cl_2$ (20.21 mg, 0.028 mmol, 0.10 equiv), $Et_3N$ (83.83 mg, 0.828 mmol, 3.00 equiv) in DMF (2.00 mL). The resulting solution was stirred for 14 hr at 120° C. The mixture was purified by Prep-HPLC. This resulted in 34 mg of (E)-3-(3-fluoro-1H-indazol-6-yl)-N-((1S,2S)-2-methoxy-2,3-dihydro-1H-inden-1-yl)acrylamide as a off-white solid. LC-MS1 (ES, m/z): $[M+H]^+$=352

$^1$H-NMR (300 MHz, DMSO-$d_6$, ppm) δ12.72 (s, 1H), 8.62 (d, J=8.7 Hz, 1H), 7.75-7.66 (m, 3H), 7.41 (d, J=8.7 Hz, 1H), 7.27-7.18 (m, 4H), 6.79 (d, J=15.9 Hz, 1H), 5.35-5.30 (m, 1H), 4.08-4.01 (m, 1H), 3.39 (s, 3H), 3.35-3.27 (m, 1H), 2.84-2.78 (m, 1H)

Example 74: (E)-3-(3-cyano-1H-indazol-6-yl)-N-((1S,2S)-2-methoxy-2,3-dihydro-1H-inden-1-yl) acrylamide

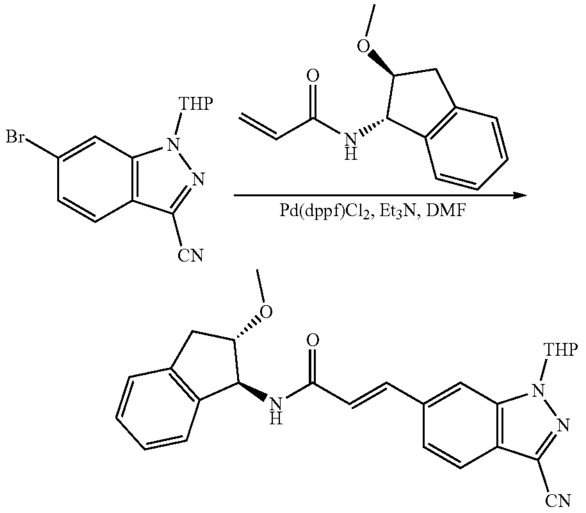

Step 1: Into a 8-mL vial, was placed N-[(1S,2S)-2-methoxy-2,3-dihydro-1H-inden-1-yl]prop-2-enamide (see Example 54, Step 1, 70.0 mg, 0.322 mmol, 1.00 equiv), 6-bromo-1-(oxan-2-yl) indazole-3-carbonitrile (98.64 mg, 0.322 mmol, 1.00 equiv), Pd(dppf)$Cl_2$ (23.57 mg, 0.032 mmol, 0.10 equiv), $Et_3N$ (97.81 mg, 0.967 mmol, 3.00 equiv) in DMF (4.00 mL). The resulting solution was stirred for 3 hr at 120° C. The mixture was applied onto a silica gel column and eluted with ethyl acetate/petroleum ether (1/1). This resulted in 60 mg (42% yield) of (E)-3-(3-cyano-1-(tetrahydro-2H-pyran-2-yl)-1H-indazol-6-yl)-N-((1S,2S)-2-methoxy-2,3-dihydro-1H-inden-1-yl)acrylamide as a light yellow solid.

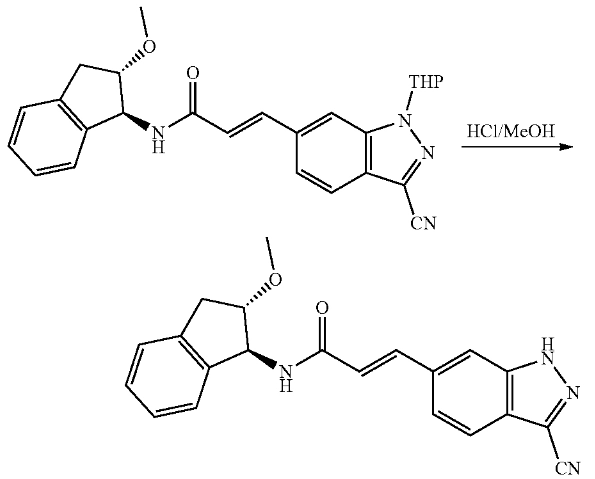

Step 2: Into a 8-mL vial, was placed (E)-3-(3-cyano-1-(tetrahydro-2H-pyran-2-yl)-1H-indazol-6-yl)-N-((1S,2S)-2-methoxy-2,3-dihydro-1H-inden-1-yl)acrylamide (60.00 mg, 0.136 mmol, 1.00 equiv) in 2M HCl(g) in MeOH (2.00 mL) and MeOH (2.00 mL). The resulting solution was stirred for 2 hr at 10° C. The resulting mixture was concentrated. The residue was purified by Prep-HPLC. This resulted in 31 mg of (E)-3-(3-cyano-1H-indazol-6-yl)-N-((1S,2S)-2-methoxy-2,3-dihydro-1H-inden-1-yl)acrylamide as an off-white solid. LC-MS (ES, m/z): $[M+H]^+=359$ $^1$H-NMR (300 MHz, DMSO-$d_6$, ppm) δ 14.52 (s, 1H), 8.64 (d, J=8.4 Hz, 1H), 7.94-7.91 (m, 2H), 7.73 (d, J=15.9 Hz, 1H), 7.62 (d, J=8.7 Hz, 1H), 7.26-7.18 (m, 4H), 6.83 (d, J=15.6 Hz, 1H), 5.34-5.30 (m, 1H), 4.07-4.01 (m, 1H), 3.38 (s, 3H), 3.35-3.27 (m, 1H), 2.84-2.73 (m, 1H).

BIOLOGICAL EXAMPLES

Biological Example 1—mPTP Activity Assay in Isolated Rat Liver Mitochondria, Human Platelet Mitochondria and Isolated Rat Brain Mitochondria Rat Liver Mitochondria Assay Pharmacological inhibition or modulation of the mPTP can be measured in well characterised '$Ca^{2+}$ retention' assays performed in isolated mitochondria. In vitro, isolated mitochondria rapidly sequester exogenous $Ca^{2+}$ until the intramitochondrial $Ca^{2+}$ concentration reaches the threshold for mPTP activation. Once the pore is activated, mitochondrial integrity is compromised and the stored $Ca^{2+}$ is released. The distribution of $Ca^{2+}$ between extra- and intra-mitochondrial compartments can be measured in real time with the use of membrane-impermeant $Ca^{2+}$ sensitive fluorescent dyes. Depending on the configuration of the assay, inhibition or modulation of the mPTP either delays the opening of the pore or increases the concentration of $Ca^{2+}$ required to induce mPTP opening.

MPTP activity was measured in mitochondria freshly isolated from female Sprague Dawley (250 to 300 gram) rat livers using the following method. Cervical dislocation was performed on the rat. The liver was then perfused in-situ with ~40 ml cold Dulbecco's Phosphate Buffered Saline (DPBS) prior to dissection and transferred into 30 ml Isolation Buffer (250 mM Sucrose, 10 mM KCl, 1 mM EGTA, 1 mM EDTA, 25 mM HEPES, adjusted to pH 7.5 with 1M NaOH). Each lobe of the liver was then removed from the buffer, minced using tweezers and a scalpel into ~5 mm pieces then transferred into a 50 ml Potterton dounce homogenization tube on ice containing 30 ml ice-cold centrifugation buffer (300 mM Trehalose, 25 mM HEPES, 1 mM EGTA, 1 mM EDTA, 10 mM KCl, adjusted to pH 7.5 with 1M NaOH and supplemented with 0.1% bovine serum albumin (BSA) and complete protease inhibitor cocktail (one tablet of inhibitor per 50 mls of buffer). Homogenisation was carried out using a teflon pestle at 1800 rpm. The slurry was centrifuged at 800 g for 10 min at 4° C., then the supernatant centrifuged at 10,000 g for 10 min. The pellet was washed once with FLIPR assay buffer (75 mM Mannitol, 25 mM Sucrose, 5 mM Potassium Phosphate Monobasic, 20 mM Tr is base, 100 mM KCl, 0.1% BSA adjusted to pH 7.4 with 5M HCl) centrifuged again, then resuspended in FLIPR assay buffer to a concentration of 8.8 mg/ml protein.

Tested compounds (10 mM stock in DMSO) were serially diluted in DMSO in half log steps to generate 10 test concentrations (final concentrations in assay 30 μM to 1 nM). An intermediate dilution of 5 μl DMSO samples into 247 μl FLIPR assay buffer was carried out prior to transfer of 5 μl into duplicate wells of a 384 well polypropylene assay plate. Control wells were 0.5% (v/v) DMSO and 5 μM cyclosporin A.

A stock mitochondria/Fluo5N assay solution was prepared in 5.6 ml FLIPR assay buffer (at RT) supplemented with succinate disodium salt (10 mM), rotenone (1 μM), Fluo5N pentapotassium salt (2 μM) and 1 ml mitochondria suspension, then transferred (15 μl) into the assay plate containing test compounds and incubated for 10 min at RT. Assay plates were then transferred to a FLIPR Tetra plate reader (Molecular Devices). Dye fluorescence was then measured every 3 sec for a total of 10 min. After 12 sec, a 2.5 μl bolus of $CaCl_2$ (75 μM) was added from a source plate containing 675 μM $CaCl_2$ in FLIPR assay buffer. IC50 values for tested compounds were calculated using the fluorescence value collected at the 10 min timepoint with % inhibition calculated using the DMSO control and cyclosporin A values as 100 and 0% respectively.

Human Platelet Mitochondria Assay

The mPTP cell based assay was performed using a mitochondria membrane potential flow cytometry assay in stimulated human platelets. Simulation of platelets results in the rapid influx of $Ca^{2+}$ across the platelet membrane. The $Ca^{2+}$ is then sequestered by mitochondria until the threshold for mPTP opening is reached, at which point the pore opens and the mitochondrial membrane potential is dissipated. Changes in mitochondria membrane potential due to mPTP opening can be quantified in live platelets using standard mitochondrial membrane potential dyes e.g. 3,3'-dihexyloxacarbocyanine Iodide; DiOC6(3), enabling pharmacological characterisation of mPTP inhibitors.

Fresh human blood (20 ml) was collected from consented donors into 3.2% sodium citrate. Platelets were isolated by centrifugation at 200 g for 20 min at room temperature, then the platelet rich plasma layer transferred to a fresh tube. Prostaglandin 12 is added to the platelets at a final concentration of 20 ng/ml. After centrifugation at 640 g for 10 min, the platelet rich pellet was resuspended in 4 ml HEPES assay buffer (137 mM NaCl, 2.7 mM KCl, 11.9 mM $NaHCO_3$, 0.42 mM $NaH_2PO_4$, 1 mM $MgCl_2$, 5.5 mM glucose, 0.1% bovine serum albumin, 10 mM HEPES adjusted to pH 7.4) and stored on ice.

Test compounds were prepared from 10 mM stocks in DMSO and serially diluted in assay buffer containing 0.4% DMSO and 25 μl transferred into a 96 well plate. Platelets were loaded with the mitochondrial membrane potential dye DiOC6(3)(3,3'-dihexyloxacarbocyanine Iodide; Invitrogen) at 200 nM for 30 min, then 50 μl plated into each well of the 96 well plate containing diluted test compound and incubated for 15 min. Control wells included DMSO(0.1% final concentration) only or 5 μM cyclosporin A. Platelets were then stimulation with the addition of assay buffer (25 μl) containing $CaCl_2$, alpha thrombin and Convulxin to achieve a final concentrations of 2 mM, 0.017 U/ml and 0.167 μg/ml respectively and incubated for 14 min. The reaction was stopped by the addition of 25 μl 15 mM EDTA in assay buffer. The mitochondrial membrane potential across the population of platelets in each well was then quantified by flow cytometry using a Guava easyCyte 5 Benchtop Flow Cytometer with 3000 events per well. The percentage of platelets with a depolarised mitochondrial membrane potential was calculated for each well. A pIC50 for each compound was then calculated using a standard four parameter curve fit model (GraphPad Prism).

Rat Brain Mitochondria Assay

MPTP activity was measured in brain mitochondria freshly isolated from female Sprague Dawley (250 to 300 gram) rats. Anaesthetised rats were perfused in-situ with ~40 ml cold Dulbecco's Phosphate Buffered Saline (DPBS), then brains dissected and transferred into 30 ml Isolation Buffer (225 mM mannitol, 75 mM sucrose, 1 mM EGTA, adjusted to pH 7.4 with 1M NaOH). The brain was minced using tweezers and a scalpel into ~5 mm pieces then transferred into a 50 ml Potterton Dounce homogenization tube on ice containing 10 ml ice-cold isolation buffer (as above with addition of Complete Protease inhibitor; 1 tablet per 50 ml buffer). Homogenisation was carried out using a teflon pestle at 1800 rpm. The slurry was centrifuged at 2000 g for 10 min at 4° C., then the supernatant centrifuged at 12,000 g for 9 min. The pellet was resuspended with a dounce homogeniser in isolation buffer as above but with the addition of 0.02% digitonin, centrifuged at 12,000 g for 11 min and finally resuspended in 5 ml modified isolation buffer (as above but with EGTA reduced to 0.1 mM).

Test compounds were prepared in 384 well polypropylene assay plates as described above for the liver mitochondria assay. A stock mitochondria/Fluo5N assay solution was prepared in 5.6 ml assay buffer (120 mM mannitol, 40 mM MOPS, 5 mM $KH_2PO_4$, 60 mM KCl, 10 mM pyruvate, 2 mM malate, 2 mM $MgCl_2$, 20 μM ADP, 1.26 μM oligomycin A, adjusted to pH 7.4) supplemented with Fluo5N pentapotassium salt (2 μM) and 1 ml mitochondria suspension, then transferred (15 μl) into the assay plate containing test compounds and incubated for 10 min at RT. Assay plates were then transferred to a FLIPR Tetra plate reader (Molecular Devices). Dye fluorescence was then measured every 3 sec for a total of 10 min. After 12 sec, a 2.5 μl bolus of Ca2+ (75 μM) was added from a source plate containing 675 μM $CaCl_2$ in FLIPR assay buffer. IC50 values for test compounds were calculated using the fluorescence value collected at the 10 min timepoint with % inhibition calculated using the DMSO control and cyclosporin A values at 100% and 0% respectively.

General cytotoxicity was assessed using standard cell viability methods (Cell Titre Glo; Promega) in HEK293 and SHSY5Y cells, following incubation of test compound for between 24 and 96 hours.

Results: mPTP $pIC_{50}$ values for certain Example compounds of the invention in a range of mPTP assays are provided in Table 3 below. Table 3 also provides the $pIC_{50}$ values for Comparative Example 1. The results indicate that the tested compounds of the invention display inhibition of mPTP, with many Example compounds displaying $pIC_{50}$ values of 6.0 or greater. Examples 37 and 51 showed the highest activity in the rat liver mitochondria assay and Example 51 also showed the highest activity in the rat brain mitochondria assay. Table 3 also presents mPTP human platelet $pIC_{50}$ values for certain Example compounds and Comparative Example 1. Table 3 also presents mPTP rat brain mitochondria $pIC_{50}$ values for certain Example compounds and Comparative Example 1. These results indicate that the tested Example compounds are active against isolated rat liver mitochondria, isolated rat brain mitochondria and human platelet mitochondria.

Biological Example 2—Cytochrome P450 Assays

Studies to assess tested compound mediated inhibition of cytochrome P450 enzyme isoform CYP2D6 were performed using human liver microsomes (BD Gentest) using either a single concentration (1 μM) of test compound or concentration response (0.1, 0.3, 1, 3, 10 and 30 μM) to derive an IC50. Tested compound solutions were prepared from 10 mM stocks in DMSO and diluted to 200 μM in DMSO. Reactions were prepared in a 96 deep well plate by combining 1 μl test compound with 179 μl reaction mixture (100 mM phosphate buffered saline (PBS), 0.2 mg/mL microsomes and 2 μM Dextromethorphan prepared from stocks as detailed below).

TABLE 2

Summary of incubation mixtures

| Buffer | Stock Concentration | Volume | Final Concentration |
|---|---|---|---|
| Microsomes | 20 mg/mL | 2 μL | 0.2 mg/mL |
| Phosphate buffer | 100 mM | 176 μL | 100 mM |
| Substrate | — | 1 μL | — |

The positive control inhibitor, quinidine, was used at a final concentration of 0.5 μM when used at a single concentration. The final concentrations of quinidine used to derive an IC50 were 0, 0.1, 0.3, 1, 3, 10 and 30 μM. Plates were warmed at 37° C. for 15 min before starting reactions with 20 μl 10 mM NADPH solution in PBS and incubated for 20 min at 37□ C. The assay is performed in duplicate. Reactions were quenched with 200 μl cold acetonitrile containing internal standards (200 nM labetalol, 200 nM alprazolam and 100 nM tolbutamide). The plate was centrifuged at 4000 rpm for 30 minutes, placed on ice for 20 minutes and then centrifuged at 4000 rpm for 30 minutes again to precipitate protein. 100 μL of the supernatant was transferred to a new plate and diluted with 100 μL pure water before being analysed using UPLC/MS/MS. The products of the transformation for dextromethorphan to dextrophan was monitored by UPLC-MS/MS. The inhibition of CYP2D6 in human liver microsomes was measured as the percentage decrease in the activity of dextrophan formation compared to non-inhibited controls (=100% activity). The $IC_{50}$ value was calculated (test compound concentration which produces 50% inhibition) by using Excel XLfit.

Results: CYP2D6% inhibition values for certain compounds of the invention are presented in Table 3. Table 3 also presents the CYP2D6% inhibition value for Comparative Example 1. The results indicate that the tested compounds displayed a significantly reduced inhibition of CYP2D6 than Comparative Example 1. Negative values indicate that there was no effective inhibition of CYP2D6 at 1 uM concentration of the tested compound. Table 3 also presents CYP2D6 $IC_{50}$ values for certain Example compounds and for Comparative Example 1. The results show that Comparative Example 1 is a highly potent inhibitor of CYP2D6, and significantly more potent than the tested Example compounds. This is consistent with the potent CYP2D6% inhibition value displayed for Comparative Example 1. Therefore, the tested compounds of the invention are expected to display improved in vivo properties, such as the reduction of deleterious drug-drug interactions and reduced inhibition in the production of neurotransmitters in the central nervous system, in particular dopamine.

TABLE 3

Summary of results from Biological Examples 1 and 2

| Example No. | mPTP Rat liver pIC50* | mPTP Human Platelets pIC50 | mPTP Rat brain pIC50 | CYP2D6 % inh @ 1 uM** | CYP2D6 IC50 uM** |
|---|---|---|---|---|---|
| Comparative Example 1 | 8.0 | 6.9 | 7.6 | 86.5 | 0.074 |
| 1 | 7.3 | | | −2.11 | |
| 2 | 6.0 | | | | |
| 3 | 6.4 | | | −1.87 | |
| 4 | 6.5 | | | 2.89 | |
| 5 | 6.7 | | | −2.57 | |
| 6 | 6.8 | 7.0 | | 5.08 | 19.02 |
| 7 | 6.8 | 7.2 | 6.9 | 2.27 | >30 |
| 8 | 5.9 | | | 3.13 | |
| 9 | 7.4 | | | −2.59 | |
| 10 | 6.7 | 7.0 | 6.5 | 3.66 | >30 |
| 11 | 6.1 | | | −0.63 | |
| 12 | 6.5 | | | 3.05 | |
| 13 | 6.0 | | | 3.84 | |
| 14 | 6.5 | | | −0.52 | |
| 15 | 6.9 | | | −0.28 | |
| 16 | 6.8 | | | 1.72 | |
| 17 | 6.4 | | | 1.91 | |
| 18 | 6.0 | | | 1.20 | |
| 19 | 6.2 | | | −3.04 | |
| 20 | 6.8 | | | −1.76 | |
| 21 | 6.1 | | | 0.91 | |
| 22 | 6.6 | | | 2.05 | |
| 23 | 6.6 | | | 0.7 | |
| 24 | 6.1 | | | 0.77 | |
| 25 | 6.9 | | | 2.05 | 13.80 |
| 26 | 7.2 | | | 3.49 | 8.80 |
| 27 | 6.6 | | | 14.28 | |
| 28 | 6.7 | | | 8.27 | |
| 29 | 6.9 | | | −3.03 | |
| 30 | 7.4 | | 7.6 | −3.33 | |
| 31 | 7.7 | | | 19.89 | |
| 32 | 6.6 | | | 4.01 | |
| 33 | 6.3 | | | −0.55 | |
| 34 | 6.7 | | | 4.37 | |
| 35 | 7.2 | | | 2.83 | |
| 36 | 7.2 | | | −2.57 | |
| 37 | 8.1 | | | 5.04 | |
| 38 | 7.2 | | | 7.30 | |
| 39 | 7.5 | | | 3.83 | |
| 40 | 6.6 | | | 6.65 | |
| 41 | 7.1 | | | 1.20 | |
| 42 | 6.1 | | | −1.97 | |
| 43 | 6.3 | | | | |
| 44 | 7.1 | | | 8.94 | |
| 45 | 6.3 | | | | |
| 46 | 6.3 | | | | |
| 47 | 5.9 | | | 1.91 | |
| 48 | 5.9 | | | 6.34 | |
| 49 | 5.8 | | | 4.52 | |
| 50 | 7.3 | | | 1.30 | |
| 51 | 7.9 | | 8.3 | | |
| 52 | 6.9 | | | | |
| 53 | 6.7 | | | | |
| 54 | 7.6 | | 7.7 | | |
| 55 | 7.1 | | | | |
| 56 | 5.8 | | | | |
| 57 | 5.8 | | | | |

TABLE 3-continued

Summary of results from Biological Examples 1 and 2

| Example No. | mPTP Rat liver pIC50* | mPTP Human Platelets pIC50 | mPTP Rat brain pIC50 | CYP2D6 % inh @ 1 uM** | CYP2D6 IC50 uM** |
|---|---|---|---|---|---|
| 58 | 5.5 | | | | |
| 59 | 5.5 | | | | |
| 60 | 5.7 | | | | |
| 61 | 5.6 | | | | |
| 62 | 5.6 | | | | |
| 63 | 4.9 | | | | |
| 64 | 4.9 | | | | |
| 65c | 7.7 | | | | |
| 66 | 7.2 | | 7.3 | | |
| 67 | 7.2 | | 7.3 | | |
| 68 | 7.8 | | 7.7 | | |
| 69 | 7.7 | | 7.6 | | |
| 70 | 7.5 | | | | |
| 71 | 7.0 | | | | |
| 72 | 8.2 | | | 9.98 | |
| 73 | 8.1 | | 7.7 | 34.57 | |
| 74 | 8.0 | | 8.0 | | |

*average value from multiple experiments (n ≥ 2)

**average value from two experiments.

Biological Example 3—PBS and FaSSIF Solubility

Test compounds were prepared as 10 mM stocks in DMSO and 15 μl samples transferred in duplicate into 1.5 mL glass flat bottom vials (BioTech Solutions). Fasted state simulated intestinal fluid (FaSSIF) or PBS (pH 7.4) was added to each vial to final volume of 500 μl. One PTFE encapsulated stir stick (V&P Scientific) was placed in each vial before sealing with PTFE/SIL plugs (BioTech Solutions). Vials were shaken at 1100 rpm for 2 hr at 25° C. Samples were then filtered through MultiScreen Solvinert filter plates (Millipore) via vacuum filtration. Aliquots of filtrate (5 μl) plus 5 μl DMSO were diluted in 490 μl 50% acetonitrile in water containing internal standard. The filtrate was analysed and quantified against a standard of known concentration using LC-MS/MS. Solubility values of the test compound and control compound were calculated as follows:

$$[Sample]=(\text{Area ratios}_{sample}*\text{INJ VOL STD}*\text{DF}_{Sample}*[STD])/(\text{Area ratio STD}*\text{INJ VOL}_{Sample}).$$

Results: The solubility values for certain compounds of the invention are provided in Table 4 below. Table 4 also presents results for Comparative Example 1. The results indicate that certain compounds of the invention display higher solubility in PBS and/or FaSSIF than Comparative Example 1. Certain compounds of the invention display solubility in either PBS or FaSSIF, whilst certain compounds display higher solubility values in both PBS and FaSSIF. Therefore, certain compounds of the invention may be expected to display improved bioavailability and/or improved systemic exposure than Comparative Example 1, particularly when said compounds are dosed orally.

Biological Example 4—Liver Microsome and Hepatocyte Intrinsic Clearance Assays

Hepatocyte Clearance Assay

In vitro clearance studies were performed in primary rat and human hepatocytes (BioIVT). Vials of cryopreserved rat or human hepatocytes were thawed in a 37° C. water bath for 2 min. Cells were transferred into thawing medium (Williams' Medium E containing 30% Percoll, 1×GlutaMAX-1, 15 mM HEPES, 5% fetal bovine serum (FBS), 4 μg/ml insulin, 1 μM dexamethasone), centrifuged at 100 g for 10 min then resuspended in culture medium (Leibovitz's L-15 Medium) at a concentration of $0.5\times10^6$ viable cells/mL (number of viable cells assessed using AO/PI staining). Hepatocytes (198 μL) were transferred into wells of a 96-well non-coated plate and placed in a 37° C. incubator for 10 min. Test compound solutions were prepared from 10 mM stocks in DMSO, diluted to 100 μM in 50% (v/v in water) acetonitrile. Test compound samples (2 μl) were added to each well of hepatocytes and incubated at 37° C. Samples (25 μl) were collected at t=0, 15, 30, 60, 60 and 120 min, mixed with 6 volumes (150 μl) of acetonitrile containing internal standard (100 nM alprazolam, 200 nM caffeine and 100 nM tolbutamide), vortexed for 5 min and centrifuged for 45 min at 3220 g. An aliquot of supernatant (100 μL) was diluted with 100 μL ultra-pure water, and the mixture was used for LC/MS/MS analysis. All incubations were performed in duplicate. Peak areas were determined from extracted ion chromatograms. The slope value, k, was determined by linear regression of the natural logarithm of the remaining percentage of the parent drug vs. incubation time curve. The in vitro half-life (in vitro t½) was determined from the slope value: in vitro t½=0.693/k. Conversion of the in vitro t½ (in min) into the in vitro intrinsic clearance (in vitro $CL_{int}$, in μL/min/$1\times10^6$ cells) was done using the following equation (mean of duplicate determinations):

$$\text{in vitro } CL_{int}=kV/N$$

V=incubation volume (0.2 mL)

N=number of hepatocytes per well ($0.1\times10^6$ cells).

Microsomal Clearance Assay

The microsomal stability of test compounds was evaluated using rat liver microsomes (BioIVT) with and without the cofactors nicotinamide adenine dinucleotide phosphate (NADPH) and uridine-diphosphate-glucuronic acid (UDPGA). Reactions were performed in a final volume of 250 μl pre-warmed (37° C.) 100 mM phosphate buffer containing 5 mM $MgCl_2$, 0.025 mg/ml alamethicin, and 0.5 mg/ml rat liver microsomes. NADPH and UDPGA were included at 1 mM and 2 mM respectively, where appropriate. Reactions were started with the addition of 1 μM (final concentration) test compound. Verapamil was used as the positive control. Solutions were incubated in a water bath at 37° C. and aliquots collected at 0.5, 5, 15, 30 and 60 min. Reactions were stopped by the addition of 5 volumes of cold acetonitrile with internal standards (200 nM caffeine and 100 nM tolbutamide). Samples were centrifuged at 3220 g for 40 min. An aliquot of supernatant was diluted 1:1 In ultra-pure H20, then used for LC-MS/MS analysis. Peak areas were determined from extracted ion chromatograms. The slope value, k, was determined by linear regression of the natural logarithm of the remaining percentage of the parent drug vs. incubation time curve. The in vitro half-life (in vitro t1/2) was determined from the slope value: in vitro t1/2=0.693/k. Conversion of the in vitro t1/2 (min) into the in vitro intrinsic clearance (in vitro $CL_{int}$, in μL/min/mg protein) was done using the following equation (mean of duplicate determinations):

$$\text{in vitro Clint}=(0.693/t1/2)*(\text{Vol of incubation } (\mu l)/\text{amount of protein (mg)}).$$

Results: Intrinsic clearance values for certain compounds of the invention are presented in Table 4. Table 4 also presents intrinsic clearance values for Comparative Example 1. These results indicate that certain compounds of the invention may be expected to have improved oral bioavailability and/or improved systemic exposure when compared to Comparative Example 1 i.e. they exhibited lower intrinsic clearance ($CL_{int}$) values in at least human or rat species. Certain compounds exhibited lower intrinsic clearance ($CL_{int}$) values than Comparative Example 1 in both human and rat species.

TABLE 4

Summary of results from Biological Examples 3 and 4

| Example | Solubility PBS uM (pH 7.4) | Solubility FaSSIF uM | Rat heps $Cl_{int}$ uL/min/$10^6$ cells* | Rat liver microsomes $Cl_{int}$ uL/min/mg* | Human heps $Cl_{int}$ uL/min/$10^6$ cells* |
|---|---|---|---|---|---|
| Comparative Example 1 | 0.9 | 4 | 89 | 43 | 13 |
| 1 | 22.2 | | | 106 | |
| 3 | 1.75 | | | | |
| 4 | 0.31 | | | | |
| 5 | 6.78 | 66 | 27 | 17 | |
| 6 | 3.71 | 18 | 53.3 | 17 | <3 |
| 7 | 1.4 | 22.5 | 27 | 6.5 | 7.63 |
| 8 | 33.64 | 219.97 | 46 | 13 | |
| 9 | 0.6 | | | | |
| 10 | 4.7 | 74 | 21.1 | 13 | 3.3 |
| 13 | 5.3 | | | | |
| 14 | 16 | | | | |
| 15 | 0.03 | | | | |
| 17 | 0.15 | | | | |
| 18 | 1.11 | | | 23 | |
| 19 | 134.23 | | 9.1 | 20.04 | 4.02 |
| 20 | | | 11.9 | | 6.08 |
| 21 | 25.99 | | | 38.04 | |
| 22 | 0.4 | | 26.12 | 9.85 | 16.2 |
| 23 | 6.13 | | 35.74 | 9.8 | 17.4 |
| 25 | 3.69 | | 36.3 | 52.88 | 21.8 |
| 26 | | | 87.55 | | |
| 28 | | | 73.64 | | |
| 29 | 33.48 | 69.83 | 16.1 | | |
| 30 | 5.73 | 135.43 | 12.08 | | 18.1 |
| 36 | 65.93 | | 9.41 | | 7.26 |
| 37 | | 2.95 | | | |
| 47 | 0.5 | | | 36.8 | |
| 50 | | 23.7 | 47.81 | | 15.59 |
| 51 | | | 48.08 | | 11.02 |
| 65c | | 9.2 | 37.9 | | 9.4 |
| 66 | | | 36.1 | | 25.4 |
| 67 | | | 73.3 | | 42.1 |
| 68 | | 61.7 | 34.9 | | 12 |
| 69 | | 180.7 | 73 | | 17.9 |
| 70 | | 18.4 | 70.1 | | 24.6 |
| 71 | | 19.94 | 72 | | 8.9 |
| 72 | | 24.4 | 77 | | 11.3 |
| 73 | | 37.5 | 73.5 | | 7.7 |
| 74 | 1.2 | | | | |

*average value from two experiments.

Conclusion: The results of Biological Examples 1 and 2 demonstrate that the tested compounds of the invention are inhibitors of mPTP in a range of mPTP assays. The tested compounds of the invention also showed a reduced inhibition of CYP2D6 compared to Comparative Example 1. The results of Biological Examples 3 and 4 demonstrate that certain compounds of the invention show improved solubility and/or lower intrinsic clearance compared to Comparative Example 1 and as such are expected to display improved oral bioavailability and/or improved systemic exposure compared to Comparative Example 1.

Therefore, the compounds of the invention are believed to be useful pharmaceuticals, particularly for the treatment or prophylaxis of diseases and disorders in which inhibition of mPTP provides a therapeutic or prophylactic effect.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

All publications, including but not limited to patents and patent applications, cited in this specification are herein incorporated by reference as if each individual publication were specifically and individually indicated to be incorporated by reference herein as though fully set forth.

REFERENCES

Yu et al., TDP-43 Triggers Mitochondrial DNA Release via mPTP to Activate cGAS/STING in ALS, Cell, Volume 183, Issue 3, 2020, pages 636-649.e18. Jang et al., Proximal tubule cyclophilin D mediates kidney fibrogenesis in obstructive nephropathy, 2021, American Journal of Physiology: Renal physiology, doi: 10.1152/ajprenal.00171.2021. Epub ahead of print. PMID: 34396791.

Plyte et al., Cinnamic Anilides as New Mitochondrial Permeability Transition Pore Inhibitors Endowed with Ischemia-Reperfusion Injury Protective Effect in Vivo, J. Med Chem. 2014, 57, 5333-47

Chen et al., Probing Mitochondrial Permeability Transition Pore Activity in Nucleated Cells and Platelets by High-Throughput Screening Assays Suggests Involvement of Protein Phosphatase 2B in Mitochondrial Dynamics, Assay and Drug Development Technologies, 2018, 16, 445-45.

The invention claimed is:

1. A compound of formula (I):

(I)

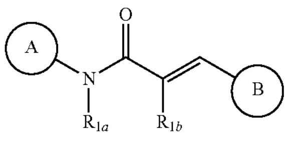

wherein:

$R_{1a}$ is H or methyl;

$R_{1b}$ is H or F;

A is group (Aa), (Ab), (Ac) or (Ad):

wherein group (Aa) is:

(Aa)

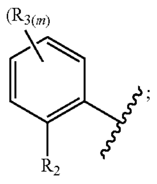

wherein:

$R_2$ is H, $C_{1-4}$alkyl, $C_{1-4}$alkylene(aryl), $C_{1-4}$alkylene(OH), $C_{1-4}$alkylene($C_{3-6}$cycloalkyl), $C_{1-4}$alkylene(4-7 membered heterocycloalkyl), $C_{1-4}$alkoxy, $OC_{1-4}$alkylene(aryl), $C_{1-4}$alkyleneO$C_{1-4}$alkyl, $C_{1-4}$alkyleneO$C_{3-6}$cycloalkyl, $C_{1-4}$alkyleneO(4-7 membered heterocycloalkyl), $C_{1-4}$alkyleneO(aryl), $C_{3-6}$alkynyl or $C_{1-4}$alkenylO($C_{3-6}$alkynyl); wherein said aryl, heterocycloalkyl and cycloalkyl are optionally substituted by 1, 2 or 3 substituents each independently selected from $C_{1-4}$alkyl, $C_{3-6}$cycloalkyl, $C_{1-4}$alkoxy, $C_{1-4}$haloalkyl, halo, CN, OH, $NR_{2a}R_{2b}$, $SO_2R_{2c}$ and $NHSO_2R_{2c}$;

$R_{2a}$ is selected from H and $C_{1-4}$alkyl;

$R_{2b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{2c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

each $R_3$ is independently halo, methyl, ethyl or n-propyl;

m is 0, 1, 2, 3 or 4;

wherein group (Ab) is:

(Ab)

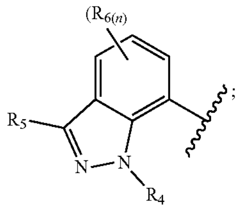

wherein:

$R_4$ is H, $C_{1-4}$alkyl or $C_{1-4}$alkylene(aryl); wherein said aryl is optionally substituted by 1, 2 or 3 substituents each independently selected from $C_{1-4}$alkyl, $C_{3-6}$cycloalkyl, $C_{1-4}$alkoxy, $C_{1-4}$haloalkyl, halo, CN, OH, $NR_{4a}R_{4b}$, $SO_2R_{4c}$ and $NHSO_2R_{4c}$;

$R_{4a}$ is selected from H and $C_{1-4}$alkyl;

$R_{4b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{4c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

$R_5$ is H or $C_{1-4}$alkyl;

each $R_6$ is independently $C_{1-4}$alkyl or halo;

n is 0, 1, 2 or 3;

wherein group (Ac) is:

(Ac)

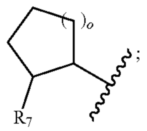

wherein:

$R_7$ is $C_{1-4}$alkyl, $C_{1-4}$alkylene(OH) or $C_{1-4}$alkyleneO$C_{1-4}$alkyl;

is 1 or 2;

wherein group (Ad) is:

(Ad)

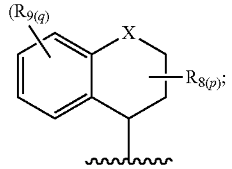

wherein:

X is a bond, O or $CH_2$;

each $R_8$ is independently halo, $C_{1-4}$alkyl, $C_{1-4}$alkoxy, $OC_{1-4}$haloalkyl, $OC_{1-4}$alkylene($C_{3-6}$cycloalkyl), $OC_{1-4}$alkylene (4-7 membered heterocycloalkyl) or OH; wherein said heterocycloalkyl and cycloalkyl are optionally substituted by 1, 2 or 3 substituents independently selected from $C_{1-4}$alkyl, $C_{3-6}$cycloalkyl, $C_{1-4}$alkoxy, $C_{1-4}$haloalkyl, halo, CN, OH, $NR_{8a}R_{8b}$, $SO_2R_{8c}$ and $NHSO_2R_{8c}$;

$R_{8a}$ is selected from H and $C_{1-4}$alkyl;

$R_{8b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{8c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

each $R_9$ is independently halo or $C_{1-4}$alkyl;

p is 0, 1 or 2;

q is 0, 1, 2, 3 or 4;

wherein B is group (Ba), (Bb) or (Bc):

wherein group (Ba) is:

(Ba)

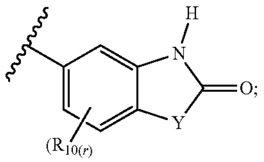

wherein:

Y is $C(R_{11})(R_{12})$, $N(R_{13})$, O or S;

each $R_{10}$ is independently halo or $C_{1-4}$alkyl;

r is 0, 1, 2 or 3;

$R_{11}$ is H or $C_{1-4}$alkyl;

$R_{12}$ is H or $C_{1-4}$alkyl; or $R_{11}$ and $R_{12}$ together with the carbon atom to which they are attached form a $C_{3-6}$cycloalkyl;

$R_{13}$ is H, $C_{1-4}$alkyl or $C_{3-6}$cycloalkyl;

wherein said cycloalkyl is optionally substituted by 1, 2 or 3 substituents independently selected from $C_{1-4}$alkyl, $C_{3-6}$cycloalkyl, $C_{1-4}$alkoxy, $C_{1-4}$haloalkyl, halo, CN, OH, $NR_{13a}R_{13b}$, $SO_2R_{13c}$ and $NHSO_2R_{13c}$;

$R_{13a}$ is selected from H and $C_{1-4}$alkyl;

$R_{13b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{13c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

wherein group (Bb) is:

(Bb)

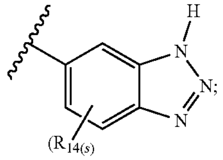

wherein:

each $R_{14}$ is independently halo or $C_{1-4}$alkyl;

sis 0, 1, 2 or 3;

wherein group (Bc) is:

(Bc)

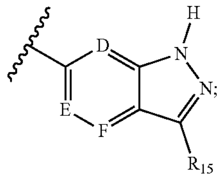

wherein:

$R_{15}$ is $C_{1-4}$alkyl, $C_{1-4}$alkoxy, $C_{3-6}$cycloalkyl, $C_{1-4}$haloalkyl, halo or CN; wherein said cycloalkyl is optionally substituted by 1, 2 or 3 substituents independently selected from $C_{1-4}$alkyl, $C_{3-6}$cycloalkyl, $C_{1-4}$alkoxy, $C_{1-4}$haloalkyl, halo, CN, OH, $NR_{15a}R_{15b}$, $SO_2R_{15c}$ and $NHSO_2R_{15c}$;

$R_{15a}$ is selected from H and $C_{1-4}$alkyl;

$R_{15b}$ is selected from H, $C_{1-4}$alkyl, $C_{3-6}$cycloalkyl, $C_{1-4}$alkoxy, $C_{1-4}$haloalkyl, aryl and 4-7 membered heterocycloalkyl;

$R_{15c}$ is selected from $C_{1-4}$alkyl, $C_{3-6}$cycloalkyl, $C_{1-4}$alkoxy, $C_{1-4}$haloalkyl, aryl and 4-7 membered heterocycloalkyl;

$R_{16}$ is H, halo or $C_{1-4}$alkyl; and

D, E and F are each independently $C(R_{16})$; or one of D, E and F is N, and the two remaining D, E and F groups are independently $C(R_{16})$;

or a pharmaceutically acceptable salt and/or solvate thereof.

2. The compound, pharmaceutically acceptable salt and/or solvate thereof according to claim 1, which is a compound of formula (I):

(I)

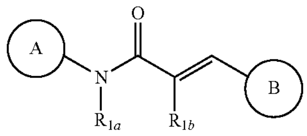

wherein:

$R_{1a}$ is H or methyl;

$R_{1b}$ is H or F;

A is group (Aa), (Ab), (Ac) or (Ad):

wherein group (Aa) is:

(Aa)

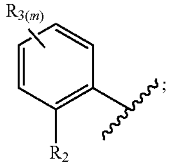

wherein:

$R_2$ is H, $C_{1-4}$alkyl, $C_{1-4}$alkylene(aryl), $C_{1-4}$alkylene(OH), $C_{1-4}$alkylene($C_{3-6}$cycloalkyl), $C_{1-4}$alkylene(4-7 membered heterocycloalkyl), $C_{1-4}$alkoxy, $OC_{1-4}$alkylene(aryl), $C_{1-4}$alkyleneO$C_{1-4}$alkyl, $C_{1-4}$alkyleneO$C_{3-6}$cycloalkyl, $C_{1-4}$alkyleneO(4-7 membered heterocycloalkyl), $C_{1-4}$alkyleneO(aryl), $C_{3-6}$alkynyl or $C_{1-4}$alkenylO($C_{3-6}$alkynyl); wherein said aryl, heterocycloalkyl and cycloalkyl may be optionally substituted by up to 3 substituents each independently selected from $C_{1-4}$alkyl, $C_{3-6}$cycloakyl, $C_{1-4}$alkoxy, $C_{1-4}$haloalkyl, halo and CN;

each $R_3$ is independently halo, methyl, ethyl or n-propyl;

m is 0, 1, 2, 3 or 4;

wherein group (Ab) is:

(Ab)

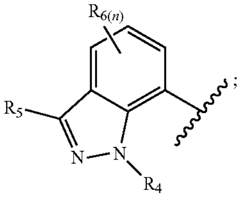

wherein:

$R_4$ is H, $C_{1-4}$alkyl or $C_{1-4}$alkylene(aryl); wherein said aryl may be optionally substituted by up to 3 substituents each independently selected from $C_{1-4}$alkyl, $C_{3-6}$cycloalkyl, $C_{1-4}$alkoxy, $C_{1-4}$haloalkyl, halo and CN;

$R_5$ is H or $C_{1-4}$alkyl;

each $R_6$ is independently $C_{1-4}$alkyl or halo;

n is 0, 1, 2 or 3;

wherein group (Ac) is:

(Ac)

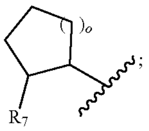

wherein:

$R_7$ is $C_{1-4}$alkyl, $C_{1-4}$alkylene(OH) or $C_{1-4}$alkyleneO$C_{1-4}$alkyl;

is 1 or 2;

wherein group (Ad) is:

(Ad)

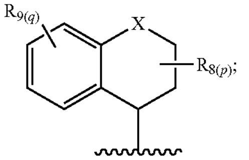

wherein:

X is a bond, O or $CH_2$;

each $R_8$ is independently halo, $C_{1-4}$alkyl, $C_{1-4}$alkoxy or OH;

each $R_9$ is independently halo or $C_{1-4}$alkyl;

p is 0, 1 or 2;

q is 0, 1, 2, 3 or 4;

wherein B is group (Ba), (Bb) or (Bc):

wherein group (Ba) is:

(Ba)

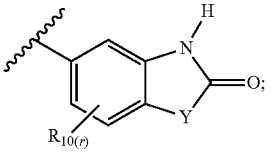

wherein:

Y is $C(R_{11})(R_{12})$, $N(R_{13})$, O or S;

each $R_{10}$ is independently halo or $C_{1-4}$alkyl;

r is 0, 1, 2 or 3;

$R_{11}$ is H or $C_{1-4}$alkyl;

$R_{12}$ is H or $C_{1-4}$alkyl; or $R_{11}$ and $R_{12}$ together with the carbon atom to which they are attached form a $C_{3-6}$cycloalkyl;

$R_{13}$ is H, $C_{1-4}$alkyl or $C_{3-6}$cycloalkyl;

wherein group (Bb) is:

(Bb)

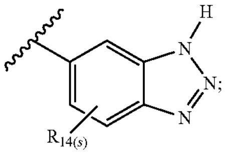

wherein:

each $R_{14}$ is independently halo or $C_{1-4}$alkyl;

s is 0, 1, 2 or 3;

wherein group (Bc) is:

(Bc)

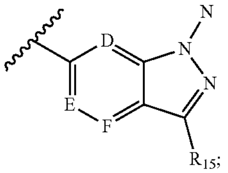

wherein:

$R_{15}$ is $C_{1-4}$alkyl, $C_{3-6}$cycloalkyl, $C_{1-4}$haloalkyl or CN;

$R_{16}$ is H, halo or $C_{1-4}$alkyl; and

D, E and F are each independently $C(R_{16})$; or one of D, E and F is N, and the two remaining D, E and F groups are independently $C(R_{16})$;

or a pharmaceutically acceptable salt and/or solvate thereof.

3. The compound, pharmaceutically acceptable salt and/or solvate thereof according to claim 1, wherein A is group (Aa):

(Aa)

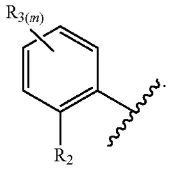

4. The compound, pharmaceutically acceptable salt and/or solvate thereof according to claim 1, wherein $R_2$ is $C_{1-4}$alkyl, $C_{1-4}$alkylene(aryl), $C_{1-4}$alkylene(OH), $C_{1-4}$alkyleneO$C_{1-4}$alkyl, $C_{1-4}$alkyleneO$C_{3-6}$cycloalkyl, $C_{1-4}$alkyleneO(aryl), $C_{1-4}$alkylene (4-7 membered heterocycloalkyl), $C_{1-4}$alkyleneO(4-7 membered heterocycloalkyl) or $C_{1-4}$alkyleneO($C_{3-6}$alkynyl); wherein said aryl, heterocycloalkyl and cycloalkyl may be optionally substituted by up to 3 substituents each independently selected from $C_{1-4}$alkyl, $C_{3-6}$cycloalkyl, $C_{1-4}$alkoxy, $C_{1-4}$haloalkyl, halo and CN.

5. The compound, pharmaceutically acceptable salt and/or solvate thereof according to claim 1, wherein $R_2$ is methyl, $CH_2OH$ or $CH_2OMe$.

6. The compound, pharmaceutically acceptable salt and/or solvate thereof according to claim 1, wherein each $R_3$ is independently fluoro or methyl.

7. The compound, pharmaceutically acceptable salt and/or solvate thereof according to claim 1, wherein m is 1 or 2.

8. The compound, pharmaceutically acceptable salt and/or solvate thereof according to claim 1, wherein m is 1 and $R_3$ is in the 3-position.

9. The compound, pharmaceutically acceptable salt and/or solvate thereof according to claim 1, wherein m is 1 and $R_3$ is in the 6-position.

10. The compound, pharmaceutically acceptable salt and/or solvate thereof according to claim 1, wherein m is 2, one $R_3$ is in the 3-position, and the other $R_3$ is in the 6-position.

11. The compound, pharmaceutically acceptable salt and/or solvate thereof according to claim 1, wherein group B is group (Bc):

(Bc)

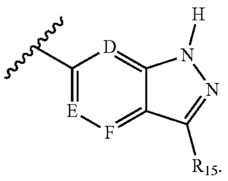

12. The compound, pharmaceutically acceptable salt and/or solvate thereof according to claim 11, wherein $R_{15}$ is methyl, ethyl, cyclopropyl, $CF_3$, CN, OMe, chloro or fluoro.

13. The compound, pharmaceutically acceptable salt and/or solvate thereof according to claim 12, wherein $R_{15}$ is OMe, chloro or fluoro.

14. The compound, pharmaceutically acceptable salt and/or solvate thereof according to claim 12, wherein $R_{15}$ is methyl, CN, chloro or fluoro.

15. The compound, pharmaceutically acceptable salt and/or solvate thereof according to claim 1, wherein D, E and F are $C(R_{16})$.

16. The compound, pharmaceutically acceptable salt and/or solvate thereof according to claim 1, wherein each $R_{16}$ is independently H, fluoro, chloro or methyl.

17. The compound, pharmaceutically acceptable salt and/or solvate thereof according to claim 1, which is a compound of formula (Ia'):

(Ia')

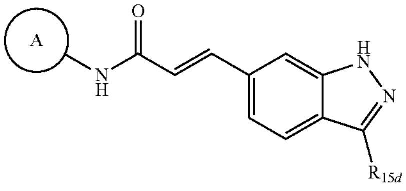

wherein:

A is group (Aa'), group (Ab'), group (Ad') or group (Ad");

$R_{15d}$ is methyl, ethyl, cyclopropyl, CN, $CF_3$, OMe, chloro or fluoro;

wherein group (Aa') is:

(Aa')

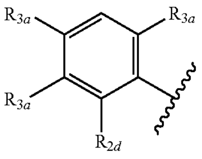

wherein:

$R_{2d}$ is H, methyl or $CH_2OMe$;

each $R_{3a}$ is independently H, fluoro or methyl; and wherein group (Ab') is:

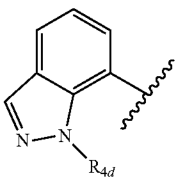

wherein:

$R_{4d}$ is methyl;

wherein group (Ad') is:

(Ad')

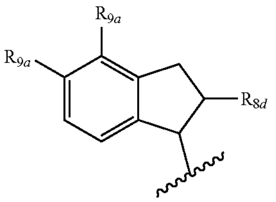

wherein:

$R_{8d}$ is H, methyl, $OCH_2$-cyclopropyl, $OCH_2$-oxetanyl, $OCH_2CH_2F$, OMe or OEt;

each $R_{9a}$ is independently H or fluoro;

wherein group (Ad") is:

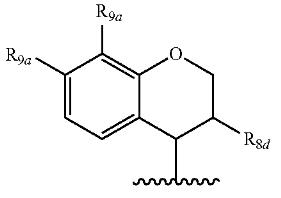

(Ad")

wherein:

$R_{8d}$ is methyl; and each $R_{9a}$ is independently H or fluoro;

or a pharmaceutically acceptable salt and/or solvate thereof.

18. The compound, pharmaceutically acceptable salt and/or solvate thereof according to claim 1, which is selected from the group consisting of:

(E)-3-(1H-benzo[d][1,2,3]triazol-6-yl)-N-(3-fluoro-2-methylphenyl)acrylamide;

(E)-N-(3-fluoro-2-methylphenyl)-3-(2-oxo-2,3-dihydrobenzo[d]thiazol-5-yl)acrylamide;

(E)-3-(3,3-dimethyl-2-oxoindolin-6-yl)-N-(3-fluoro-2-methylphenyl)acrylamide;

(E)-N-(3-fluoro-2-methylphenyl)-3-(2'-oxospiro[cyclopropane-1,3'-indolin]-6'-yl)acrylamide;

(E)-N-(3-fluoro-2-methylphenyl)-3-(7-fluoro-2-oxoindolin-6-yl)acrylamide;

(E)-N-(3-fluoro-2-methylphenyl)-3-(2-oxo-2,3-dihydrobenzo[d]oxazol-5-yl)acrylamide;

(E)-N-(3-fluoro-2-methylphenyl)-3-(1-methyl-2-oxo-2,3-dihydro-1H-benzo[d]imidazol-5-yl) acrylamide;

(E)-N-(3-fluoro-2-methylphenyl)-3-(3-methyl-2-oxoindolin-6-yl)acrylamide;

(E)-N-(3-chloro-2-methylphenyl)-3-(2-oxo-2,3-dihydrobenzo[d]oxazol-5-yl)acrylamide;

(E)-N-(3-fluoro-2-methylphenyl)-3-(2-oxoindolin-6-yl) acrylamide;

(E)-N-(2,3-dihydro-1H-inden-1-yl)-3-(2-oxo-2,3-dihydrobenzo[d]oxazol-5-yl)acrylamide;

(E)-3-(2-oxo-2,3-dihydrobenzo[d]oxazol-5-yl)-N-(o-tolyl)acrylamide;

(E)-N-(2-isopropylphenyl)-3-(2-oxo-2,3-dihydrobenzo[d]oxazol-5-yl)acrylamide;

(E)-N-(2-isopropyl-6-methylphenyl)-3-(2-oxo-2,3-dihydrobenzo[d]oxazol-5-yl)acrylamide;

(E)-N-(5-chloro-2-isopropylphenyl)-3-(2-oxo-2,3-dihydrobenzo[d]oxazol-5-yl)acrylamide;

(E)-N-(4,5-difluoro-2-methylphenyl)-3-(2-oxo-2,3-dihydrobenzo[d]oxazol-5-yl)acrylamide;

(E)-N-(5-fluoro-2-methylphenyl)-3-(2-oxo-2,3-dihydrobenzo[d]oxazol-5-yl)acrylamide;

(E)-N-(3-fluoro-2-methylphenyl)-3-(4-fluoro-2-oxoindolin-6-yl)acrylamide;

(E)-N-(2,6-dimethylphenyl)-3-(2-oxoindolin-6-yl)acrylamide;

(E)-N-(3-fluoro-2,6-dimethylphenyl)-3-(2-oxoindolin-6-yl)acrylamide;

(E)-N-(2-methyl-2,3-dihydro-1H-inden-1-yl)-3-(2-oxoindolin-6-yl)acrylamide;

(E)-3-(1-ethyl-2-oxo-2,3-dihydro-1H-benzo[d]imidazol-5-yl)-N-(3-fluoro-2-methylphenyl) acrylamide;

(E)-3-(1-cyclopropyl-2-oxo-2,3-dihydro-1H-benzo[d]imidazol-5-yl)-N-(3-fluoro-2-methylphenyl)acrylamide;

(E)-N-(2,3-dihydro-1H-inden-1-yl)-3-(1-methyl-2-oxo-2,3-dihydro-1H-benzo[d]imidazol-5-yl) acrylamide;

(E)-N-(2,3-dihydro-1H-inden-1-yl)-3-(3-methyl-1H-indazol-6-yl)acrylamide;

(E)-3-(3-cyano-1H-indazol-6-yl)-N-(2,3-dihydro-1H-inden-1-yl)acrylamide;

(E)-N-(2,3-dihydro-1H-inden-1-yl)-3-(5-fluoro-1H-benzo[d][1,2,3]triazol-6-yl)acrylamide;

(E)-N-(2,3-dihydro-1H-inden-1-yl)-3-(3-(trifluoromethyl)-1H-indazol-6-yl)acrylamide;

(E)-N-(2,6-dimethylphenyl)-3-(1-methyl-2-oxo-2,3-dihydro-1H-benzo[d]imidazol-5-yl)acrylamide;

(E)-N-(3-fluoro-2,6-dimethylphenyl)-3-(1-methyl-2-oxo-2,3-dihydro-1H-benzo[d]imidazol-5-yl)acrylamide;

(E)-N-(2,6-dimethylphenyl)-3-(3-methyl-1H-indazol-6-yl)acrylamide;

(E)-N-(2,3-dihydro-1H-inden-1-yl)-3-(3-ethyl-1H-indazol-6-yl)acrylamide;

(E)-3-(3-cyclopropyl-1H-indazol-6-yl)-N-(2,3-dihydro-1H-inden-1-yl)acrylamide;

(E)-N-(2,3-dihydro-1H-inden-1-yl)-3-(4-fluoro-3-methyl-1H-indazol-6-yl)acrylamide;

(E)-N-(3,5-difluoro-2,6-dimethylphenyl)-3-(2-oxoindolin-6-yl)acrylamide;

(E)-N-(3,4-difluoro-2,6-dimethylphenyl)-3-(2-oxoindolin-6-yl)acrylamide;

(E)-N-(3-fluoro-2-methylphenyl)-3-(3-methyl-1H-indazol-6-yl)acrylamide;

(E)-3-(3-methyl-1H-indazol-6-yl)-N-(2-methyl-2,3-dihydro-1H-inden-1-yl)acrylamide;

(E)-3-(3-methyl-1H-indazol-6-yl)-N-(1-methyl-1H-indazol-7-yl)acrylamide;

(E)-N-(5-fluoro-2,3-dihydro-1H-inden-1-yl)-3-(3-methyl-1H-indazol-6-yl)acrylamide;

(E)-N-(4-fluoro-3-methylphenyl)-3-(3-methyl-1H-indazol-6-yl)acrylamide;

(E)-N-(3-fluoro-4-methylphenyl)-3-(3-methyl-1H-indazol-6-yl)acrylamide;

Racemic-(E)-3-(3-methyl-1H-indazol-6-yl)-N-((1R,2R)-2-methylcyclohexyl)acrylamide;

(E)-3-(3-cyano-1H-indazol-6-yl)-N-(2-methyl-2,3-dihydro-1H-inden-1-yl)acrylamide;

(E)-N-(2-methyl-2,3-dihydro-1H-inden-1-yl)-3-(1-methyl-2-oxo-2,3-dihydro-1H-benzo[d]imidazol-5-yl) acrylamide;

(E)-N-(2-methyl-2,3-dihydro-1H-inden-1-yl)-3-(2-oxo-2,3-dihydrobenzo[d]oxazol-5-yl)acrylamide;

(Z)-2-fluoro-N-(3-fluoro-2-methylphenyl)-3-(2-oxoindolin-6-yl)acrylamide;

(E)-N-(3-chloro-2-methylphenyl)-N-methyl-3-(2-oxo-2,3-dihydrobenzo[d]oxazol-5-yl)acrylamide;

(E)-N-(2-methylcyclopentyl)-3-(2-oxo-2,3-dihydrobenzo[d]oxazol-5-yl)acrylamide;

(E)-N-(3-fluoro-2-(methoxymethyl)phenyl)-3-(3-methyl-1H-indazol-6-yl)acrylamide;

(E)-3-(3-cyano-1H-indazol-6-yl)-N-(3-fluoro-2-methylphenyl)acrylamide;

(E)-3-(3-methyl-1H-indazol-6-yl)-N-(3-methylchroman-4-yl)acrylamide;

(E)-N-(2-methyl-1,2,3,4-tetrahydronaphthalen-1-yl)-3-(3-methyl-1H-indazol-6-yl)acrylamide;

(E)-N-((1S,2S)-2-methoxy-2,3-dihydro-1H-inden-1-yl)-3-(3-methyl-1H-indazol-6-yl)acrylamide;

(R,E)-N-(2,3-dihydro-1H-inden-1-yl)-3-(3-methyl-1H-indazol-6-yl)acrylamide;

(E)-N-(chroman-4-yl)-3-(2-oxo-2,3-dihydrobenzo[d]oxazol-5-yl)acrylamide;

(E)-3-(2-oxo-2,3-dihydrobenzo[d]oxazol-5-yl)-N-(1,2,3,4-tetrahydronaphthalen-1-yl)acrylamide;

(E)-N-(2-methyl-1,2,3,4-tetrahydronaphthalen-1-yl)-3-(2-oxoindolin-6-yl)acrylamide;

(E)-N-(2,3-dihydro-1H-inden-1-yl)-3-(2-oxoindolin-6-yl)acrylamide;

(E)-N-(3,5-difluoro-2-methylphenyl)-3-(2-oxoindolin-6-yl)acrylamide;

(E)-N-(2,3-dihydro-1H-inden-1-yl)-3-(7-fluoro-1H-benzo[d][1,2,3]triazol-6-yl)acrylamide;

(E)-N-(2,3-dihydro-1H-inden-1-yl)-3-(4-fluoro-1H-benzo[d][1,2,3]triazol-6-yl)acrylamide;

(E)-N-(5-chloro-2-methylphenyl)-3-(2-oxo-2,3-dihydrobenzo[d]oxazol-5-yl)acrylamide;

(E)-N-(2-methylcyclohexyl)-3-(2-oxoindolin-6-yl)acrylamide;

(E)-3-(3-methyl-1H-indazol-6-yl)-N-(-3-methylchroman-4-yl)acrylamide;

(E)-3-(3-methyl-1H-indazol-6-yl)-N-((3R,4S)-3-methylchroman-4-yl)acrylamide;

(E)-3-(3-methyl-1H-indazol-6-yl)-N-((3S,4R)-3-methylchroman-4-yl)acrylamide;

(E)-3-(3-methyl-1H-indazol-6-yl)-N-((3R,4R)-3-methylchroman-4-yl)acrylamide;

(E)-3-(3-methyl-1H-indazol-6-yl)-N-((3S,4S)-3-methylchroman-4-yl)acrylamide;

(E)-3-(3-methyl-1H-indazol-6-yl)-N-((1S,2S)-2-(oxetan-3-ylmethoxy)-2,3-dihydro-1H-inden-1-yl)acrylamide;

(E)-N-((1S,2S)-2-(cyclopropylmethoxy)-2,3-dihydro-1H-inden-1-yl)-3-(3-methyl-1H-indazol-6-yl)acrylamide;

(E)-N-((1S,2S)-2-(2-fluoroethoxy)-2,3-dihydro-1H-inden-1-yl)-3-(3-methyl-1H-indazol-6-yl)acrylamide;

(E)-N-((1S,2S)-2-ethoxy-2,3-dihydro-1H-inden-1-yl)-3-(3-methyl-1H-indazol-6-yl)acrylamide;

(E)-3-(3-cyclopropyl-1H-indazol-6-yl)-N-((1S,2S)-2-methoxy-2,3-dihydro-1H-inden-1-yl)acrylamide;

(E)-3-(3-methoxy-1H-indazol-6-yl)-N-((1S,2S)-2-methoxy-2,3-dihydro-1H-inden-1-yl)acrylamide;

(E)-3-(3-chloro-1H-indazol-6-yl)-N-((1S,2S)-2-methoxy-2,3-dihydro-1H-inden-1-yl)acrylamide;

(E)-3-(3-fluoro-1H-indazol-6-yl)-N-((1S,2S)-2-methoxy-2,3-dihydro-1H-inden-1-yl)acrylamide; and (E)-3-(3-cyano-1H-indazol-6-yl)-N-((1S,2S)-2-methoxy-2,3-dihydro-1H-inden-1-yl)acrylamide;

or a pharmaceutically acceptable salt and/or solvate of any one thereof.

19. A method of treating a disease selected from Parkinson's disease, dementia with Lewy bodies, Alzheimer's disease, amyotrophic lateral sclerosis, frontotemporal dementia, non-alcoholic steatohepatitis, obesity, and chronic kidney disease in a subject, which comprises administering to a subject suffering from the said disease an effective amount of a compound, pharmaceutically acceptable salt and/or solvate thereof according to claim 1.

20. A pharmaceutical composition comprising a compound, pharmaceutically acceptable salt and/or solvate thereof according to claim 1, and a pharmaceutically acceptable carrier or excipient.

* * * * *